US012787640B2

(12) United States Patent
Li et al.

(10) Patent No.: US 12,787,640 B2
(45) Date of Patent: Nov. 3, 2026

(54) ORGANIC MATERIAL COMPOSITION AND APPLICATIONS THEREOF

(71) Applicant: Ningbo Lumilan Advanced Materials Co., Ltd., Ningbo City (CN)

(72) Inventors: Xiangzhi Li, Ningbo City (CN); Ye Cai, Ningbo City (CN); Ting-Wei Wei, Ningbo City (CN); Zhi-Kuan Chen, Ningbo City (CN)

(73) Assignee: Ningbo Lumilan Advanced Materials Co., Ltd., Ningbo City (CN)

( * ) Notice: Subject to any disclaimer, the term of this patent is extended or adjusted under 35 U.S.C. 154(b) by 1078 days.

(21) Appl. No.: 17/950,312

(22) Filed: Sep. 22, 2022

(65) Prior Publication Data

US 2023/0157161 A1 May 18, 2023

(30) Foreign Application Priority Data

Nov. 18, 2021 (CN) ......................... 202111367059.0

(51) Int. Cl.

| | |
|---|---|
| ***H10K 85/60*** | (2023.01) |
| ***C07D 263/52*** | (2006.01) |
| ***C07D 403/04*** | (2006.01) |
| ***C07D 403/14*** | (2006.01) |
| ***C07D 405/14*** | (2006.01) |
| ***C07D 413/12*** | (2006.01) |
| ***H10K 50/11*** | (2023.01) |

(52) U.S. Cl.

CPC ......... *H10K 85/654* (2023.02); *C07D 263/52* (2013.01); *C07D 403/04* (2013.01); *C07D 403/14* (2013.01); *C07D 405/14* (2013.01); *C07D 413/12* (2013.01); *H10K 85/636* (2023.02); *H10K 85/6572* (2023.02); *H10K 85/6574* (2023.02); *H10K 50/11* (2023.02); *H10K 85/657* (2023.02)

(58) Field of Classification Search

CPC .. H10K 50/11; H10K 2101/90; H10K 85/654; H10K 85/636; H10K 85/6572; H10K 85/6574; H10K 85/657; H10K 85/656; C07D 263/52; C07D 403/04; C07D 403/14; C07D 405/14; C07D 413/12

See application file for complete search history.

(56) References Cited

U.S. PATENT DOCUMENTS

| | | | | |
|---|---|---|---|---|
| 2021/0328154 A1* | 10/2021 | Kim | ................... | H10K 85/6574 |
| 2021/0359216 A1* | 11/2021 | Kim | ..................... | H10K 85/624 |
| 2022/0123230 A1* | 4/2022 | Kang | ................... | C07D 403/04 |

* cited by examiner

*Primary Examiner* — Dylan C Kershner

(74) *Attorney, Agent, or Firm* — MUNCY, GEISSLER, OLDS & LOWE, P.C.

(57) ABSTRACT

The present invention provides an organic material composition and applications thereof. By the combination of the compounds comprised in the organic material composition, the organic material composition makes the element have a lower driving voltage, a higher current efficiency and a longer service life.

11 Claims, No Drawings

ORGANIC MATERIAL COMPOSITION AND APPLICATIONS THEREOF

CROSS-REFERENCE TO RELATED APPLICATION

Pursuant to 35 U.S.C. § 119(a), this application claims the benefit of the priority to Chinese Patent Application No. 202111367059.0, filed on Nov. 18, 2021. The content of the prior application is incorporated herein by its entirety.

BACKGROUND OF THE INVENTION

1. Field of the Invention

The present invention belongs to the field of electroluminescence material, which relates to an organic material composition and applications thereof.

2. Description of the Prior Arts

An electroluminescence (EL) device is a self-luminous display device which is advantageous for its wider angle of view, higher contrast ratio, and faster response time.

The most important key factor to decide the light-emitting efficiency of an EL device is the light-emitting material. A light-emitting material needs to have the following characteristics: high quantum efficiency, high mobility of electrons and holes, and the uniformity and stability of the light-emitting layer formed by the light-emitting material.

Recently, it is urgent to develop an organic EL device having higher light-emitting efficiency and longer service life. Specifically, in light of the EL characteristics needed for medium and large organic light-emitting diodes (OLED) panels, an excellent light-emitting material superior to regular materials is urgently needed. Thus, a high glass transition temperature and a high pyrolysis temperature are required for the host material in order to achieve high thermal stability and high electrochemical stability, thereby resulting in a longer service life, good formability of amorphous films, good adhesion with adjacent layers, and good immobility between layers.

To enhance color purity, light-emitting efficiency and stability, the light-emitting material as a host material can be used in a combination of a host material and a dopant. Generally, an EL device with good characteristics has an emitting layer structure formed by a material in which a dopant is doped into a host material. When the dopant/host material system is used as the light-emitting material, the host material will greatly influence the efficiency and service life of the EL device. Thus, the host material is important.

SUMMARY OF THE INVENTION

To overcome the shortcomings of the existing technology, the objective of the present invention is to provide an organic material composition and applications thereof.

To achieve the above objective, the present invention uses the following technical approaches:

In one aspect, the present invention provides an organic material composition comprising at least one compound having a structure represented by Formula (1) and at least one compound having a structure represented by Formula (2), Formula (1)

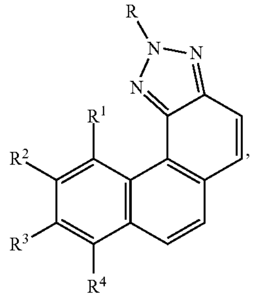

wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is $-L^1Ar^1$; $R^2$ is $-L^2Ar^2$; $R^3$ is $-L^3Ar^3$; $R^4$ is $-L^4Ar^4$;

$L^1$ to $L^4$ are each independently selected from a bond, a substituted or unsubstituted C6-C30 arylene group, and a substituted or unsubstituted C3-C30 heteroarylene group;

$Ar^1$ to $Ar^4$ are each independently selected from hydrogen, deuterium, halogen, a cyano group, a substituted or unsubstituted C6-C60 aryl group, and a substituted or unsubstituted C3-C60 heteroaryl group;

Formula (2)

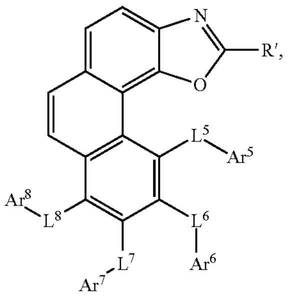

wherein, R' is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$L^5$ to $L^8$ are each independently selected from a bond, a substituted or unsubstituted C6-C30 arylene group, and a substituted or unsubstituted C3-C30 heteroarylene group;

$Ar^5$ to $Ar^8$ are each independently selected from hydrogen, deuterium, halogen, a cyano group, a substituted or unsubstituted C6-C60 aryl group, and a substituted or unsubstituted C3-C60 heteroaryl group.

In the present invention, by the combination of at least one compound having a structure represented by Formula (1) and at least one compound having a structure represented by Formula (2), the organic material composition not only has an energy level that can be aligned with the energy levels of the adjacent layers, but also has a higher triplet energy level, which are advantageous for the recombination of charge carriers in the emitting layer, thereby increasing light-emitting efficiency.

Preferably, in Formula (1), at least one of $Ar^1$ to $Ar^4$ is a group represented by Formula (a):

Formula (a)

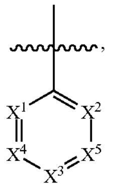

wherein the wavy line represents the connection position of the group;

$X^1$ is selected from N and $CR^{X1}$; $X^2$ is selected from N and $CR^{X2}$; $X^3$ is selected from N and $CR^{X3}$; $X^4$ is selected from N and $CR^{X4}$; $X^5$ is selected from N and $CR^{X5}$;

$R^{X1}$ to $R^{X5}$ are each independently selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group; $R^{X1}$ to $R^{X5}$ are present individually without forming a ring, or any adjacent two of $R^{X1}$ to $R^{X5}$ joined to form a ring, and the ring is a benzene ring.

Preferably, $X^1$ is N; $X^2$ is N; $X^3$ is $CR^{X3}$; $X^4$ is $CR^{X4}$; $X^5$ is $CR^{X5}$.

Preferably, $X^1$ is N; $X^3$ is N; $X^2$ is $CR^{X2}$; $X^4$ is $CR^{X4}$; $X^5$ is $CR^{X5}$.

Preferably, $X^1$ is N; $X^2$ is N; $X^3$ is N; $X^4$ is $CR^{X4}$; $X^5$ is $CR^{X5}$.

Preferably, the Formula (a) is selected from

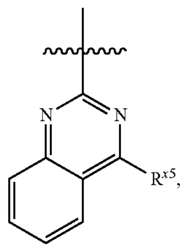

and $R^{X5}$ is the same as described above.

Preferably, the Formula (a) is selected from

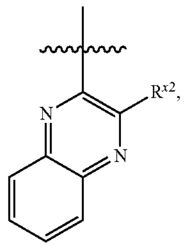

and $R^{X2}$ is the same as described above.

Preferably, in Formula (1), the $R^{X1}$ to $R^{X5}$ are each independently selected from hydrogen, deuterium, halogen, and a group selected from a phenyl group, a biphenylyl group, a terphenylyl group, a naphthyl group, a phenanthryl group, an anthryl group, a phenylnaphthyl group, a naphthylphenyl group, a pyridyl group, a bipyridyl group, a dibenzofuryl group, a dibenzothiophenyl group, a carbazolyl group, a carbazolylphenyl group, a phenylcarbazolyl group, a dimethylfluorenyl group, a diphenylfluorenyl group, a spiro-bifluorenyl group, a dibenzofurylphenyl group, a dibenzothiophenylphenyl group, a dimethylfluorenylphenyl group, a benzocarbazolyl group, a benzonaphthofuryl group, and a benzonaphthothiophenyl group, each of which is substituted or unsubstituted.

Preferably, in Formula (1), at least one of the $R^1$, $R^2$, $R^3$ and $R^4$ is hydrogen.

Preferably, at least two of the $R^1$, $R^2$, $R^3$ and $R^4$ are hydrogen.

Preferably, at least three of the $R^1$, $R^2$, $R^3$ and $R^4$ are hydrogen.

Preferably, the $R^2$ is $-L^2Ar^2$; and $R^1$, $R^3$, and $R^4$ are all hydrogen.

Preferably, the $R^3$ is $-L^3Ar^3$; and $R^1$, $R^2$, and $R^4$ are all hydrogen.

Preferably, the R is selected from a phenyl group and a biphenylyl group, each of which is substituted or unsubstituted.

Preferably, the R' is selected from a phenyl group and a biphenylyl group, each of which is substituted or unsubstituted.

Preferably, $L^1$ to $L^4$ are each independently selected from a bond, a substituted or unsubstituted phenylene group, a substituted or unsubstituted naphthylene group, and a substituted or unsubstituted biphenylene group.

In the present invention, the compound having a structure represented by Formula (1) is a compound having electron transport properties.

Preferably, the compound having a structure represented by Formula (1) is any one of the following compounds M1 to M206:

M1

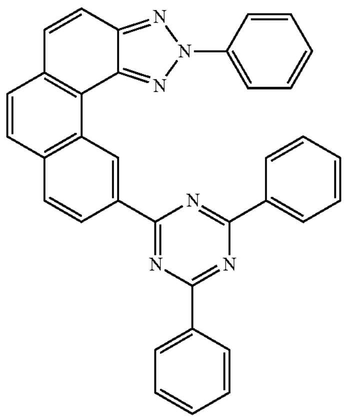

M2
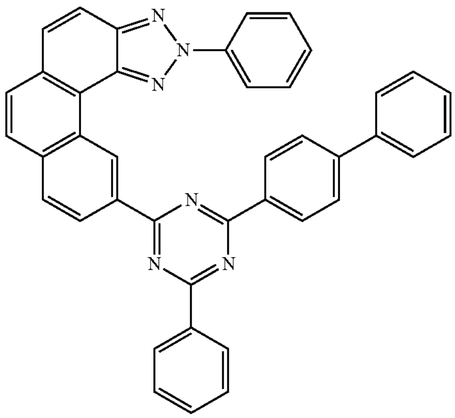
M3
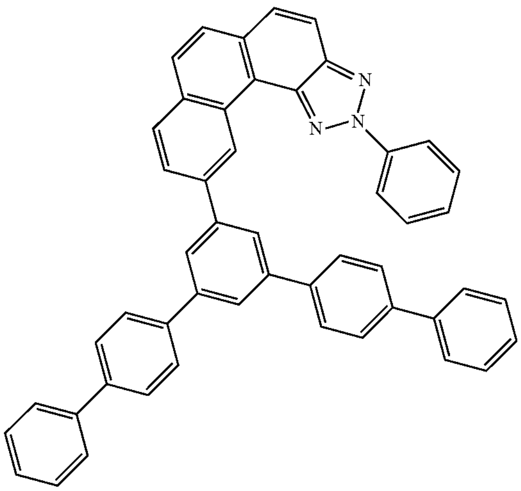
M4
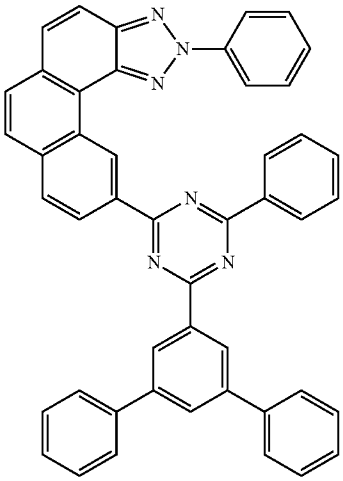
M5
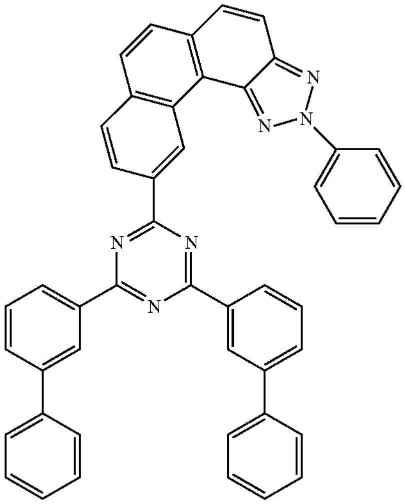
M6
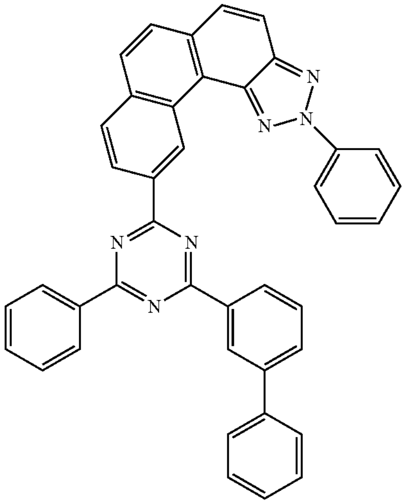
M7
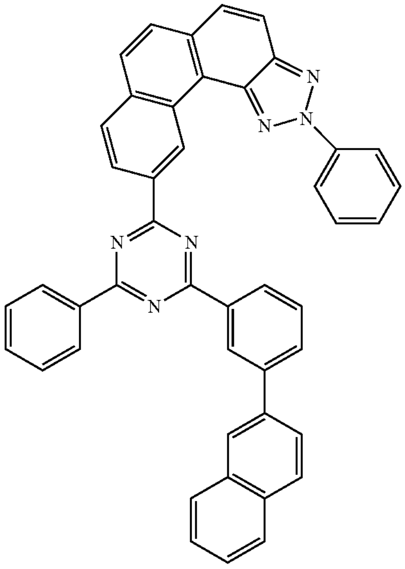

-continued
M8
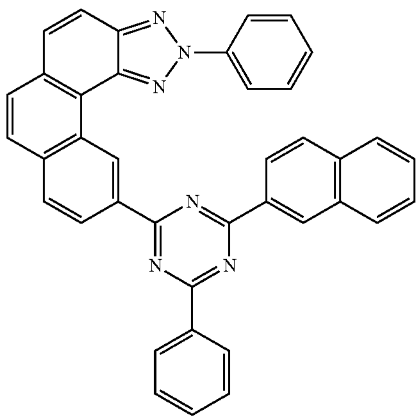
M9
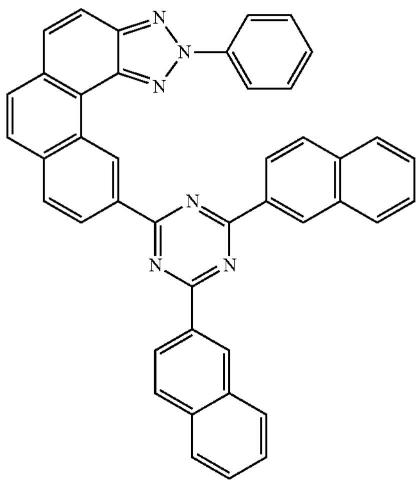
M10
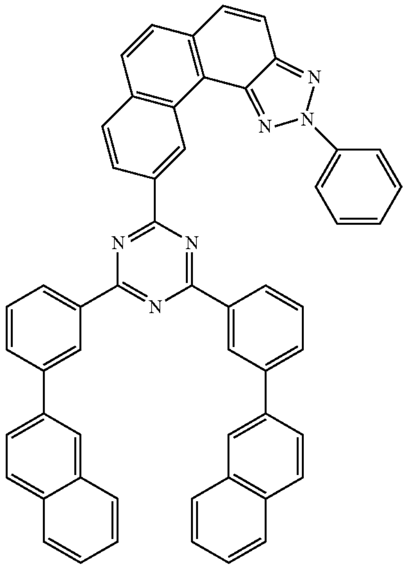
-continued
M11
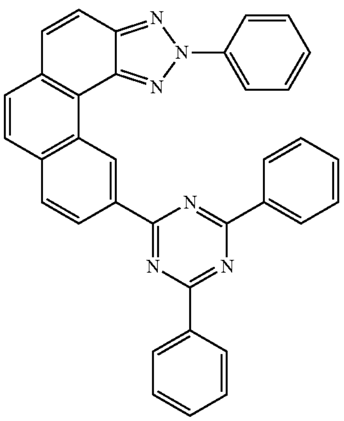
M12
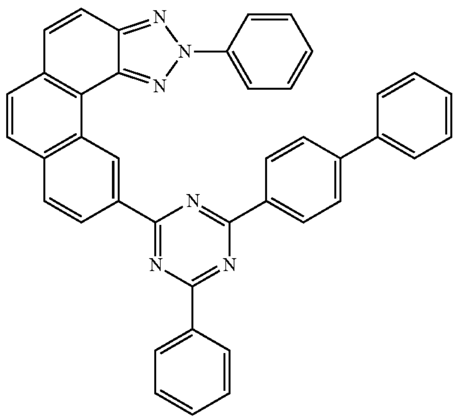
M13
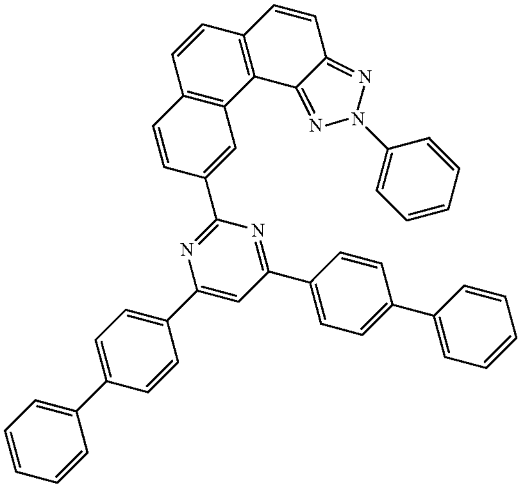

-continued
M14
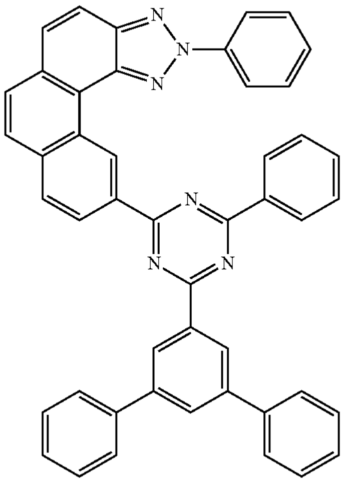
M15
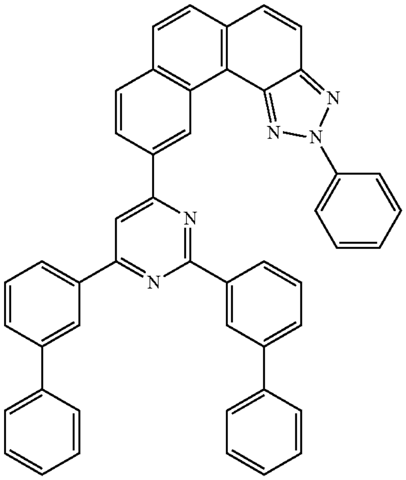
M16
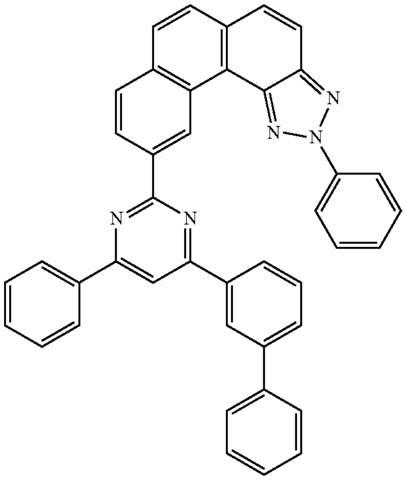
-continued
M17
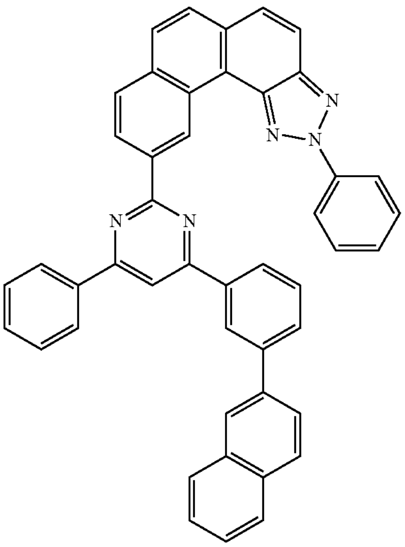
M18
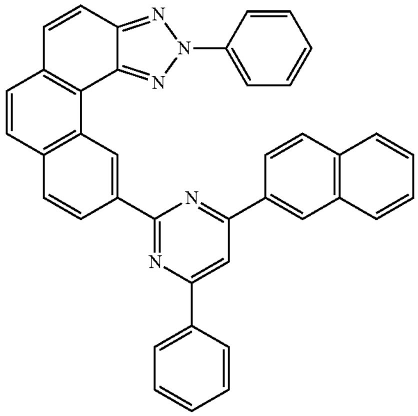
M19
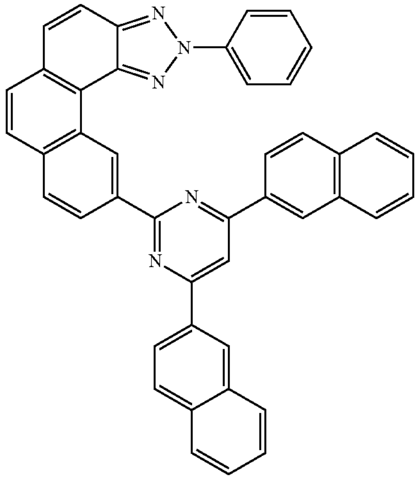

-continued
M20
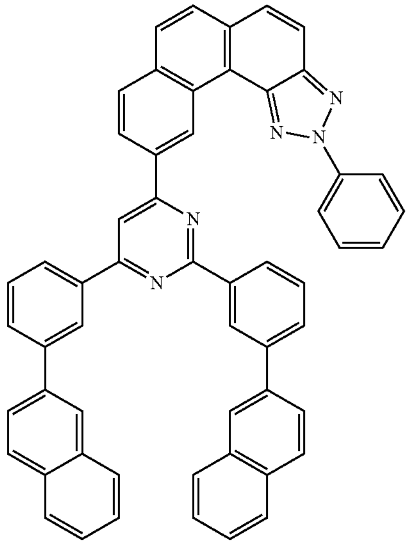
M21
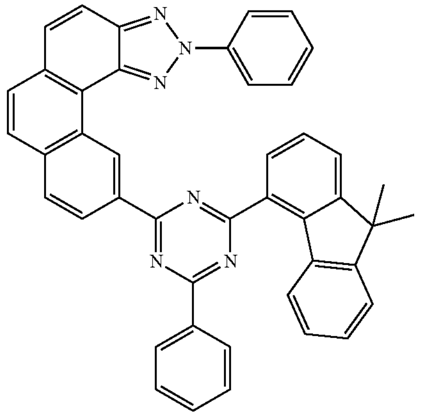
M22
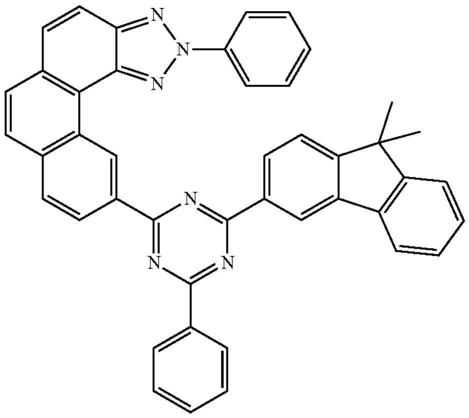
-continued
M23
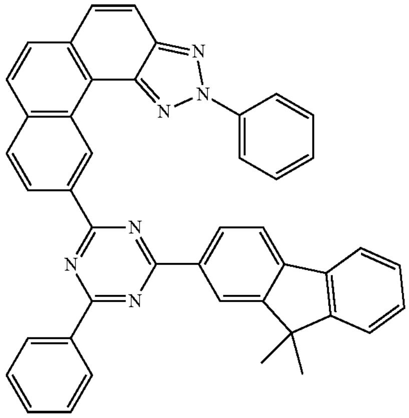
M24
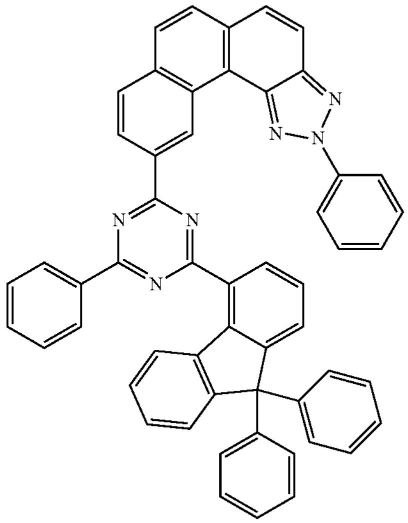
M25
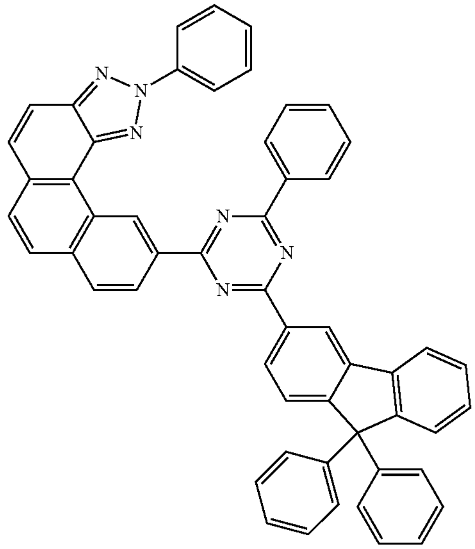

-continued
M26
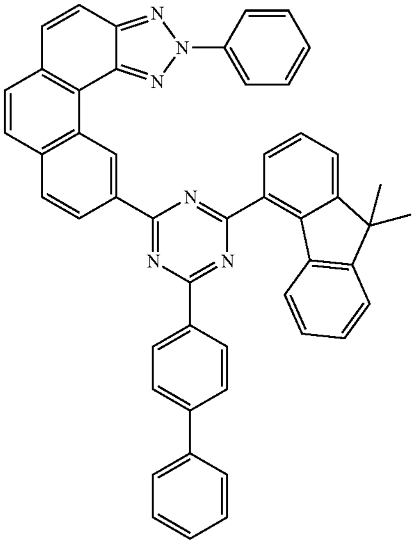
M27
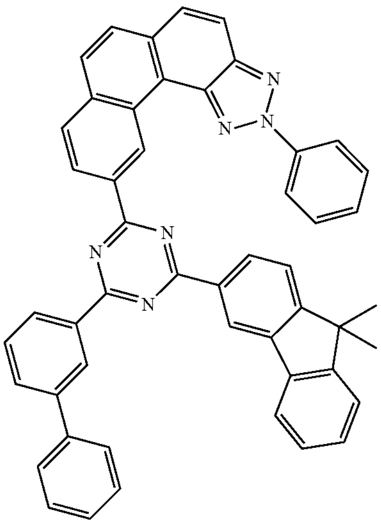
M28
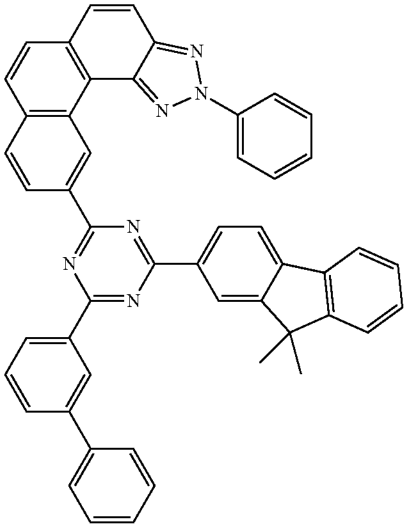
-continued
M29
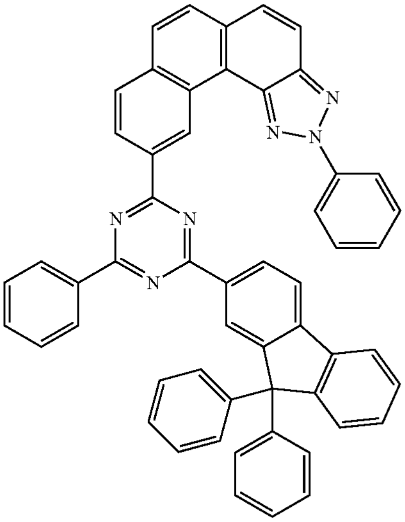
M30
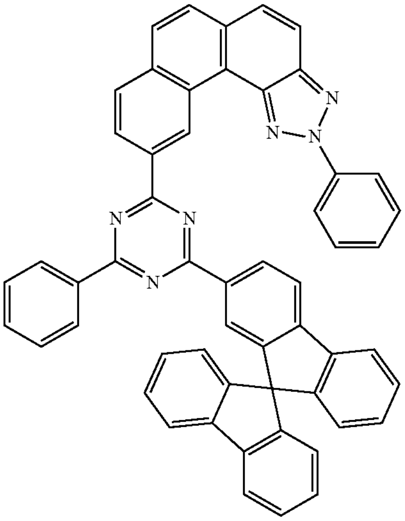
M31
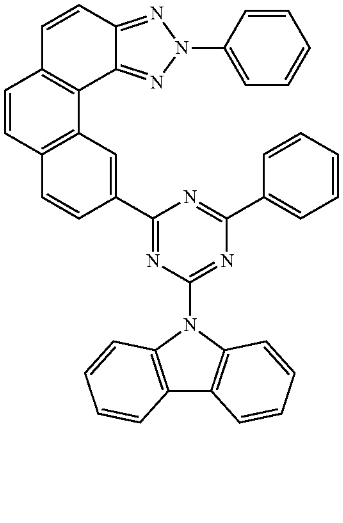

-continued
M32
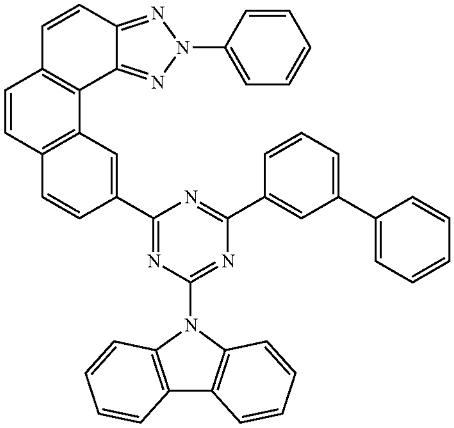
M33
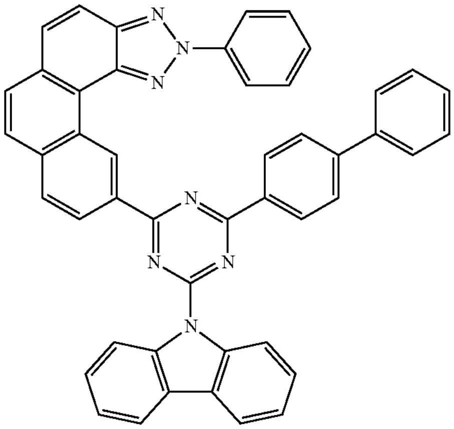
M34
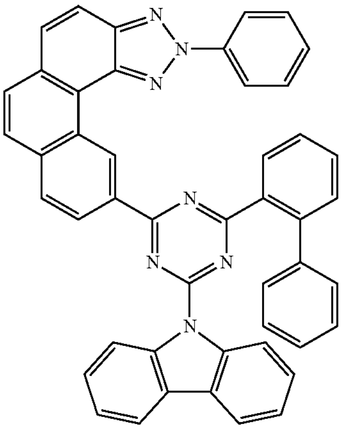
-continued
M35
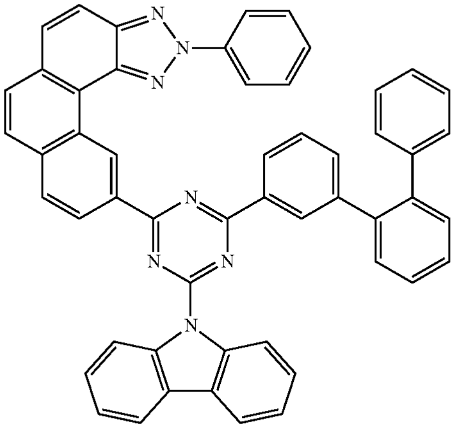
M36
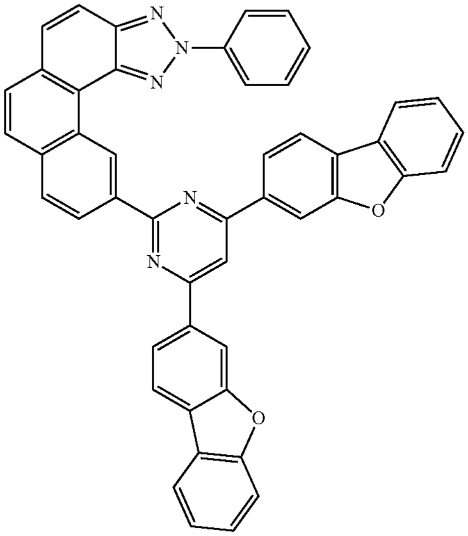
M37
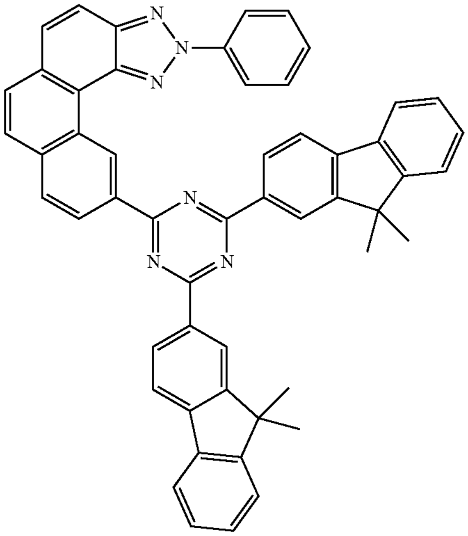

-continued
M38
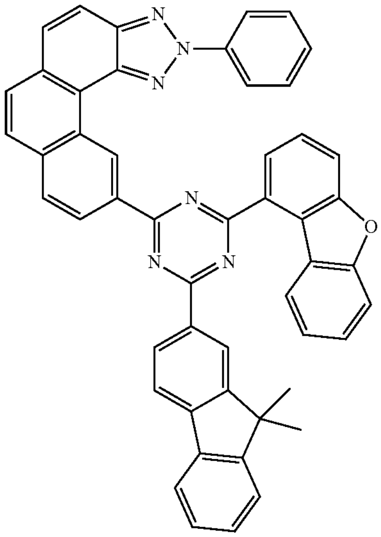
M39
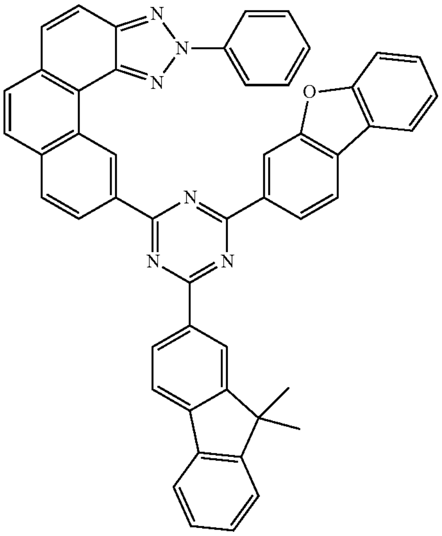
M40
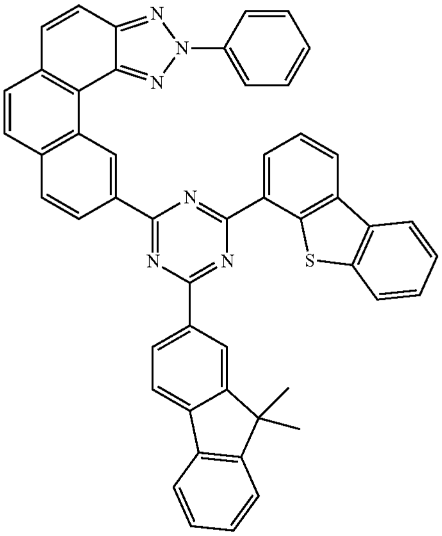
-continued
M41
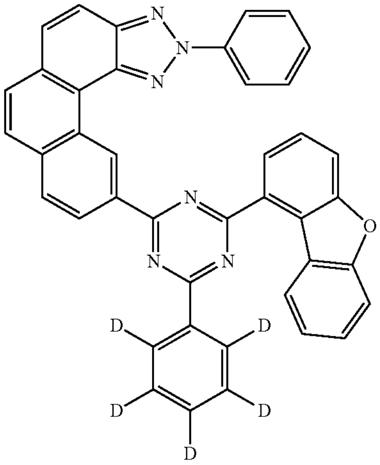
M42
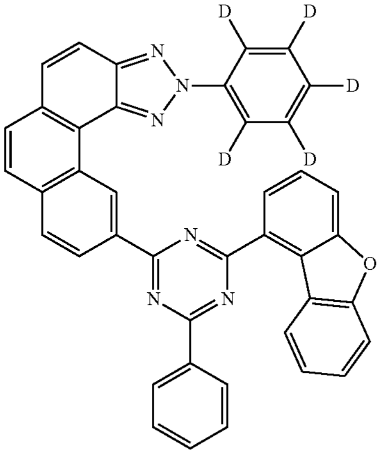
M43
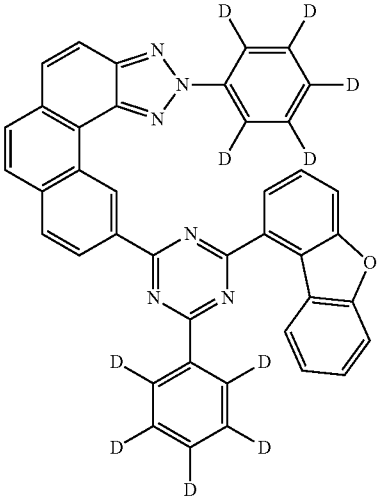

-continued
M44
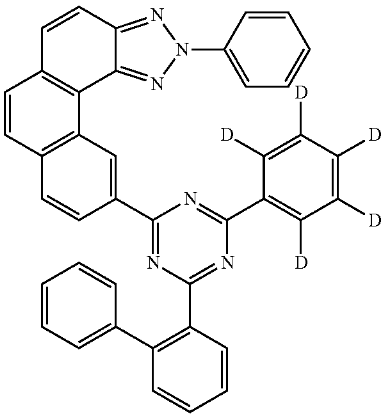
M45
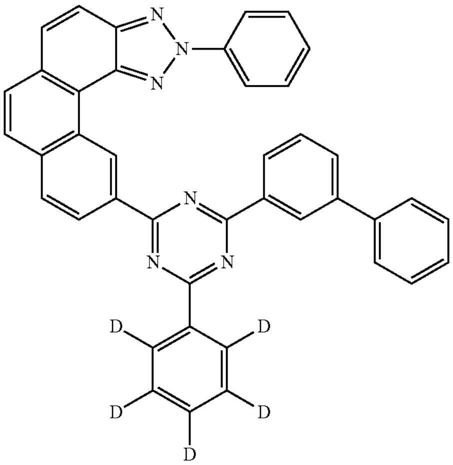
M46
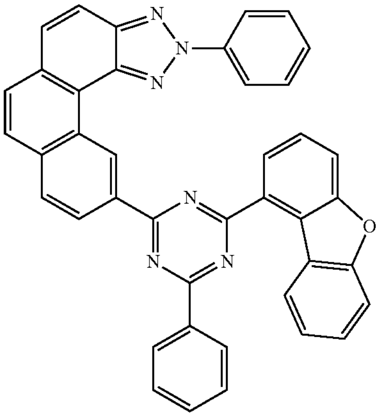
-continued
M47
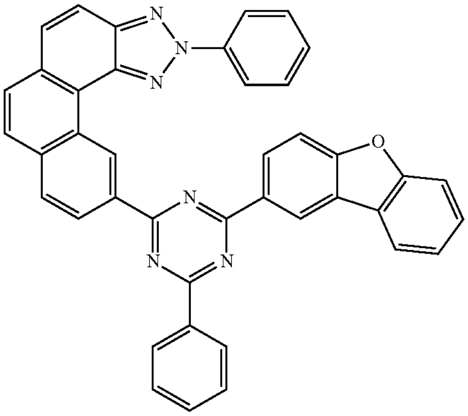
M48
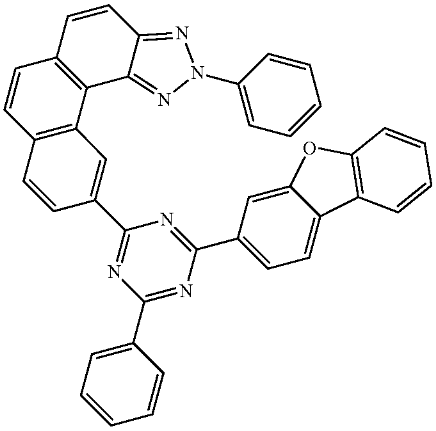
M49
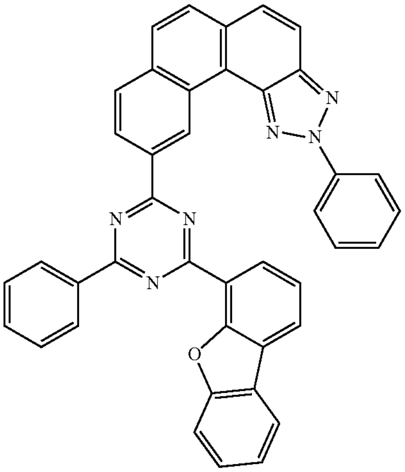

-continued
M50
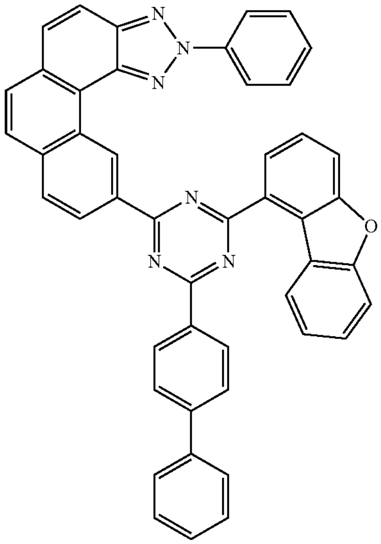
M51
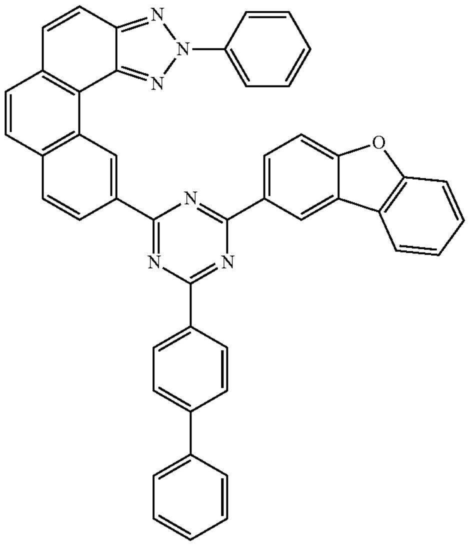
M52
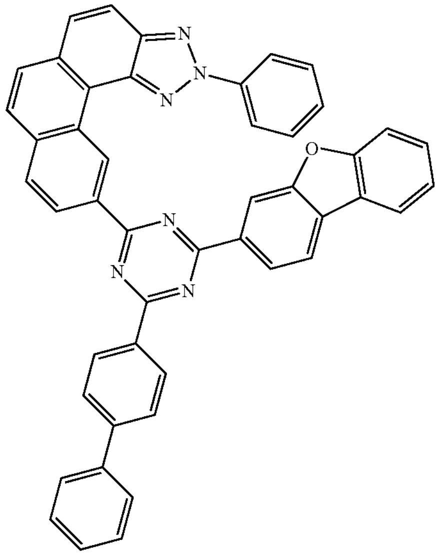
-continued
M53
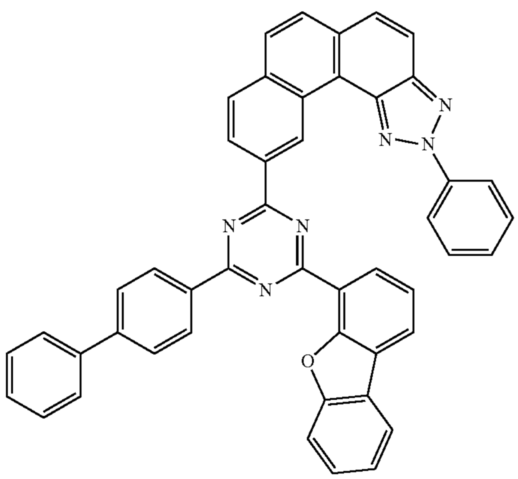
M54
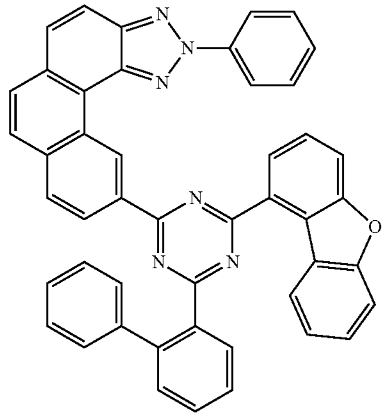
M55
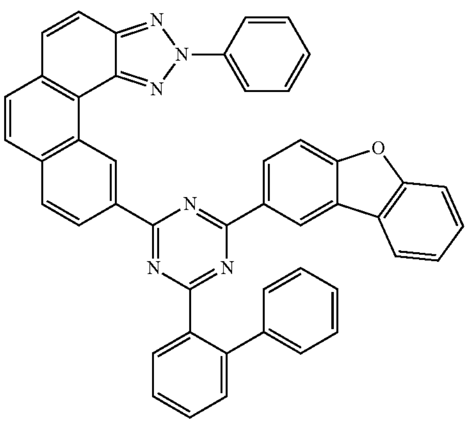

-continued
M56
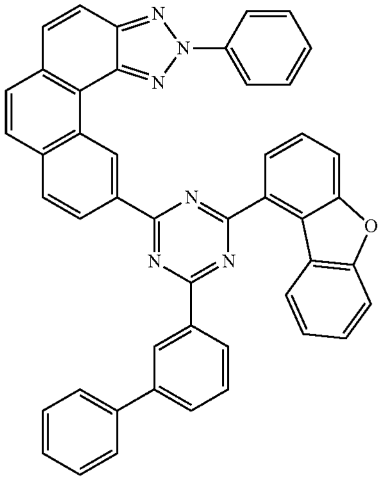
M57
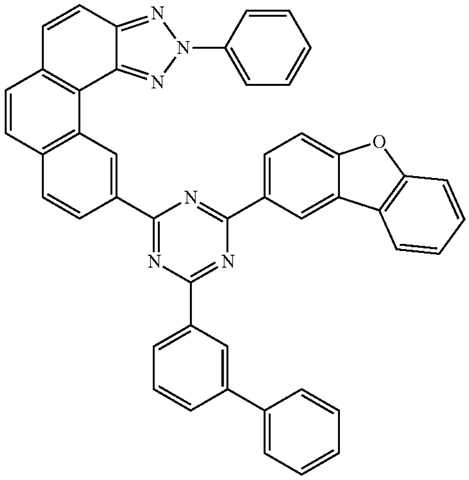
M58
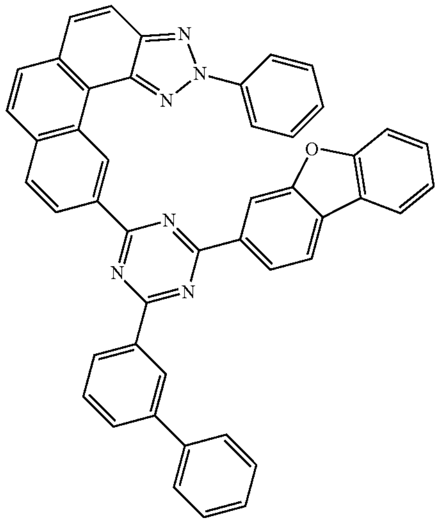
-continued
M59
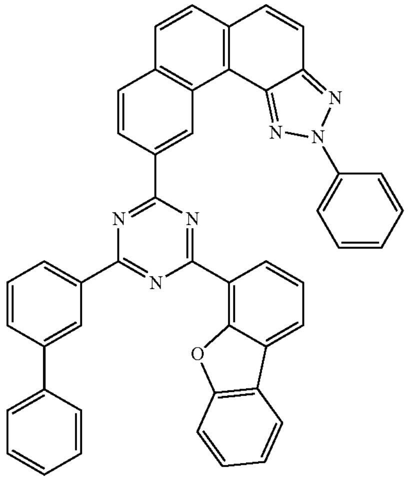
M60
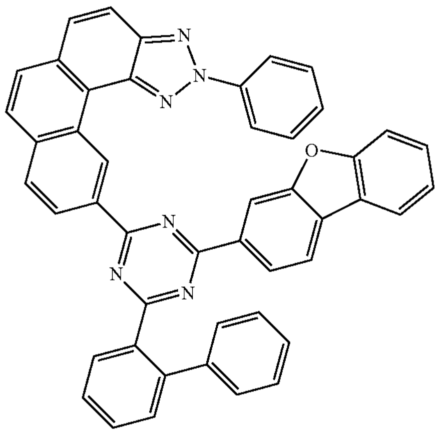
M61
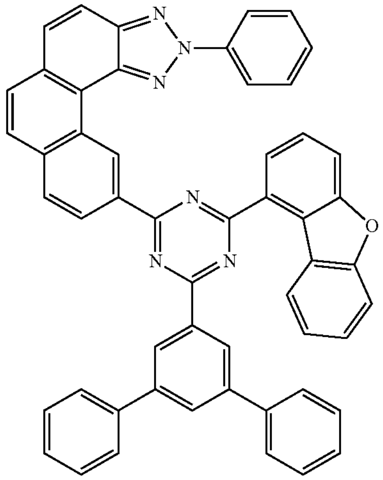

-continued
M62
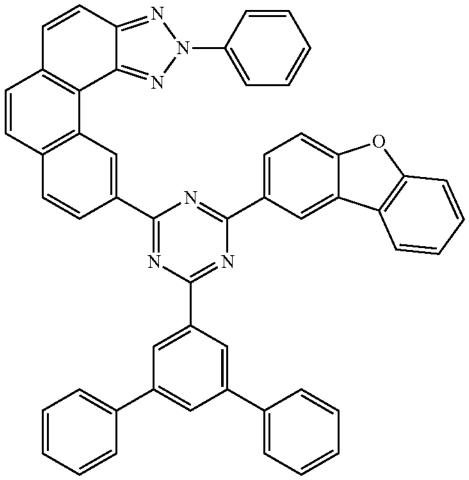
M63
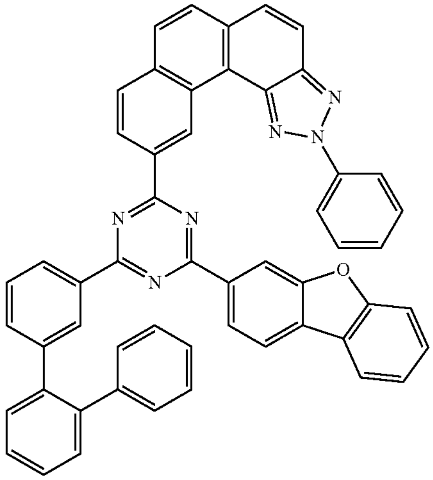
M64
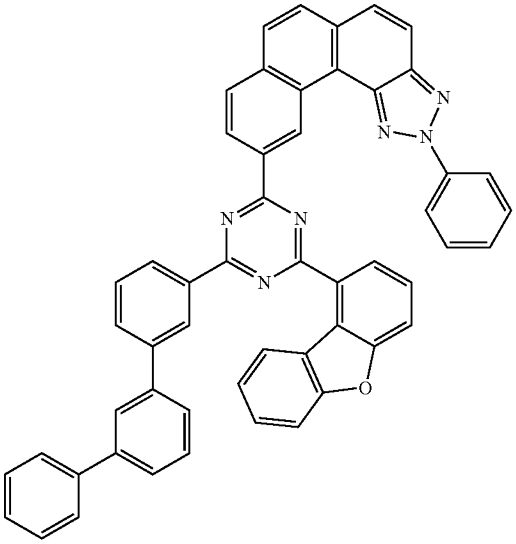
-continued
M65
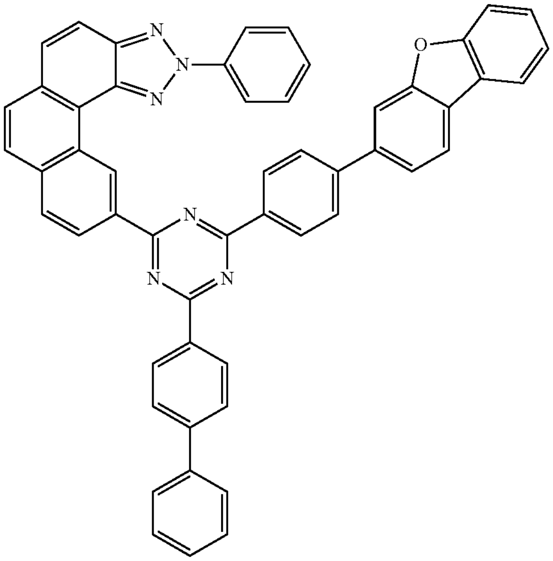
M66
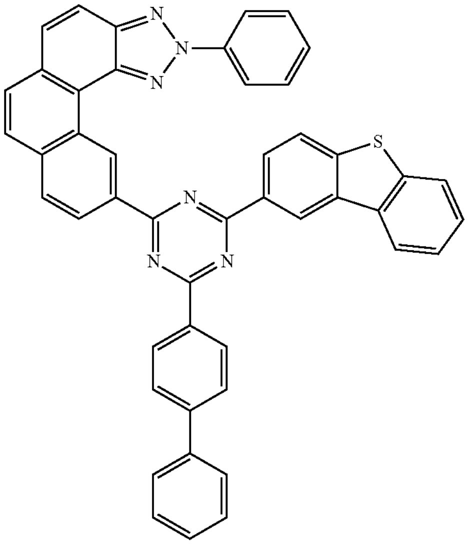

-continued
M67
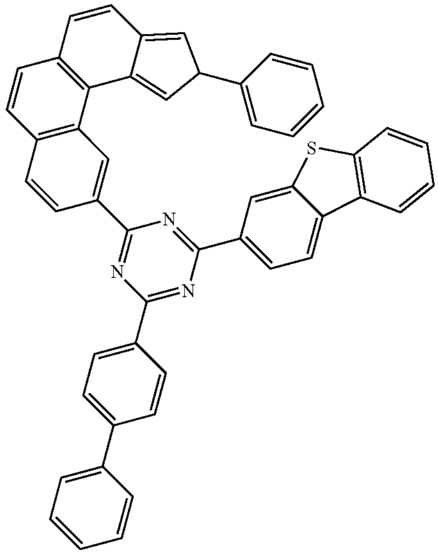
M68
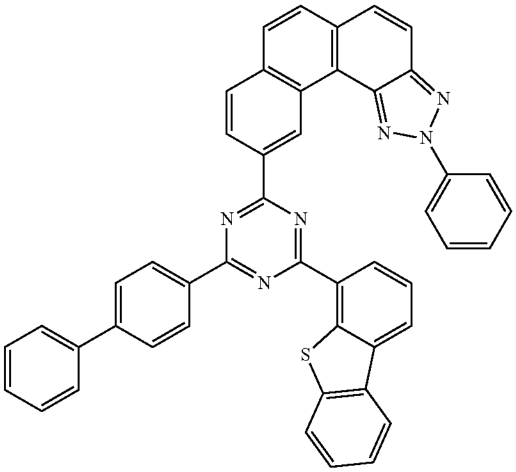
M69
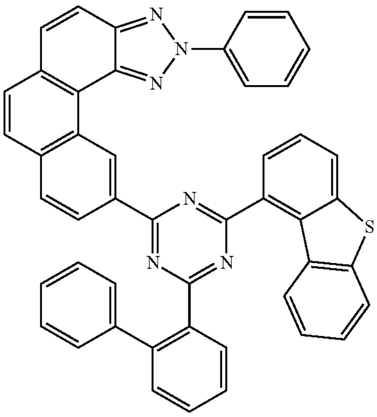
-continued
M70
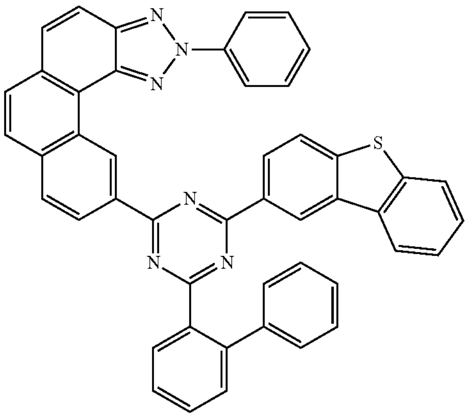
M71
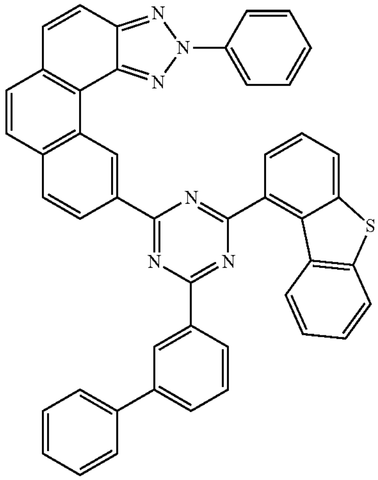
M72
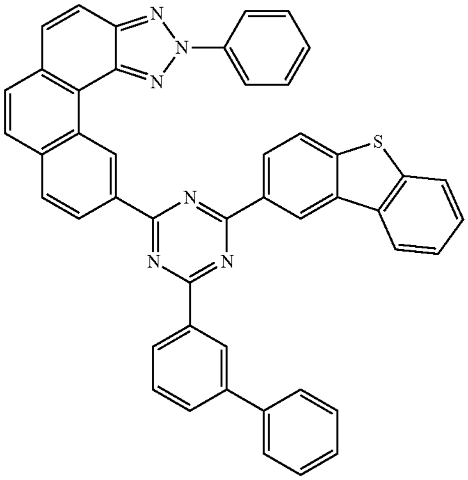

-continued
M73
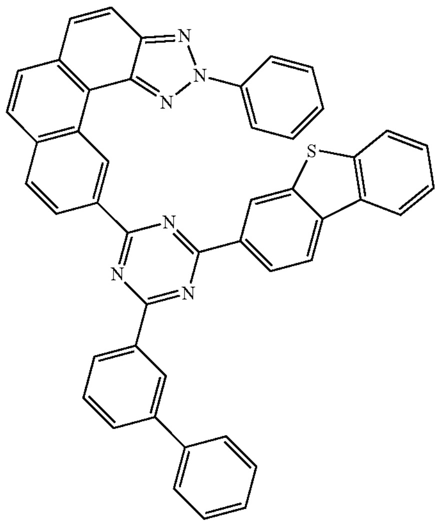
M74
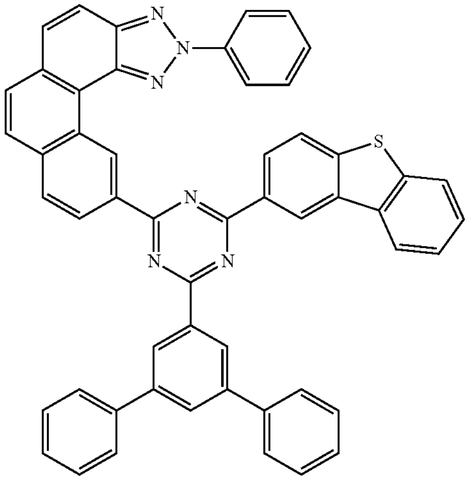
M75
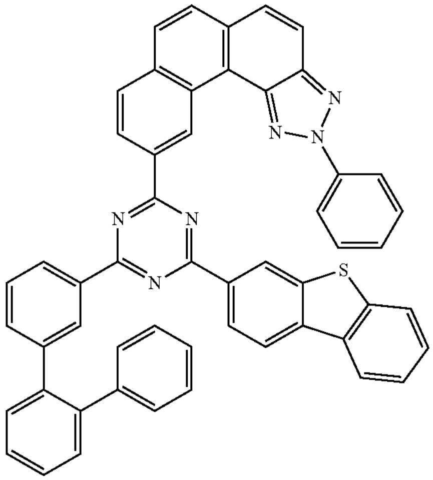
-continued
M76
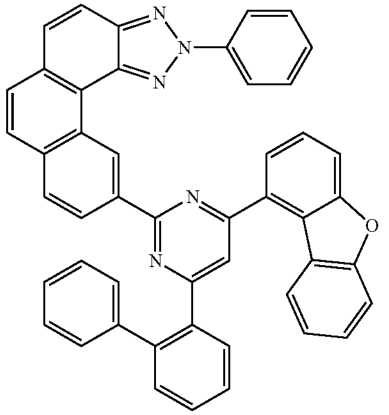
M77
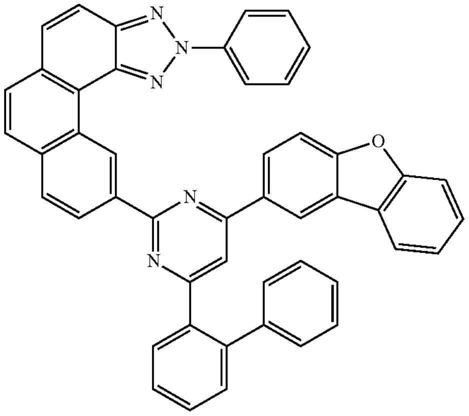
M78
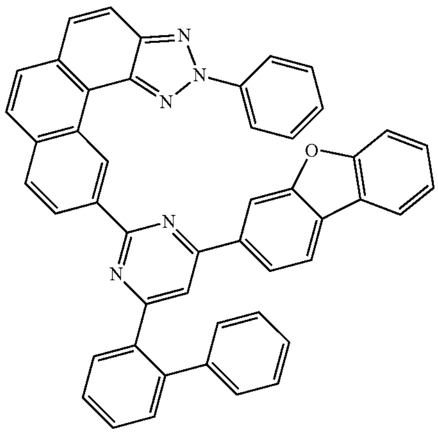

-continued
M79
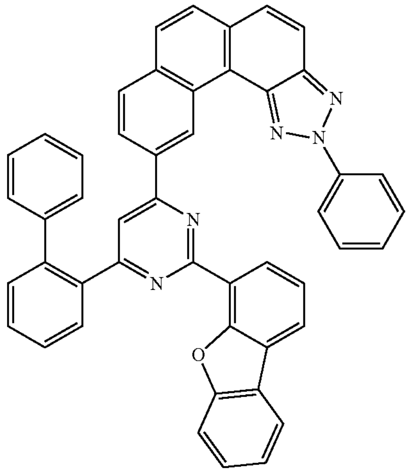
M80
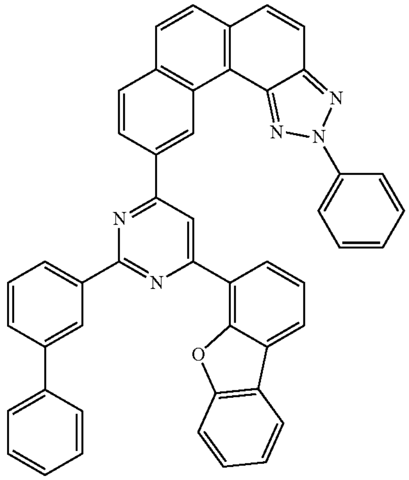
M81
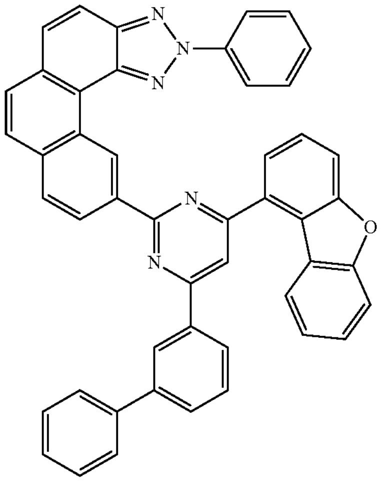
-continued
M82
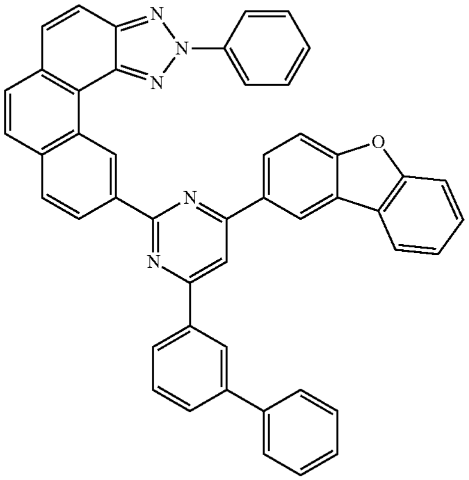
M83
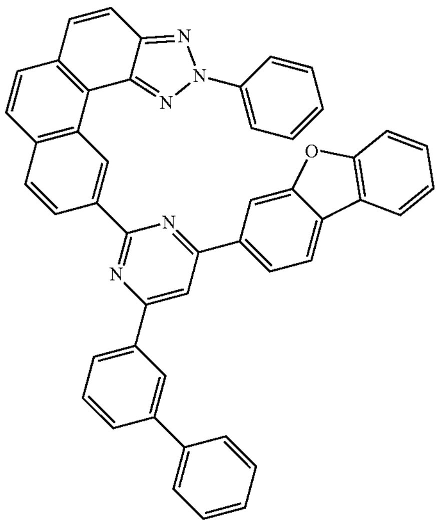
M84
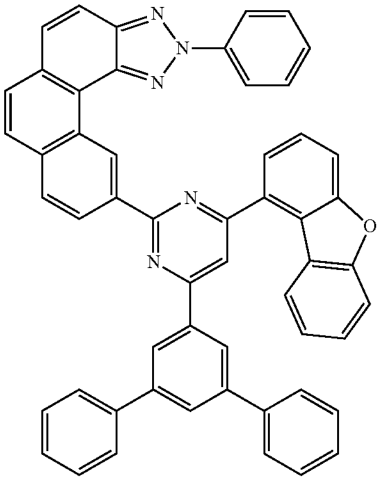

-continued
M85
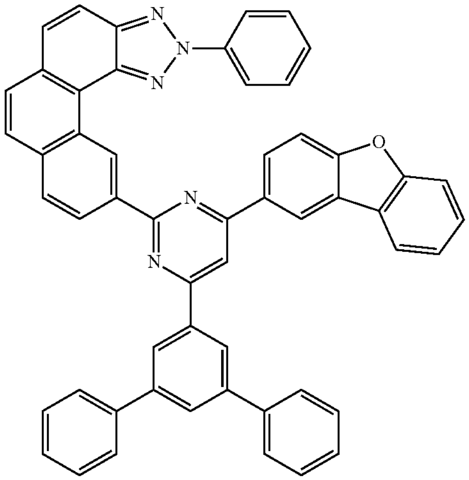
M86
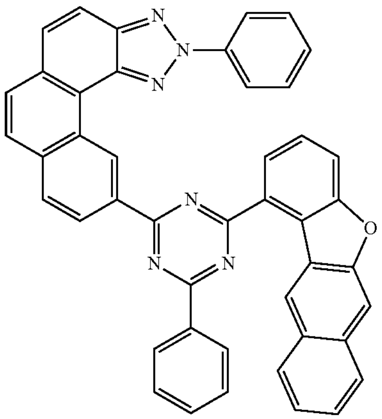
M87
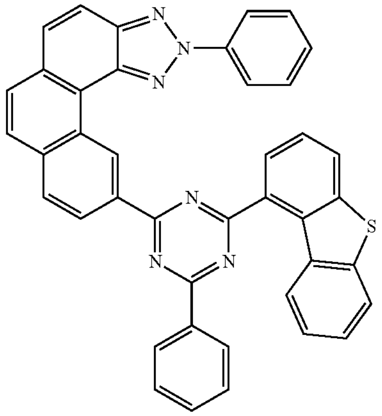
-continued
M88
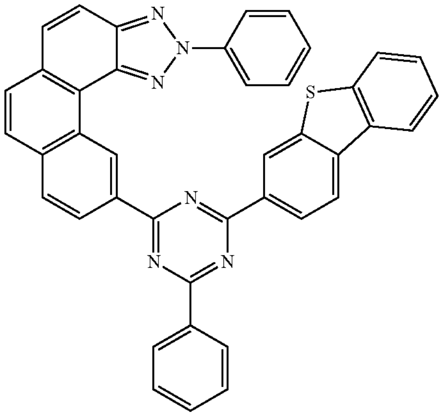
M89
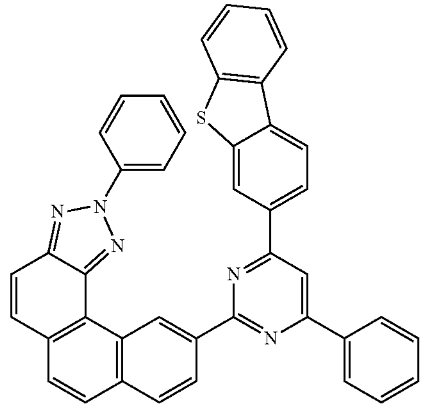
M90
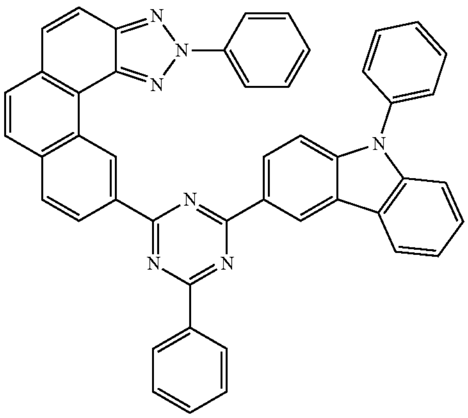

-continued
M91
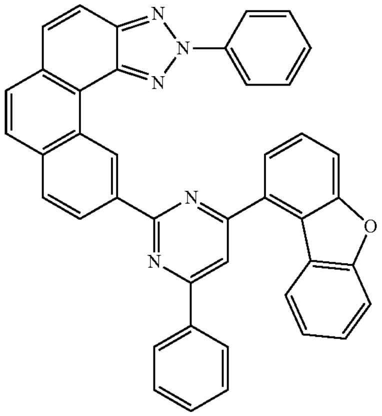
M92
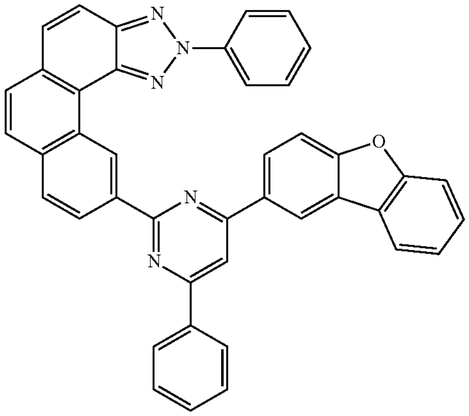
M93
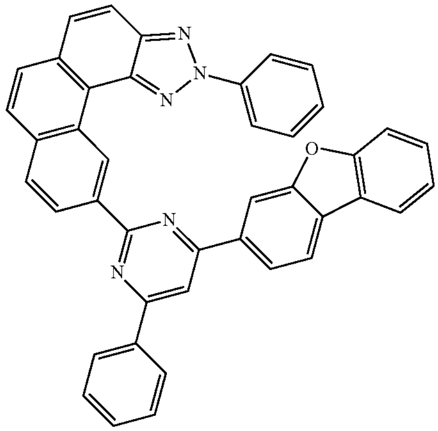
-continued
M94
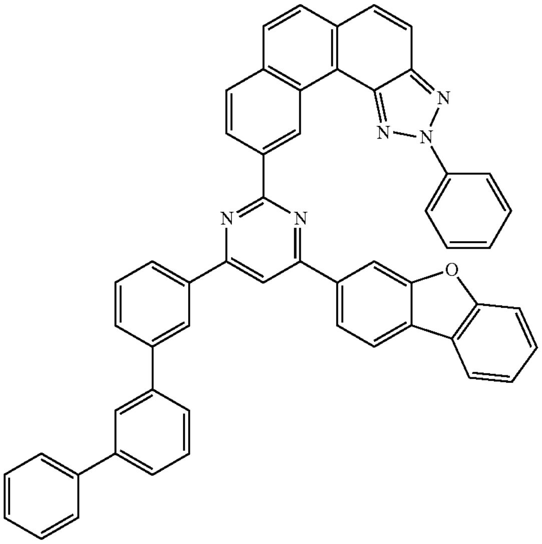
M95
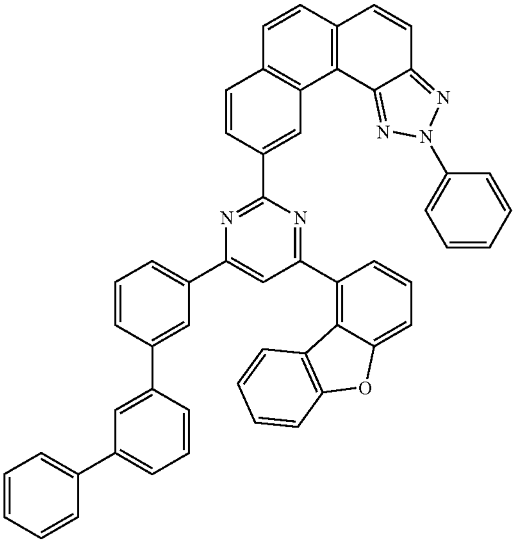
M96
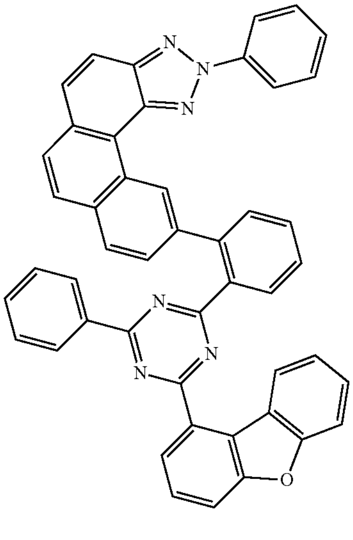

-continued
M97
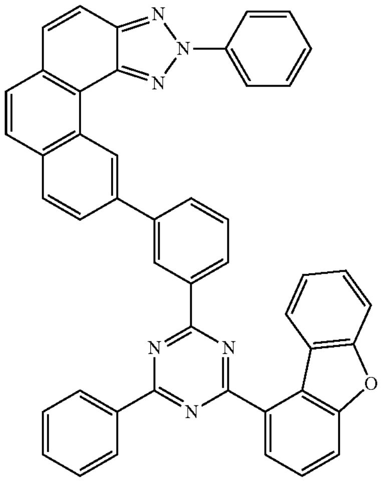
M98
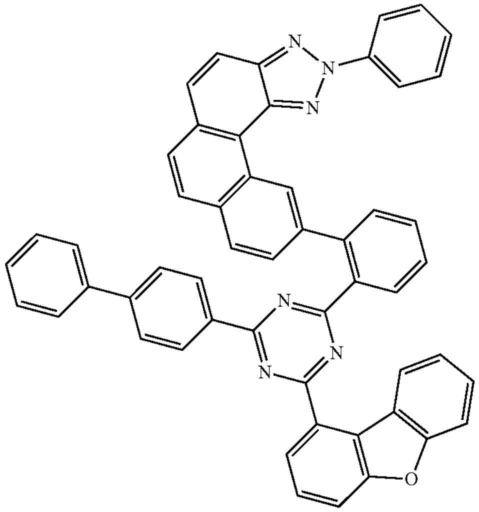
M99
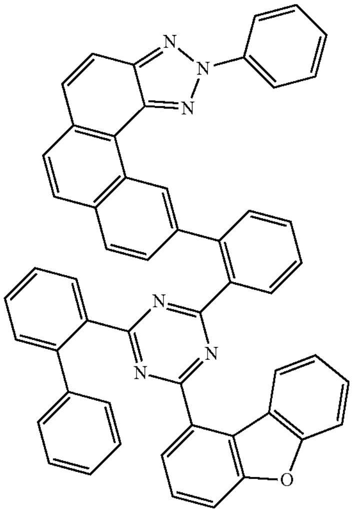
-continued
M100
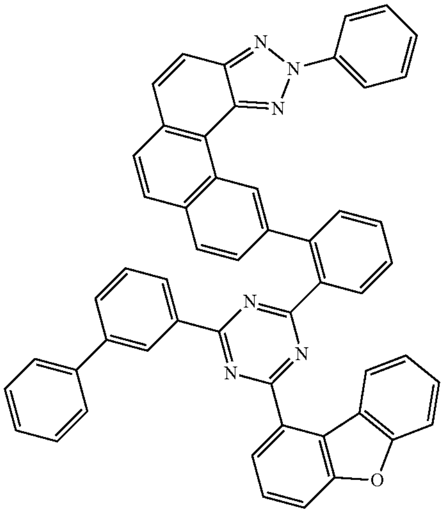
M101
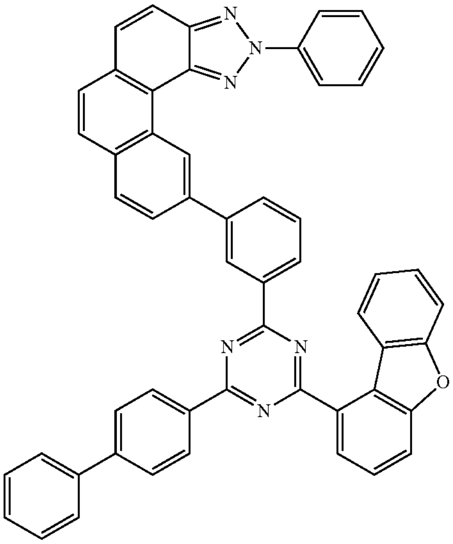
M102
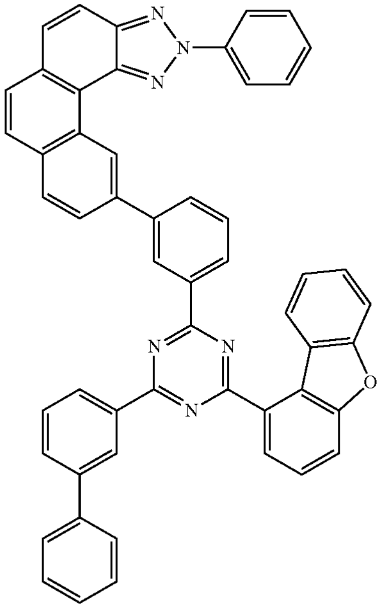

-continued
M103
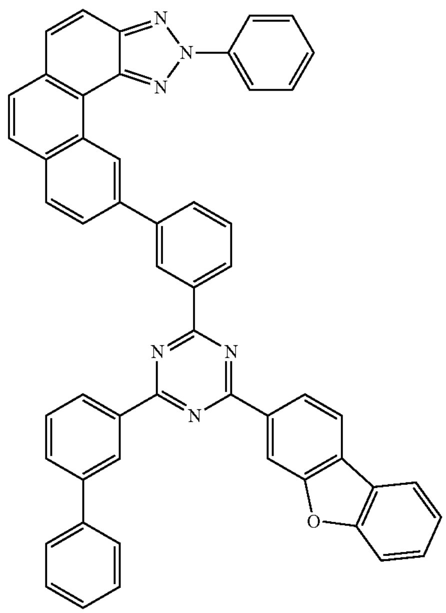
M104
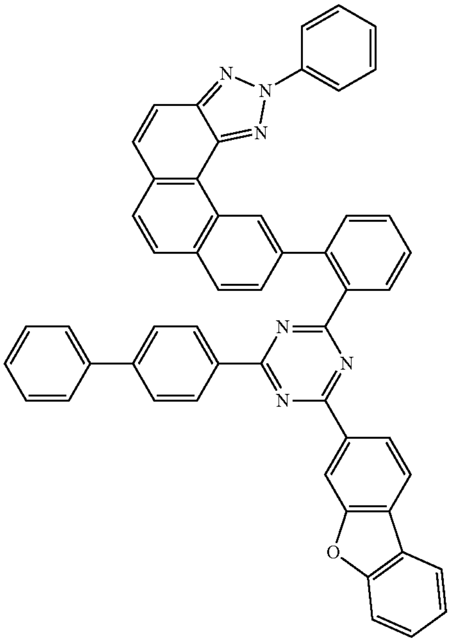
-continued
M105
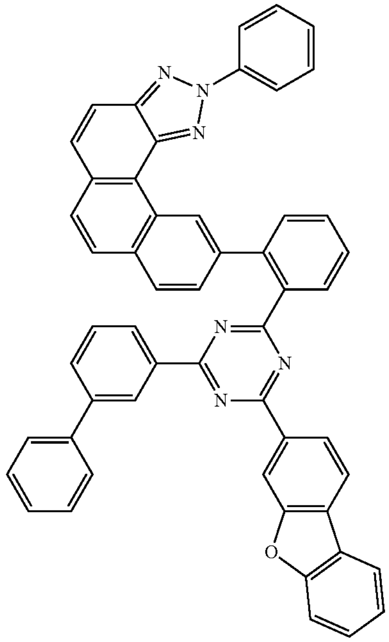
M106
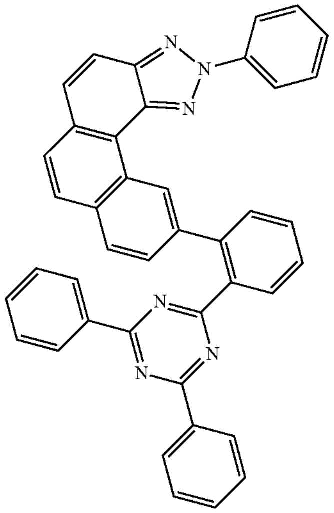
M107
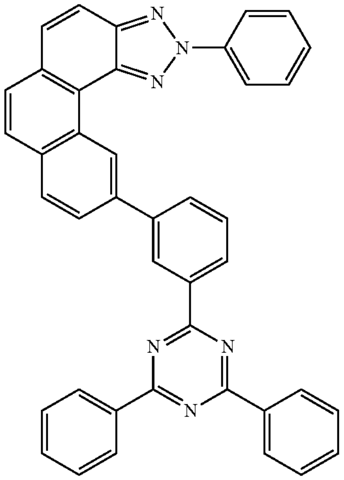

-continued
M108
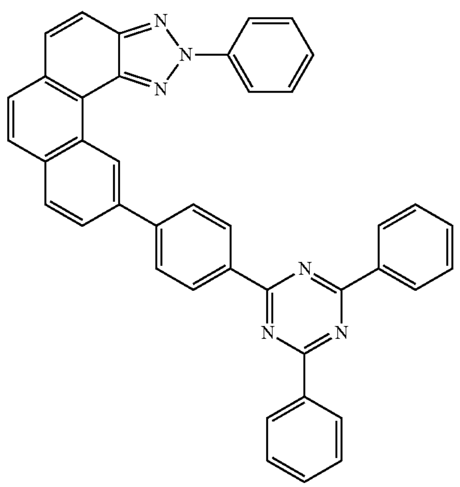
M109
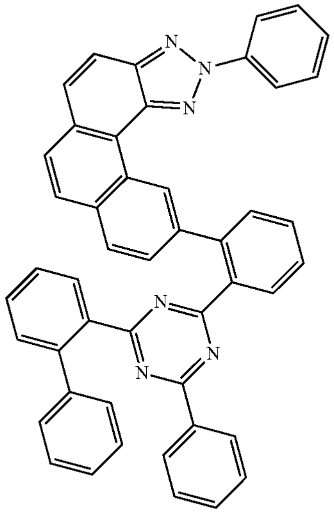
M110
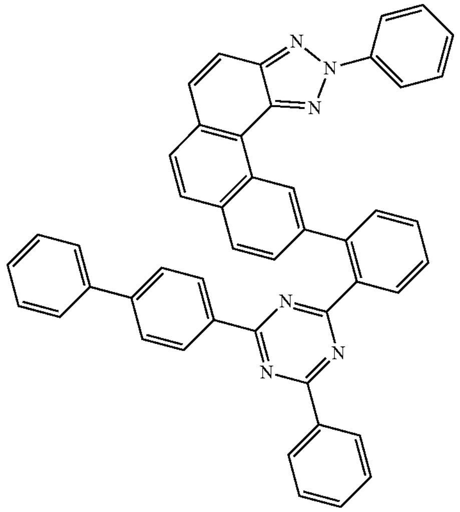
-continued
M111
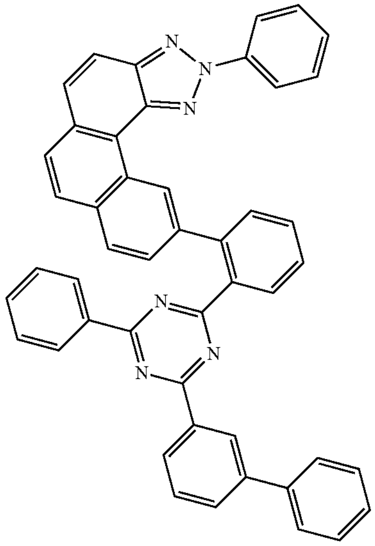
M112
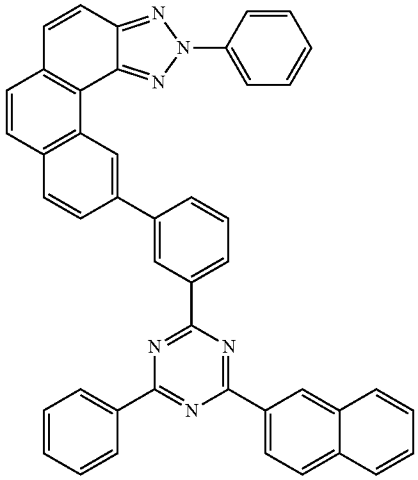
M113
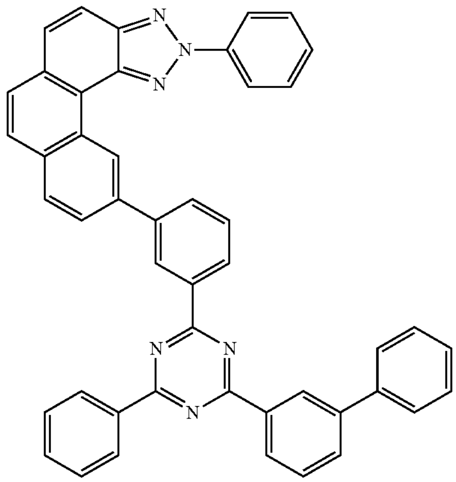

-continued
M114
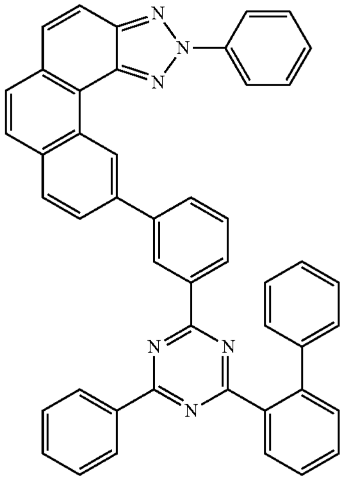
M115
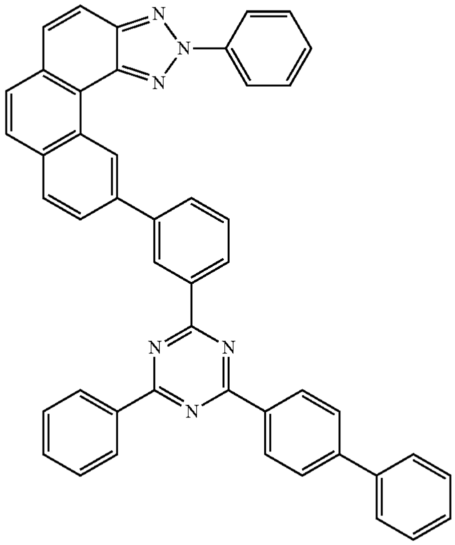
M116
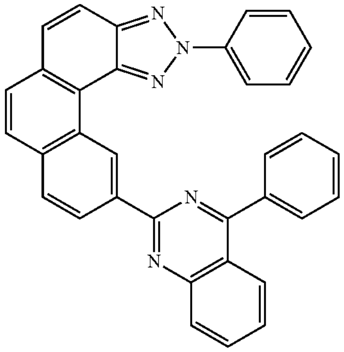
-continued
M117
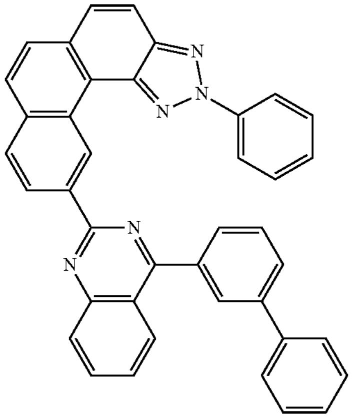
M118
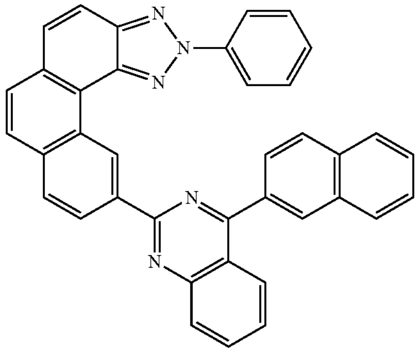
M119
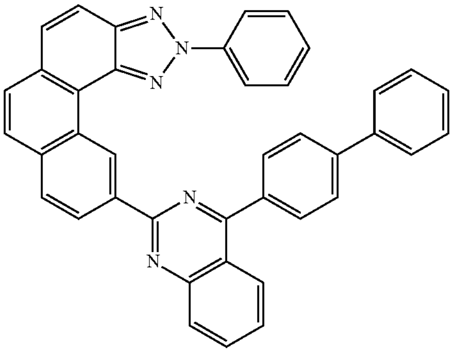
M120
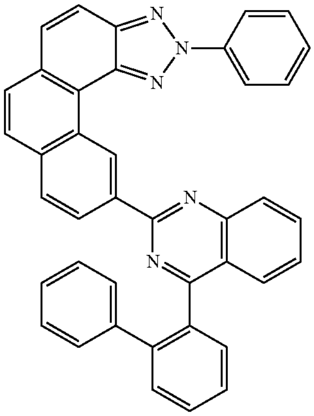

-continued
M121
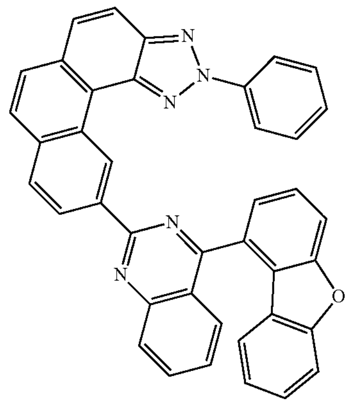
M122
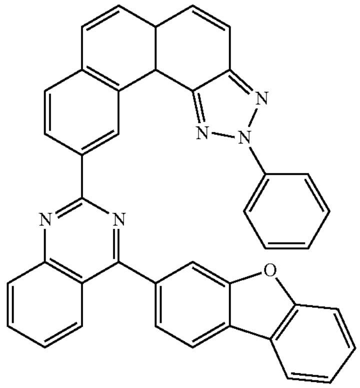
M123
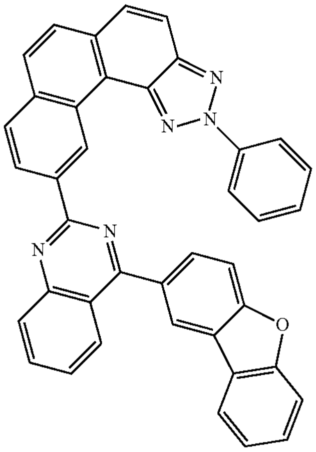
-continued
M124
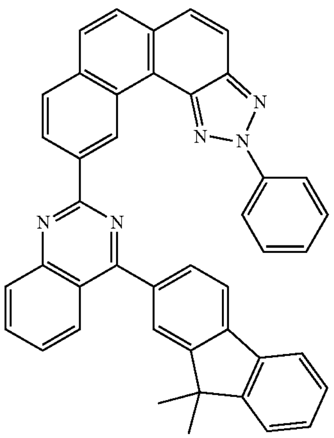
M125
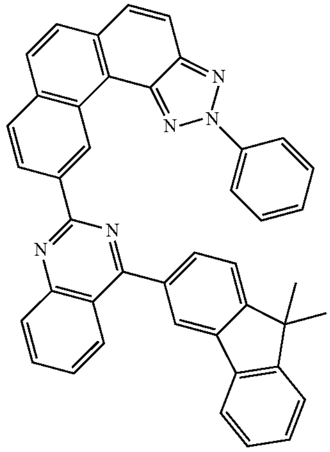
M126
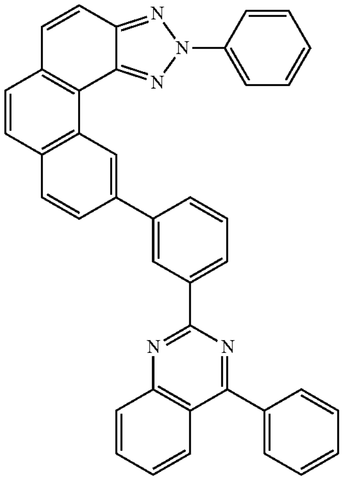

-continued
M127
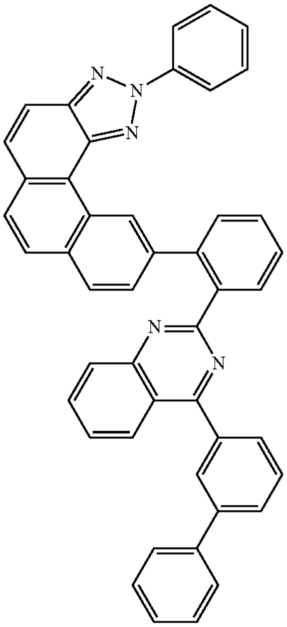
M128
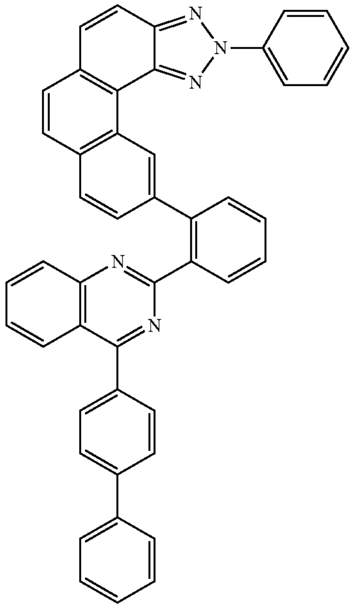
-continued
M129
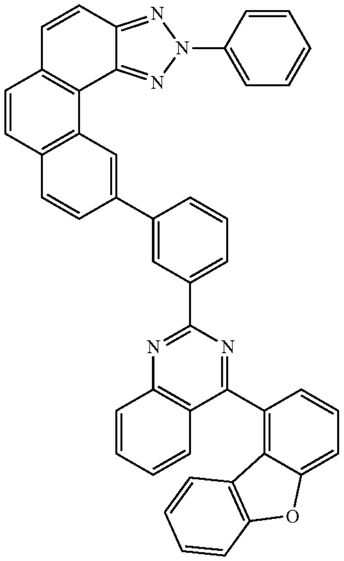
M130
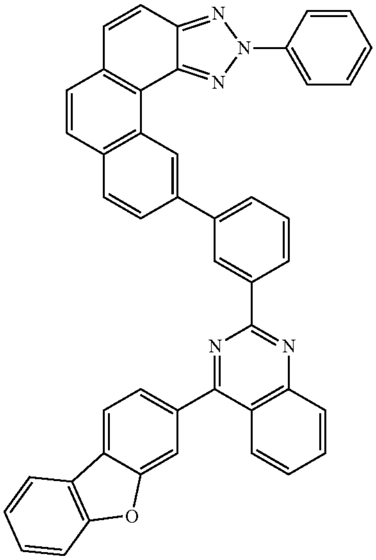
M131
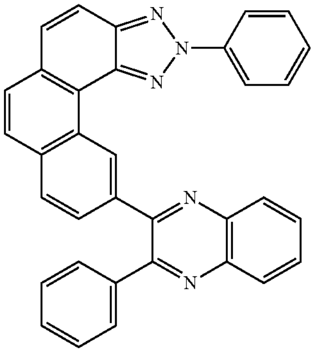

-continued
M132
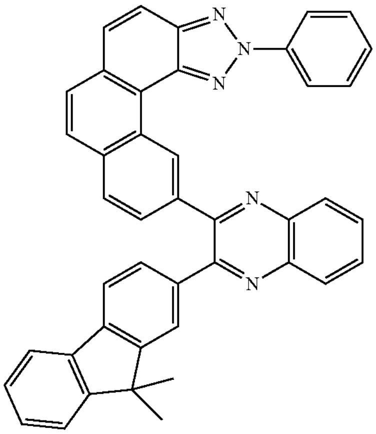
M133
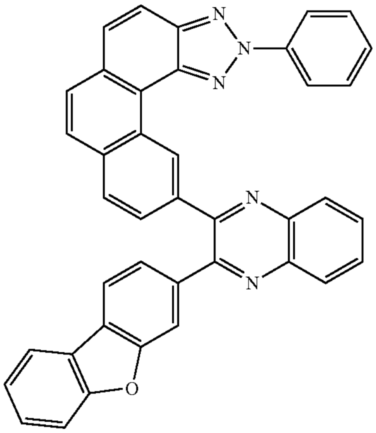
M134
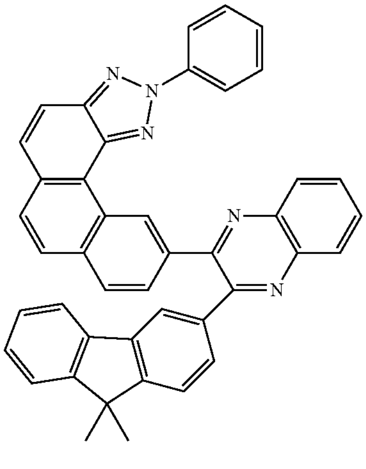
-continued
M135
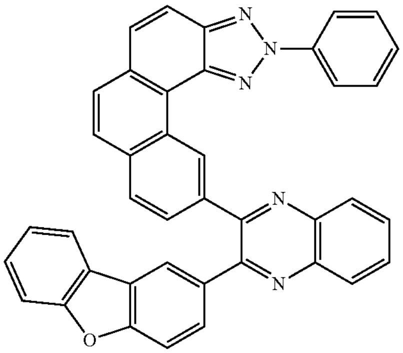
M136
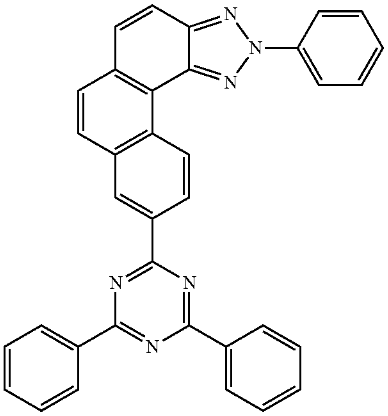
M137
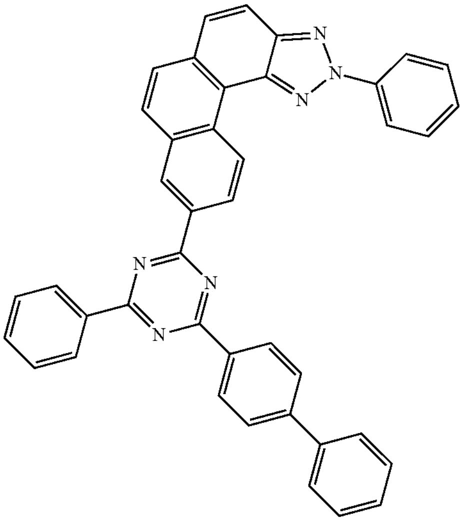

-continued
M138
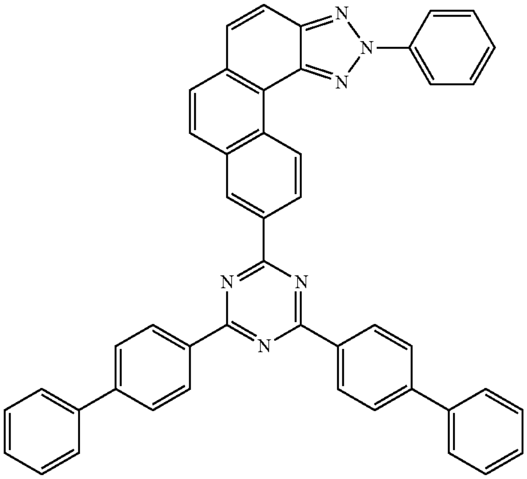
M139
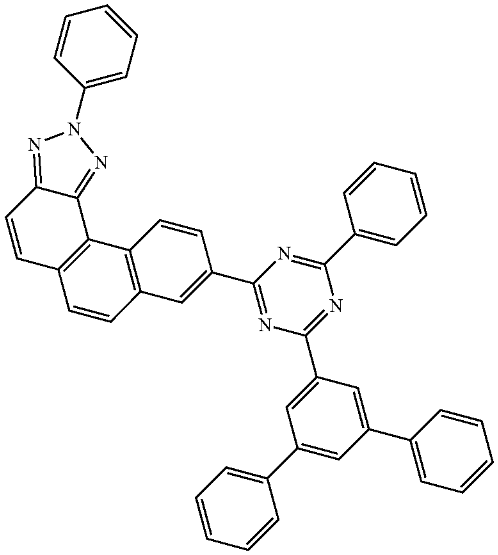
M140
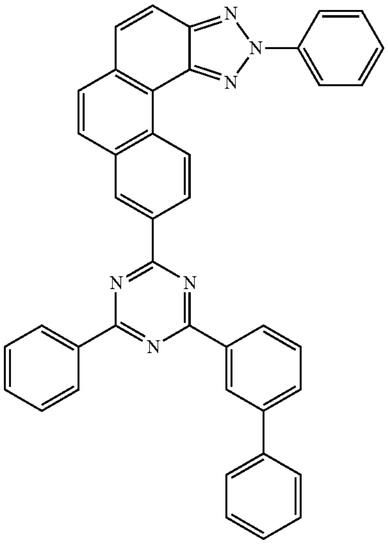
-continued
M141
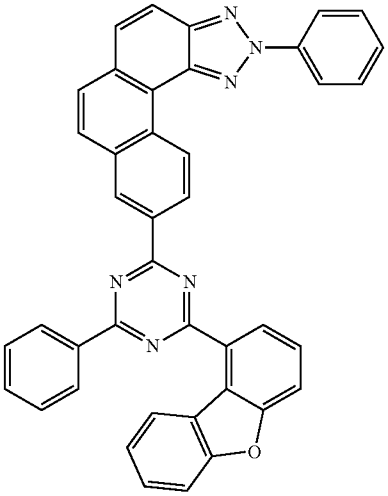
M142
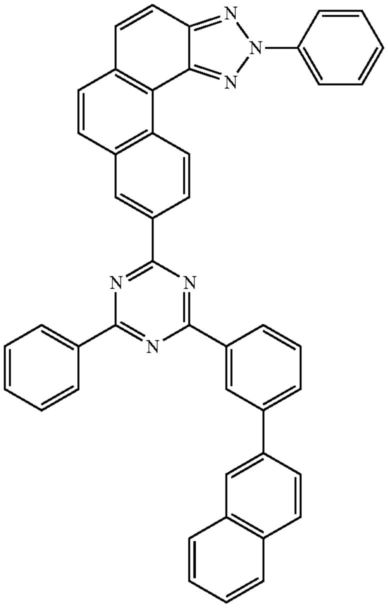
M143
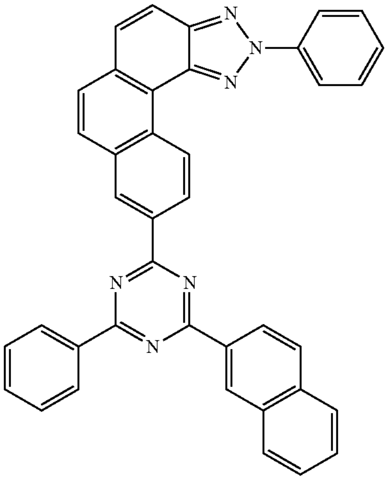

M144
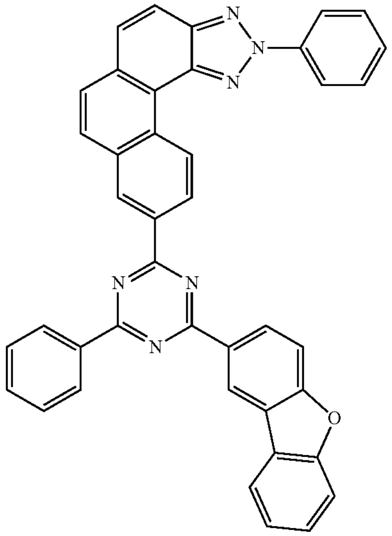
M145
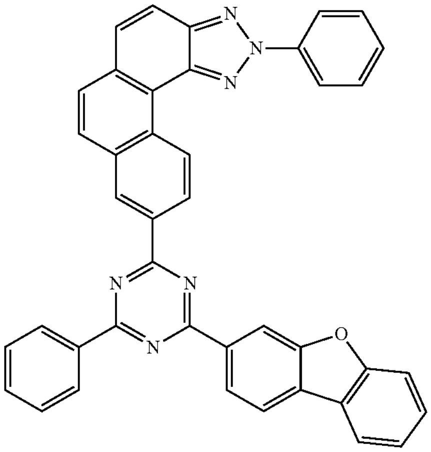
M146
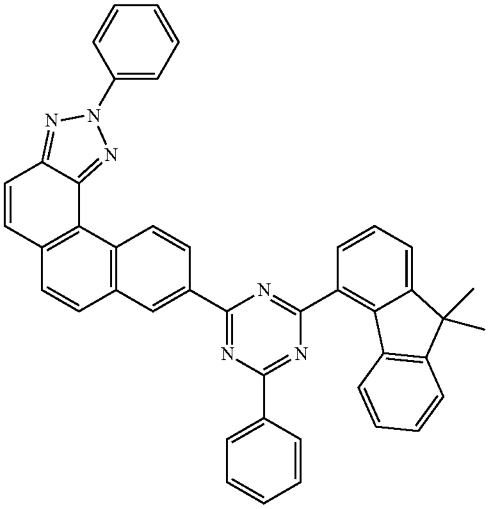
M147
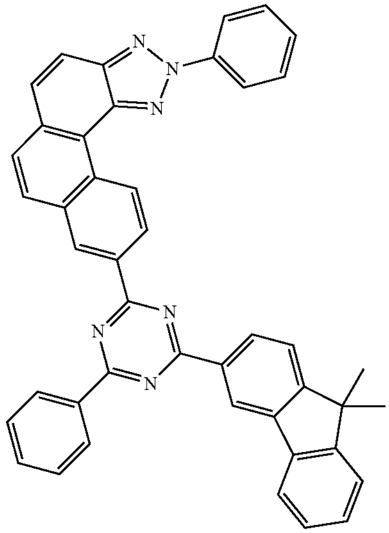
M148
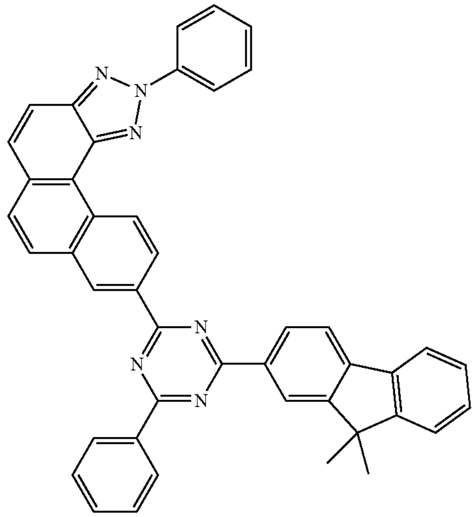
M149
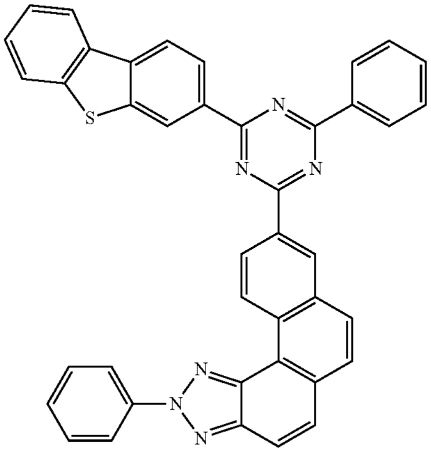

-continued
M150
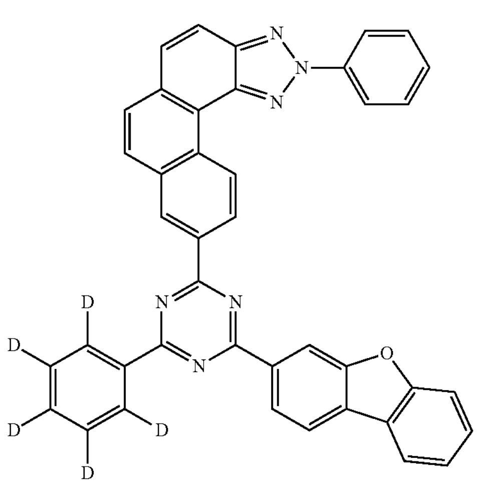
M151
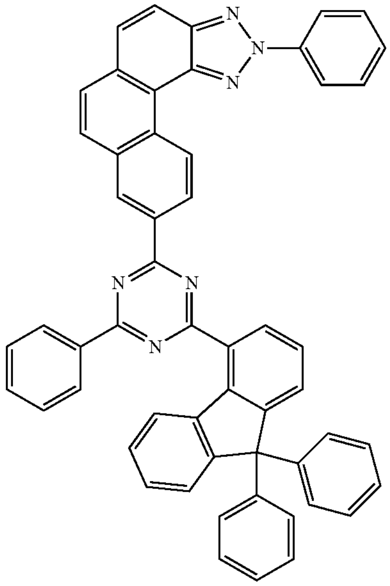
M152
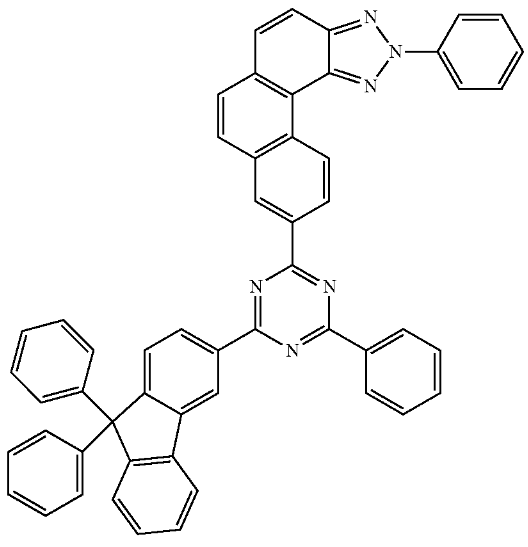
-continued
M153
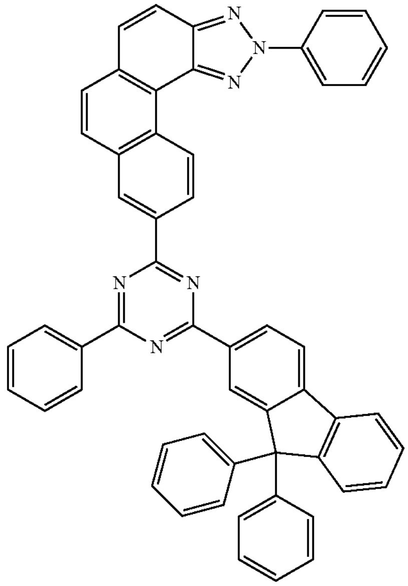
M154
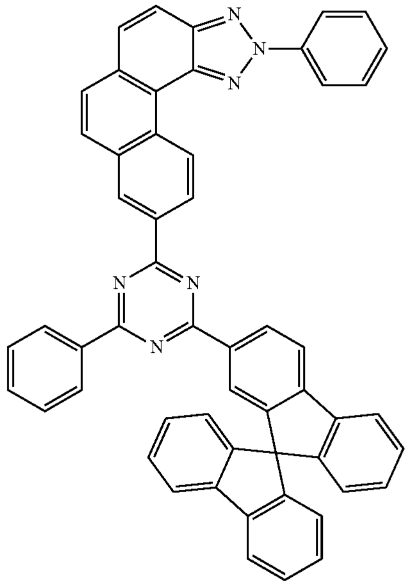

-continued
M155
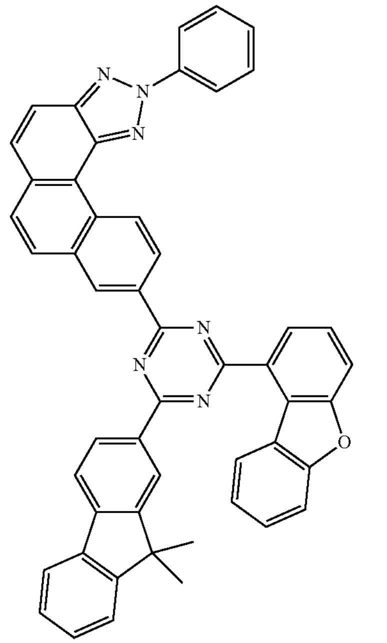
M156
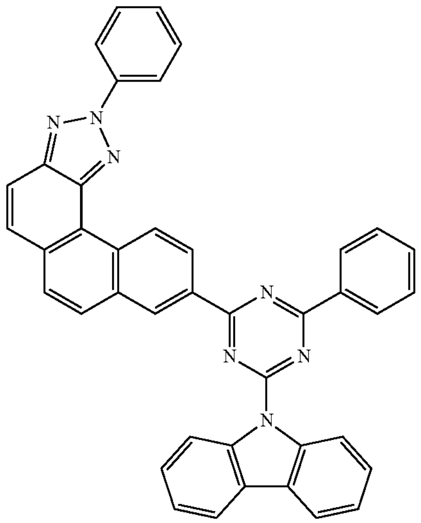
-continued
M157
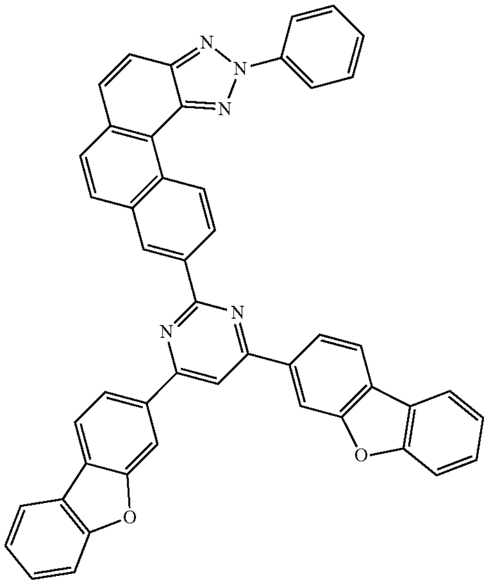
M158
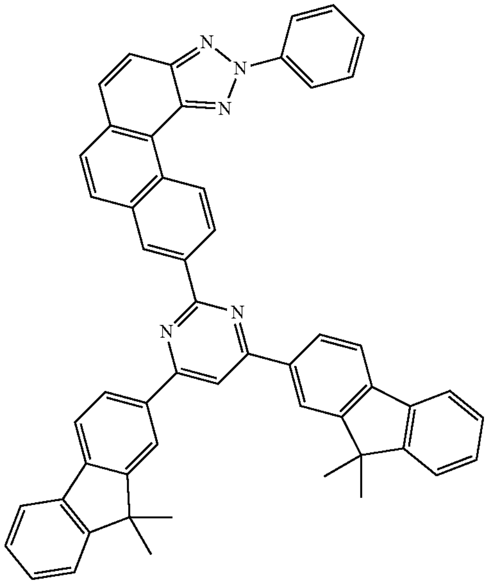
M159
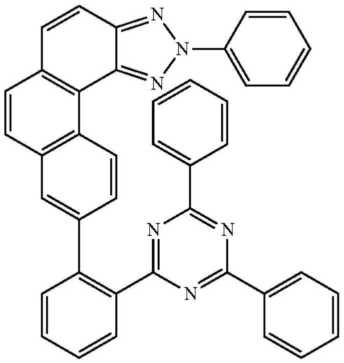

-continued
M160
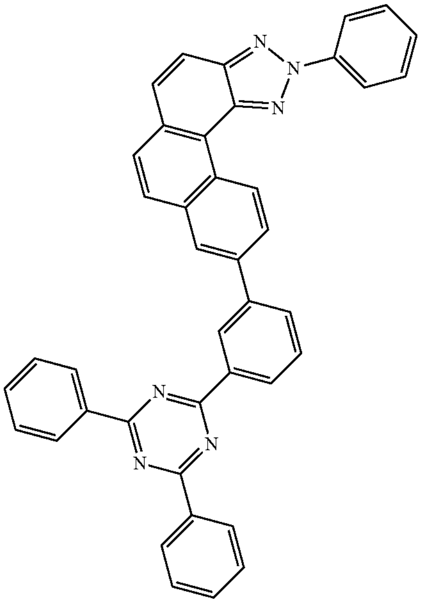
M161
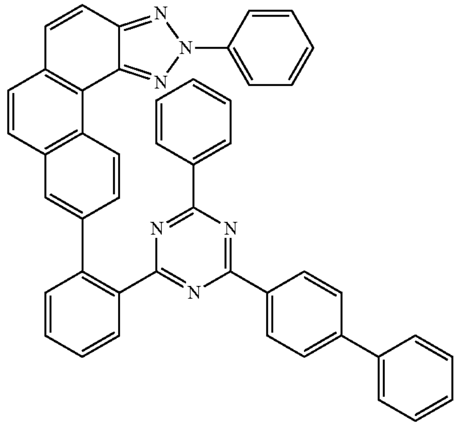
M162
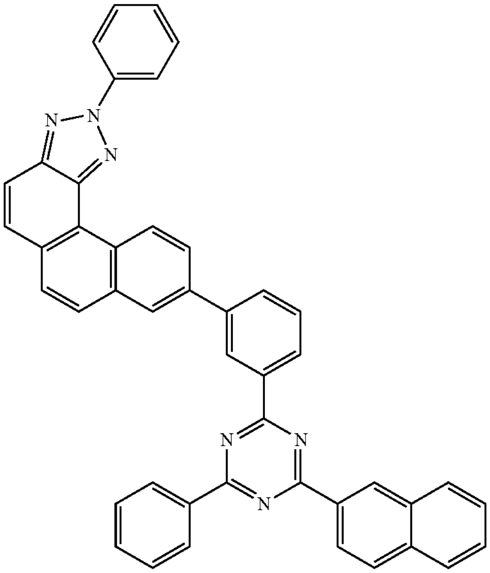
-continued
M163
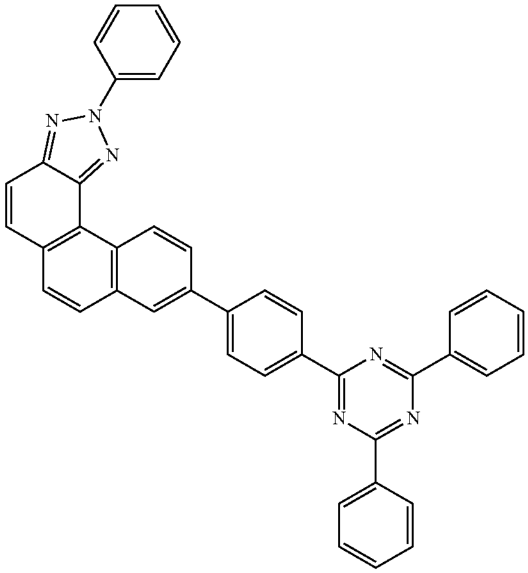
M164
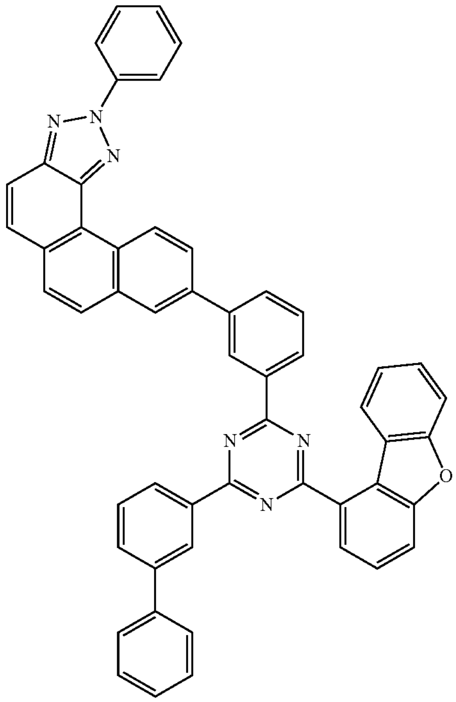

-continued
M165
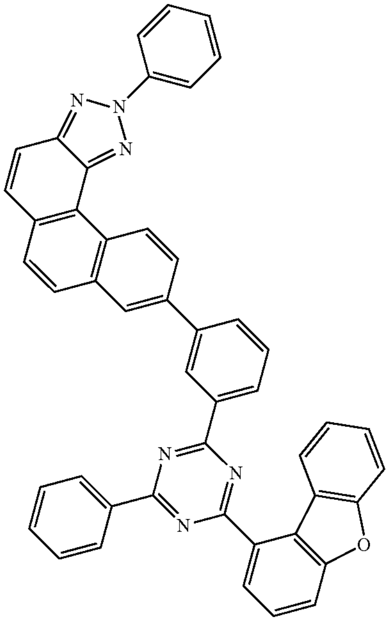
M166
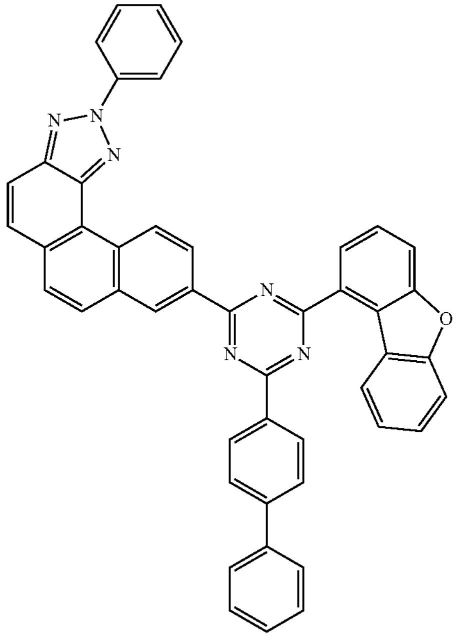
-continued
M167
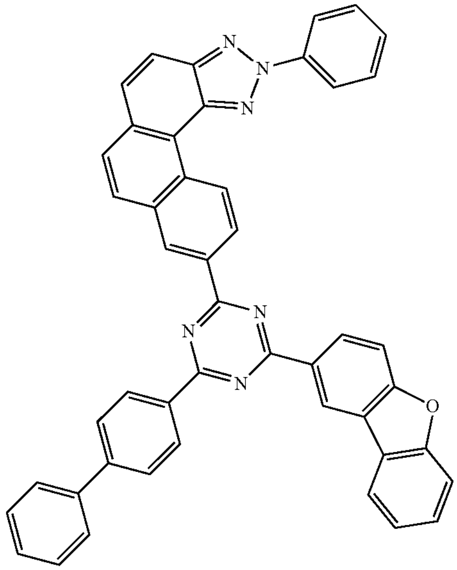
M168
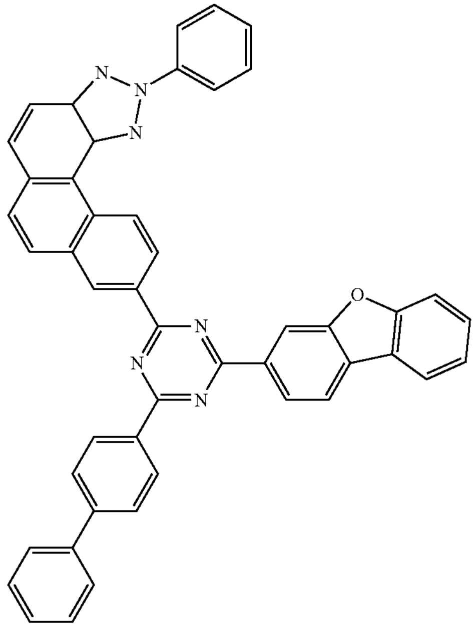

-continued
M169
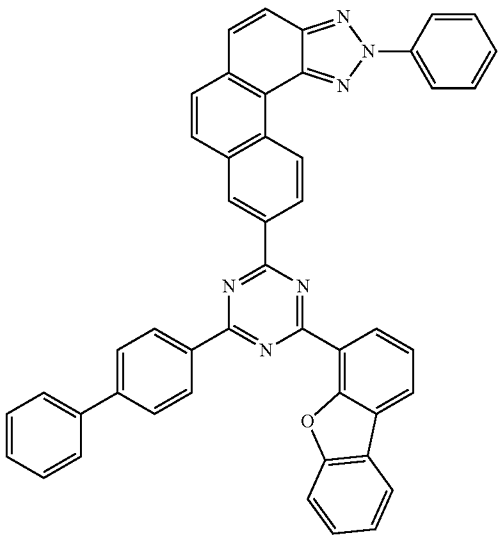
M170
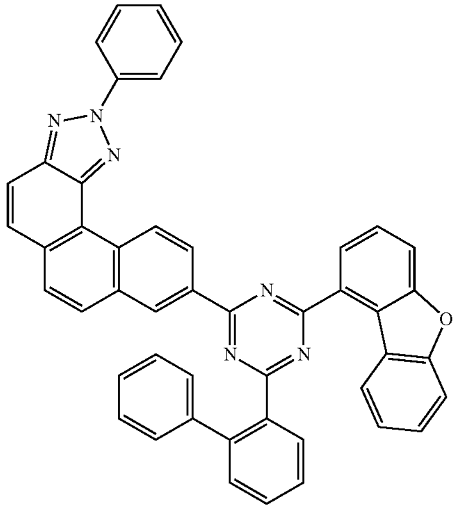
M171
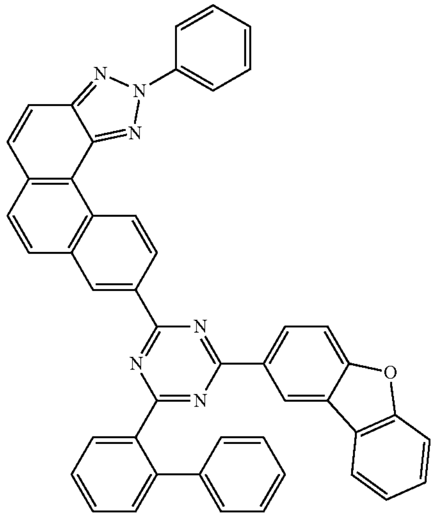
-continued
M172
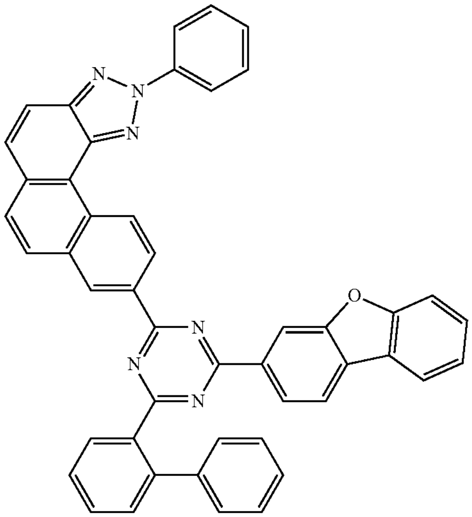
M173
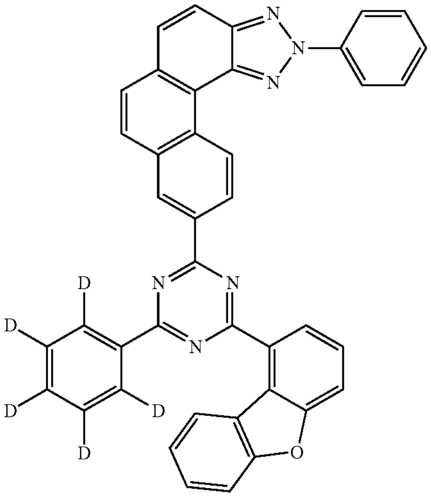
M174
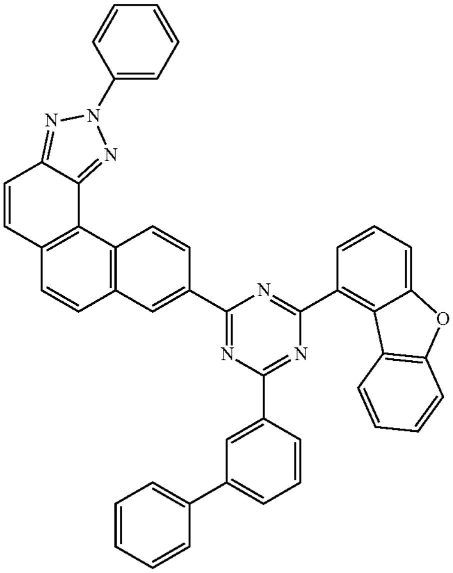

-continued
M175
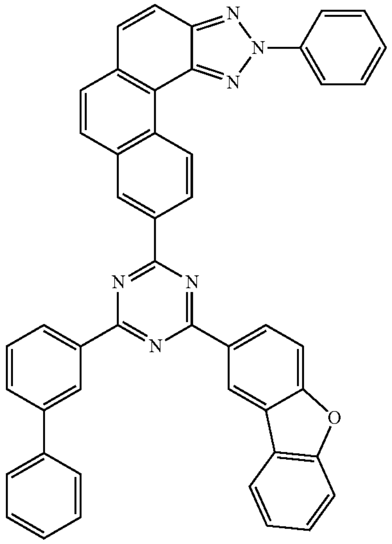
M176
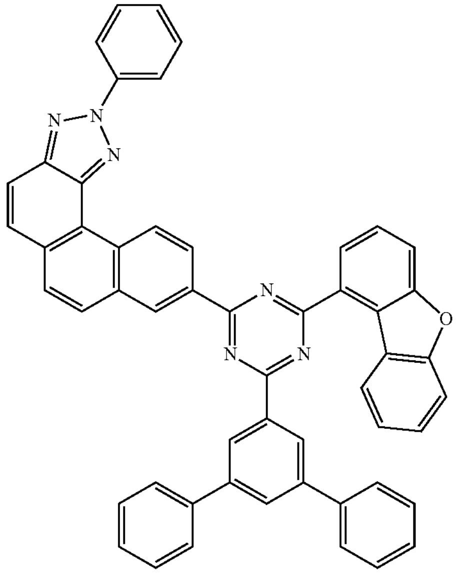
-continued
M177
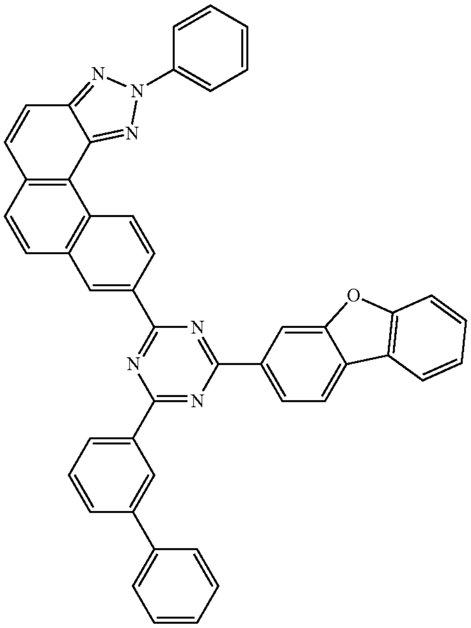
M178
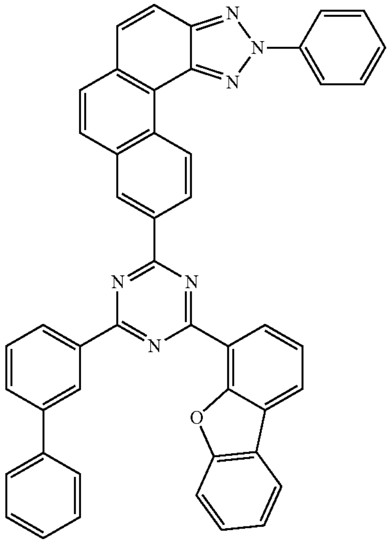

-continued
M179
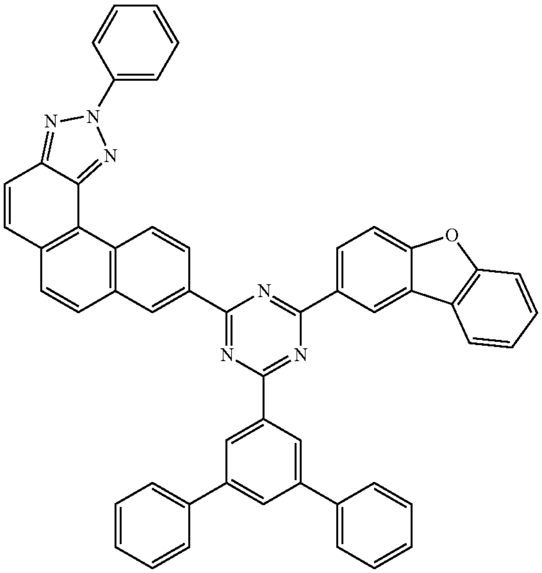
M180
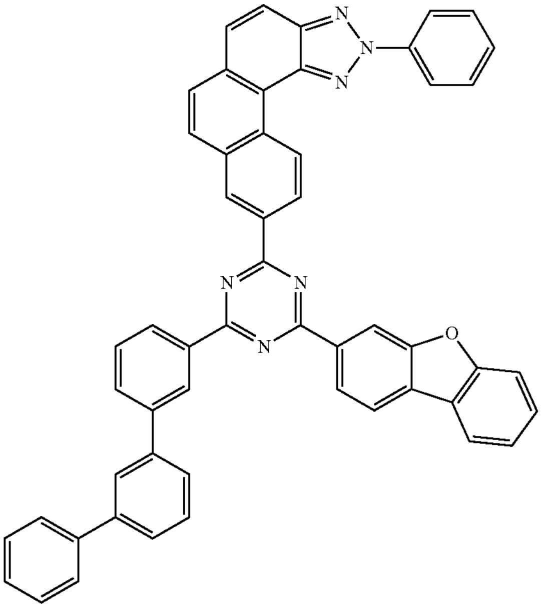
-continued
M181
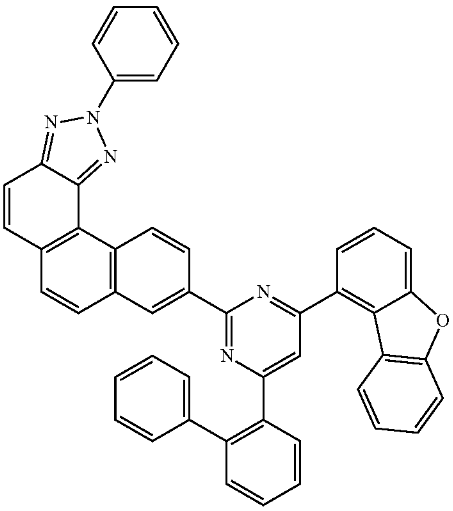
M182
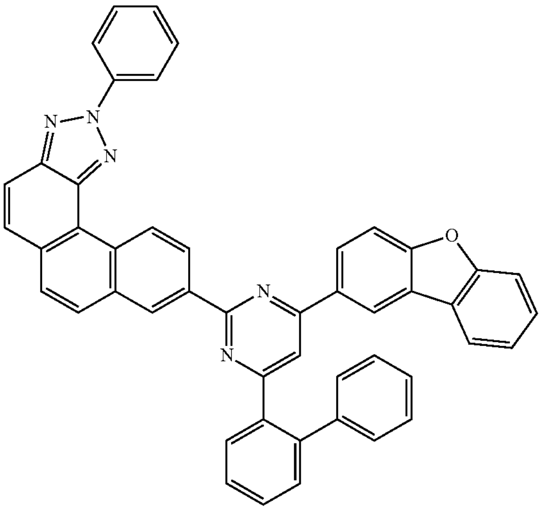
M183
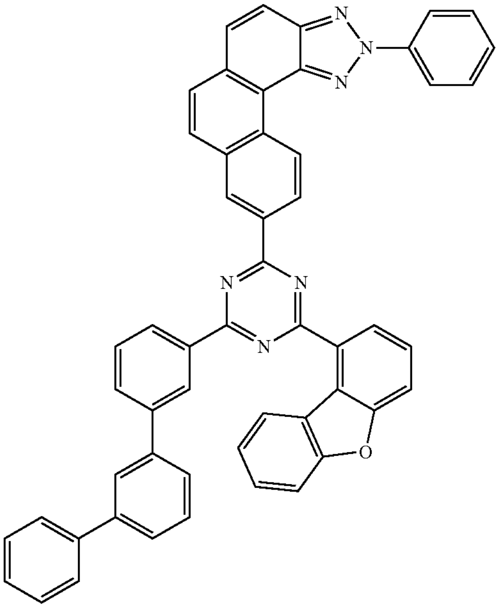

-continued
M184
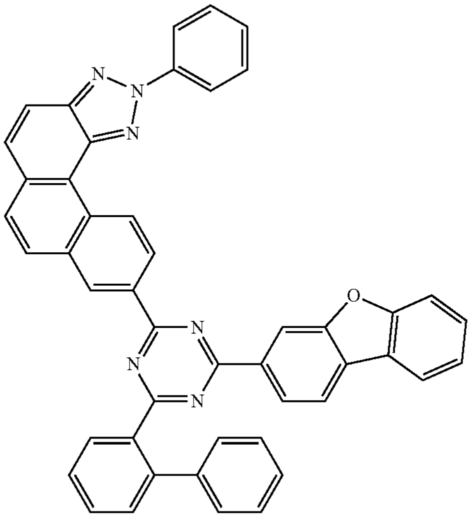
M185
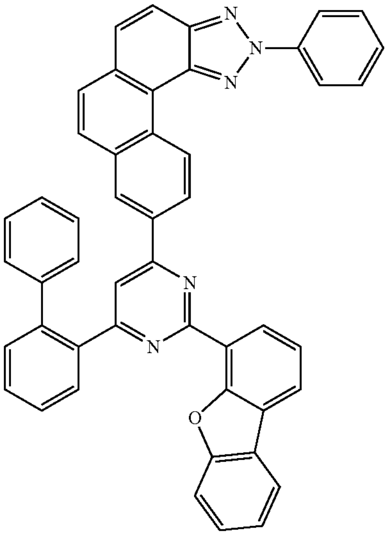
M186
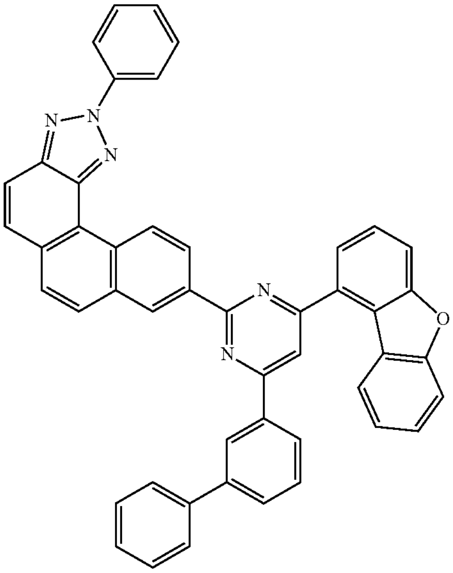
-continued
M187
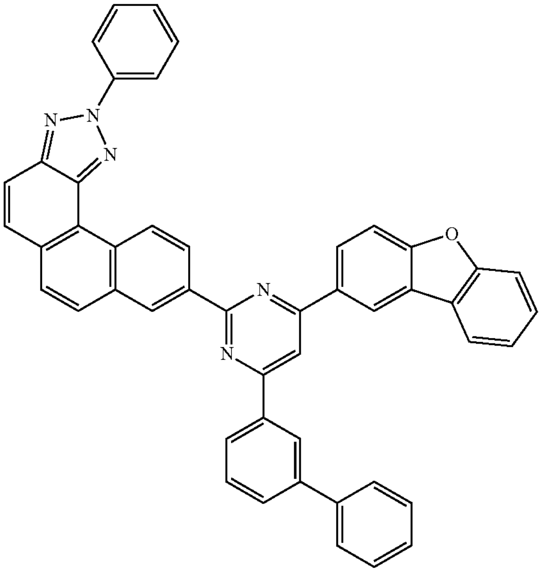
M188
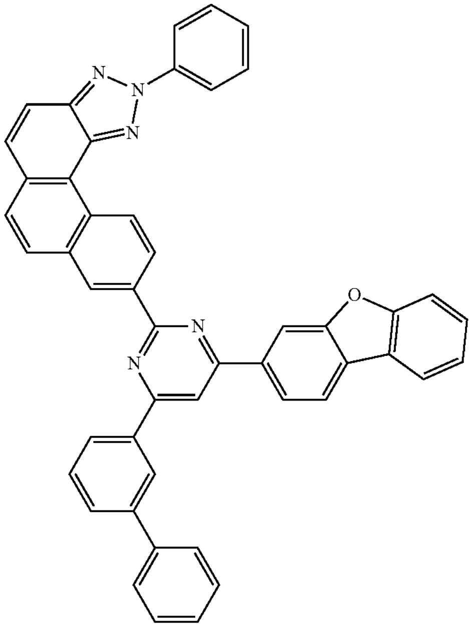

-continued
M189
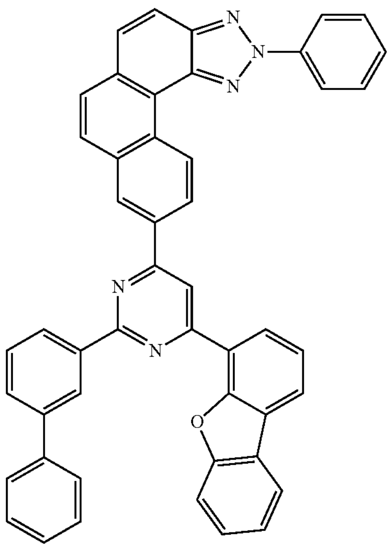
M190
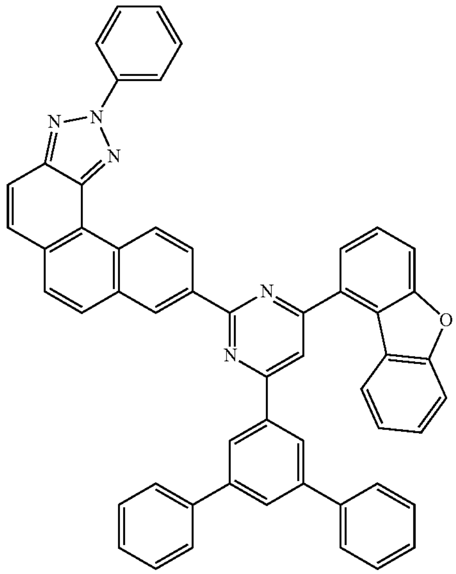
-continued
M191
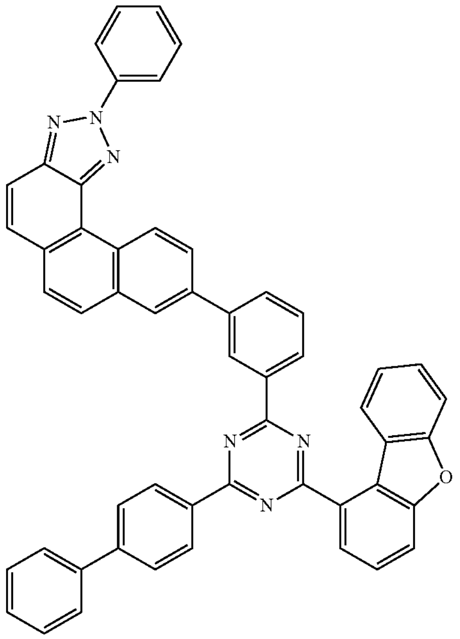
M192
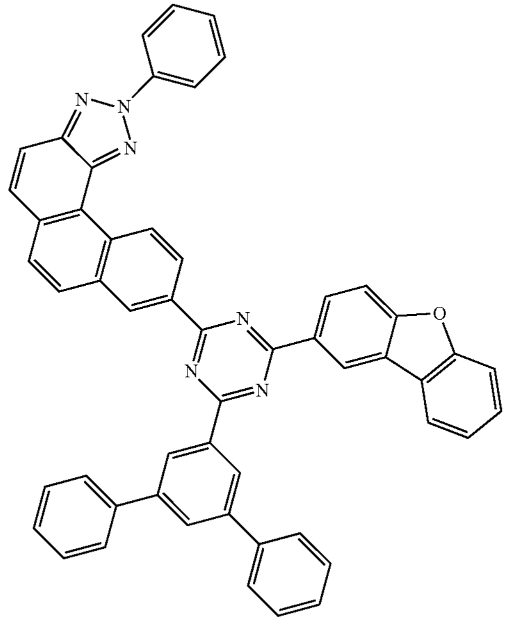

-continued
M193
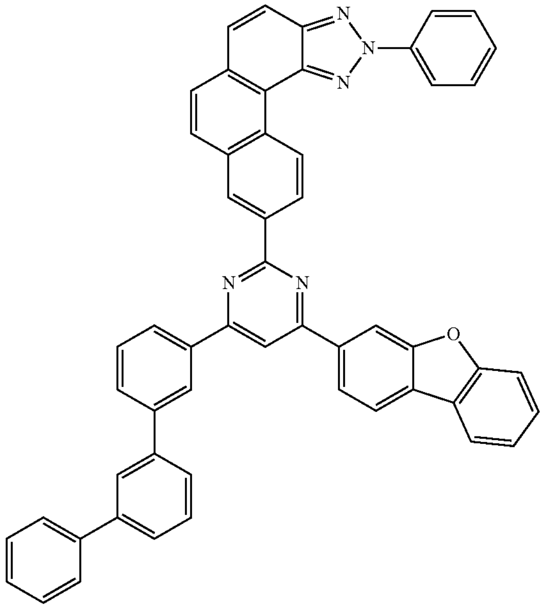
-continued
M195
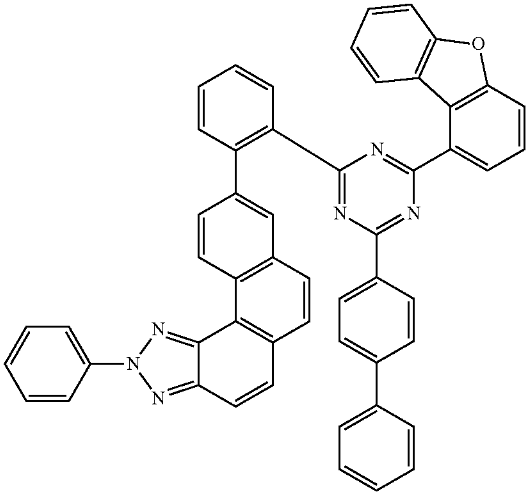
M194
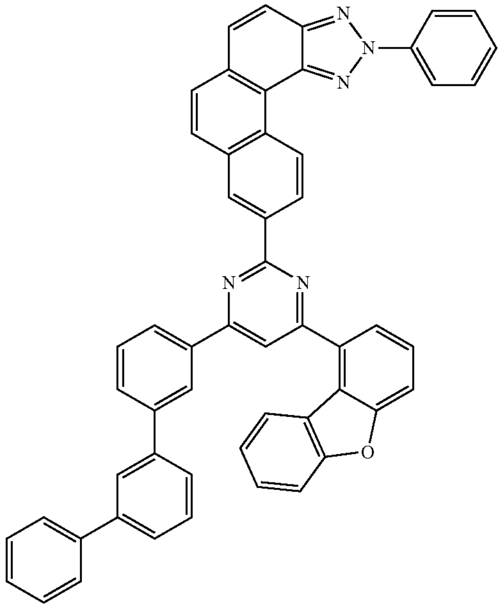
M196
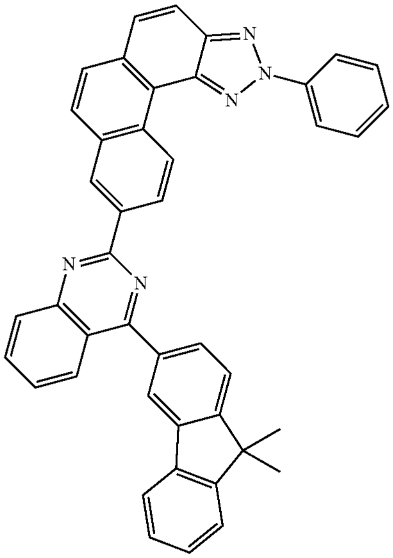

-continued
M197
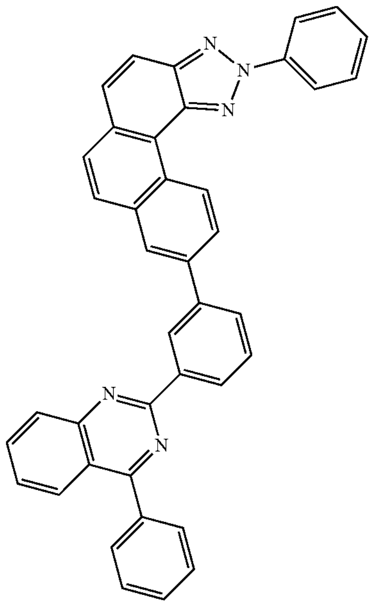
M198
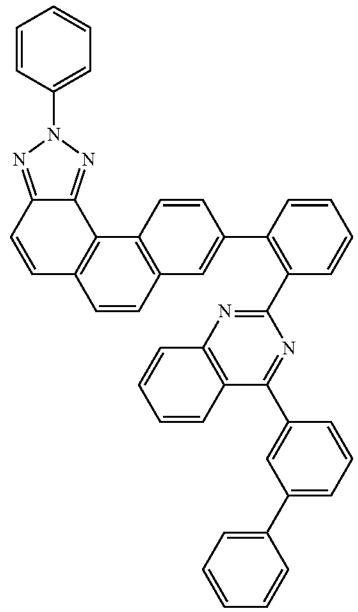
-continued
M199
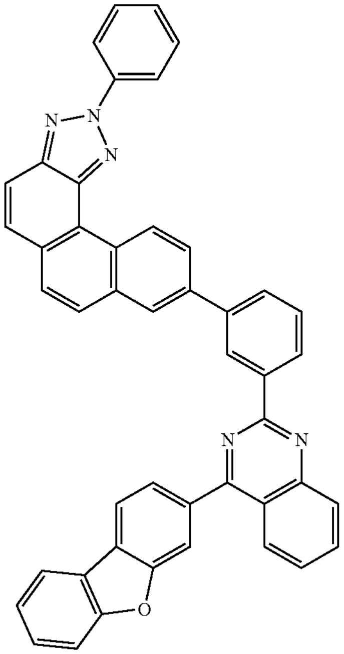
M200
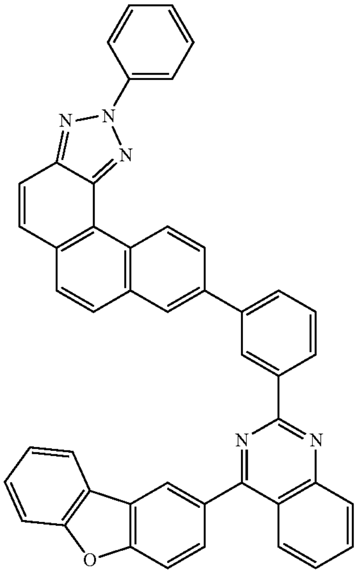

-continued
M201
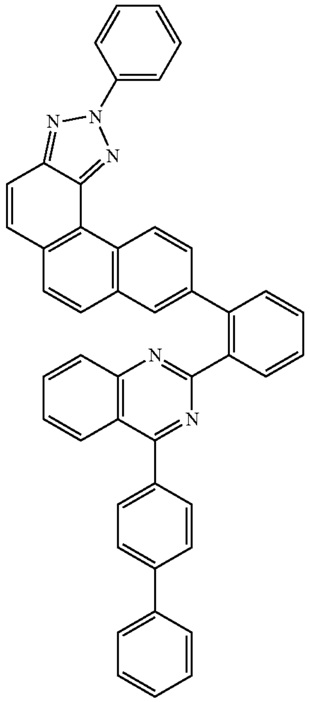
M202
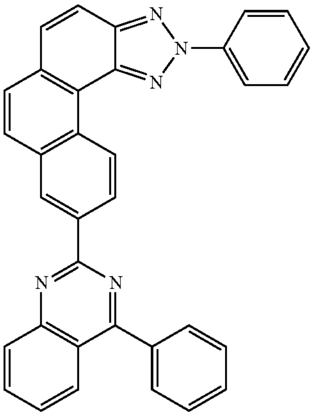
M203
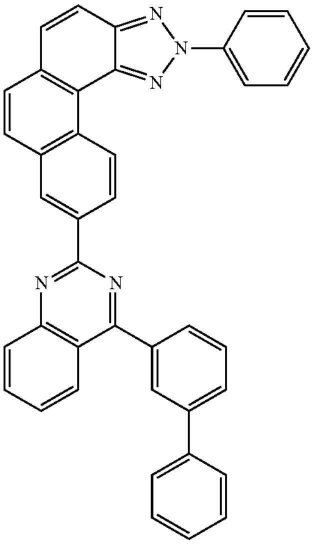
-continued
M204
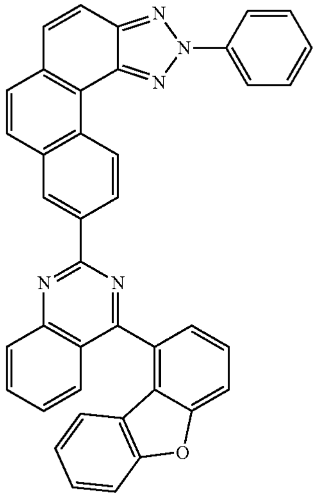
M205
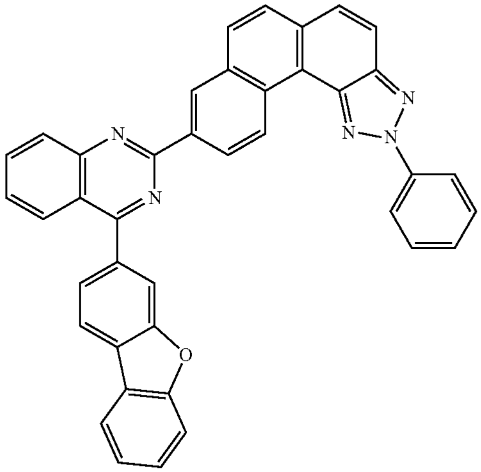
M206
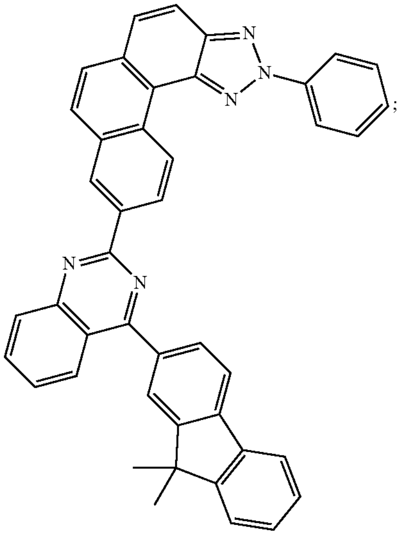
wherein D represents deuterium.

Preferably, at least one of $Ar^5$ to $Ar^8$ is

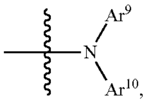

wherein $Ar^9$ and $Ar^{10}$ are each independently selected from a substituted or unsubstituted C6-C30 aryl group, and a substituted or unsubstituted C3-C30 heteroaryl group.

Preferably, $Ar^9$ and $Ar^{10}$ are each independently selected from a phenyl group, a biphenylyl group, a terphenylyl group, a naphthyl group, a phenanthryl group, an anthryl group, a triphenylenylene group, a phenylnaphthyl group, a naphthylphenyl group, a pyridyl group, a bipyridyl group, a dibenzofuryl group, a dibenzothiophenyl group, a benzonaphthofuryl group, a benzonaphthothiophenyl group, a dinaphthofuryl group, a dinaphthothiophenyl group, a dibenzofurylphenyl group, a dibenzothiophenylphenyl group, a phenylcarbazolyl group, a dimethylfluorenyl group, a benzodimethylfluorenyl group, a diphenylfluorenyl group, a spiro-bifluorenyl group, and a dimethylfluorenylphenyl group, each of which is substituted or unsubstituted.

Preferably, $Ar^5$ is

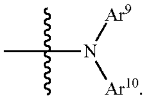

Preferably, $Ar^6$ is

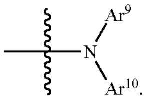

Preferably, $Ar^7$ is

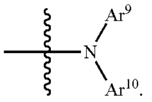

Preferably, $Ar^8$ is

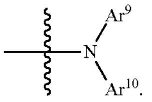

In the present invention, the compound having a structure represented by Formula (2) is a compound having hole transport properties.

Preferably, the compound having a structure represented by Formula (2) is any one of the following compounds N1 to N60:

N1

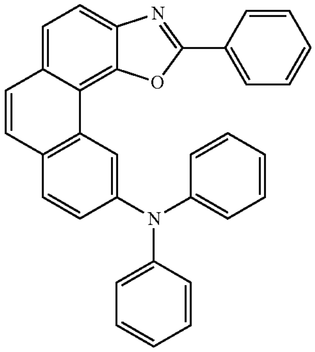

N2

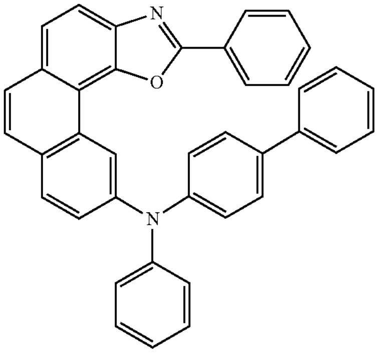

N3

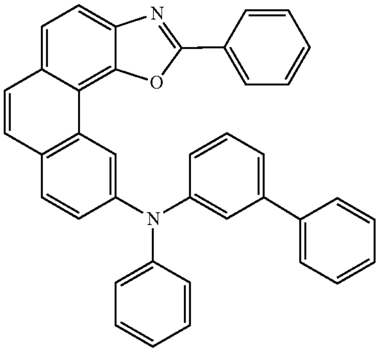

N4

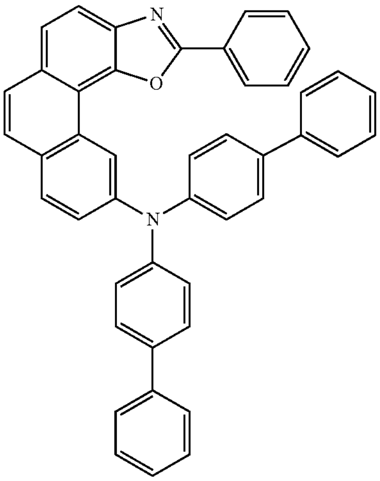

-continued
N5
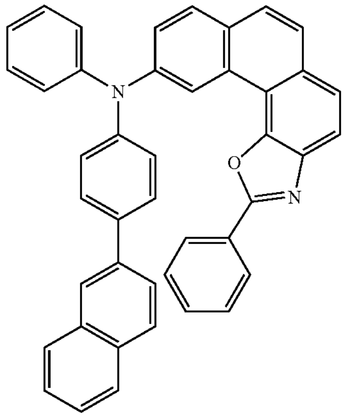
N6
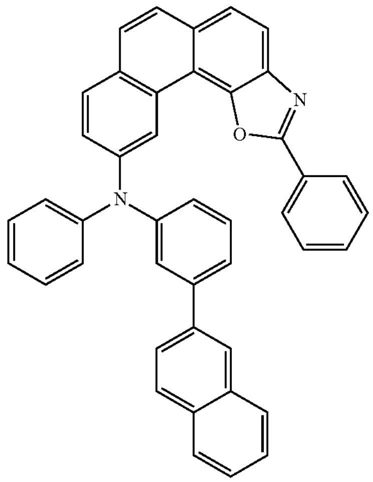
N7
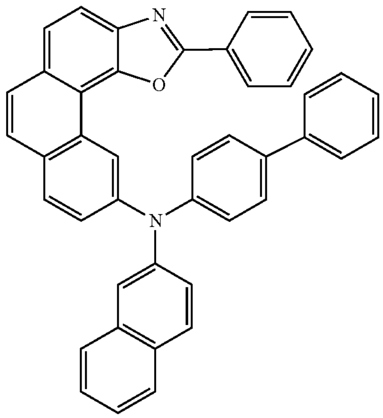
-continued
N8
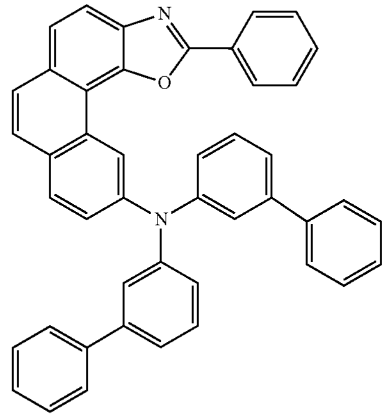
N9
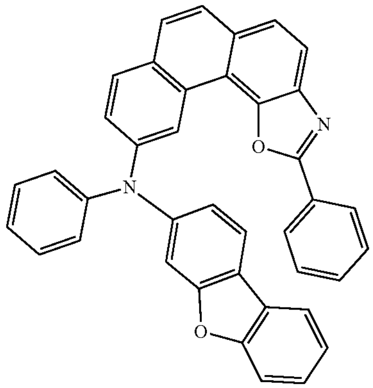
N10
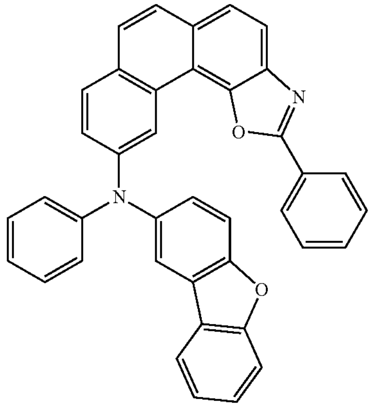
N11
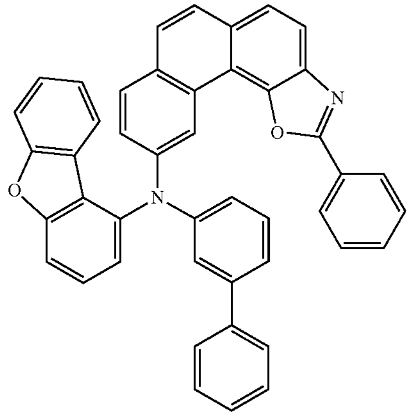

-continued
N12
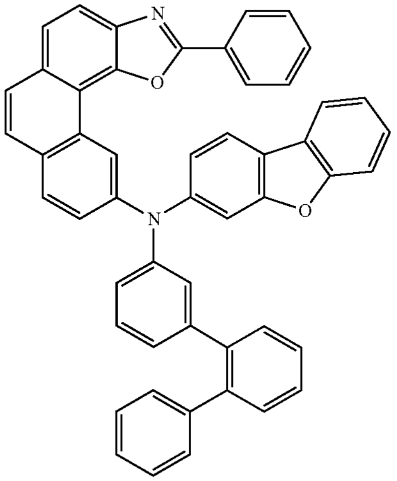
N13
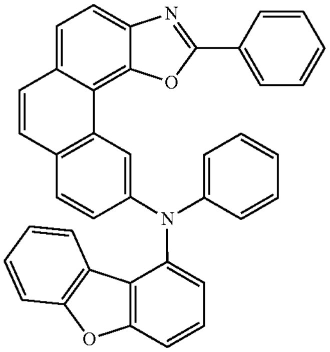
N14
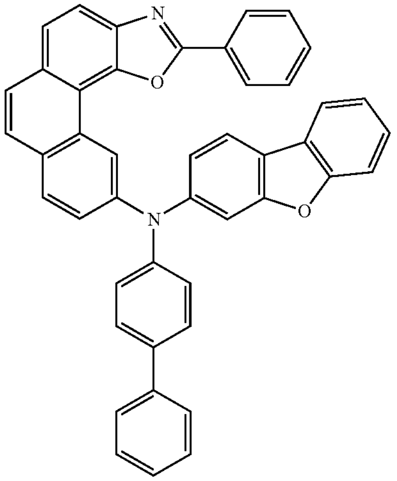
-continued
N15
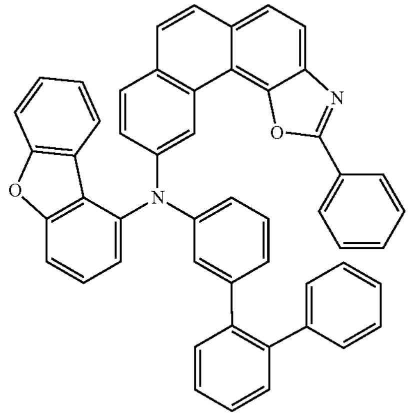
N16
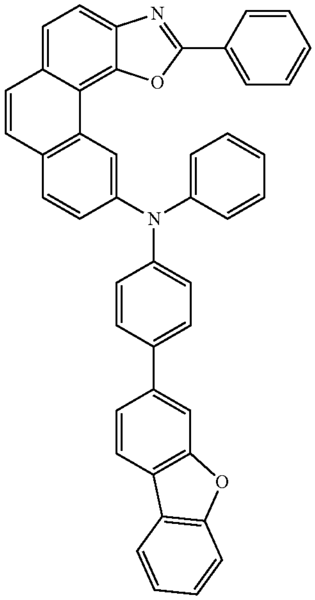
N17
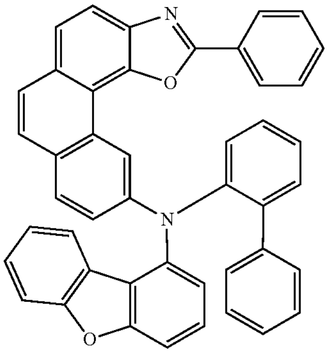

-continued
N18
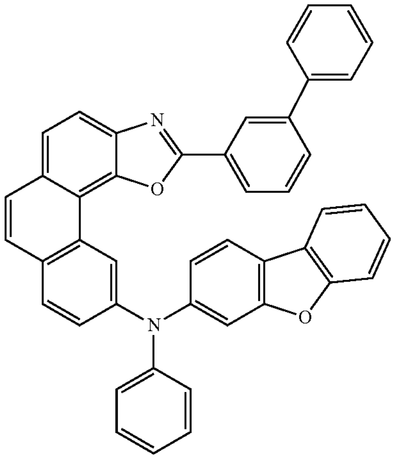
N19
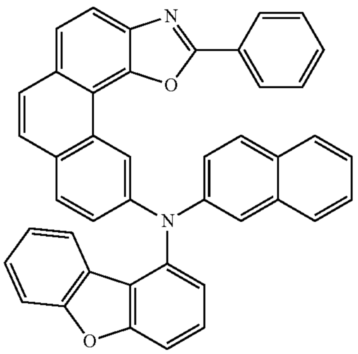
N20
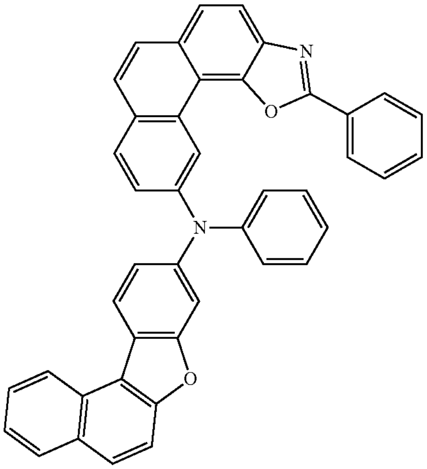
-continued
N21
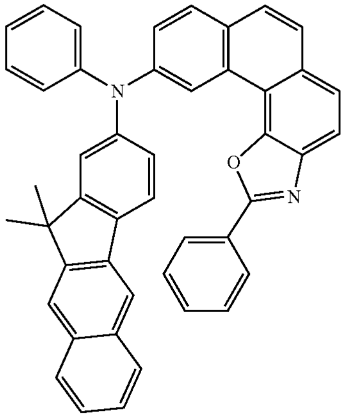
N22
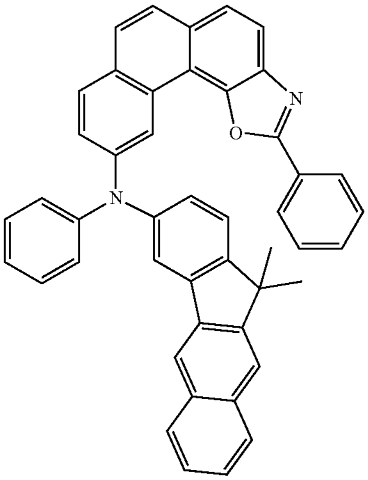
N23
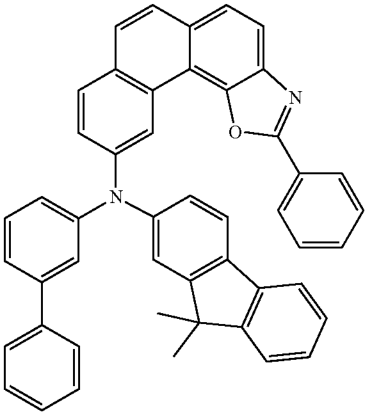

-continued
N24
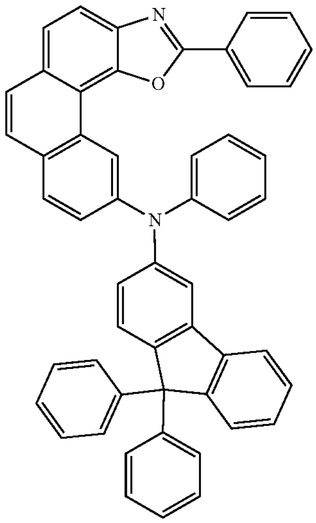
N25
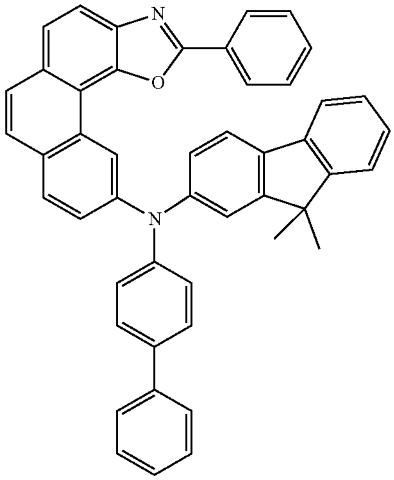
N26
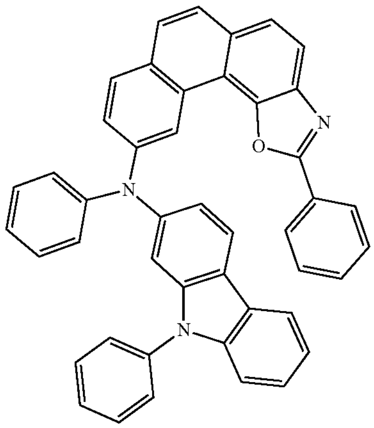
-continued
N27
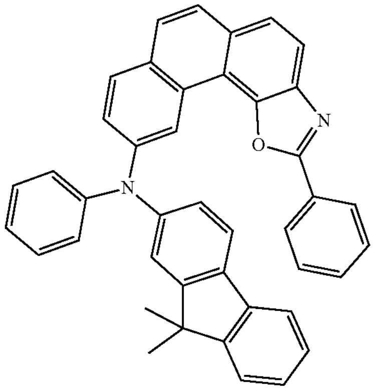
N28
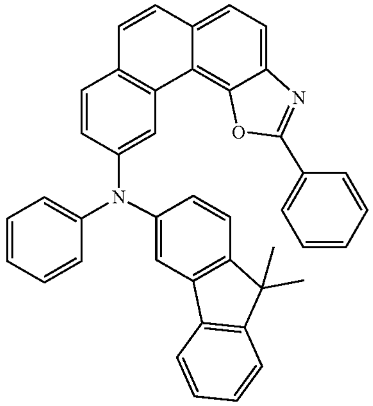
N29
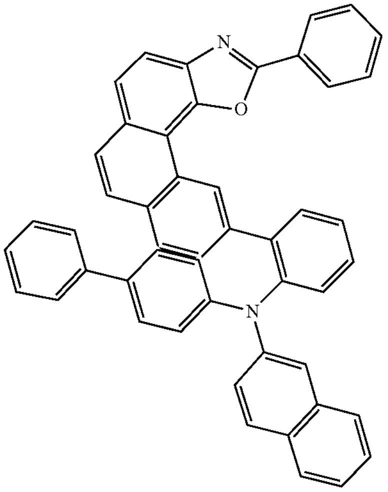

-continued
N30
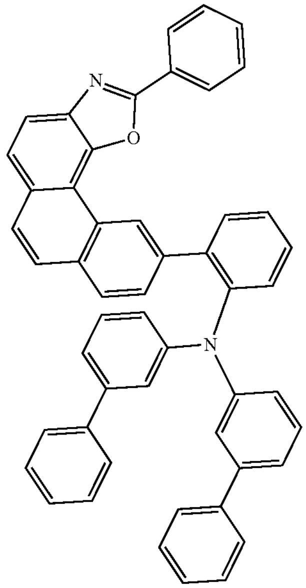
N31
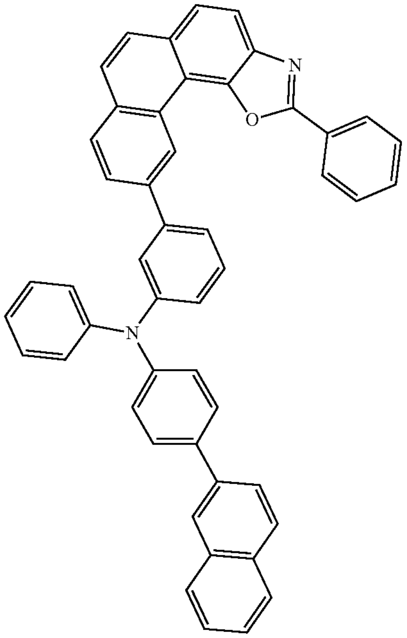
-continued
N32
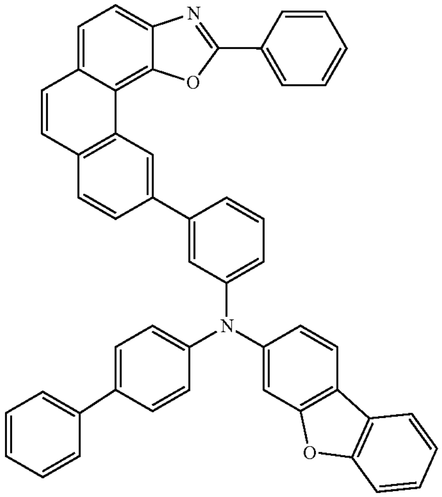
N33
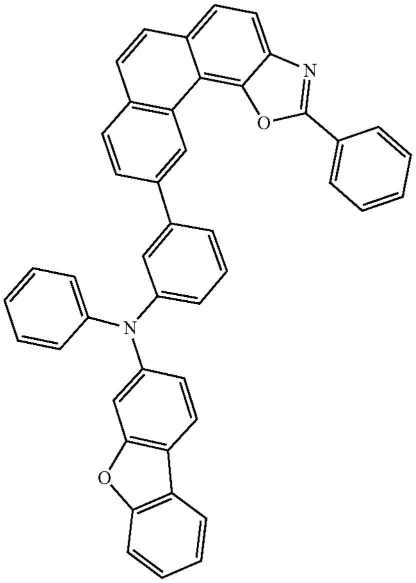
N34
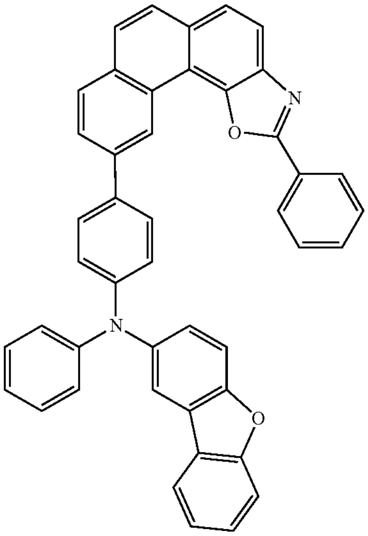

-continued
N35
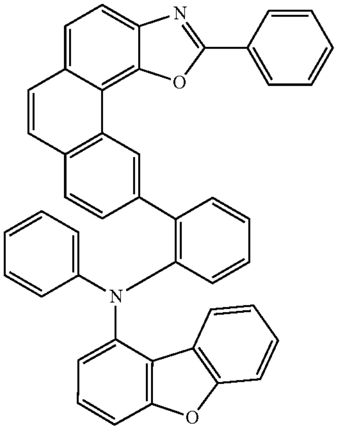
N36
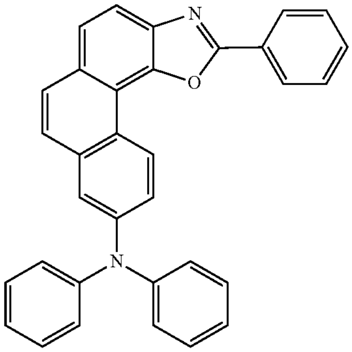
N37
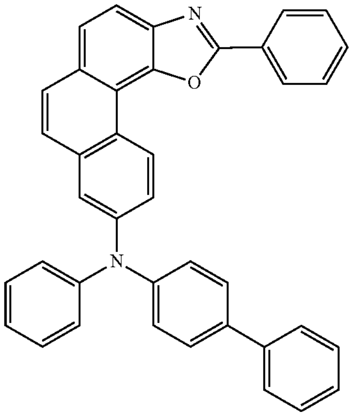
-continued
N38
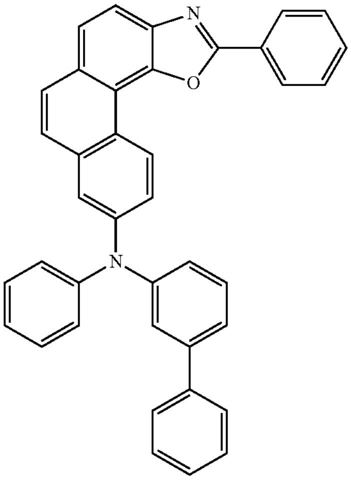
N39
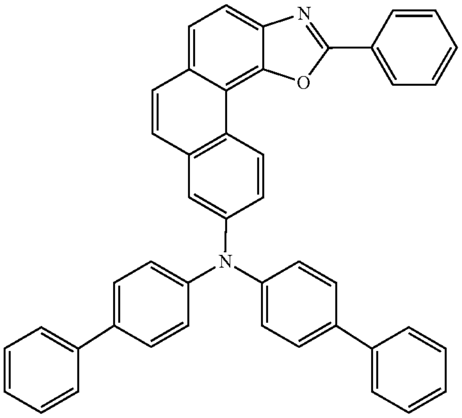
N40
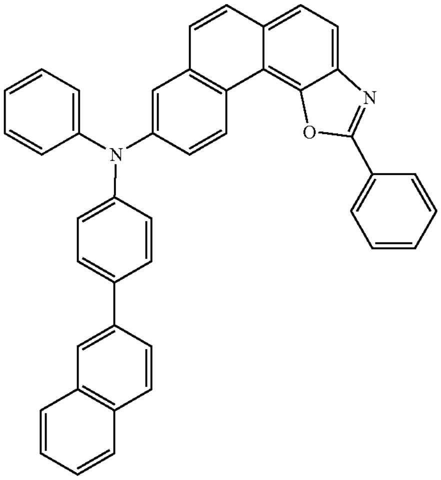

-continued
N41
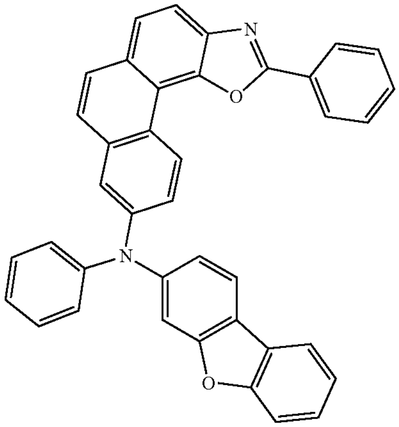
N42
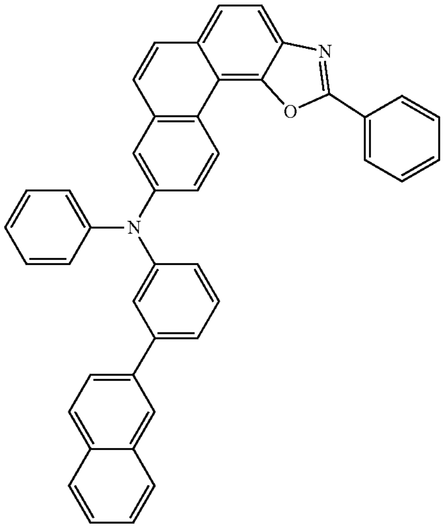
N43
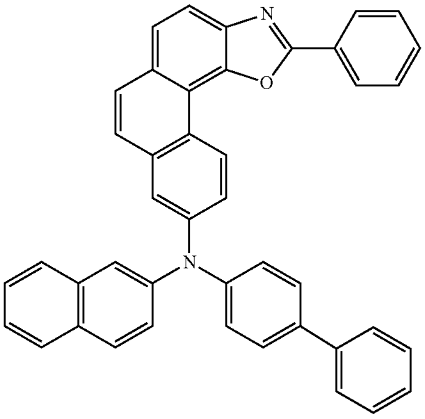
-continued
N44
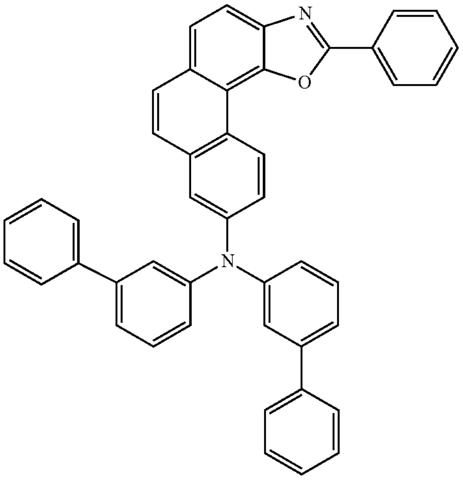
N45
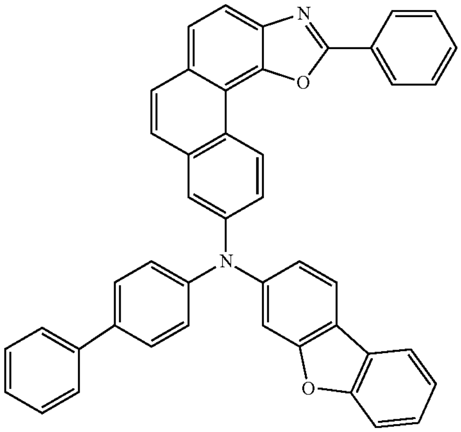
N46
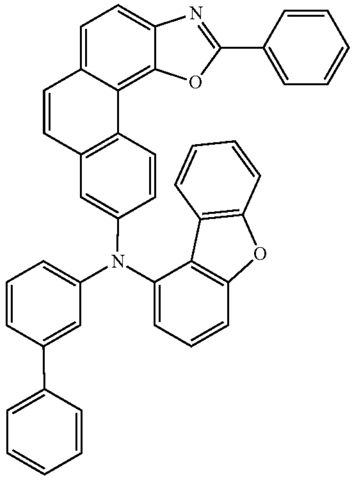

-continued
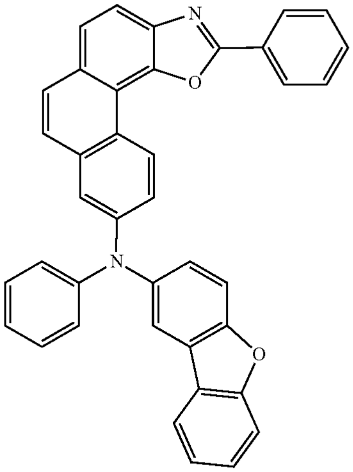
N47
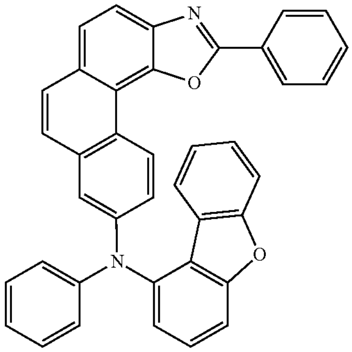
N48
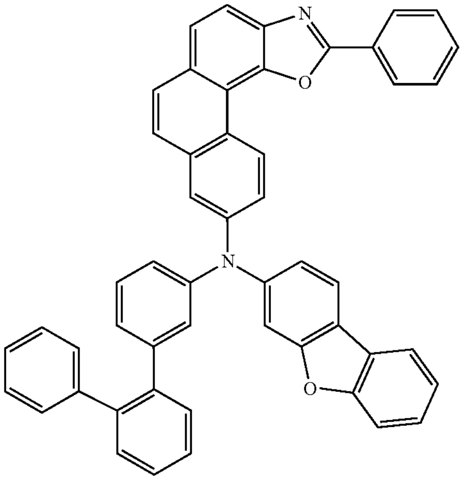
N49
-continued
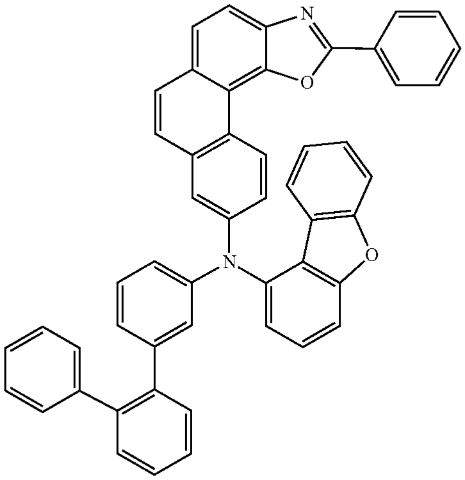
N50
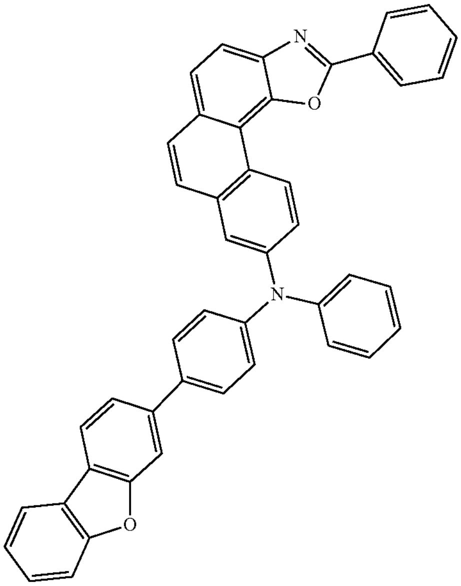
N51
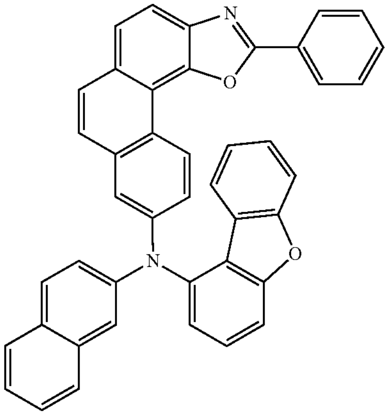
N52

-continued
N53
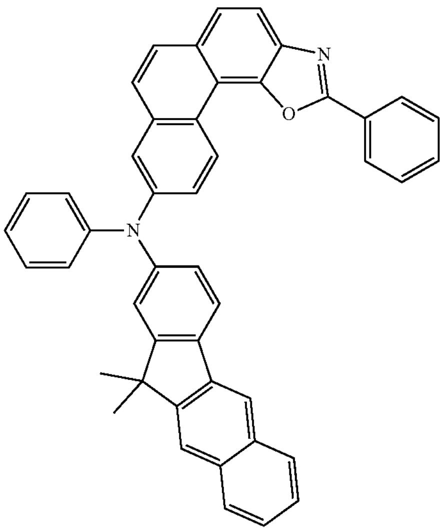
N54
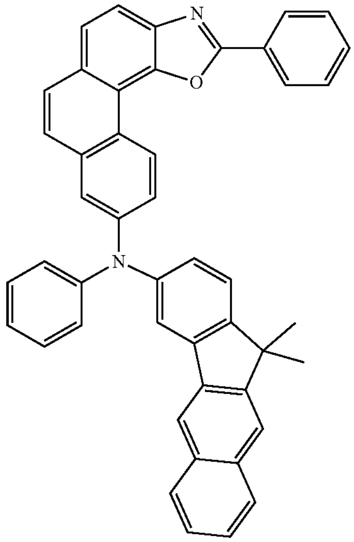
N55
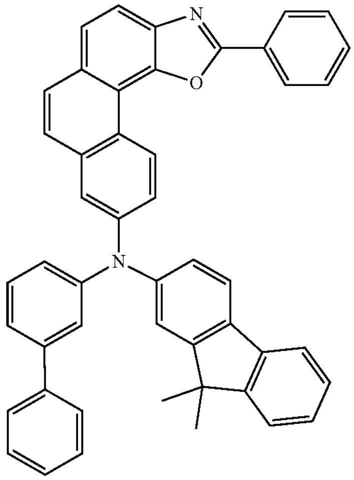
-continued
N56
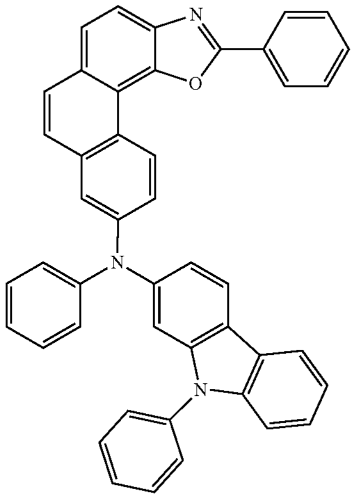
N57
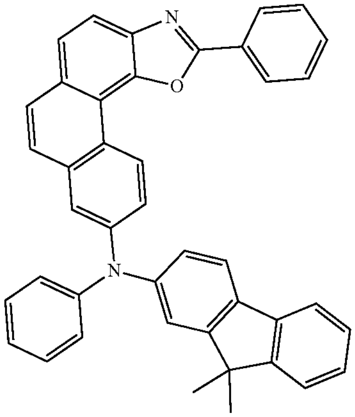
N58
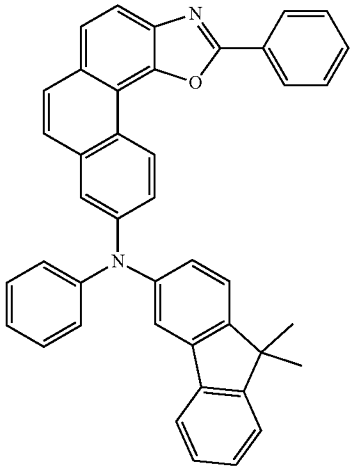

-continued

N59

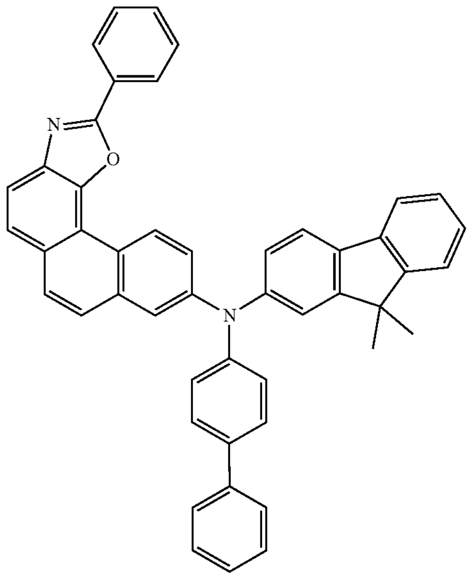

N60

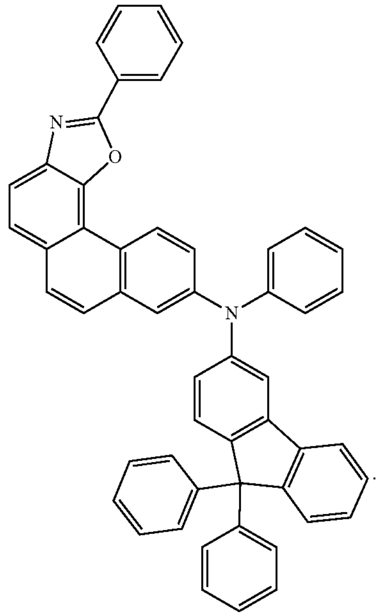

Preferably, the compound having a structure represented by Formula (1) and the compound having a structure represented by Formula (2) have a weight ratio of 1:9 to 9:1, such as 1:9, 2:8, 3:7, 4:6, 5:5, 6:4, 7:3, 8:2, 9:1, or the like; preferably 2:8 to 8:2; more preferably 3:7 to 7:3; even more preferably 4:6 to 6:4.

In the present invention, with the limitation of the group is substituted or unsubstituted, when the group is substituted, the substituent is selected from deuterium, halogen, a cyano group, a nitro group, an unsubstituted or R"-substituted C1-C4 straight or branched alkyl group, an unsubstituted or R"-substituted C6-C20 aryl group, an unsubstituted or R"-substituted C3-C20 heteroaryl group, and an unsubstituted or R"-substituted C6-C20 arylamino group; R" is selected from deuterium, halogen, a cyano group and a nitro group.

Preferably, the aryl group is selected from a phenyl group, a biphenylyl group, a terphenylyl group, a naphthyl group, an anthryl group, a phenanthryl group, a benzophenanthryl group, a naphthylphenyl group, a dimethylfluorenyl group, a diphenylfluorenyl group and a spiro-bifluorenyl group.

Preferably, the heteroaryl group is selected from a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a benzonaphthofuryl group, a benzonaphthothiophenyl group, a benzocarbazolyl group and a dibenzocarbazolyl group.

Preferably, the alkyl group is selected from a methyl group, an ethyl group, a propyl group, a tert-butyl group, a cyclohexyl group and adamantyl.

As used in the present invention, the term "halogen" may comprise fluorine, chlorine, bromine or iodine.

As used in the present invention, the term "C1-C30 alkyl group" indicates a monovalent substituent derived from a straight or branched saturated hydrocarbon having 1 to 30 carbon atoms, for example, it comprises, but is not limited to, a methyl group, an ethyl group, a propyl group, an isobutyl group, a sec-butyl group, a tert-butyl group, a pentyl group, an isopentyl group, or a hexyl.

As used in the present invention, the term "C3-C30 cycloalkyl group" indicates a group derived from a monocyclic hydrocarbon or a multicyclic hydrocarbon having 1 to 30 carbon atoms on the main chain, and the cycloalkyl group may comprise cyclopropyl, cyclobutyl, adamantyl group, or the like.

In the present invention, the aryl group and arylene group comprise a monocyclic, a multicyclic or a fused cyclic aryl group, in which the rings may be interrupted by a short non-aromatic unit, and they may comprise a spiro-structure. The aryl group and arylene group of the present invention comprise, but are not limited to, a phenyl group, a biphenylyl group, a terphenylyl group, a naphthyl group, a phenanthryl group, an anthryl group, a fluorenyl group, a spiro-bifluorenyl group, or the like.

In the present invention, the heteroaryl group and heteroarylene group comprise a monocyclic, a multicyclic or a fused cyclic heteroaryl group, in which the rings may be interrupted by a short non-aromatic unit, and the hetero atom comprises nitrogen, oxygen or sulfur. The heteroaryl group and heteroarylene group of the present invention comprise, but are not limited to, a furyl group, a thiophenyl group, a pyrrolyl group, an imidazolyl group, a pyrazolyl group, a thiazolyl group, a thiadiazolyl group, an isothiazolyl group, an isoxazolyl group, an oxazolyl group, an oxadizolyl group, a triazinyl group, a tetrazinyl group, a triazolyl group, a tetrazolyl group, a furazanyl group, a pyridyl group, a pyrazinyl group, a pyrimidinyl group, a pyridazinyl group, a benzofuryl group, a benzothiophenyl group, an isobenzofuryl group, a dibenzofuryl group, a dibenzothiophenyl group, a benzimidazolyl group, a benzothiazolyl group, a benzisothiazolyl group, a benzisoxazolyl group, a benzoxazolyl group, an isoindolyl group, an indolyl group, an indazolyl group, a benzothiadiazolyl group, a quinolyl group, an isoquinolyl group, a cinnolinyl group, a quinazolinyl group, a quinoxalinyl group, a carbazolyl group, a phenoxazinyl group, a phenothiazinyl group, a phenanthridinyl group, a 1,3-benzodioxolyl group, a dihydroacridinyl group, or derivatives thereof.

Preferably, the aryl group is selected from a phenyl group, a biphenylyl group, a terphenylyl group, a naphthyl group, an anthryl group, a phenanthryl group, a 9,9'-dimethylfluorenyl group, a 9,9'-diphenylfluorenyl group and a spiro-bifluorenyl group.

Preferably, the heteroaryl group is selected from a dibenzofuryl group, a dibenzothiophenyl group, a carbazolyl group, a triazinyl group, a pyridyl group, a pyrimidinyl group, an imidazolyl group, an oxazolyl group, a thiazolyl group, a benzimidazolyl group, a benzoxazolyl group, a benzothiazolyl, a naphthimidazolyl group, a naphthoxazolyl group, a naphthothiazolyl group, a phenanthrimidazolyl group, a phenanthroxazolyl group, a phenanthrothiazolyl group, a quinoxalinyl group, a quinazolinyl group, an indolocarbazolyl group, an indolofluorenyl group, a benzothienopyrazinyl group, a benzothienopyrimidinyl group, a benzofuropyrazinyl group, a benzofuropyrimidinyl group, an indolopyrazinyl group, an indolopyrimidinyl group, an indenopyrazinyl group, an indenopyrimidinyl group, a spiro[fluorene-9,1'-indene]-pyrazinyl group, spiro[fluorene-9,1'-indene]-pyrimidinyl group, benzofurocarbazolyl and benzothienocarbazolyl.

As used in the present invention, the term "C6-C30 aryloxy group" indicates a monovalent substituent represented by ZO—, wherein Z represents an aryl group having 6 to 30 carbon atoms. Examples of such aryloxy group comprise, but are not limited to, a phenoxy group, a naphthyloxy group, a diphenoxy group, or the like.

As used in the present invention, the term "C1-C30 alkoxy group" indicates a monovalent substituent represented by Z'O—, wherein Z' represents an alkyl group having 1 to 30 carbon atoms.

As used in the present invention, the term "substituted" indicates a hydrogen atom comprised in a compound is replaced by another substituent. The position of substitution is not specifically limited, provided that the hydrogen at the position can be replaced by the substituent. When two or more substituents are simultaneously present, the two or more substituents can be the same or different.

As used in the present invention, unless otherwise specified, the hydrogen atom comprises protium, deuterium or tritium.

In the present invention, "adjacent two groups joined to form a ring" indicates that 2 substituents at adjacent positions on the same ring or adjacent rings can be joined to form a ring by chemical bonding. The specific way to form a ring in the present invention is not limited (for example, joined via a single bond, joined via a benzene ring, joined via a naphthalene ring, fused via

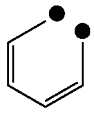

, fused via

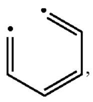

, fused via

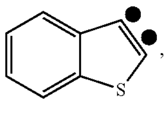

, fused via

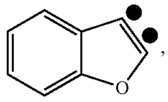

, fused via

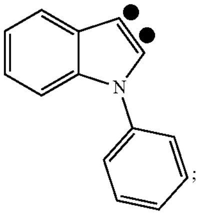 [SMILES: c1ccc(-n2ccc3ccccc32)cc1]

;

wherein the  represents fusion positions). In the same description present hereinafter, it has the same meaning.

In the present invention, when the range of carbon atom number is limited in the definition of a functional group, the functional group may have a carbon atom number of any integer in the limited range. For example, a C6-C60 aryl group represents an aryl group that may give a carbon number of any one integer comprised in the range of 6 to 60, such as 6, 8, 10, 15, 20, 30, 35, 40, 45, 50, 55 or 60, etc.

In the present invention, the organic compounds substituted at each of the described positions are prepared by a synthesis route shown as below:

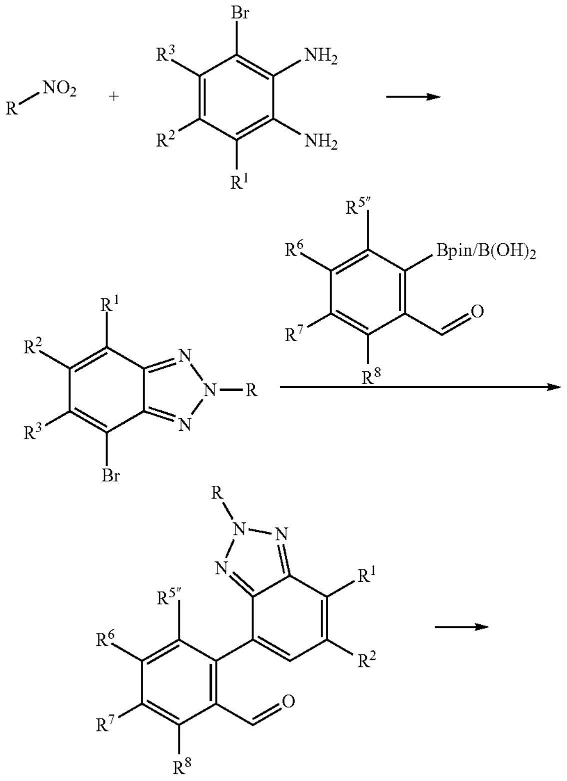

-continued
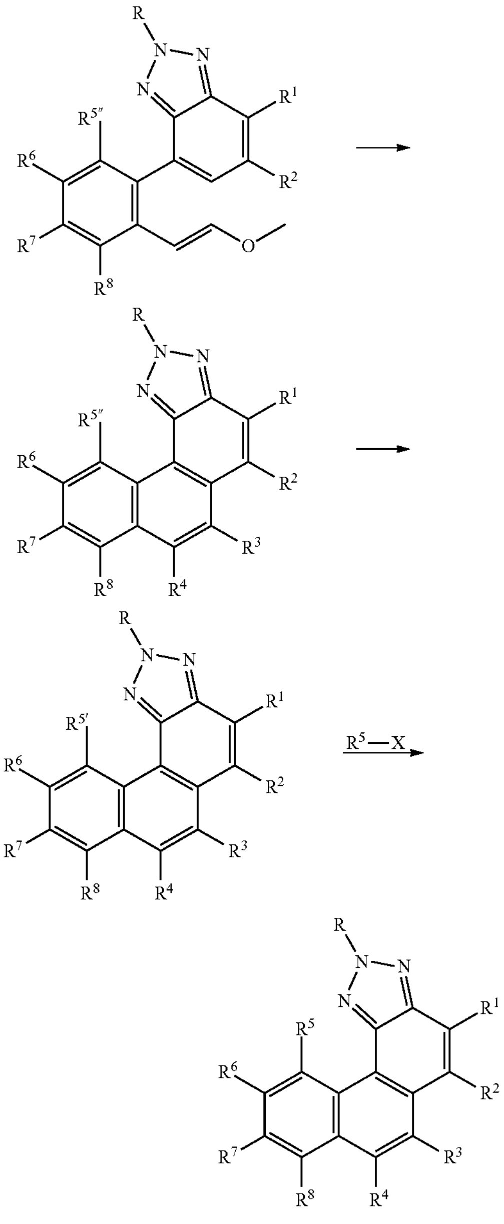
$R^{5''}$ is chlorine; $R^{5'}$ is
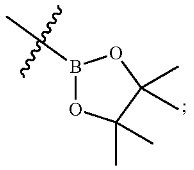
X is halogen, preferably chlorine or bromine.
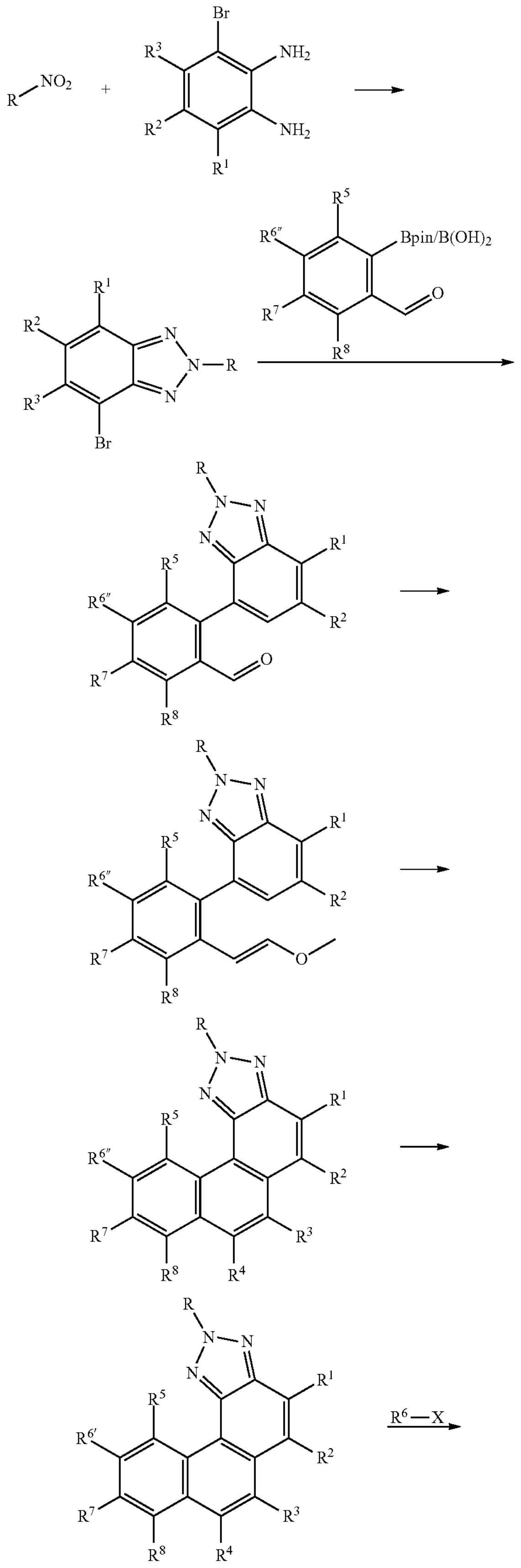

-continued
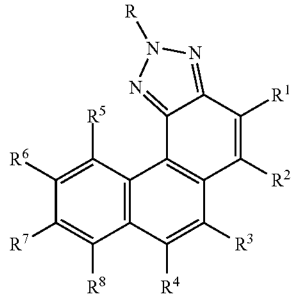
$R^{6''}$ is chlorine; $R^{6'}$ is
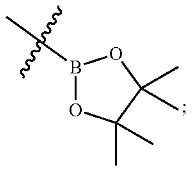 [SMILES: *B1OC(C)(C)C(C)(C)O1]
X is halogen, preferably chlorine or bromine.
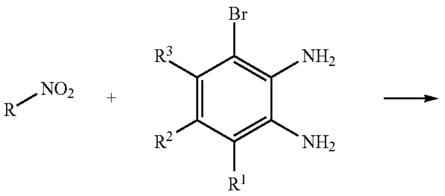
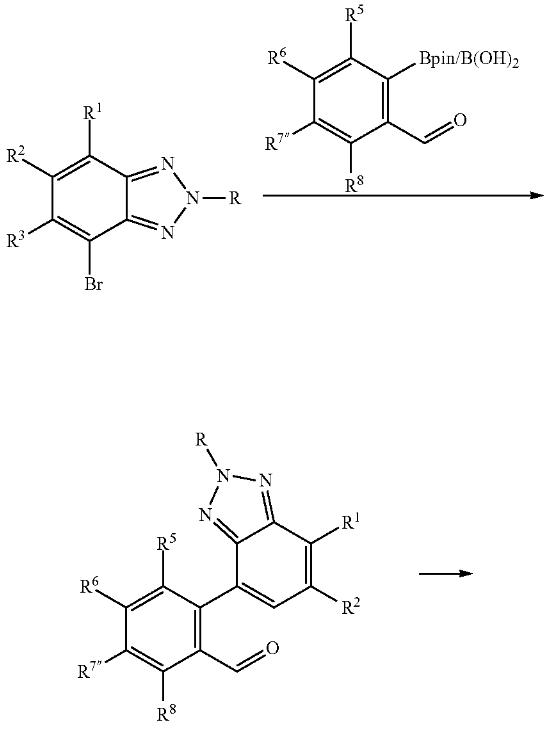
-continued
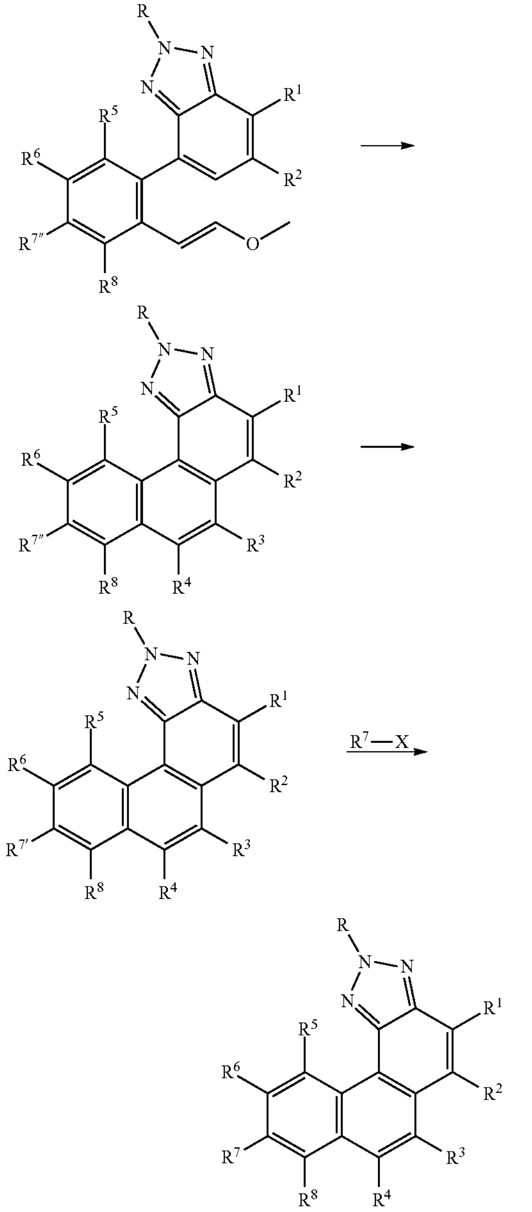
$R^{7''}$ is chlorine; $R^{7'}$ is
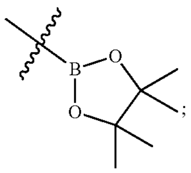 [SMILES: *B1OC(C)(C)C(C)(C)O1]
X is halogen, preferably chlorine or bromine.

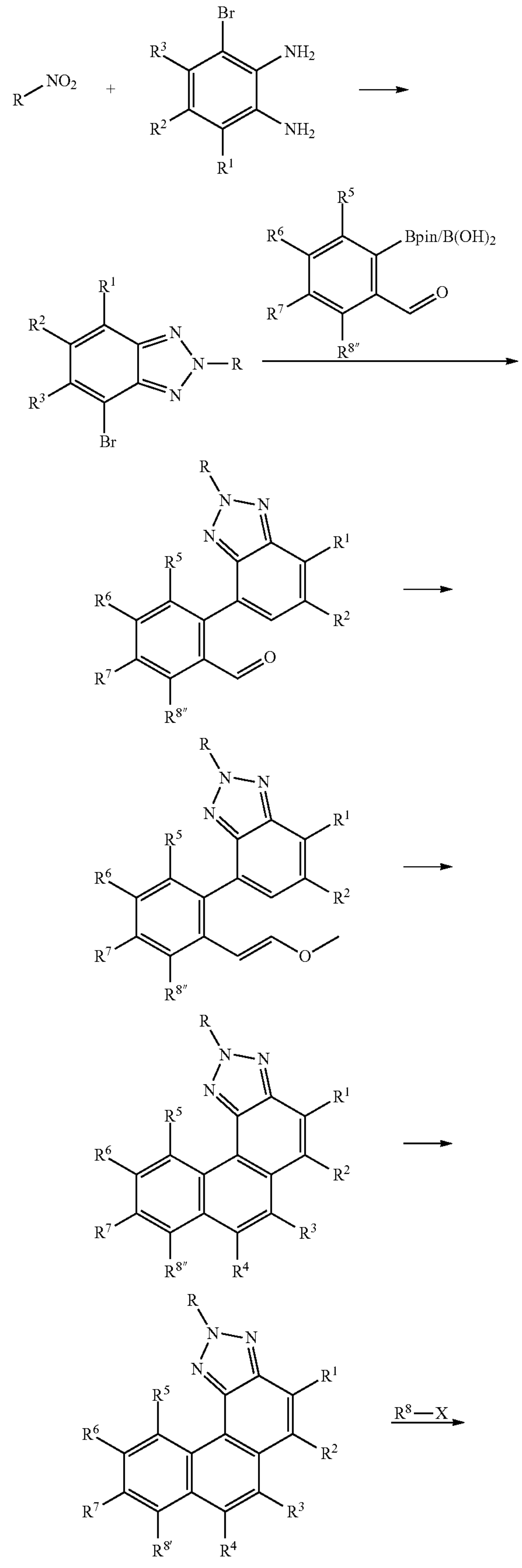

-continued

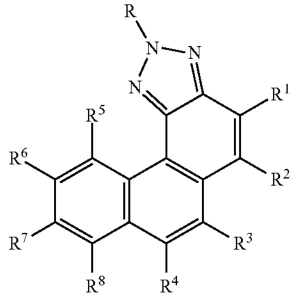

$R^{8''}$ is chlorine; $R^{8'}$ is

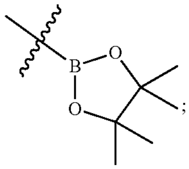 [SMILES: *B1OC(C)(C)C(C)(C)O1]

X is halogen, preferably chlorine or bromine.

Buchwald-Hartwig synthesis method is mainly used to synthesize Formula (2).

In another aspect, the present invention provides an organic electroluminescence material, and the organic electroluminescence material comprises the above-mentioned organic material composition.

In another aspect, the present invention provides an application of the above-mentioned organic material composition or the above-mentioned organic electroluminescence material in preparation of an optical element.

Preferably, the optical element comprises any one of an organic electroluminescence element, an organic field-effect transistor, an organic thin film transistor, an organic light-emitting transistor, an organic integrated circuit, an organic solar cell, an organic field quenching element, a light-emitting electrochemical cell, an organic laser diode, and an organic photoreceptor.

In another aspect, the present invention provides an organic electroluminescence element, wherein the organic electroluminescence element comprises an anode, a cathode, and an organic layer disposed between the anode and the cathode, and the organic layer comprises the above-mentioned organic material composition or the above-mentioned organic electroluminescence material.

Preferably, the organic layers comprise a hole injection layer, a hole transport layer, an emitting layer, an electron transport layer and an electron injection layer, which are sequentially layered from a side of the anode to a side of the cathode.

Preferably, the emitting layer is made of a material comprising a host material and a guest material, wherein the host material comprises the above-mentioned organic material composition or the above-mentioned organic electroluminescence material.

Preferably, the guest material comprises a phosphorescence dopant, and the phosphorescence dopant comprises a coordination complex of a transition metal.

In another aspect, the present invention provides an organic electroluminescence device, wherein the organic electroluminescence device comprises the above-mentioned organic electroluminescence element.

Compared to the existing technology, the present invention has the following advantages:

By the combination of at least one compound having a structure represented by Formula (1) and at least one compound having a structure represented by Formula (2), the organic material composition of the present invention makes an organic light-emitting element have an obviously enhanced light-emitting efficiency.

DETAILED DESCRIPTION OF THE PREFERRED EMBODIMENTS

Specific embodiments are further illustrated by the following examples to demonstrate the technical approaches of the present invention. Those skilled in the art should understand that the illustrative examples are helpful to understand the present invention; however, they should not be construed as being limiting to the scope of the present invention.

The compounds whose synthesis methods are not mentioned in the present invention are commercially available products used as raw materials. The solvents and agents used in the present invention, for example, chemical agents such as tetrahydrofuran, potassium hydroxide, nitrobenzene, palladium catalyst and the like, can be purchased in the chemical product market in China, for example, purchased from Sinopharm Chemical Reagent Co., Ltd.; Tokyo Chemical Industry (TCI) Co., Ltd.; Bide Pharmatech Ltd.; J&K Scientific Ltd. and the like. In addition, these compounds can also be synthesized with a well-known method by those skilled in the art.

Preparation Example of Compound of Formula (1)

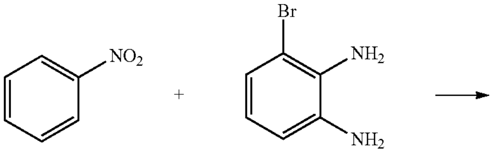

M6-A

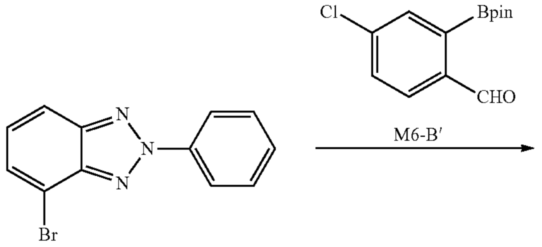

M6-B

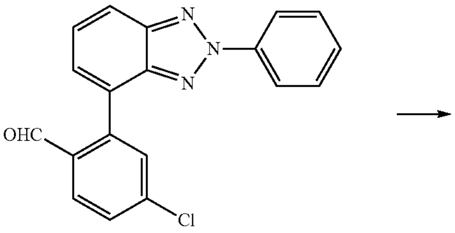

M6-C

-continued

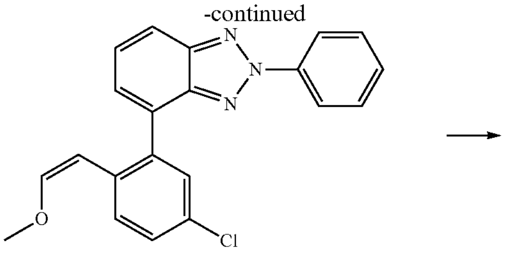

M6-D

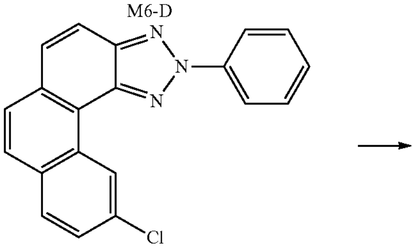

M6-E

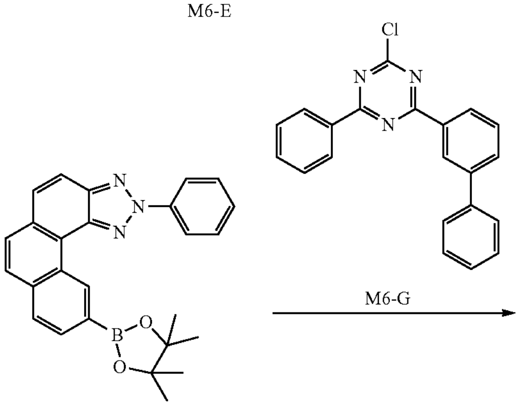

M6-F

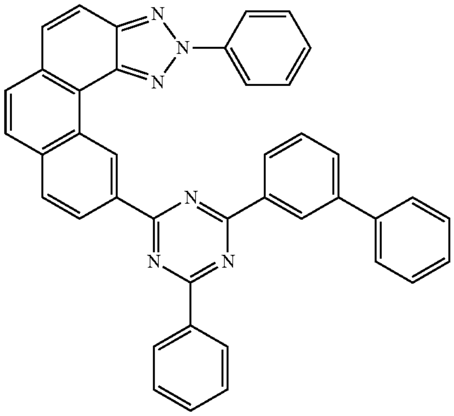

M6

Synthesis of M6-B: In a three-necked bottle of 25 milliliters (mL), M6-A (10 millimoles (mmol)), nitrobenzene (10 mmol), potassium hydroxide (22 mmol), copper(I) thiocyanate (1 mmol) and anhydrous tetrahydrofuran (10 mL) were added, nitrogen gas was purged for three times, and heated to 90° C. under nitrogen gas protection to react for 48 hours (h). After the reaction ended, the reaction mixture was quenched by water, the reaction system was extracted by ethyl acetate, and the organic solvent was removed by rotary evaporation to give a crude product. The crude product was purified by column chromatography (ethyl acetate:n-hexane=1:50 (volume ratio)), to obtain M6-B (1.34 g, 49% yield).

Synthesis of M6-B': In a three-necked bottle of 50 mL, 2-bromo chlorobenzaldehyde (10 mmol), bis(pinacolato) diboron (12 mmol), potassium acetate (100 mmol), [1,1'-bis (diphenylphosphino)ferrocene]palladium(II) dichloride (0.2 mmol) and 1,4-dioxane (25 mL) were added, nitrogen gas was purged, and heated to 100° C. under nitrogen gas protection for reaction. After the reaction ended, the reaction mixture was quenched by water, extracted by methylene dichloride to give a crude product. The crude product was purified by column chromatography (methylene dichloride: n-hexane=1:50 (volume ratio)), to obtain M6-B' (1.7 g, 64% yield).

Synthesis of M6-C: In a three-necked bottle of 50 mL, M6-B (10 mmol), M6-B' (10 mmol), sodium bicarbonate (20 mmol), tetrakis(triphenylphosphine)palladium (0.2 mmol), tetrahydrofuran (20 mL) and water (10 mL) were added, nitrogen gas was purged, and heated to 60° C. under nitrogen gas protection to react overnight. After the reaction ended, the reaction mixture was quenched by water, extracted by methylene dichloride, and the organic solvent was removed by rotary evaporation to give a crude product. The crude product was purified by column chromatography (ethyl acetate:n-hexane=1:50 (volume ratio)), to obtain M6-C (3.06 g, 92% yield).

Synthesis of M6-D: In a three-necked bottle of 50 mL, M6-C (10 mmol), (methoxymethyl)triphenylphosphonium chloride (20 mmol) and tetrahydrofuran (10 mL) were added, and the temperature was reduced to 0° C. Potassium tert-butoxide (2 mmol) was resolved in 5 mL tetrahydrofuran. The three-necked bottle was purged with nitrogen gas. Under nitrogen gas protection, the potassium tert-butoxide solution was added dropwise at 0° C. to obtain a mixture. After the addition, the mixture was stirred to react for half an hour. After the reaction ended, the reaction mixture was quenched by water, extracted by methylene dichloride, and the organic solvent was removed by rotary evaporation to give a crude product. The crude product was purified by column chromatography (ethyl acetate:n-hexane=1:50 (volume ratio)), to obtain M6-D (1.8 g, 50% yield).

Synthesis of M6-E: In a three-necked bottle of 25 mL, M6-D (1 mmol) and hexafluoroisopropanol (5 mL) were added, the temperature was reduced to 0° C., and nitrogen gas was purged. Under nitrogen gas protection, trifluoromethanesulfonic acid (1 mL) was added dropwise to obtain a mixture, and the mixture was stirred to react for half an hour to give a crude product. The crude product was purified by column chromatography (ethyl acetate:n-hexane=1:50 (volume ratio)), to obtain M6-E (0.24 g, 73% yield).

Synthesis of M6-F: In a three-necked round-bottom flask of 50 mL, M6-E (10 mmol), bis(pinacolato)diboron (12 mmol), sodium acetate (20 mmol), tris(dibenzylideneacetone)dipalladium(0) (0.5 mmol) and 2-dicyclohexylphosphino-2',6'-dimethoxybiphenyl (1.5 mmol) were added, then 1,4-dioxane (20 mL) was added, nitrogen gas was purged for three times, and heated to 100° C. under nitrogen gas protection for reaction. After the reaction ended, the reaction mixture was quenched by water, extracted by methylene dichloride, and the organic solvent was removed by rotary evaporation to give a crude product. The crude product was purified by column chromatography (ethyl acetate: n-hexane=1:50 (volume ratio)), to obtain M6-F (3.24 g, 77% yield).

Synthesis of M6: In a three-necked round-bottom flask of 100 mL, a stir bar was put at the bottom and a refluxing tube was connected on the top. The flask was dried and purged with nitrogen gas, and M6-F (10 mmol), M6-G (10 mmol, CAS1689576-03-1), sodium bicarbonate (23 mmol), tetrakis (triphenylphosphine)palladium (0.5 mmol), bis(di-tert-butyl (4-dimethylaminophenyl)phosphine)dichloropalladium(II) (0.5 mmol), toluene (25 mL), ethanol (7 mL) and water (7 mL) were separately added, nitrogen gas was purged for three times, and heated to 80° C. under nitrogen gas protection to react for 8 h. After the reaction ended, the reaction mixture was extracted by ethyl acetate, and the resulting extract was dried by magnesium sulfate, filtered, and dried by rotary evaporation to give a crude product. The crude product was purified by column chromatography (ethyl acetate:n-hexane=1:10 (volume ratio)), to obtain compound M6 (4.13 g, 67% yield).

Anal. Calcd. $C_{41}H_{26}N_6$: C, 81.71; H, 4.35; N, 13.94. Found: C, 81.78; H, 4.33; N, 13.89. HRMS (ESI) m/z $[M+H]^+$: Calcd.: 602.22. Found: 603.40.

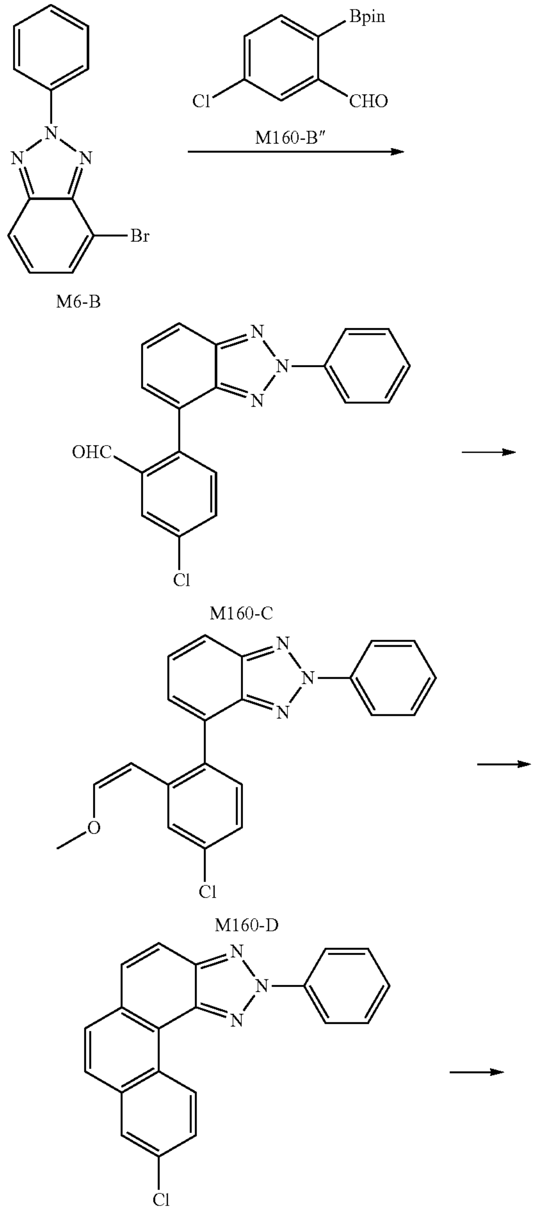

M6-B

M160-C

M160-D

M160-E

-continued

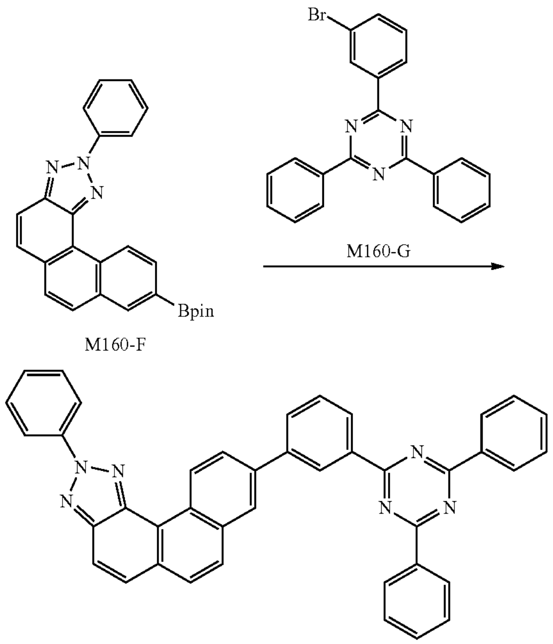

M160

Synthesis of M160-B": Similar to the synthesis of M6-B', with the difference that 2-bromo-5-chlorobenzaldehyde is used to replace 2-bromo-4-chlorobenzaldehyde, to obtain M160-B" (1.60 g, 60% yield).

Synthesis of M160-C: Similar to the synthesis of M6-C, with the difference that 4-fluoro-2-formylbenzeneboronic acid pinacol ester is used to replace 5-fluoro-2-formylbenzeneboronic acid pinacol ester, to obtain M160-C (2.13 g, 64% yield).

Synthesis of M160-D: Similar to the synthesis of M6-D, with the difference that M160-C is used to replace M6-C, to obtain M160-D (3.21 g, 89% yield).

Synthesis of M160-E: Similar to the synthesis of M6-E, with the difference that M160-D is used to replace M6-D, to obtain M160-E (0.16 g, 48% yield).

Synthesis of M160-F: Similar to the synthesis of M6-F, with the difference that M160-E is used to replace M6-E, to obtain M160-F (4.00 g, 95% yield).

Synthesis of compound M160: Similar to the synthesis of compound M6, with the difference that M160-F is used to replace M6-F, and M160-G is used to replace M6-G, to obtain compound M160 (4.70 g, 78% yield).

Anal. Calcd. $C_{41}H_{26}N_6$: C, 81.71; H, 4.35; N, 13.94. Found: C, 81.73; H, 4.37; N, 13.90. HRMS (ESI) m/z ($M^+$): Calcd.: 602.22. Found: 603.29.

The corresponding products shown in Table 1 were prepared by the above-mentioned preparation method using the Material 1 and Material 2 as raw materials. The structure and characteristic data of the products are shown in Table 2.

TABLE 1

| Material 1 | Material 2 | Product | Yield (%) |
|---|---|---|---|
| 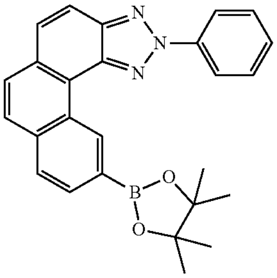 [SMILES: CC1(C)OB(c2ccc3ccc4ccc5nn(-c6ccccc6)nc5c4c3c2)OC1(C)C] | 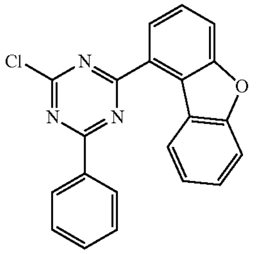 CAS2142681-84-1 | 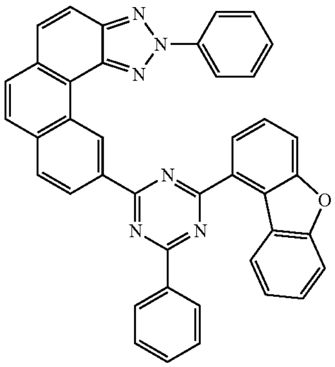 M46 | 65 |
| 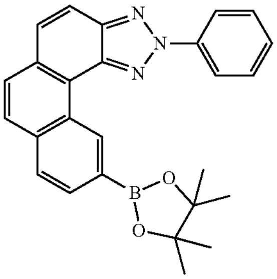 [SMILES: CC1(C)OB(c2ccc3ccc4ccc5nn(-c6ccccc6)nc5c4c3c2)OC1(C)C] | 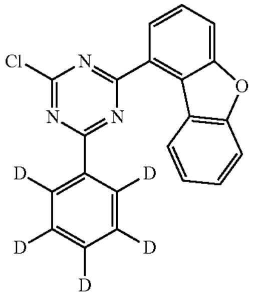 CAS2391956-00-4 | 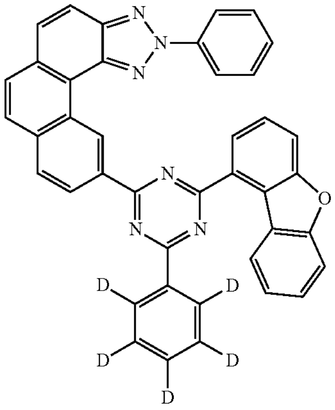 M41 | 67 |

TABLE 1-continued
| Material 1 | Material 2 | Product | Yield (%) |
|---|---|---|---|
| 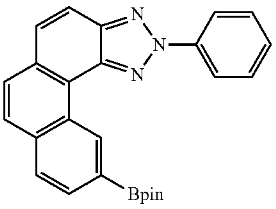 | 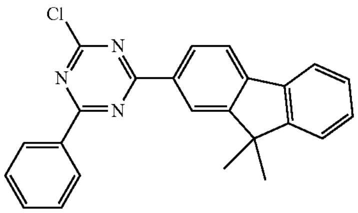 CAS1618106-98-1 | 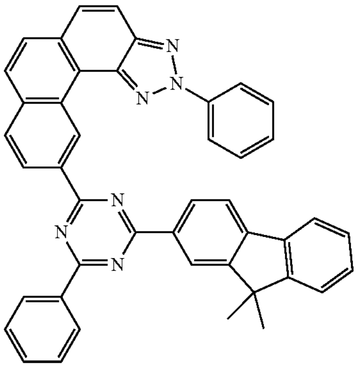 M23 | 74 |
| 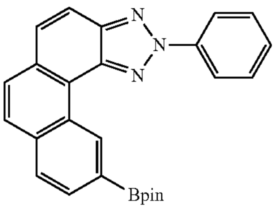 | 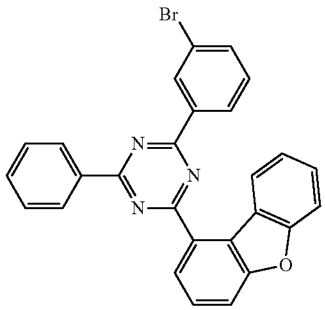 CAS2102445-28-1 | 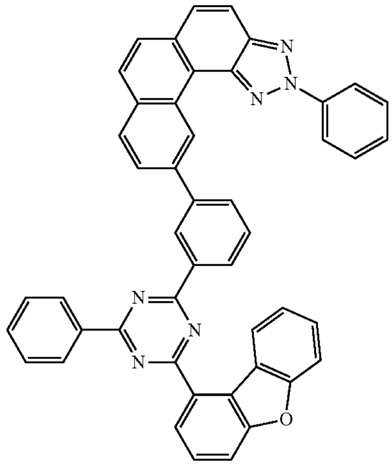 M97 | 65 |
| 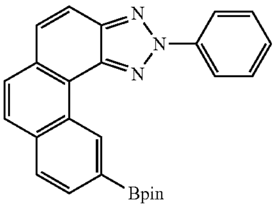 | 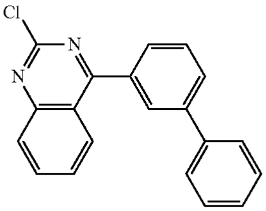 CAS1413365-66-8 | 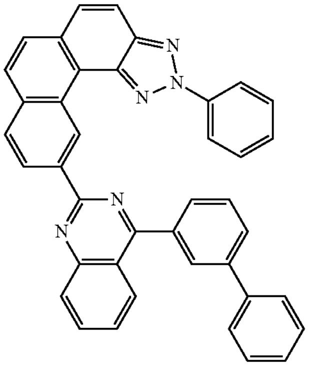 M117 | 68 |

TABLE 1-continued

| Material 1 | Material 2 | Product | Yield (%) |
|---|---|---|---|
| 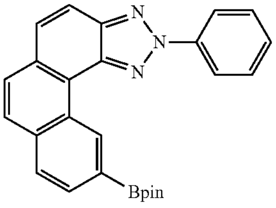 | 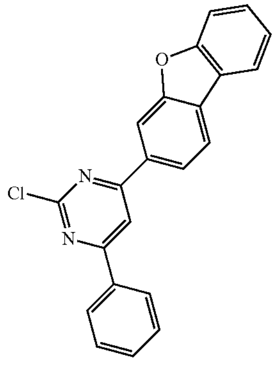 CAS2286234-09-9 | 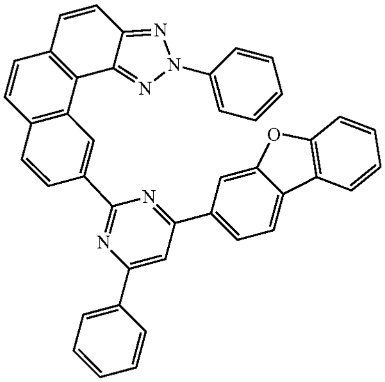 M93 | 68 |
| 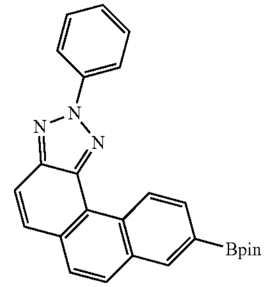 | 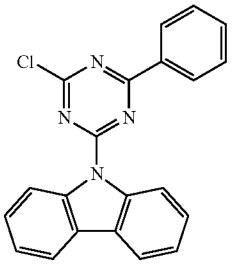 CAS1268244-56-9 | 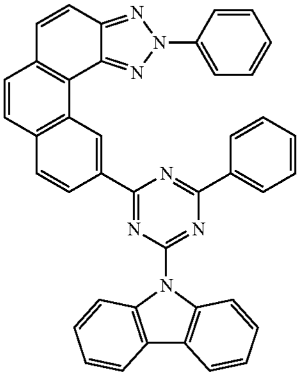 M31 | 61 |

TABLE 2

| Compound | Elemental analysis Calcd. | Elemental analysis Found | HRMS (ESI) m/z [M + H]+ Calcd. | HRMS (ESI) m/z [M + H]+ Found |
|---|---|---|---|---|
| M46 | C, 79.85; H, 3.92; N, 13.63; | C, 79.92; H, 3.91; N, 13.59; | 616.20 | 617.26 |
| M41 | C, 79.21; H, 4.70; N, 13.52; | C, 79.24; H, 4.71; N, 13.48; | 621.23 | 622.26 |
| M23 | C, 82.22; H, 4.70; N, 13.08; | C, 82.16; H, 4.72; N, 13.12; | 642.25 | 643.25 |
| M97 | C, 81.49; H, 4.07; N, 12.13; | C, 81.53; H, 4.08; N, 12.08; | 692.23 | 693.20 |
| M117 | C, 83.46; H, 4.38; N, 12.17; | C, 83.39; H, 4.40; N, 12.21; | 575.21 | 576.24 |
| M93 | C, 81.93; H, 4.09; N, 11.37; | C, 81.89; H, 4.11; N, 11.40; | 615.21 | 616.17 |

TABLE 2-continued

| Compound | Elemental analysis Calcd. | Elemental analysis Found | HRMS (ESI) m/z [M + H]+ Calcd. | HRMS (ESI) m/z [M + H]+ Found |
|---|---|---|---|---|
| M31 | C, 79.98; H, 4.09; N, 15.92; | C, 80.04; H, 4.08; N, 15.88; | 615.22 | 616.16 |

Preparation Example of Compound of Formula (2)

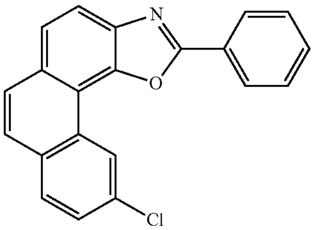 [SMILES: Clc1ccc2ccc3ccc4nc(-c5ccccc5)oc4c3c2c1]

N4-A

+

-continued

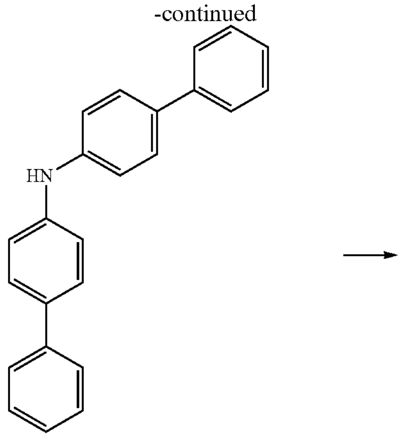

N4-B

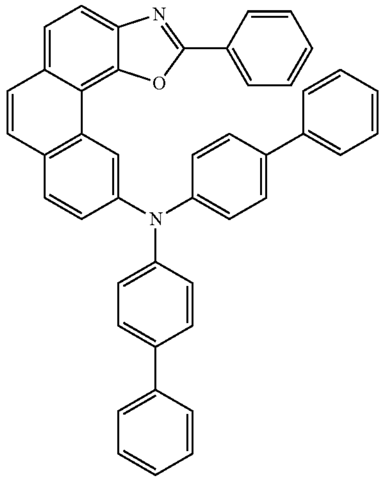

N4

Synthesis of compound N4: In a three-necked bottle of 25 mL, nitrogen gas was purged, N4-A (1 mmol, CAS 2085325-19-3), N4-B (1 mmol, CAS 102113-98-4), sodium tert-butoxide (2 mmol), tris(dibenzylideneacetone)dipalladium(0) (0.02 mmol), 50% tri-tert-butylphosphine solution (0.1 mmol) and toluene 8 mL was added, and stirred under reflux to react. After the reaction ended, the reaction mixture was cooled to room temperature, and the organic layer was extracted by ethyl acetate and $H_2O$. The extracted organic layer was dried by $MgSO_4$, filtered, and the filtrate was concentrated under vacuum to give a crude product. The crude product was purified by column chromatography (ethyl acetate: n-hexane=1:50 (volume ratio)), to obtain compound N4 (0.43 g, 69% yield).

Anal. Calcd. $C_{45}H_{30}N_2O$: C, 87.92; H, 4.92; N, 4.56. Found: C, 87.97; H, 4.90; N, 4.53. HRMS (ESI) m/z $[M+H]^+$: Calcd.: 614.24. Found: 615.33.

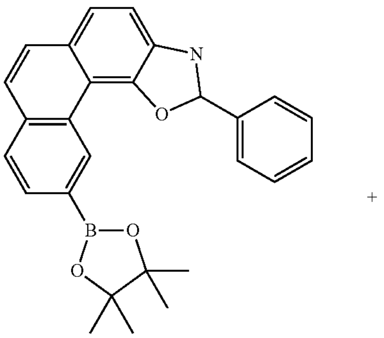

N33-A

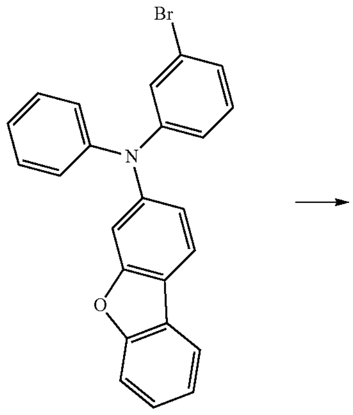

N33-B

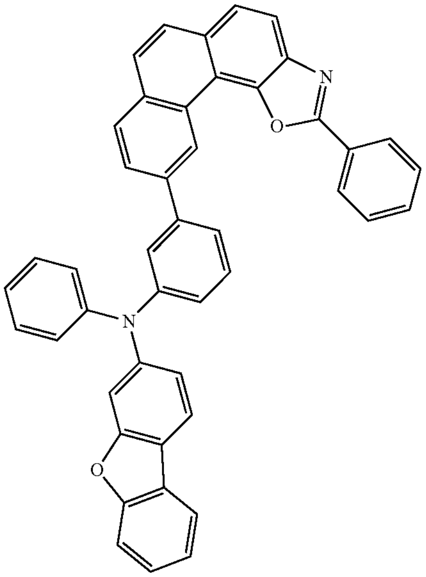

N33

Synthesis of N33: In a two-necked round-bottom flask of 25 mL, a stir bar was put at the bottom and a refluxing tube was connected on the top. The flask was dried and purged with nitrogen gas, and N33-A (1 mmol), N33-B (1 mmol, CAS 2468159-90-0), potassium carbonate (1.3 mmol), tetrakis(triphenylphosphine)palladium (0.05 mmol), toluene (7 mL), and water (2 mL) were separately added, nitrogen gas was purged for three times, and heated to 85° C. under nitrogen gas protection to react for 10 h. After the reaction ended, the reaction mixture was extracted by ethyl acetate, and the resulting extract was dried by magnesium sulfate, filtered, and dried by rotary evaporation to give a crude product. The crude product was purified by column chromatography (ethyl acetate: n-hexane=1:10 (volume ratio)), to obtain compound N33 (0.44 g, 63% yield).

Anal. Calcd. $C_{45}H_{28}N_2O_2$: C, 85.97; H, 4.49; N, 4.46. Found: C, 85.88; H, 4.52; N, 4.48. HRMS (ESI) m/z ($M^+$): Calcd.: 628.22 Found: 629.10.

Compounds in Table 3 were synthesized by the same synthesis method for preparing compound N33. The raw materials and resulting products are shown in Table 3. The structure and characteristic data of the products are shown in Table 4.

TABLE 3

| Material 1 | Material 2 | Product | Yield % |
|---|---|---|---|
| 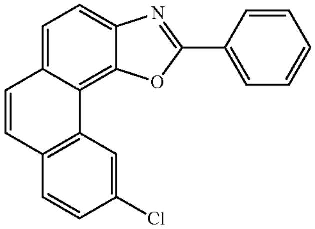 [SMILES: Clc1ccc2ccc3ccc4nc(-c5ccccc5)oc4c3c2c1] | 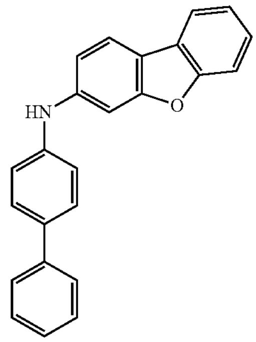 CAS 1290039-85-8 | 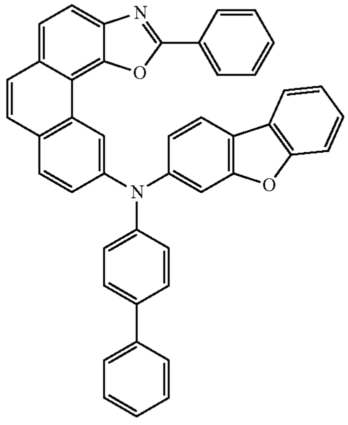 N14 | 71 |
| 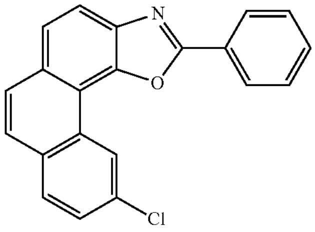 | 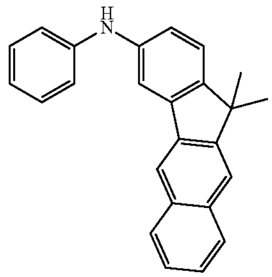 CAS 2118930-04-2 | 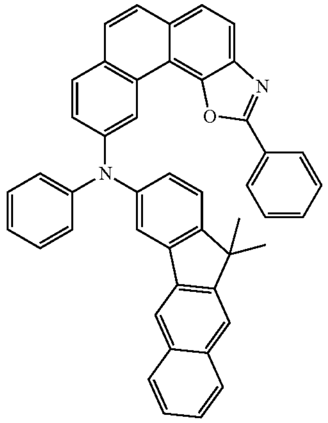 N22 | 69 |
| 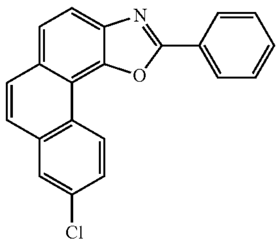 CAS 2085325-16-0 | 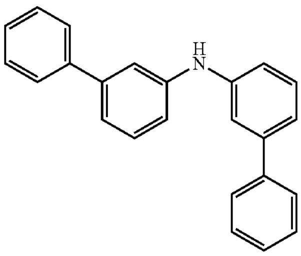 CAS 1456702-59-2 | 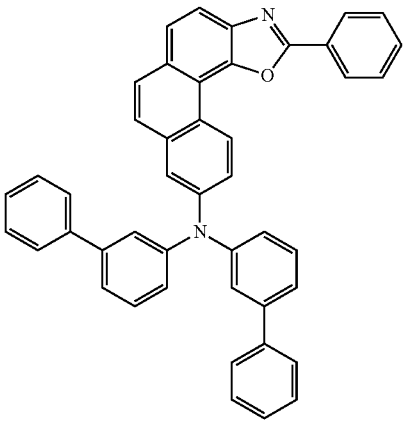 N44 | 67 |

TABLE 3-continued

| Material 1 | Material 2 | Product | Yield % |
|---|---|---|---|
| 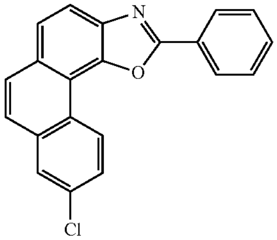 CAS 2085325-16-0 | 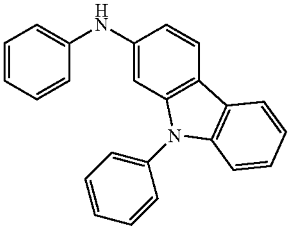 CAS 1427316-55-9 | 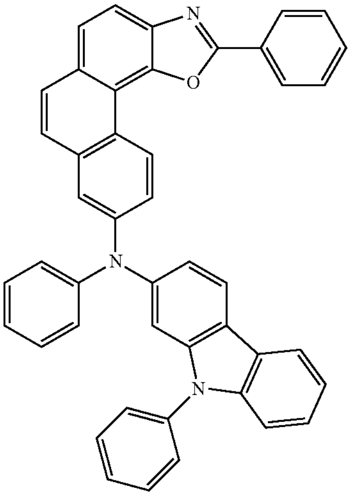 N56 | 68 |

TABLE 4

| | Elemental analysis | | HRMS (ESI) m/z [M + H]+ | |
|---|---|---|---|---|
| Compound | Calcd. | Found | Calcd. | Found |
| N14 | C, 87.87; H, 5.13; N, 4.46; | C, 87.90; H, 5.10; N, 4.47; | 628.25 | 629.32 |
| N22 | C, 85.97; H, 4.49; N, 4.46; | C, 85.91; H, 4.52; N, 4.45; | 628.22 | 629.32 |
| N44 | C, 87.92; H, 4.92; N, 4.56 | C, 87.96; H, 4.89; N, 4.55 | 614.24 | 615.15 |
| N56 | C, 86.10; H, 4.66; N, 6.69 | C, 86.07; H, 4.65; N, 6.72 | 627.23 | 628.34 |

Application Examples

An organic electroluminescence element (such as OLED) with the following layer structure was provided: base (indium tin oxide (ITO, as an anode) coated glass substrate)/hole injection layer (HIL)/hole transport layer (HTL)/emitting layer (EML)/electron transport layer (ETL)/electron injection layer (EIL), and the cathode at last.

The materials needed to prepare OLED are listed below, wherein the REF-1 is comparative compound 1:

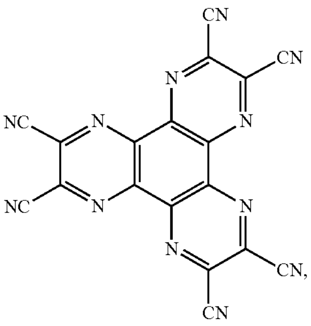

(HAT)(CN)6

-continued

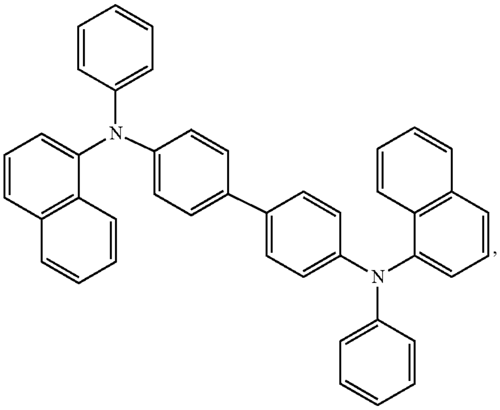

HT

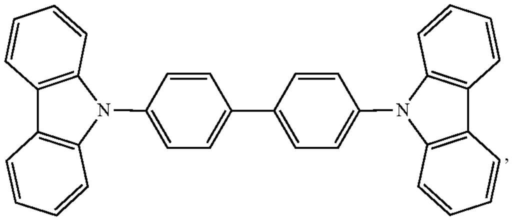

CBP

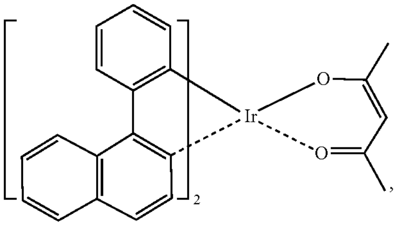

$(piq)_2Ir(acac)$

-continued

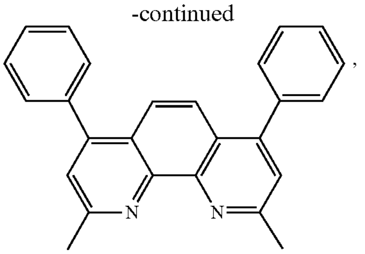

BPhen

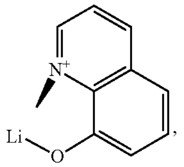

LiQ

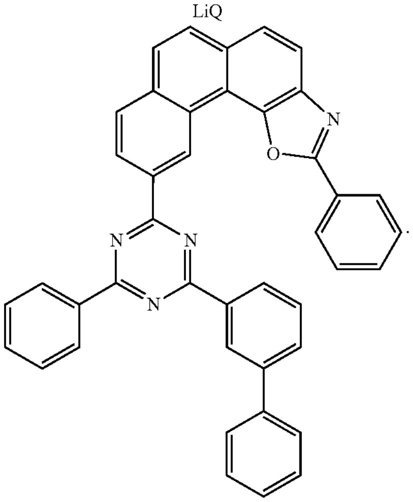

REF-1

The above-mentioned organic electroluminescence elements were prepared by the following steps:

(1) Cleaning the substrate: a glass substrate coated with transparent ITO layer (the anode) was ultrasonicated in an aqueous detergent (the content and concentration of the aqueous detergent: an ethylene glycol solvent of ≤10 percent by weight (wt %), triethanolamine of ≤1 wt %), washed in deionized water, degreased in an acetone/ethanol mixed solvent (volume ratio=1:1) by ultrasonication, baked in a clear environment until water was completely removed, and washed by ozone under ultraviolet light;

(2) Depositing organic emitting functional layers:

The glass substrate with the anode was placed in a chamber, and the chamber was vacuumized until $1\times10^{-6}$ Pascal (Pa) to $2\times10^{-4}$ Pa, and a mixture of $HAT(CN)_6$ and HT (mass ratio of $HAT(CN)_6$ and HT is 3:97) was deposited on the anode layer in vacuum to form a hole injection layer, in which the deposited thickness was 10 nanometers (nm).

A hole transport layer was deposited on the hole injection layer, in which the deposited thickness was 80 nm.

An emitting layer was deposited on the hole transport layer. Specifically, the preparation method was: the light-emitting host material and a guest material were co-deposited in vacuum, in which the total deposited thickness was 30 nm.

An electron transport layer was deposited on the emitting layer. Specifically, the preparation method was: BPhen and LiQ were co-deposited in vacuum, in which the total deposited thickness was 30 nm.

An electron injection layer was deposited on the electron transport layer, in which the total deposited thickness was 1 nm.

Al (as cathode) was deposited on the electron injection layer 6, in which the deposited thickness was 80 nm.

The materials (mat.) of each layer in the element and parameters such as thickness (thk.) of Element Examples 1 to 11 (E1 to E11) and Comparative Element Examples 1 to 2 (CE1 to CE2) are shown in Table 5.

TABLE 5

| No. | HIL mat./ thk. | HTL mat./ thk. | EML mat./ thk. | ETL mat./ thk. | EIL mat./ thk. | Cathode mat./ thk. |
|---|---|---|---|---|---|---|
| E1 | $HAT(CN)_6$: HT (mass ratio3:97)/ 10 nm | HT/ 80 nm | compound M6: compound N44: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E2 | $HAT(CN)_6$: HT (mass ratio 3:97)/ 10 nm | HT/ 80 nm | compound M6: compound N4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E3 | $HAT(CN)_6$: HT (mass ratio 3:97)/ 10 nm | HT/ 80 nm | compound M160: compound N14: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E4 | $HAT(CN)_6$: HT (mass ratio 3:97)/ 10 nm | HT/ 80 nm | compound M46: compound N4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E5 | $HAT(CN)_6$: HT (mass ratio 3:97)/ 10 nm | HT/ 80 nm | compound M41: compound N33: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E6 | $HAT(CN)_6$: HT (mass ratio 3:97)/ 10 nm | HT/ 80 nm | compound M23: compound N56: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E7 | $HAT(CN)_6$: HT (mass ratio 3:97)/ 10 nm | HT/ 80 nm | compound M97: compound N44: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E8 | $HAT(CN)_6$: HT (mass ratio 3:97)/ 10 nm | HT/ 80 nm | compound M117: compound N4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E9 | $HAT(CN)_6$: HT (mass ratio 3:97)/ 10 nm | HT/ 80 nm | compound M93: compound N22: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |

TABLE 5-continued

| No. | HIL mat./ thk. | HTL mat./ thk. | EML mat./ thk. | ETL mat./ thk. | EIL mat./ thk. | Cathode mat./ thk. |
|---|---|---|---|---|---|---|
| E10 | $HAT(CN)_6$: HT (mass ratio 3:97)/ 10 nm | HT/ 80 nm | compound M31: compound N4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| E11 | $HAT(CN)_6$: HT (mass ratio 3:97)/ 10 nm | HT/ 80 nm | compound M46: compound N4: $(piq)_2Ir(acac)$ (mass ratio 13:6:1)/ 30 nm | BPhen: LiQ (mass ratio 1:1)/ 30 nm | LiQ/ 1 nm | Al/ 80 nm |
| CE1 | $HAT(CN)_6$: HT (mass ratio 3:97)/ 10 nm | HT/ 80 nm | CBP: compound N4: $(piq)_2Ir(acac)$ (mass ratio 47.5:47.5:5)/ 30 nm | BPhen: LiQ (mass ratio 1:1)/ 30 nm | LiQ/ 1 nm | Al/ 80 nm |
| CE2 | $HAT(CN)_6$: HT (mass ratio 3:97)/ 10 nm | HT/ 80 nm | REF-1: compound N4: $(piq)_2Ir(acac)$ (mass ratio 47.5:47.5:5)/ 30 nm | BPhen: LiQ (mass ratio 1:1) 30 nm | LiQ/ 1 nm | Al/ 80 nm |

Characteristic Tests of Elements:

Instruments: the characteristics such as current, voltage, luminance, emission spectrum and the like of the elements of the above Element Examples 1 to 11 and Comparative Element Examples 1 to 2 were synchronously tested by PR 650 SpectraScan Colorimeter and Keithley K 2400 SourceMeter;

Conditions for testing electrooptical characteristics: a current density of 10 milliamperes/square centimeter ($mA/cm^2$) under room temperature;

Service life test: tested with a current density of 20 $mA/cm^2$ under room temperature, and the time period recorded when the luminance of the tested element was reduced to 98% of the original luminance (in hour).

The test results of the elements are shown in Table 6.

TABLE 6

| No. | Driving voltage (V) | Current efficiency (Cd/A) | Service life (h) |
|---|---|---|---|
| E1 | 3.89 | 23 | 235 |
| E2 | 3.87 | 25 | 250 |
| E3 | 3.88 | 24 | 240 |
| E4 | 3.93 | 23 | 230 |
| E5 | 3.87 | 20 | 218 |
| E6 | 3.96 | 22 | 245 |
| E7 | 3.95 | 21 | 220 |
| E8 | 3.92 | 24 | 225 |
| E9 | 3.90 | 24 | 240 |
| E10 | 3.88 | 23 | 245 |
| E11 | 3.90 | 24 | 235 |
| CE1 | 4.34 | 15 | 97 |
| CE2 | 4.13 | 17 | 125 |

From Table 6, it is clear that the organic material composition of the present invention obviously increases the current efficiency. When the organic material composition is used as the material of an organic functional layer, the element has a lower driving voltage (3.96 voltages (V) or lower), a higher current efficiency (20 Candelas/Ampere (Cd/A) or more) and a longer service life (218 h or more).

The applicant claims herein that even though the organic material composition of the present invention and the applications thereof are demonstrated by the above examples, the scope of the present invention is not limited by these examples. That is to say, it does not mean that the present invention has to be carried out based on the above examples. Those skilled in the art should understand that any improvement of the present invention, equivalent replacement of materials, addition of auxiliary components, selection of specific means and the like are all within the scope of protection and disclosure of the present invention.

What is claimed is:

1. An organic material composition, wherein the organic material composition comprises at least one compound having a structure represented by Formula (1) and at least one compound having a structure represented by Formula (2):

Formula (1)

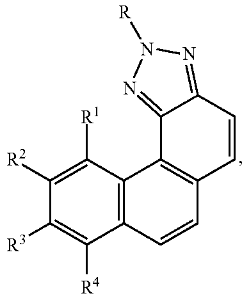

wherein, R is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$R^1$ is $-L^1Ar^1$; $R^2$ is $-L^2Ar^2$; $R^3$ is $-L^3Ar^3$; $R^4$ is $-L^4Ar^4$;

$L^1$ to $L^4$ are each independently selected from a bond, a substituted or unsubstituted C6-C30 arylene group, and a substituted or unsubstituted C3-C30 heteroarylene group;

$Ar^1$ to $Ar^4$ are each independently selected from hydrogen, deuterium, halogen, a cyano group, a substituted or unsubstituted C6-C60 aryl group, and a substituted or unsubstituted C3-C60 heteroaryl group;

at least one of $Ar^1$ to $Ar^4$ is a group represented by Formula (a):

Formula (a)

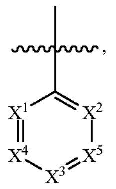

wherein the wavy line represents the connection position of the group;

$X^1$ is selected from N and $CR^{X1}$, $X^2$ is selected from N and $CR^{X2}$; $X^3$ is selected from N and $CR^{X3}$; $X^4$ is selected from N and $CR^{X4}$, $X^5$ is selected from N and $CR^{X5}$;

$R^{X1}$ to $R^{X5}$ are each independently selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group; $R^{X1}$ to $R^{X5}$ are present individually without forming a ring, or any adjacent two of $R^{X1}$ to $R^{X5}$ joined to form a ring, and the ring is a benzene ring;

Formula (2)

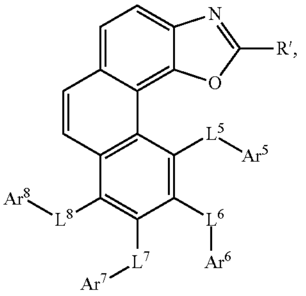

wherein, R' is selected from hydrogen, deuterium, halogen, a cyano group, a substituted or unsubstituted C1-C30 alkyl group, a substituted or unsubstituted C3-C30 cycloalkyl group, a substituted or unsubstituted C6-C30 aryl group, and a substituted or unsubstituted C3-C30 heteroaryl group;

$L^5$ to $L^8$ are each independently selected from a bond, a substituted or unsubstituted C6-C30 arylene group, and a substituted or unsubstituted C3-C30 heteroarylene group;

$Ar^5$ to $Ar^8$ are each independently selected from hydrogen, deuterium, halogen, a cyano group, a substituted or unsubstituted C6-C60 aryl group, and a substituted or unsubstituted C3-C60 heteroaryl group.

2. The organic material composition according to claim 1, wherein $R^{X1}$ to $R^{X5}$ are each independently selected from hydrogen, deuterium, halogen, and a group selected from a phenyl group, a biphenylyl group, a terphenylyl group, a naphthyl group, a phenanthryl group, an anthryl group, a phenylnaphthyl group, a naphthylphenyl group, a pyridyl group, a bipyridyl group, a dibenzofuryl group, a dibenzothiophenyl group, a carbazolyl group, a carbazolylphenyl group, a phenylcarbazolyl group, a dimethylfluorenyl group, a diphenylfluorenyl group, a spiro-bifluorenyl group, a dibenzofurylphenyl group, a dibenzothiophenylphenyl group, a dimethylfluorenylphenyl group, a benzocarbazolyl group, a benzonaphthofuryl group, and a benzonaphthothiophenyl group, each of which is substituted or unsubstituted; and in $X^1$ to $X^5$, $X^1$ is N; $X^2$ is N; $X^3$ is $CR^{X3}$; $X^4$ is $CR^{X4}$; and $X^5$ is $CR^{X5}$; or $X^1$ is N; $X^3$ is N; $X^2$ is $CR^{X2}$; $X^4$ is $CR^{X4}$; and $X^5$ is $CR^{X5}$; or $X^1$ is N; $X^2$ is N; $X^3$ is N; $X^4$ is $CR^{X4}$; and $X^5$ is $CR^{X5}$; and $L^1$ to $L^4$ are each independently selected from a bond, a substituted or unsubstituted phenylene group, a substituted or unsubstituted naphthylene group, and a substituted or unsubstituted biphenylene group.

3. The organic material composition according to claim 1, wherein the compound having a structure represented by Formula (1) is any one of the following compounds M1 to M206:

M1

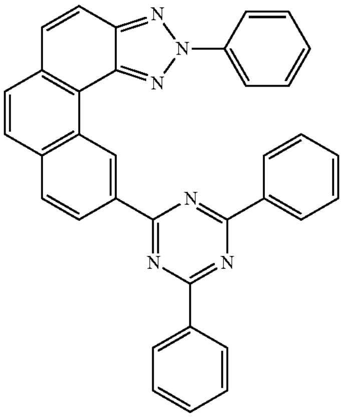

M2

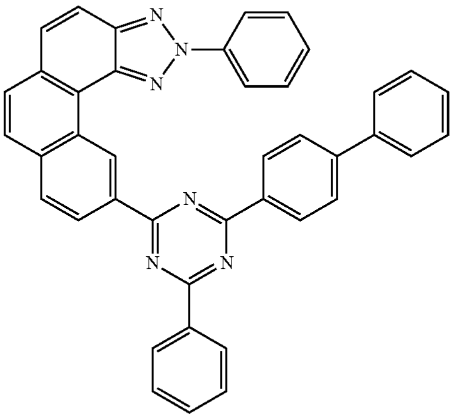

M3

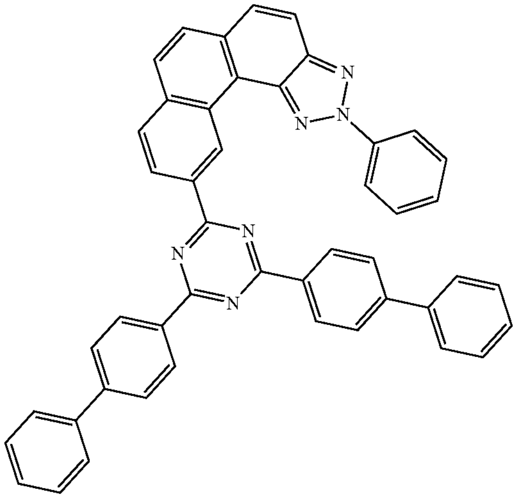

M4
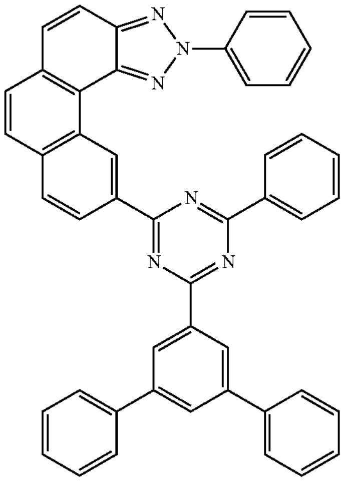
M5
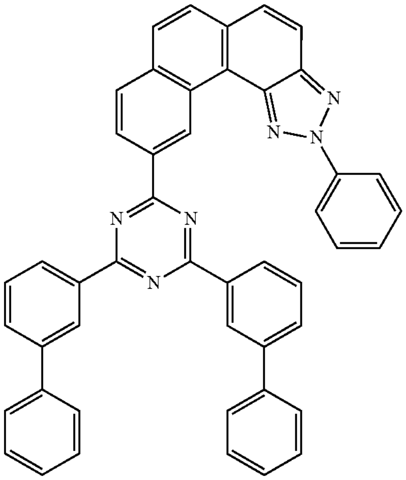
M6
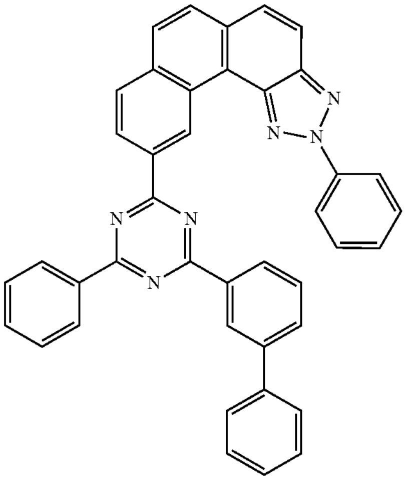
M7
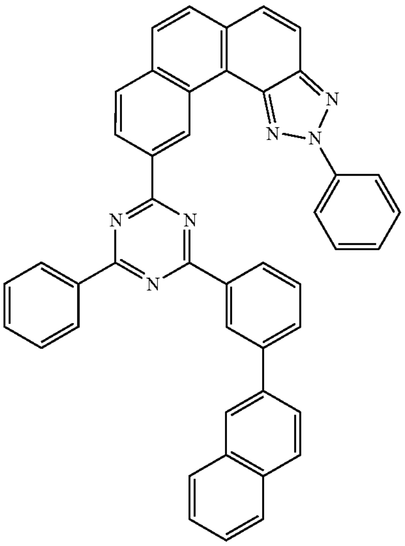
M8
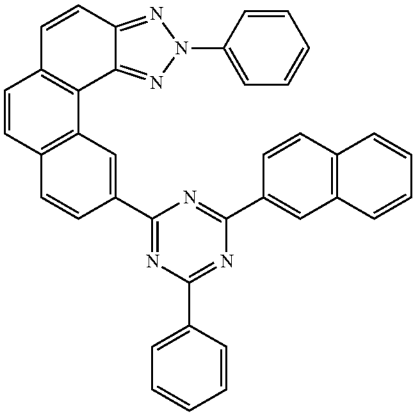
M9
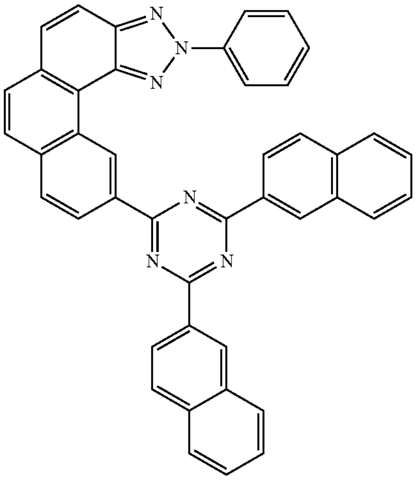

M10
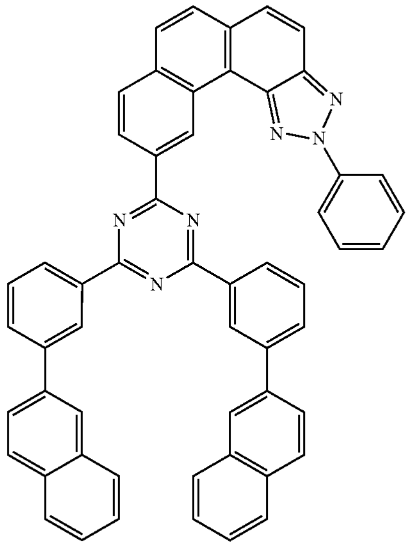
M11
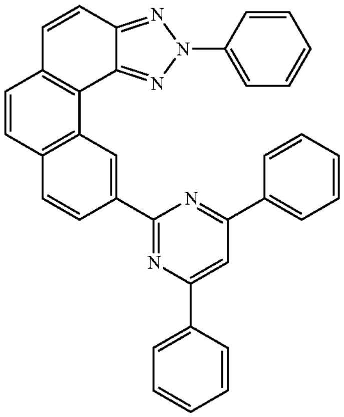
M12
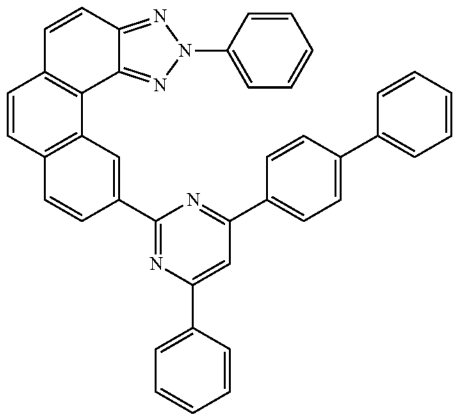
M13
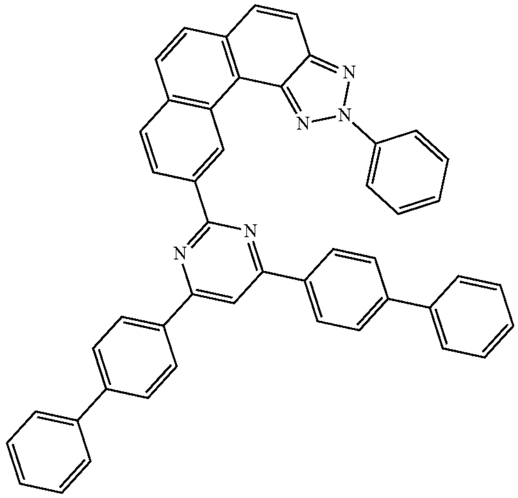
M14
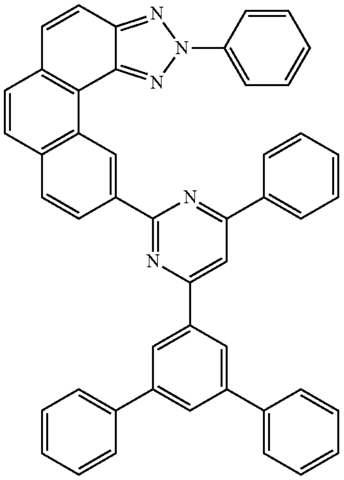
M15
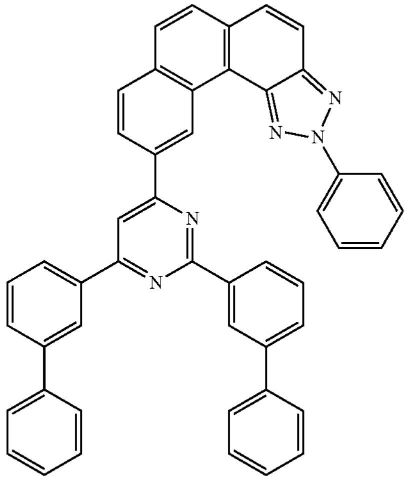

M16
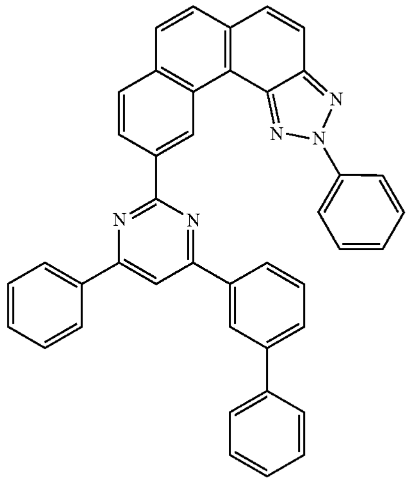
M17
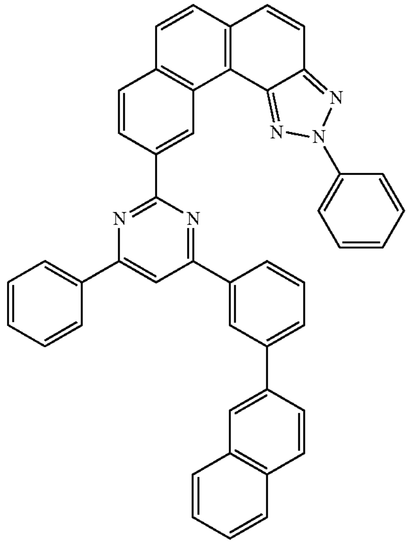
M18
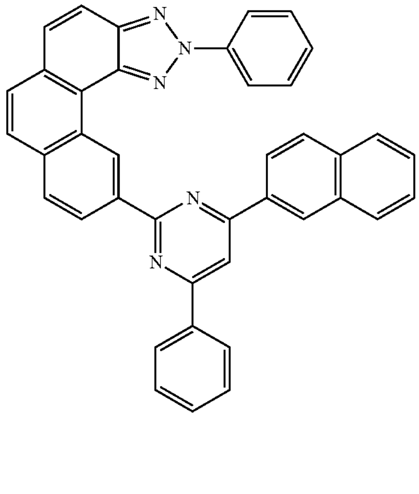
M19
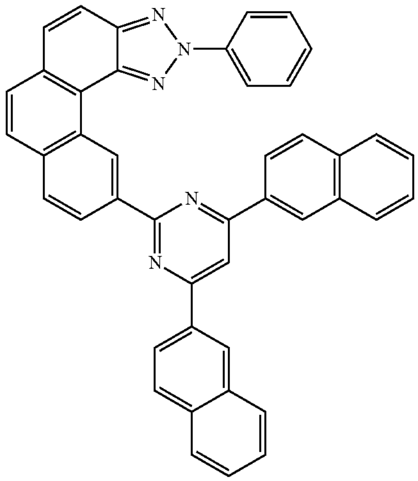
M20
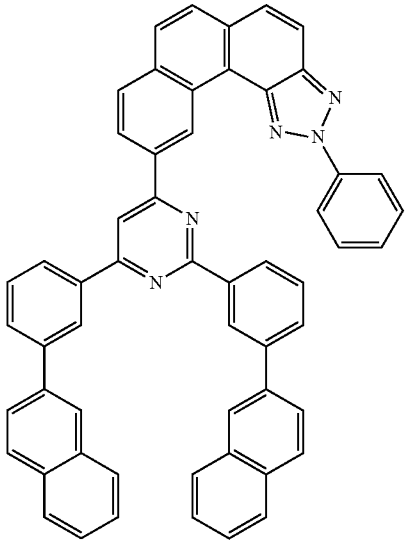
M21
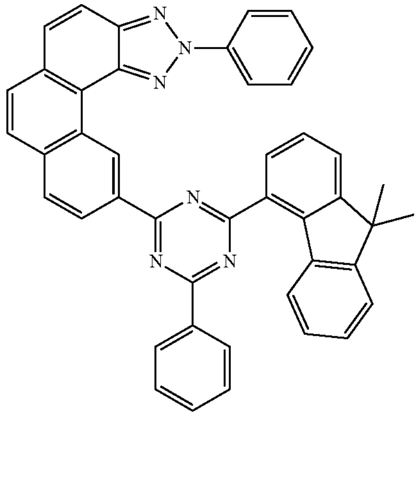

M22
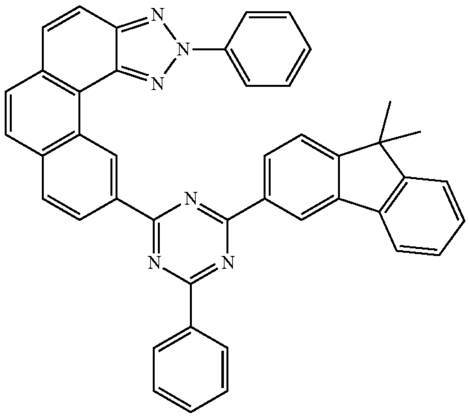
M23
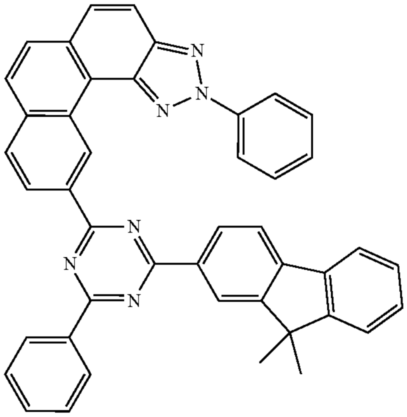
M24
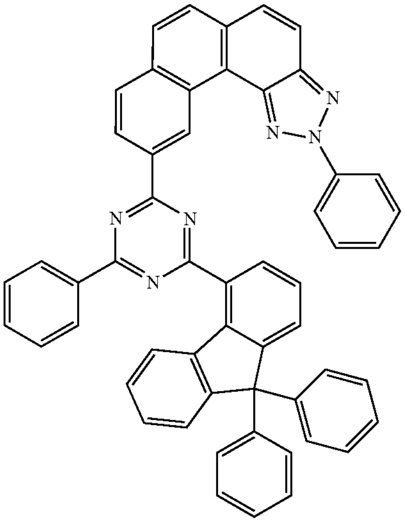
M25
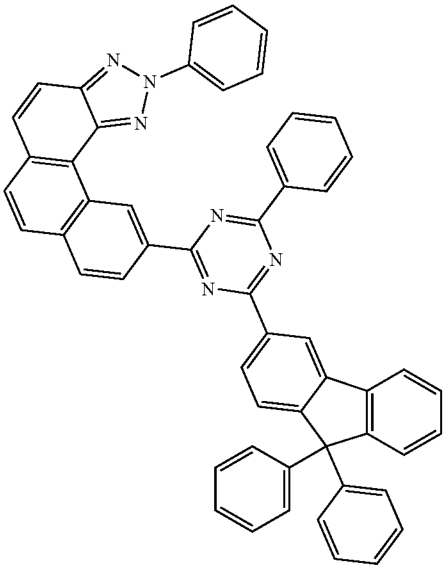
M26
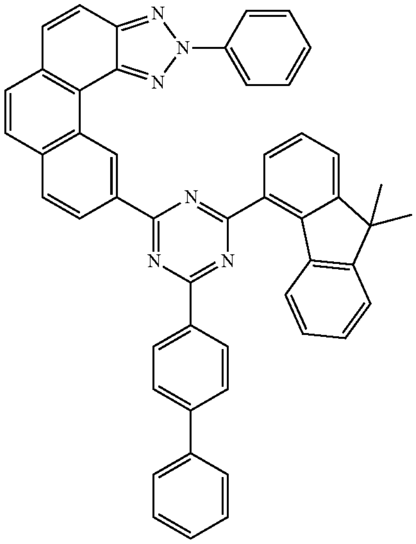
M27
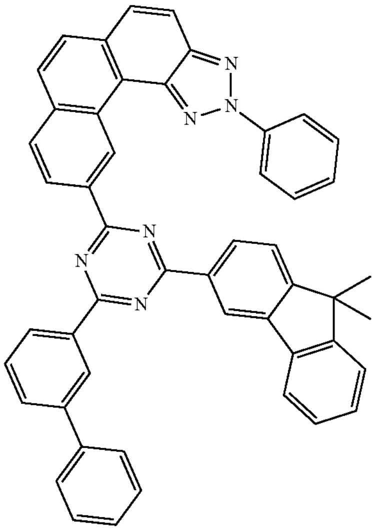

-continued
M28
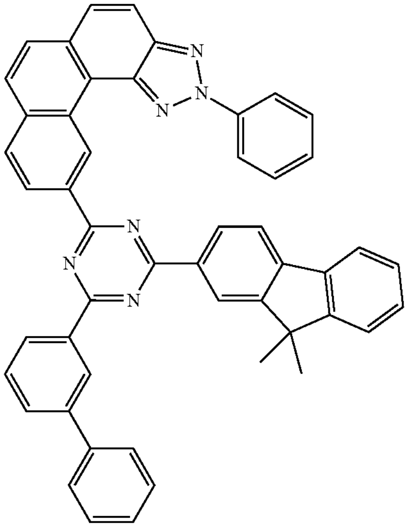
M29
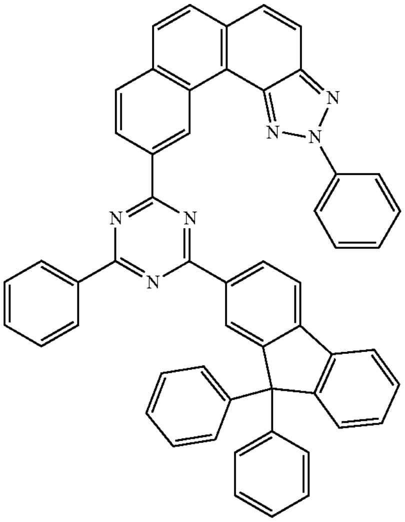
M30
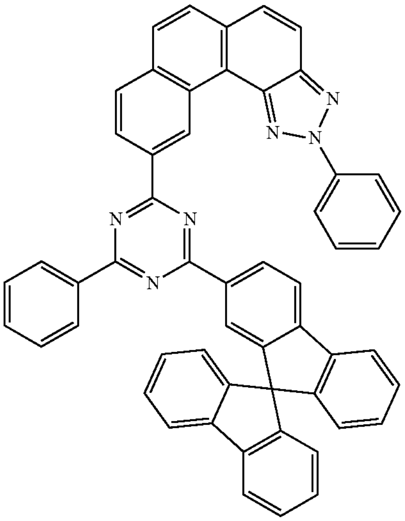
-continued
M31
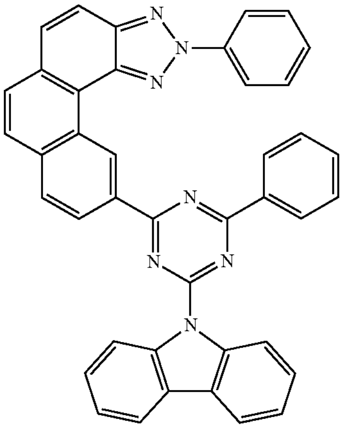
M32
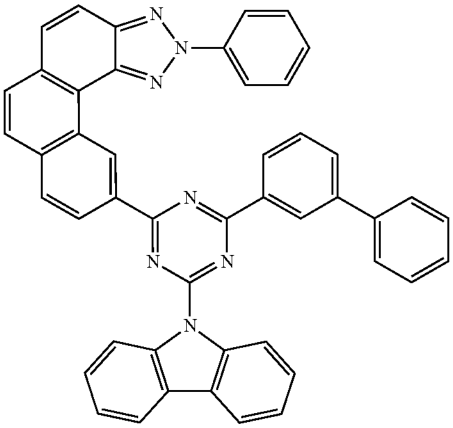
M33
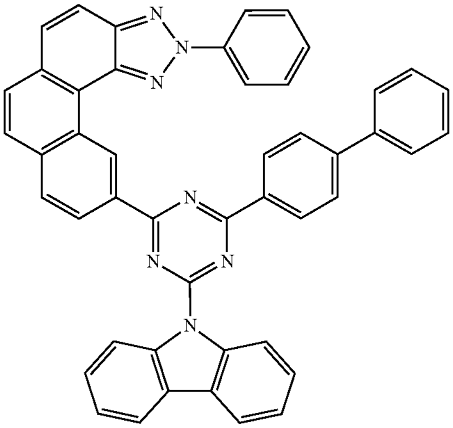

-continued
M34
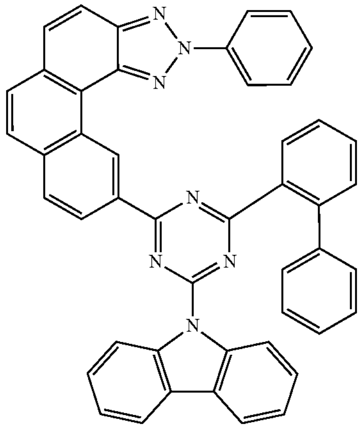
M35
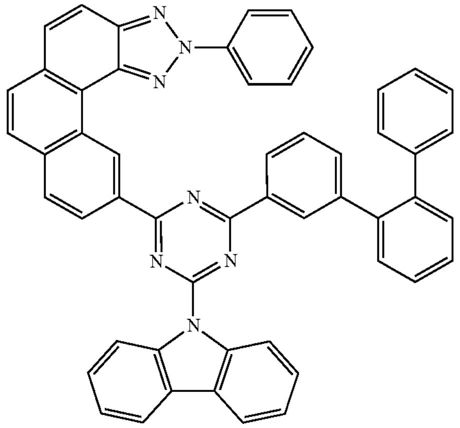
M36
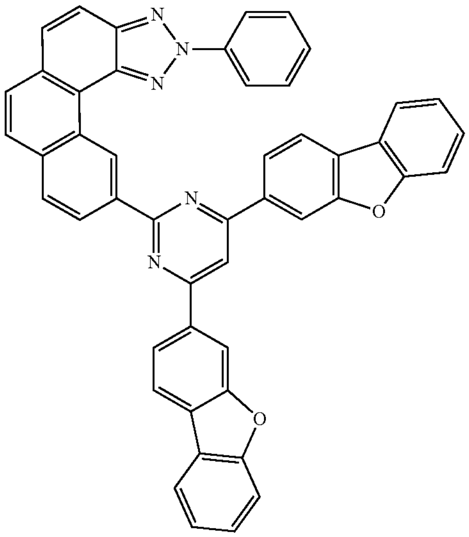
-continued
M37
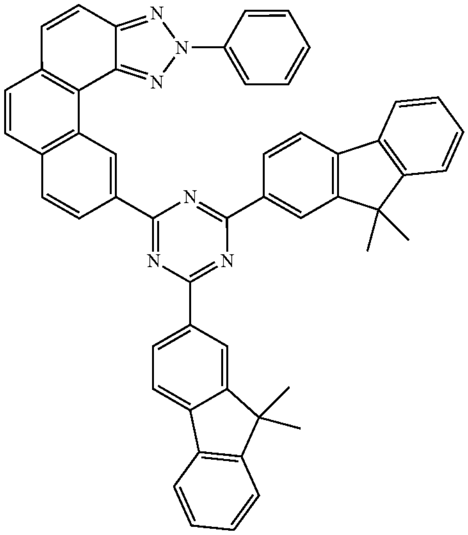
M38
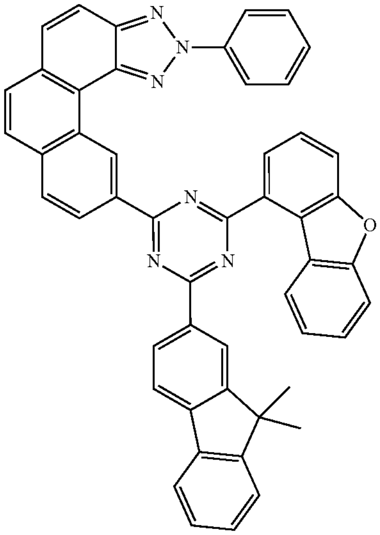
M39
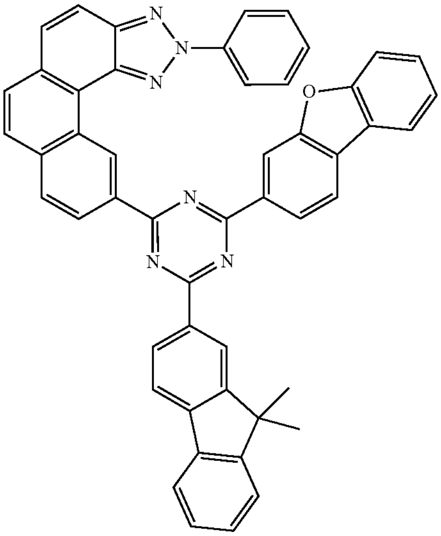

-continued
M40
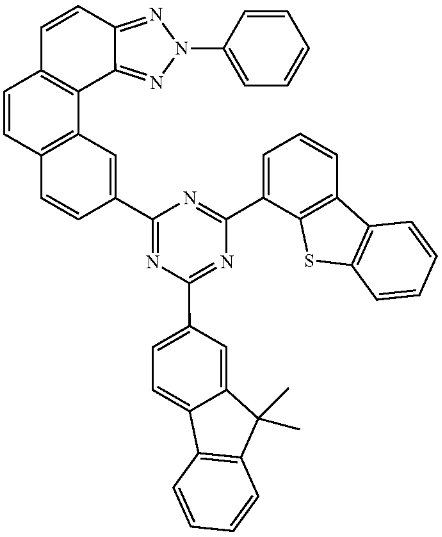
M41
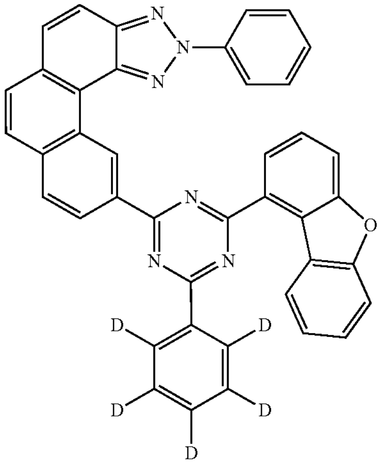
M42
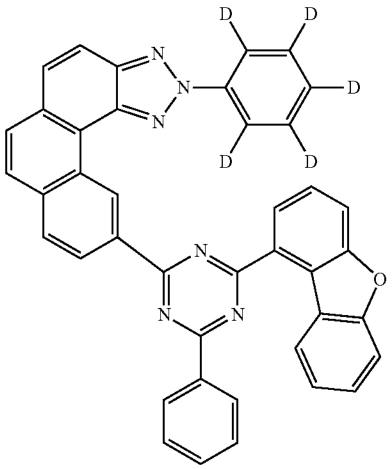
-continued
M43
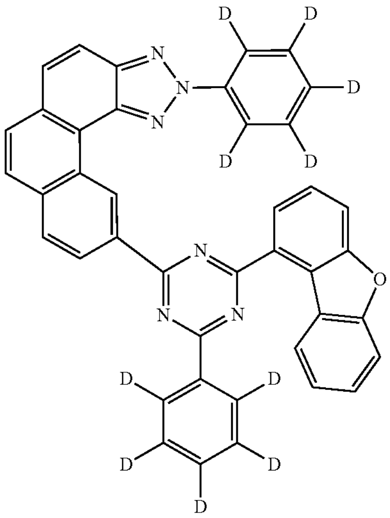
M44
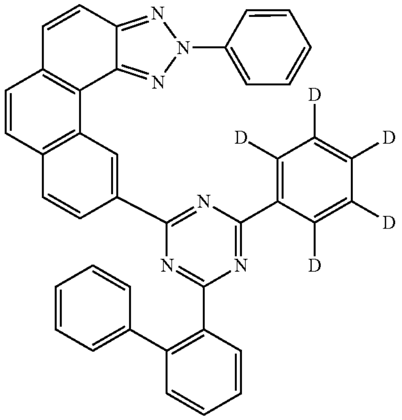
M45
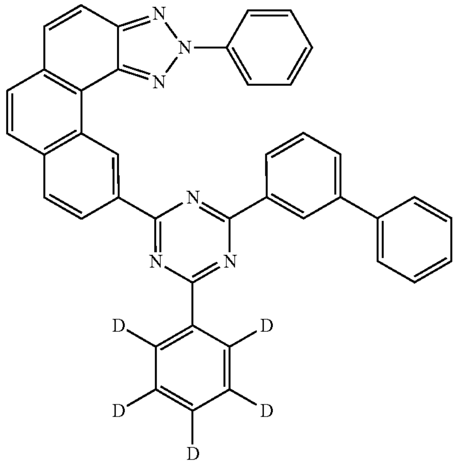

M46
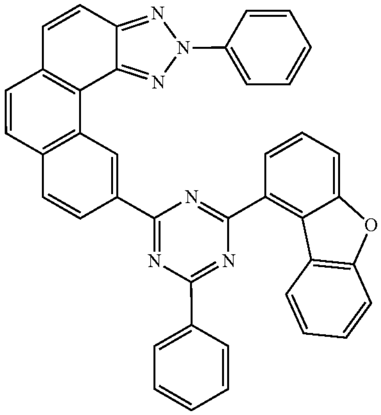
M47
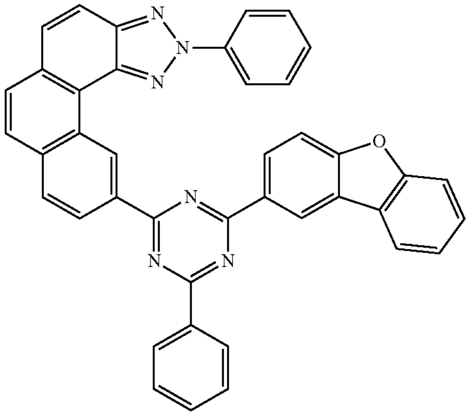
M48
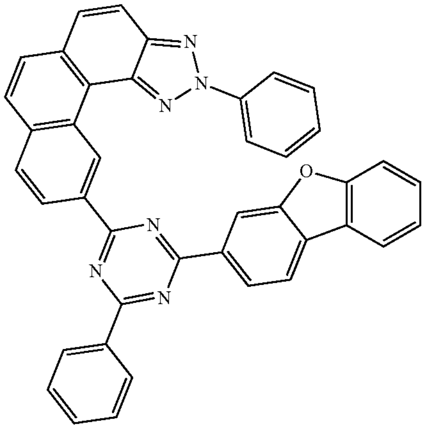
M49
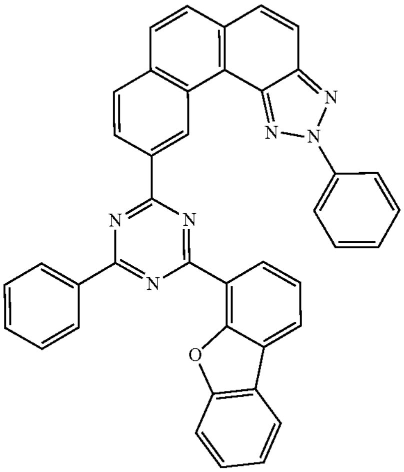
M50
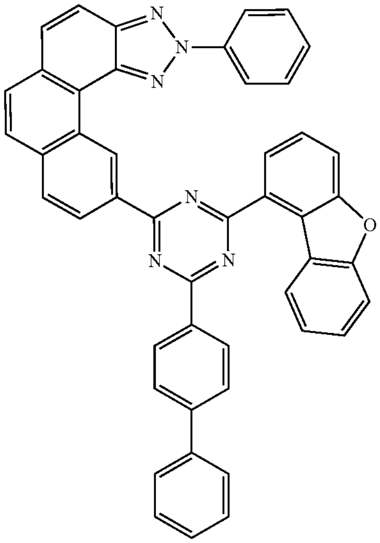
M51
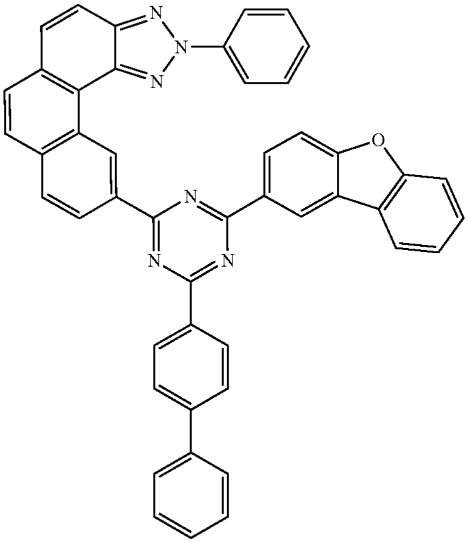

-continued
M52
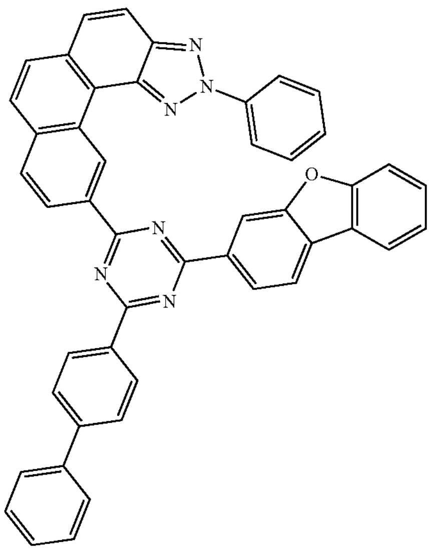
M53
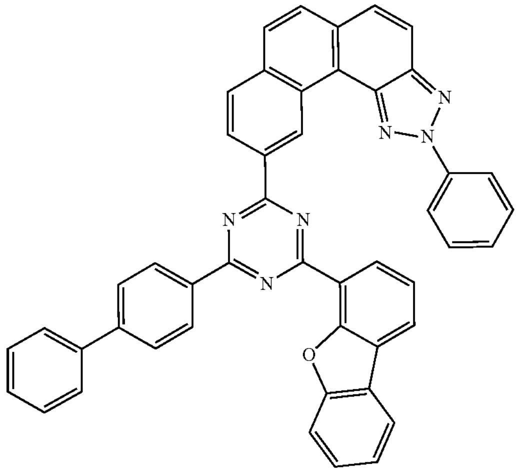
M54
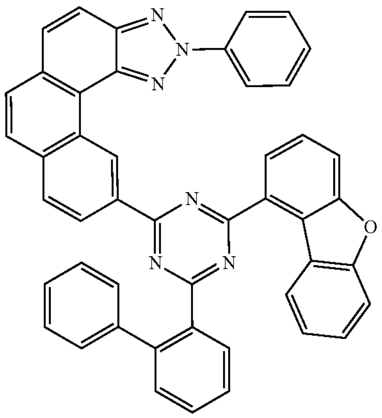
-continued
M55
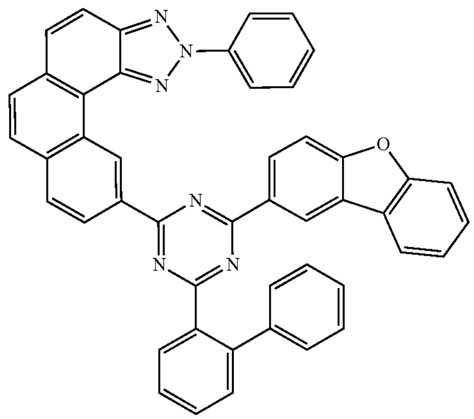
M56
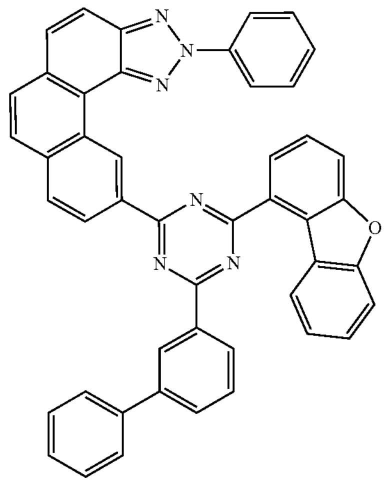
M57
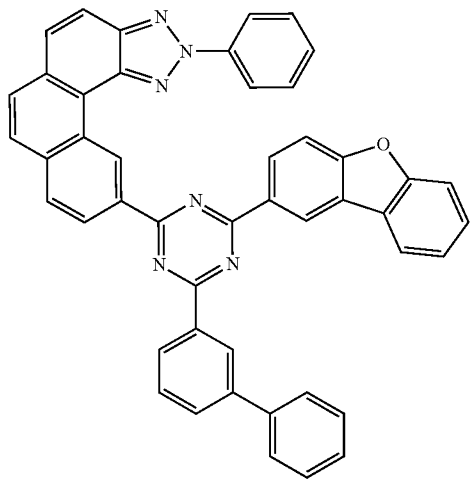

-continued
M58
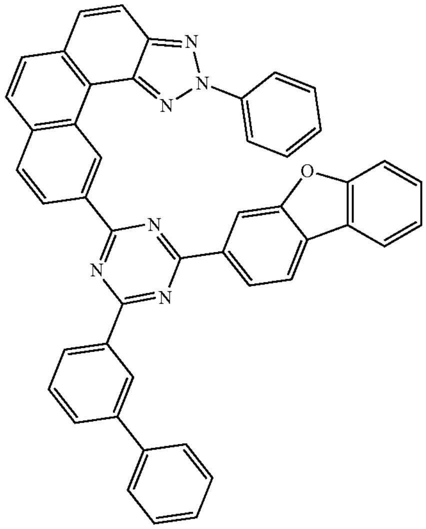
M59
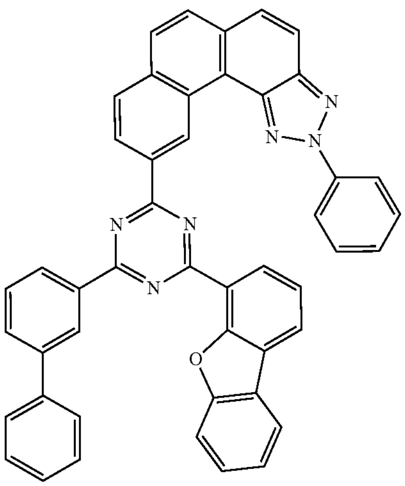
M60
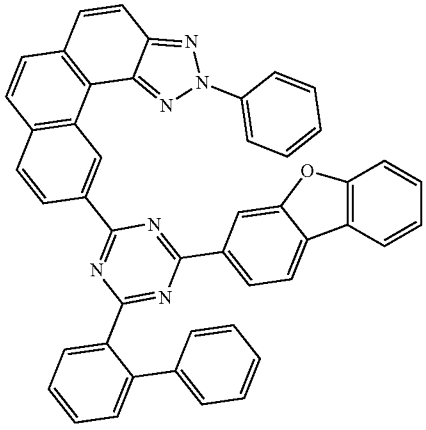
-continued
M61
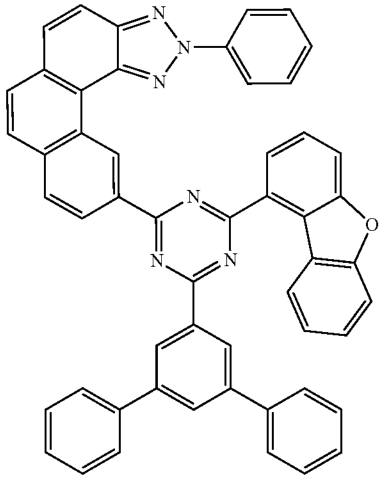
M62
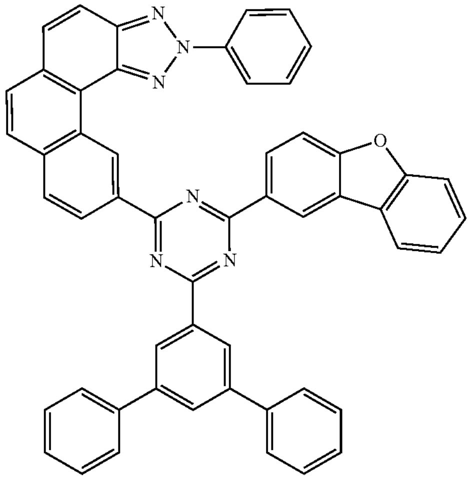
M63
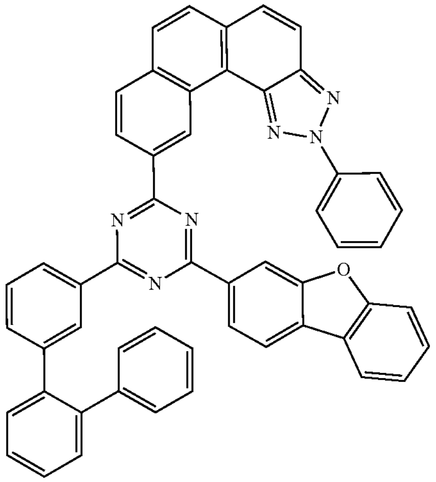

-continued
M64
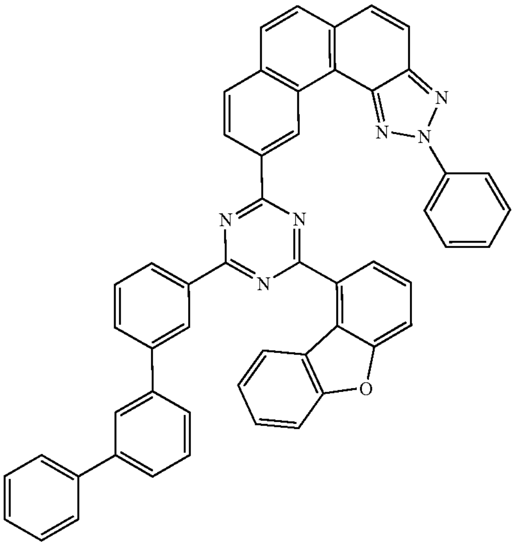
M65
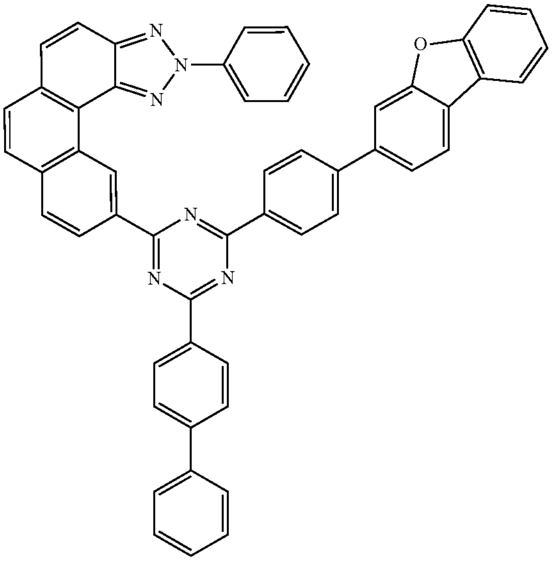
-continued
M66
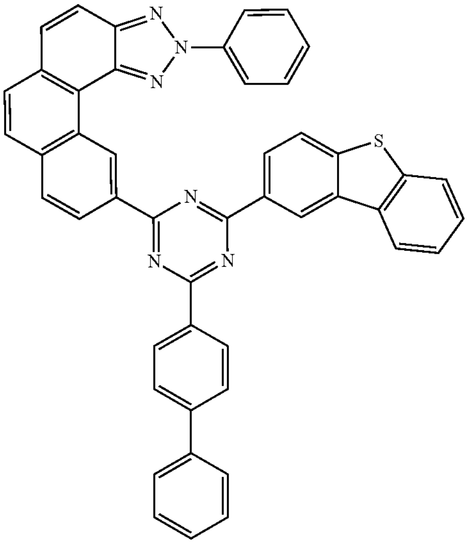
M67
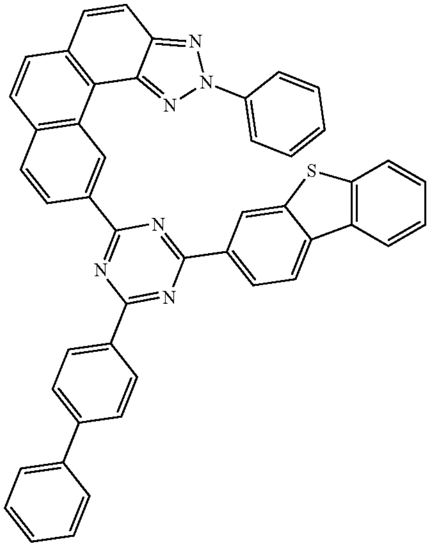
M68
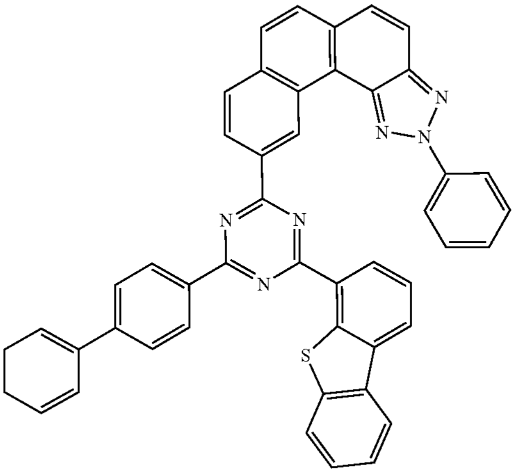

-continued
M69
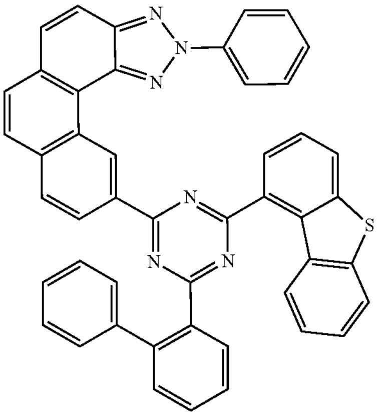
M70
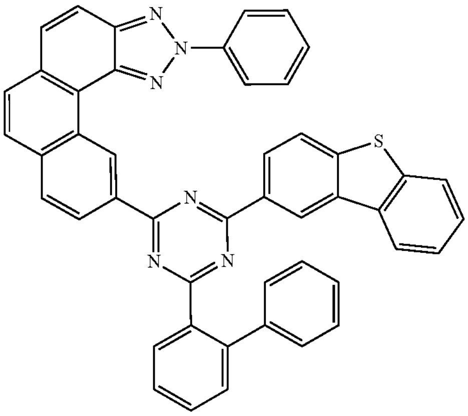
M71
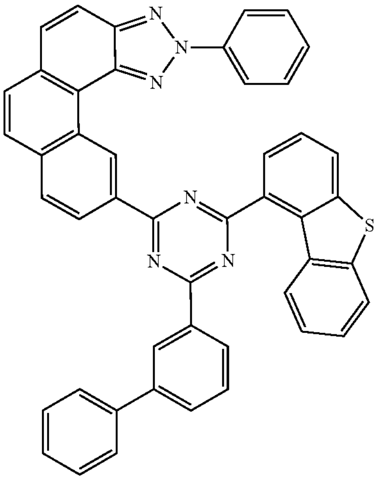
-continued
M72
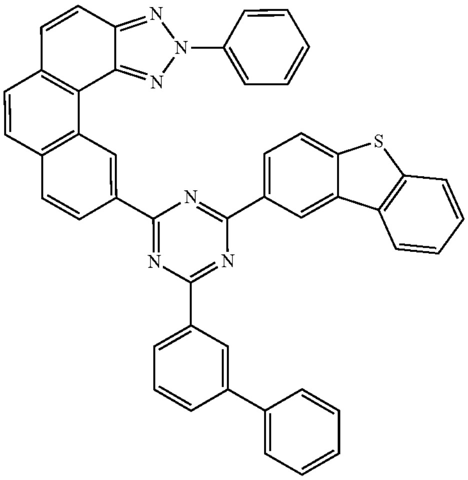
M73
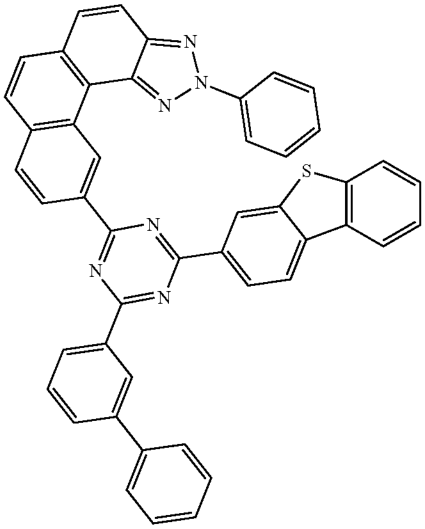
M74
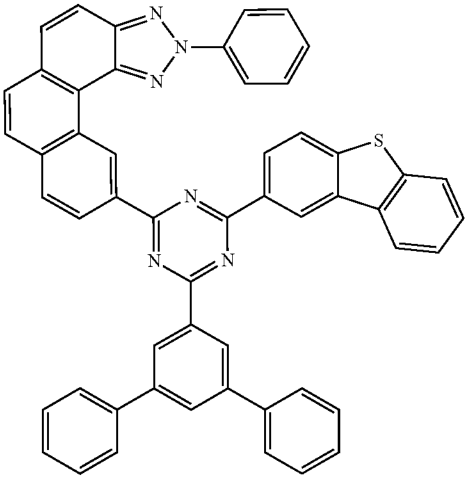

-continued
M75
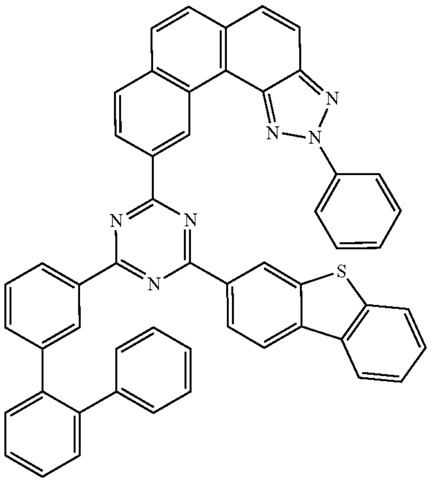
M76
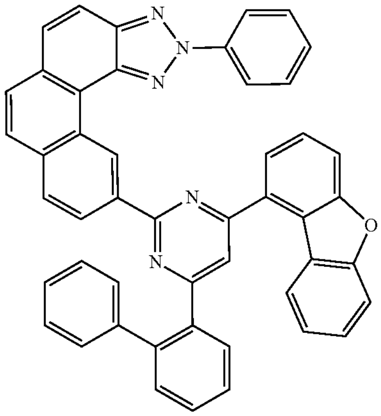
M77
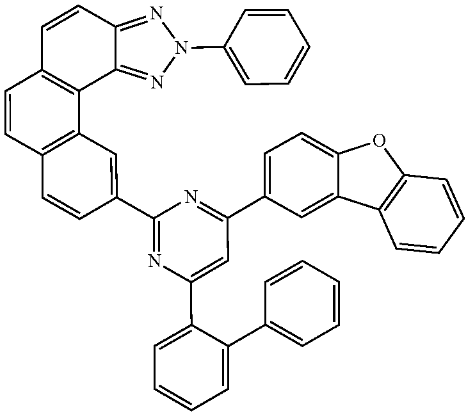
-continued
M78
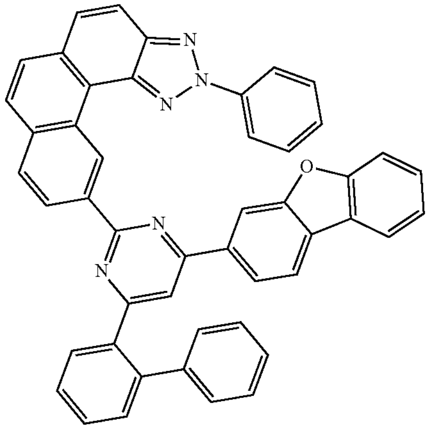
M79
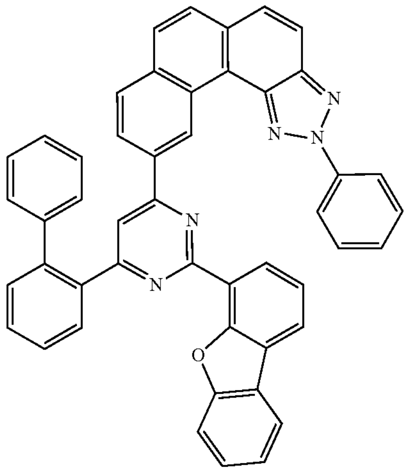
M80
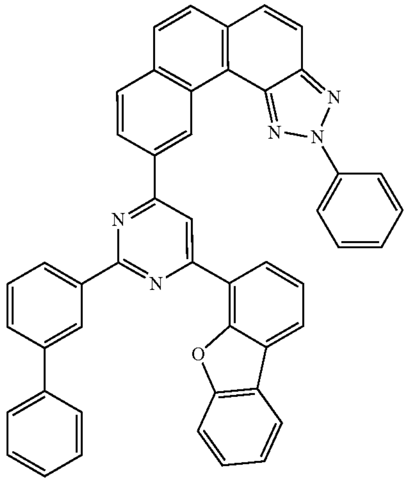

-continued
M81
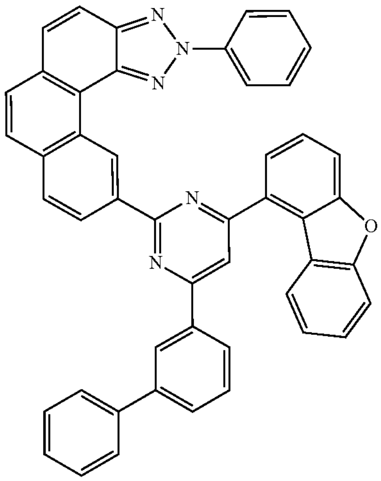
M82
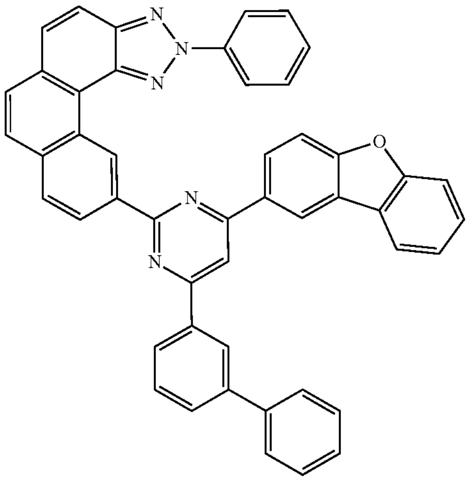
M83
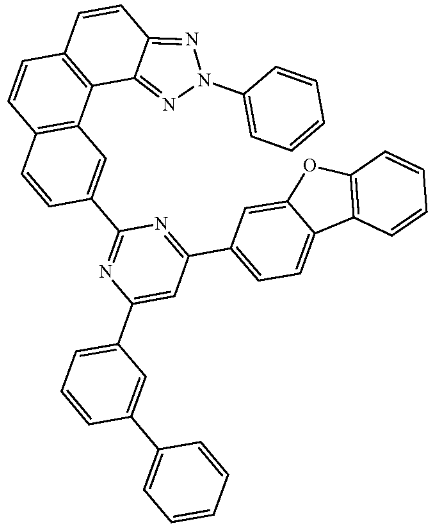
-continued
M84
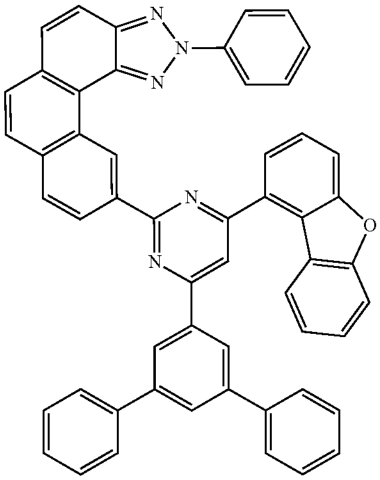
M85
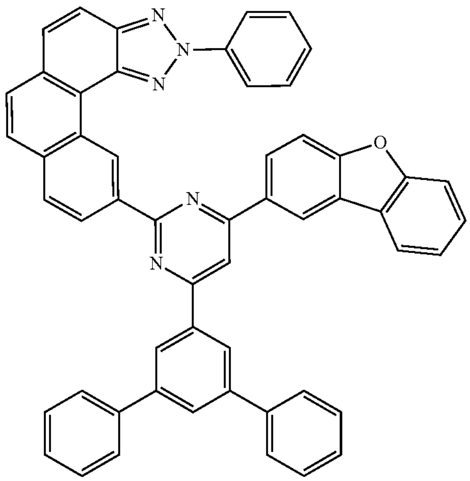
M86
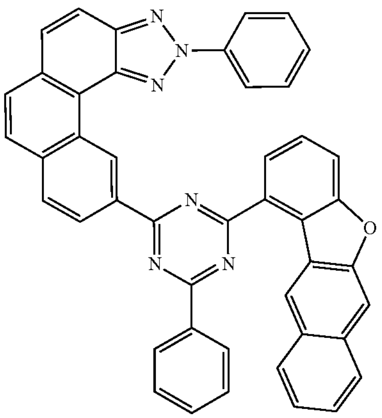

-continued
M87
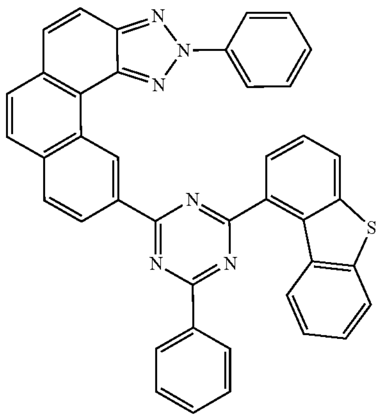
M88
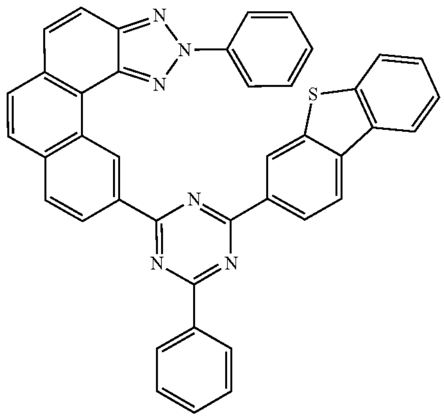
M89
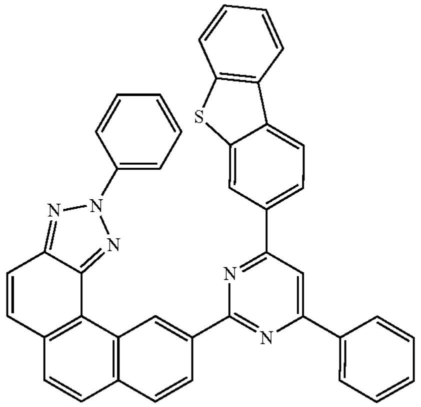
-continued
M90
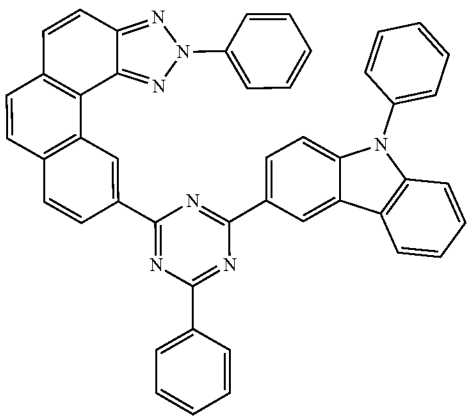
M91
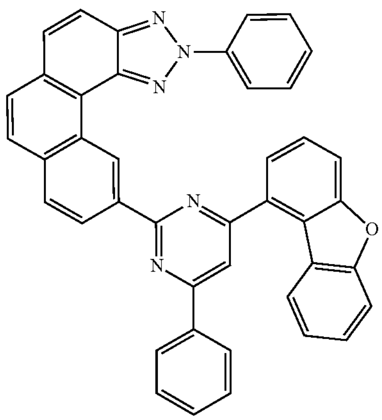
M92
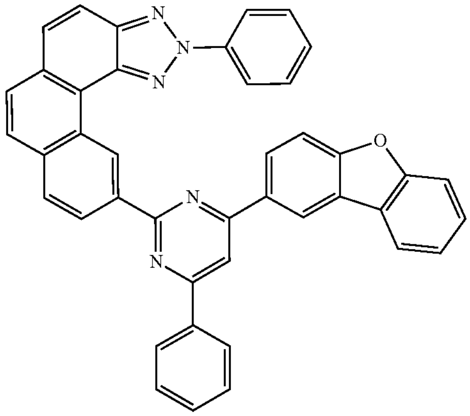

-continued
M93
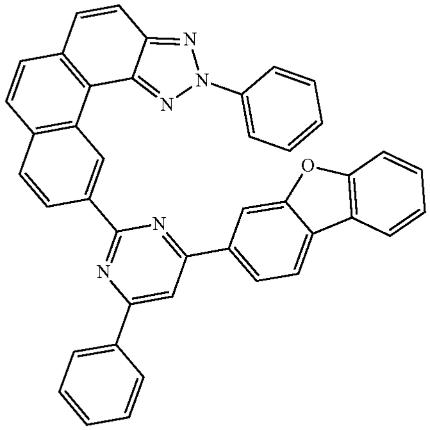
M94
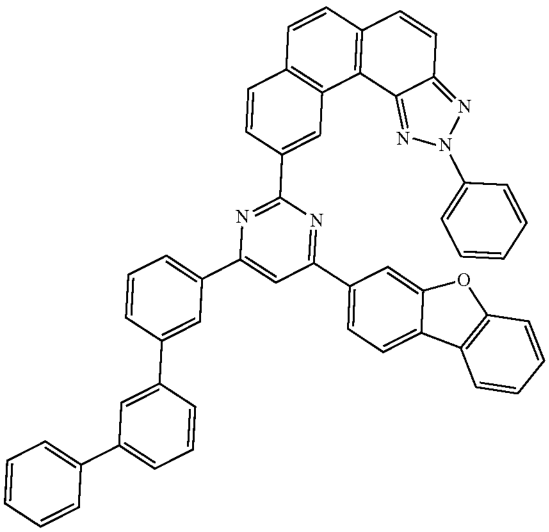
M95
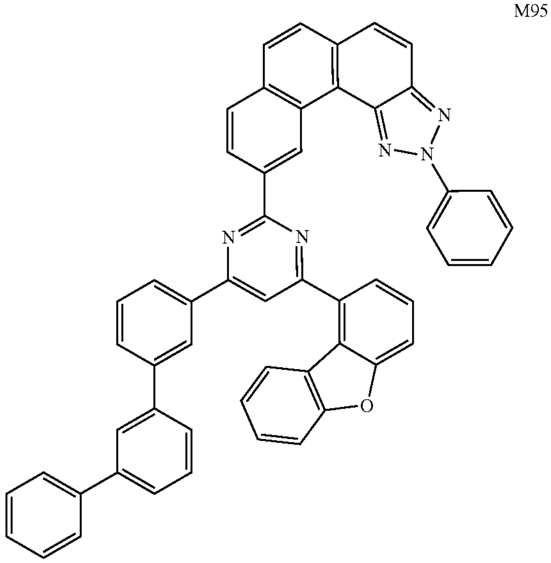
-continued
M96
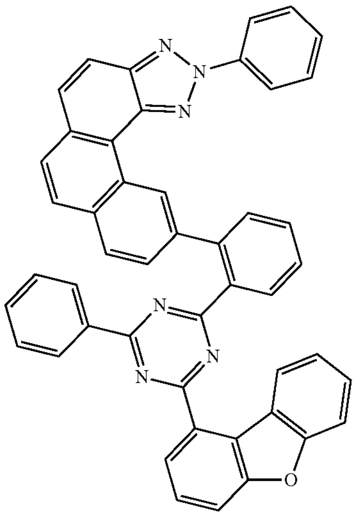
M97
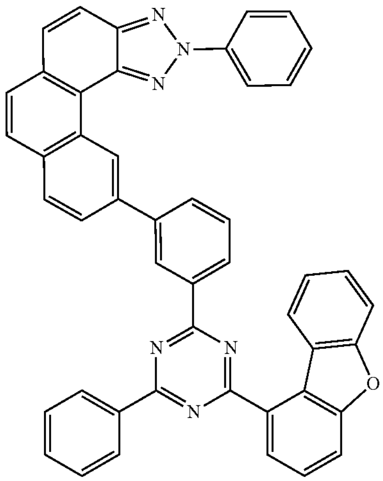
M98
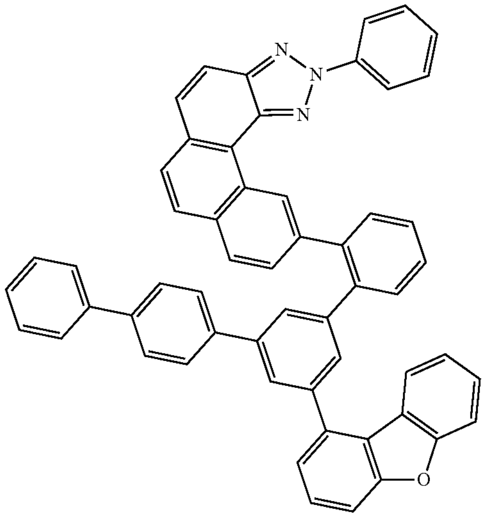

-continued
M99
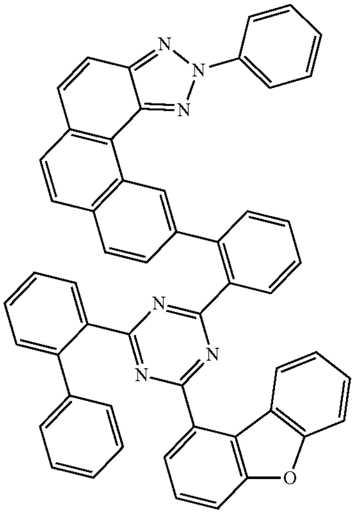
M100
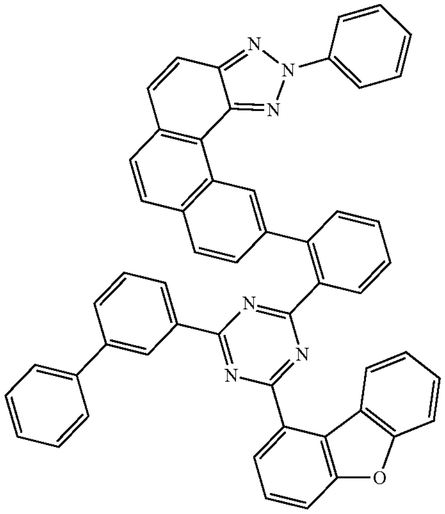
M101
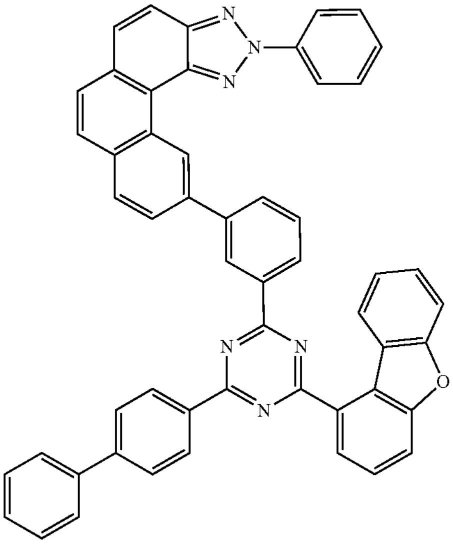
-continued
M102
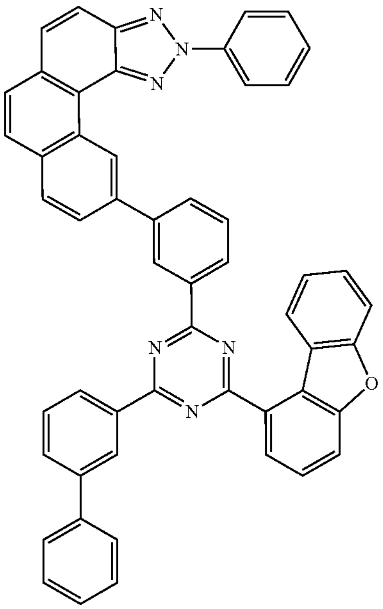
M103
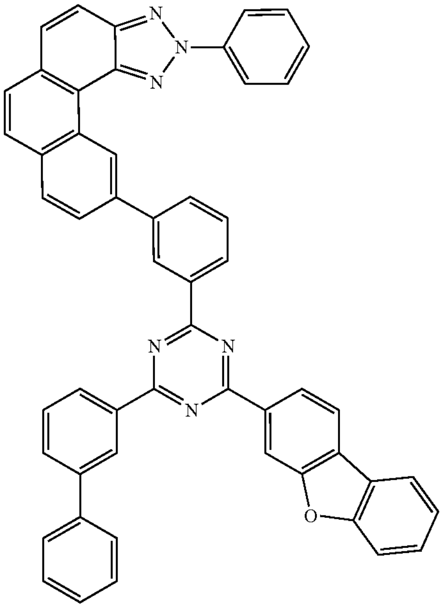

-continued
M104
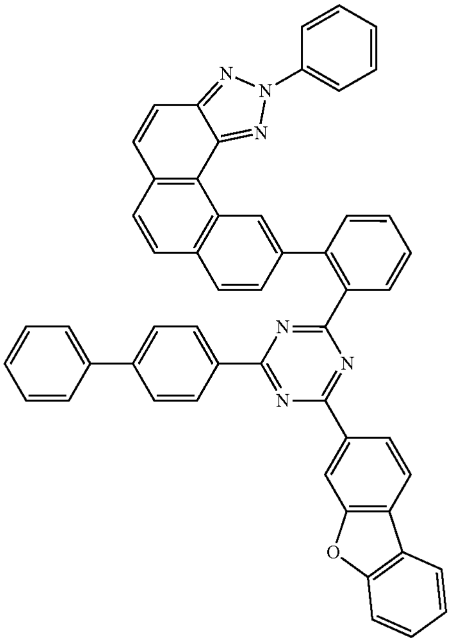
M105
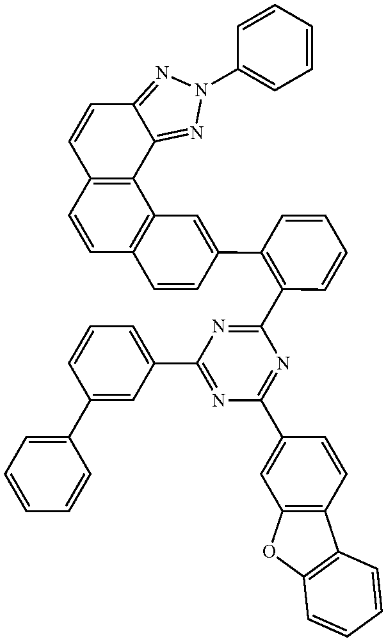
-continued
M106
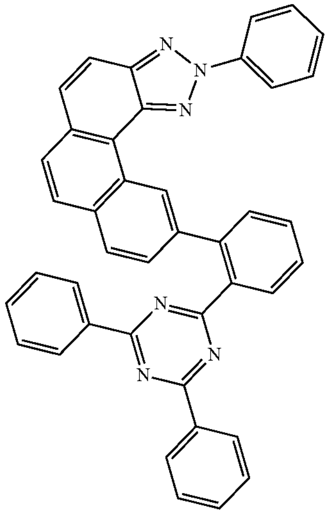
M107
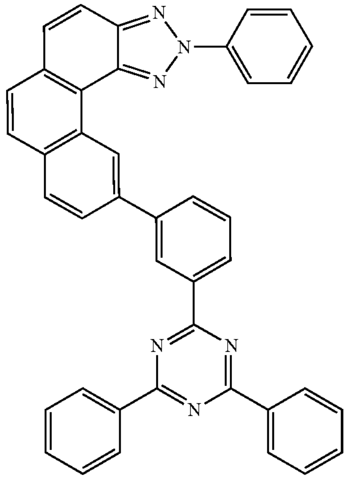
M108
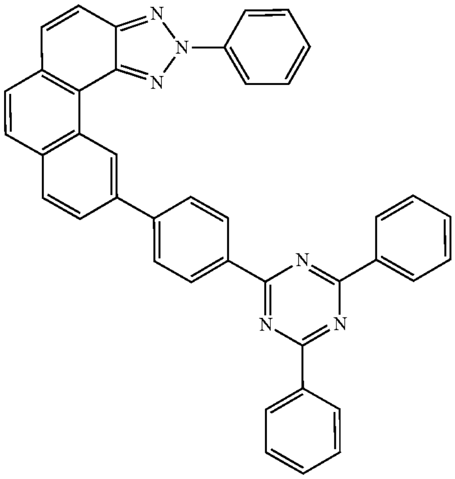

-continued
M109
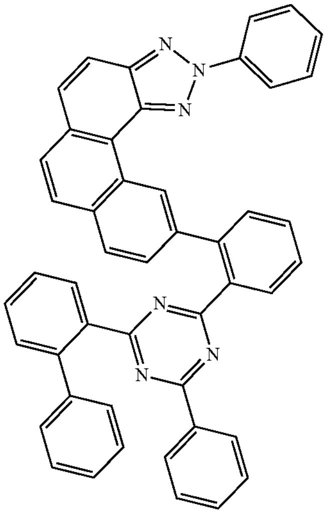
M110
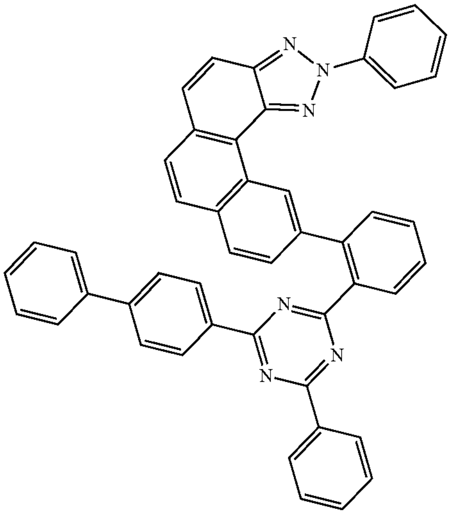
M111
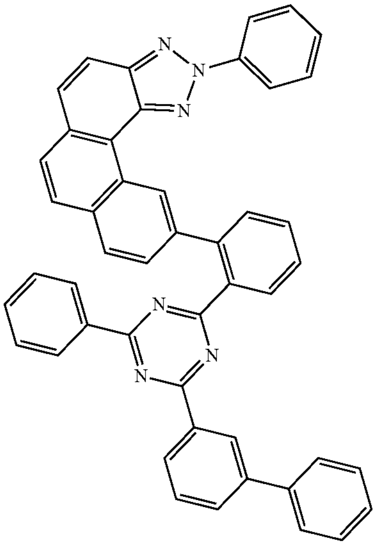
-continued
M112
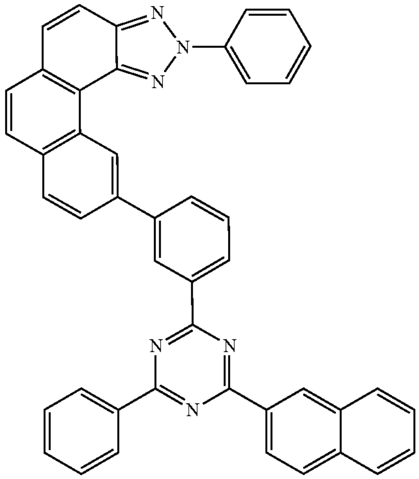
M113
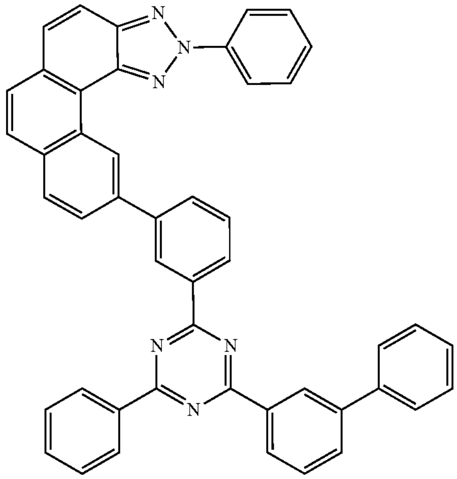
M114
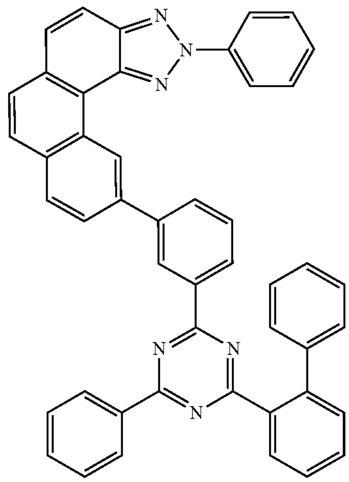

-continued
M115
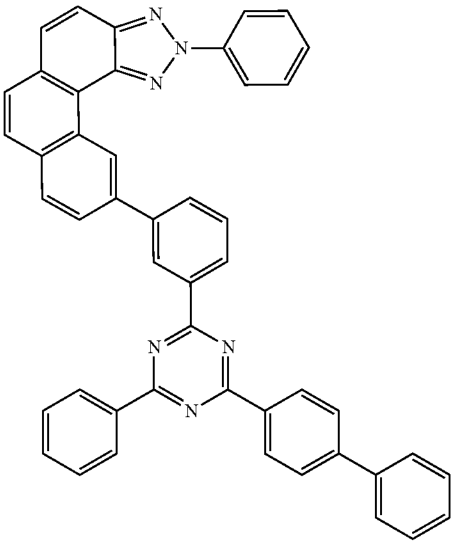
M116
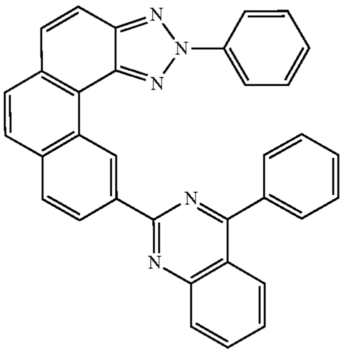
M117
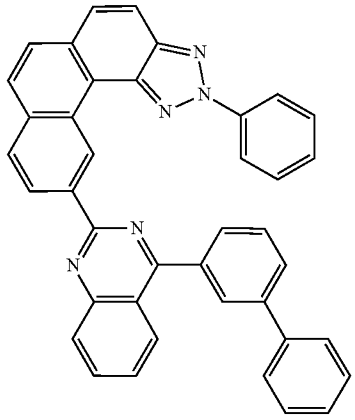
-continued
M118
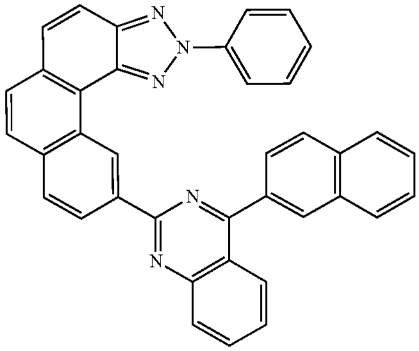
M119
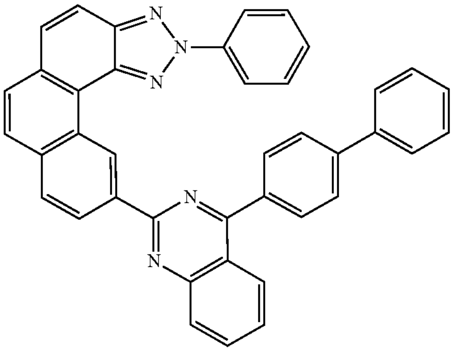
M120
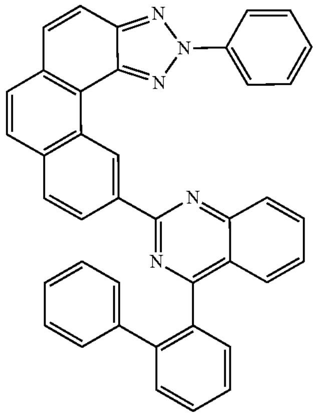
M121
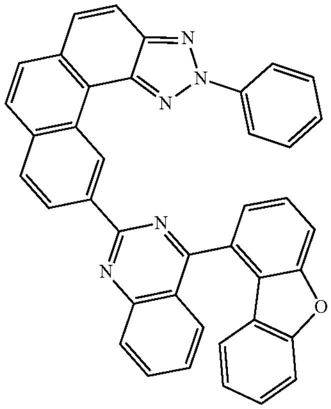

-continued
M122
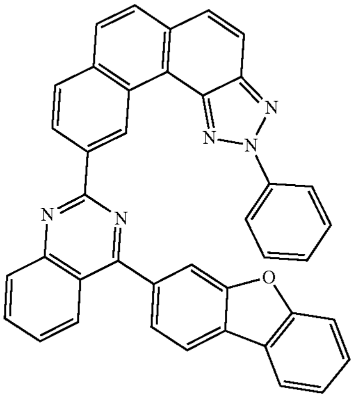
M123
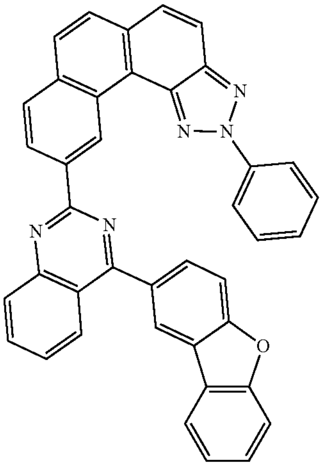
M124
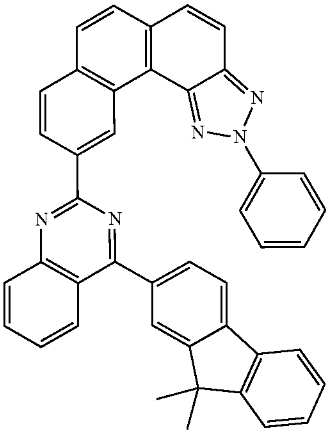
-continued
M125
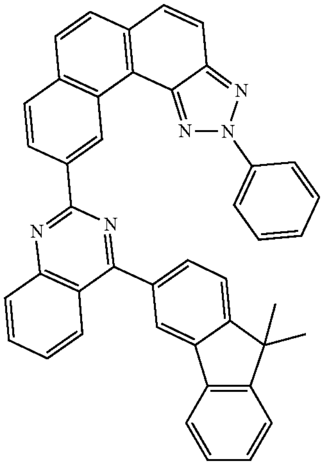
M126
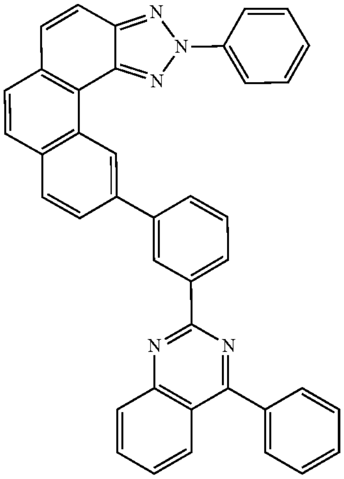
M127
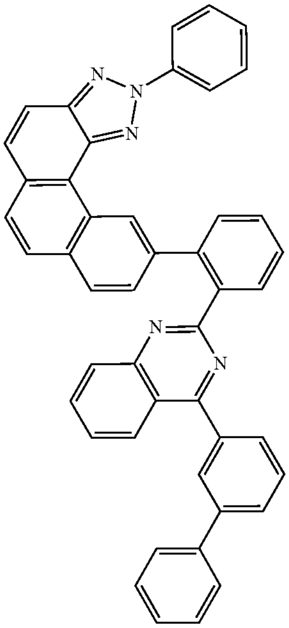

-continued
M128
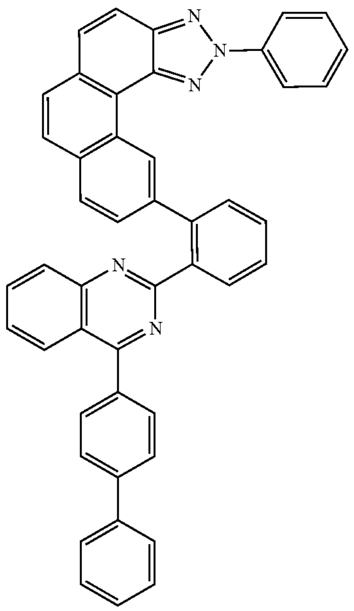
M129
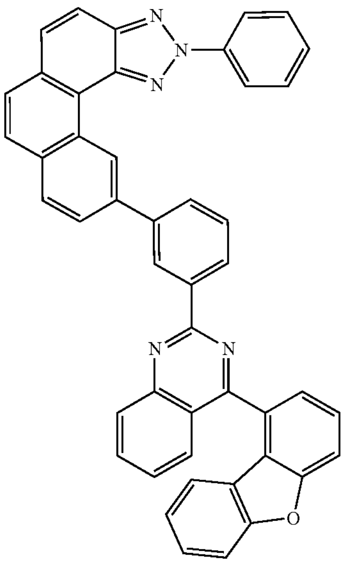
-continued
M130
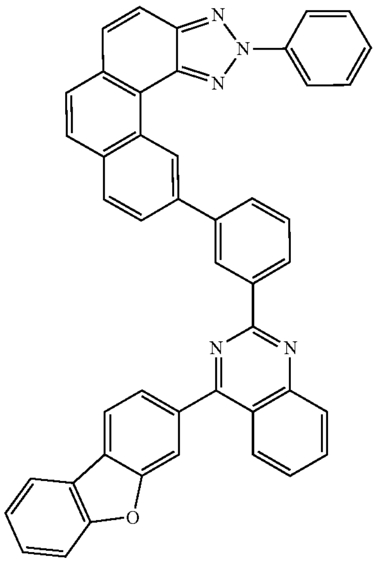
M131
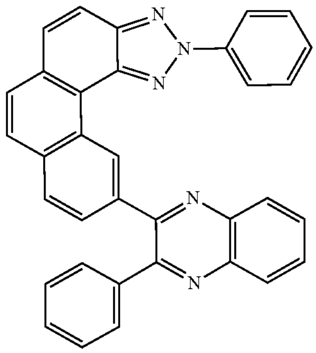
M132
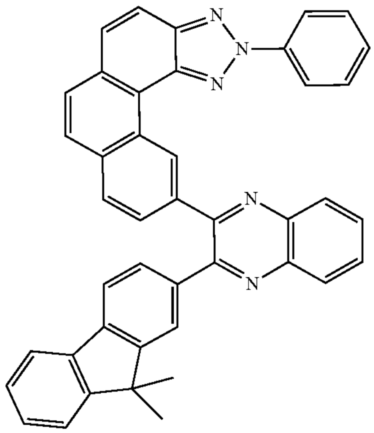

-continued
M133
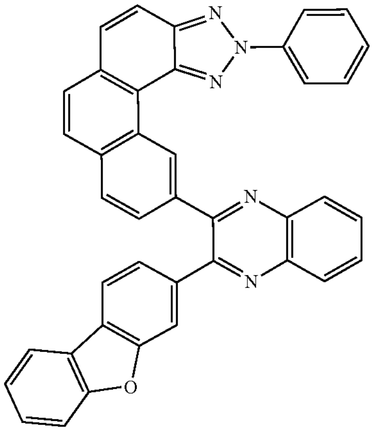
M134
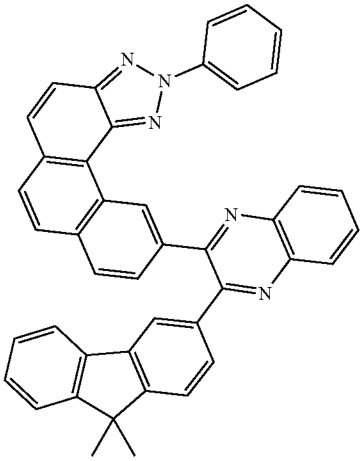
M135
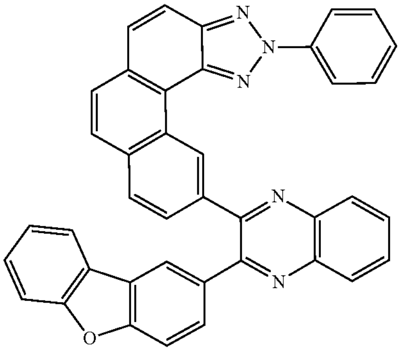
-continued
M136
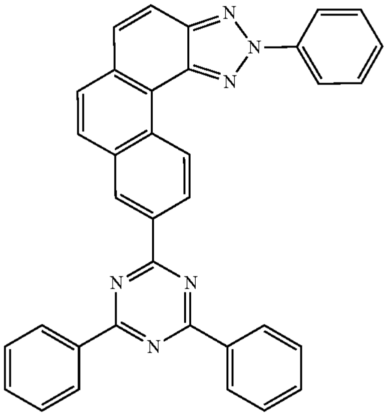
M137
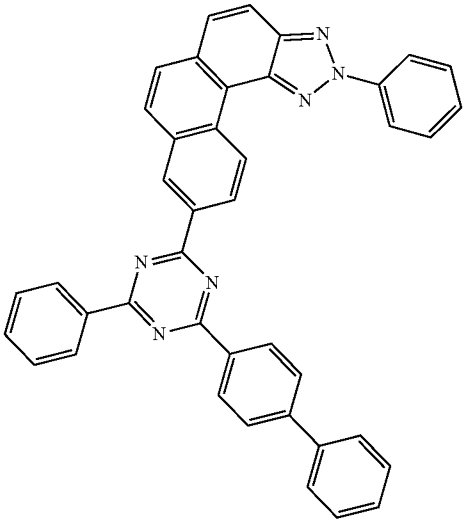
M138
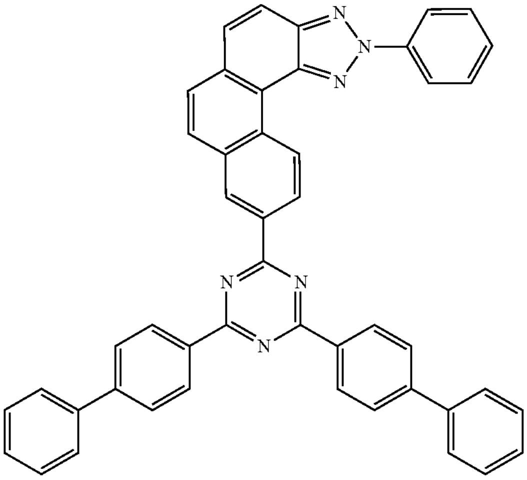

-continued
M139
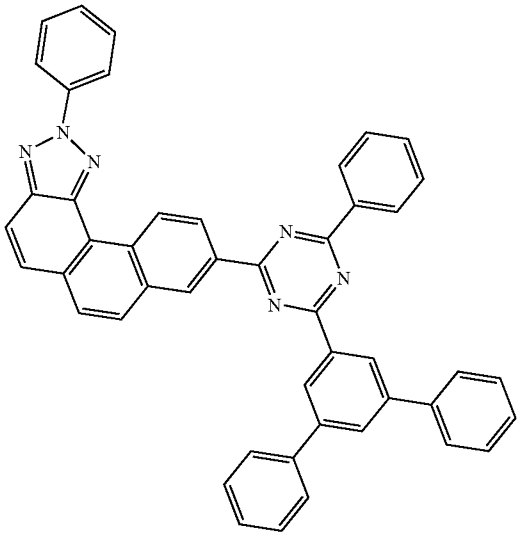
M140
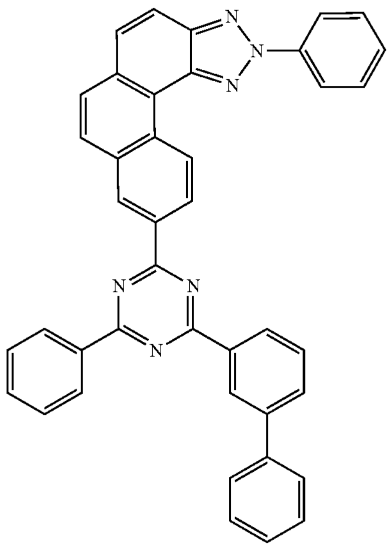
M141
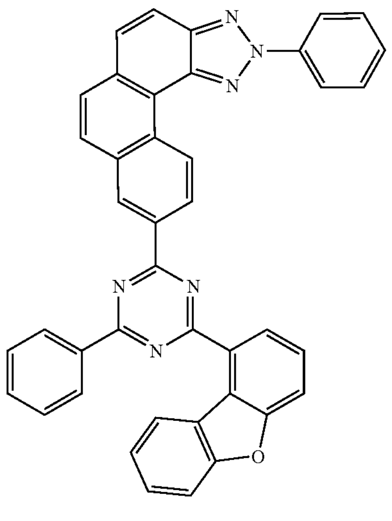
-continued
M142
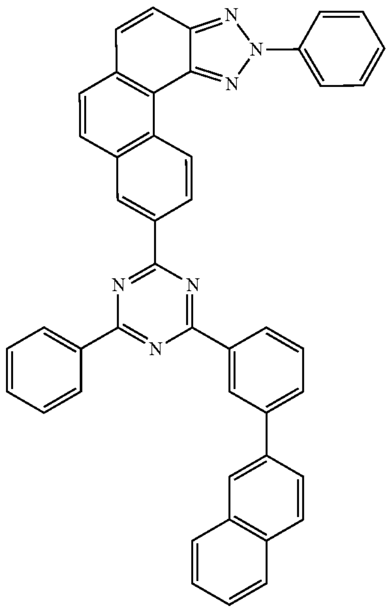
M143
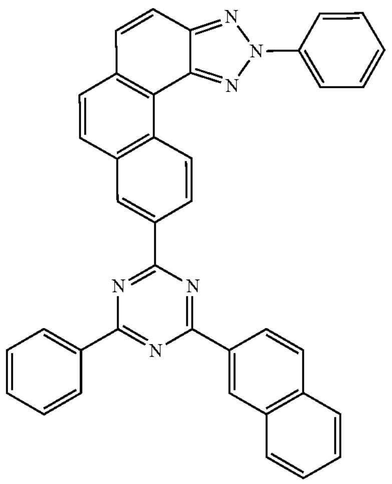
M144
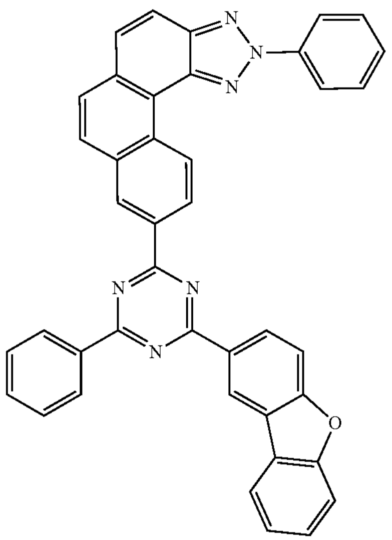

-continued
M145
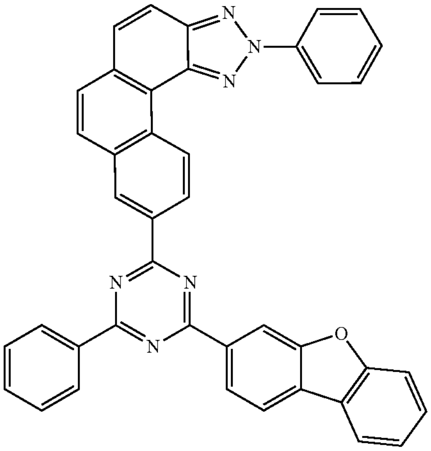
M146
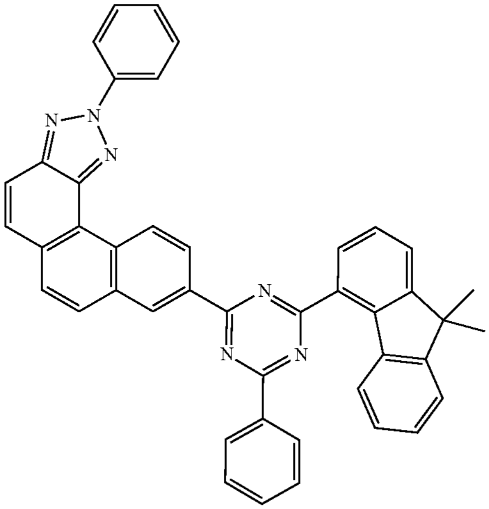
M147
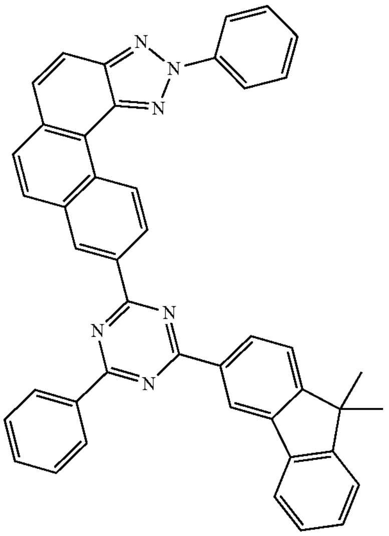
-continued
M148
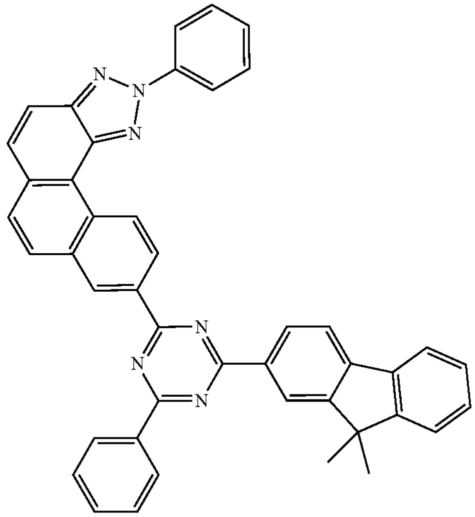
M149
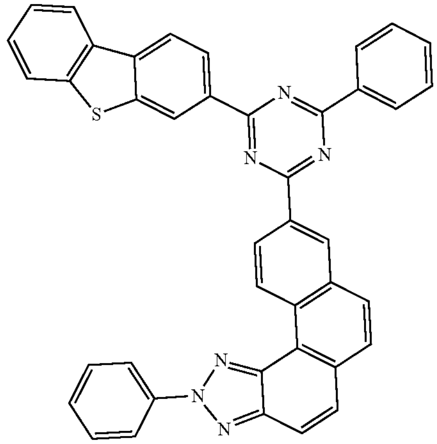
M150
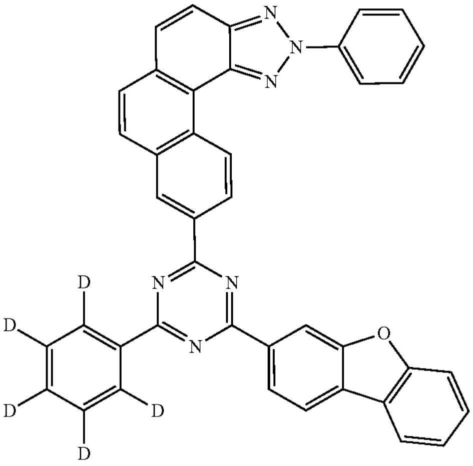

-continued
M151
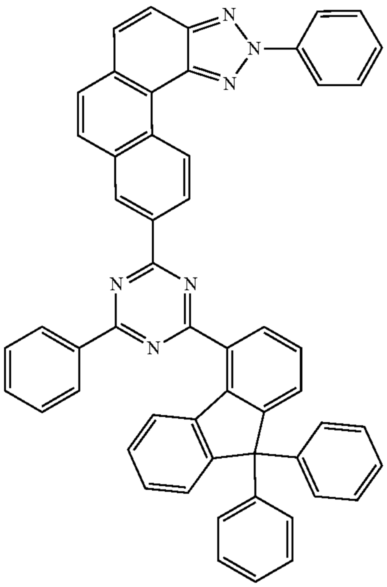
M153
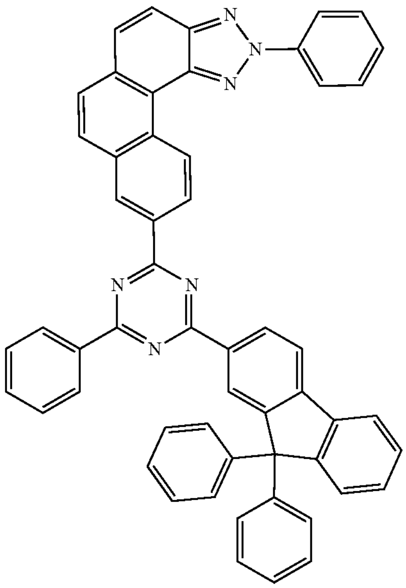
M152
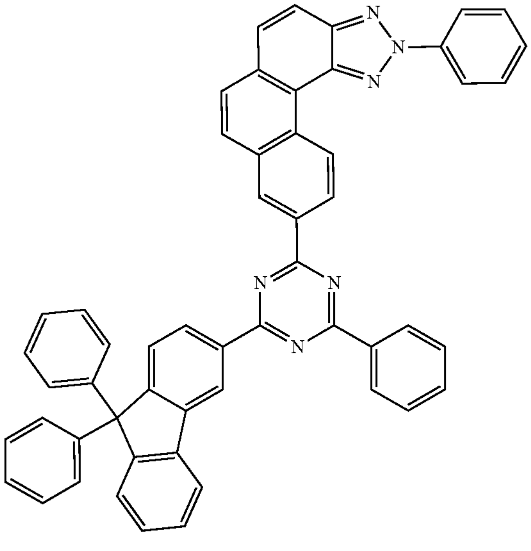
M154
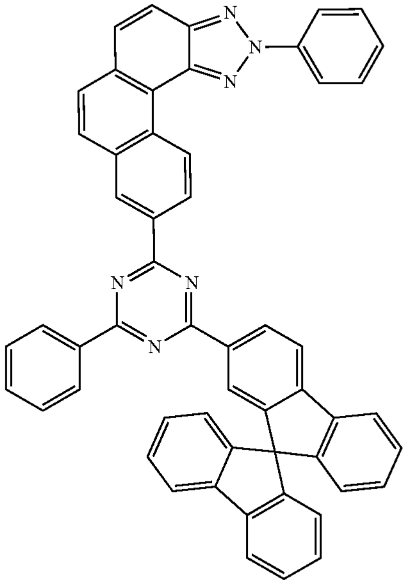

-continued
M155
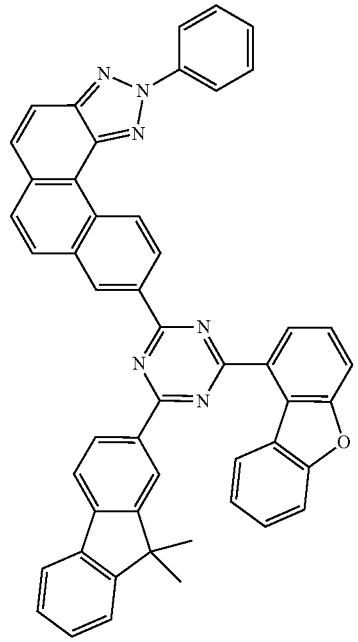
M156
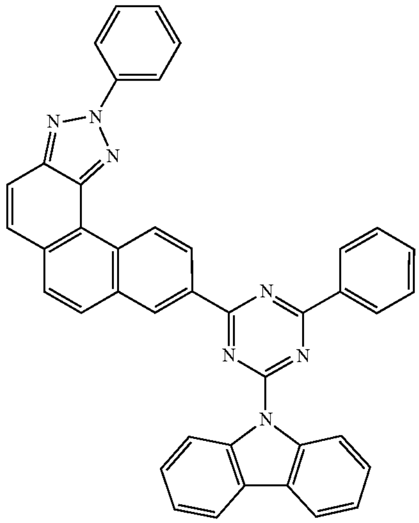
-continued
M157
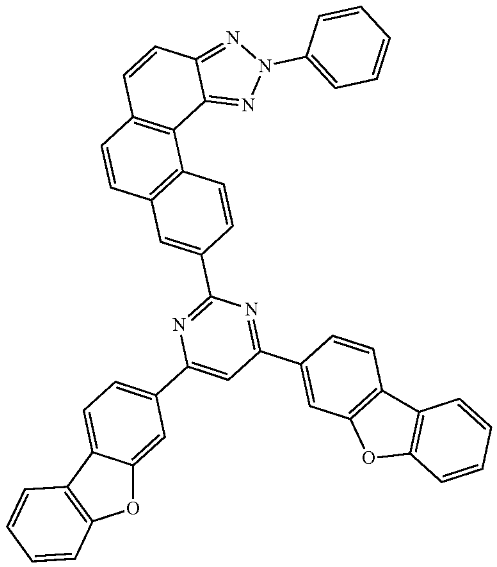
M158
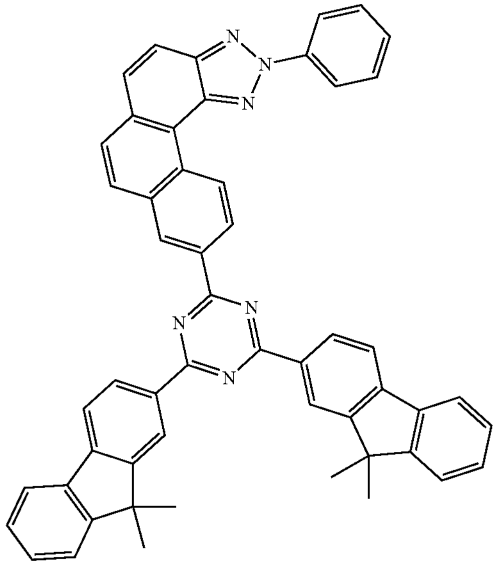
M159
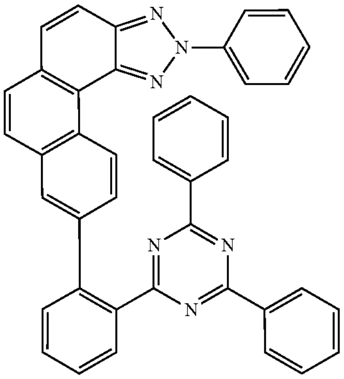

-continued
M160
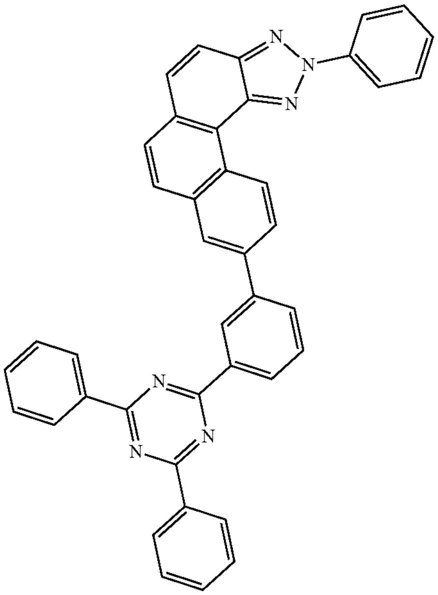
M161
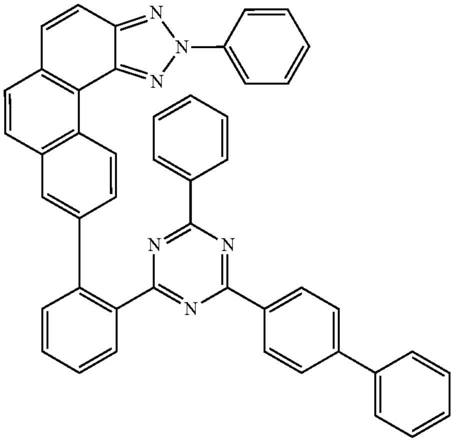
M162
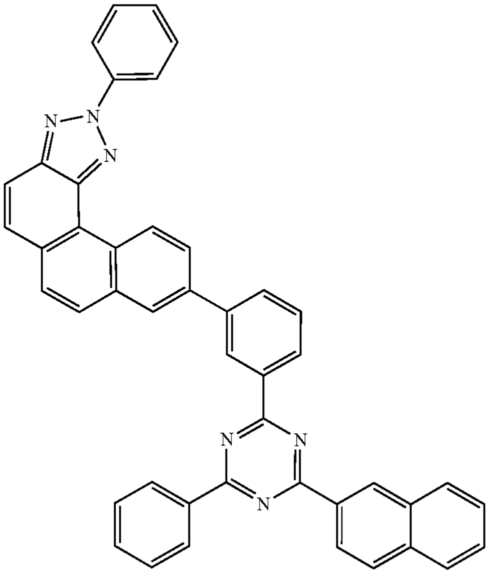
-continued
M163
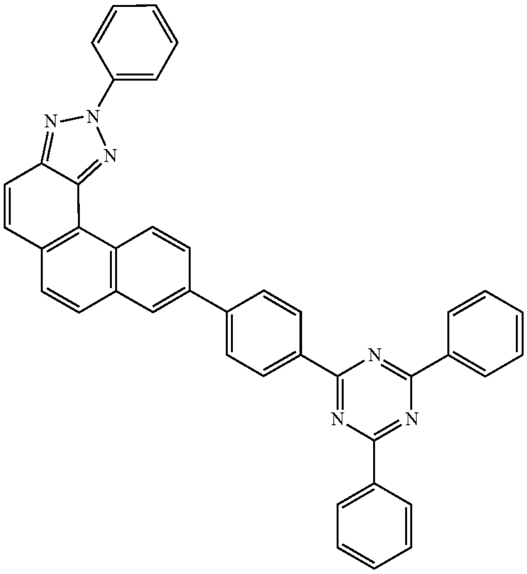
M164
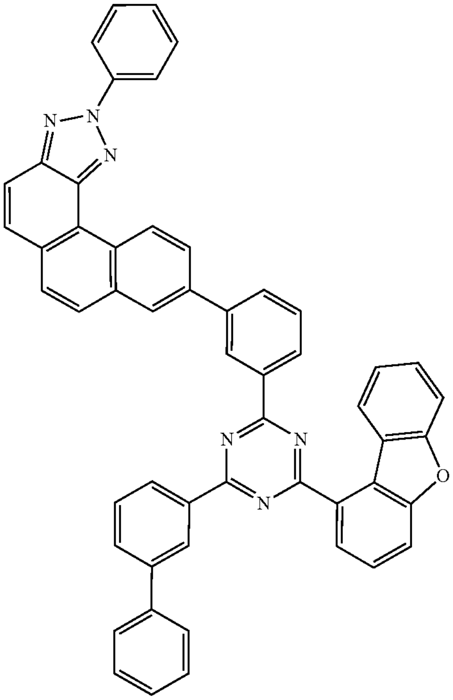

-continued
M165
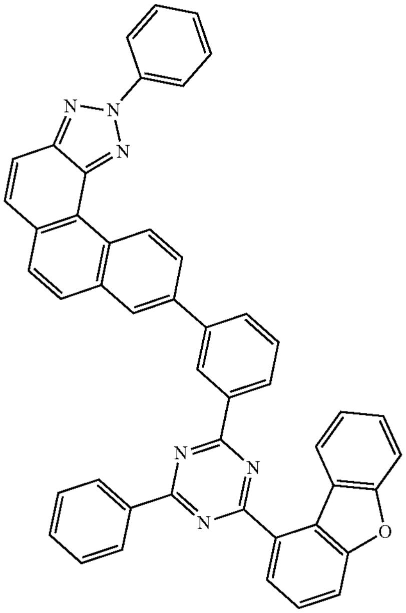
M166
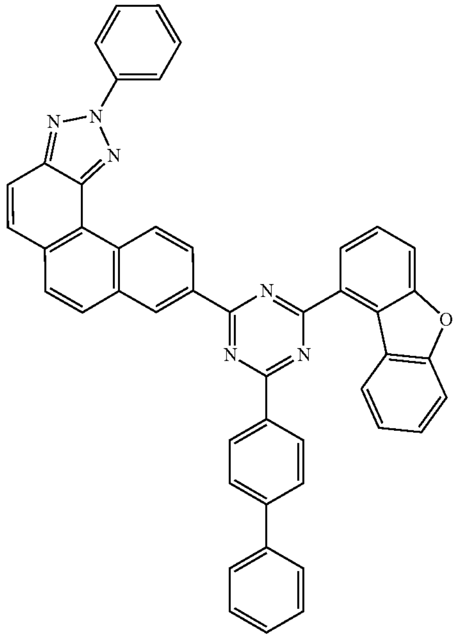
-continued
M167
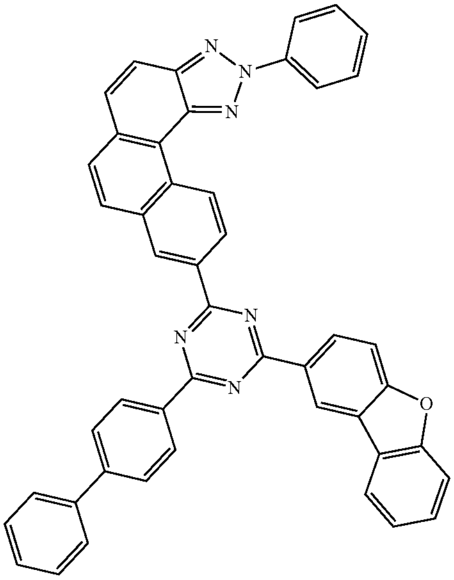
M168
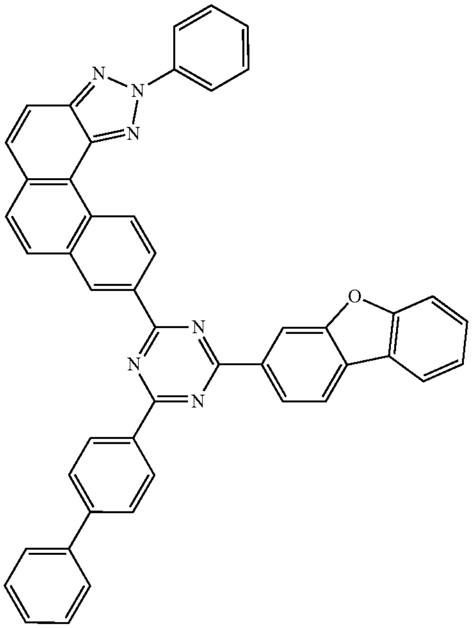

-continued
M169
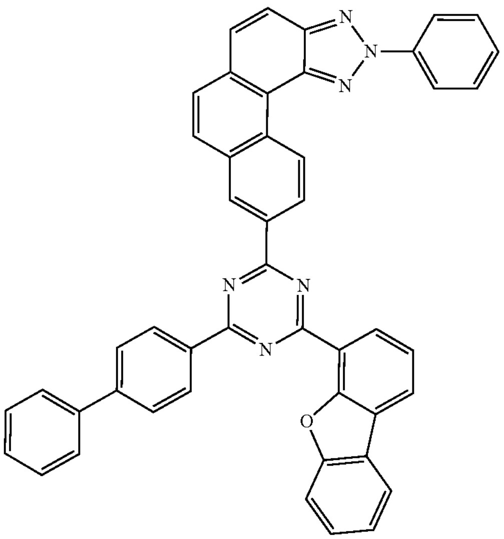
M170
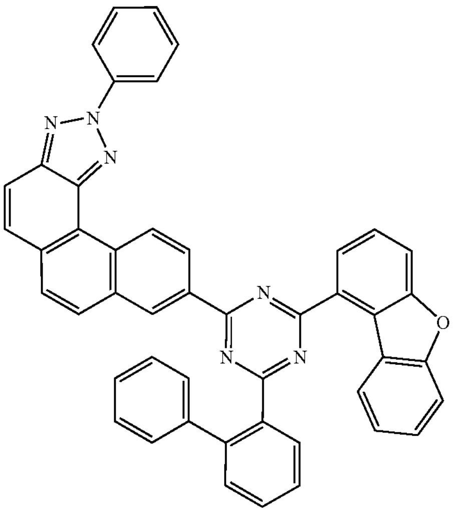
M171
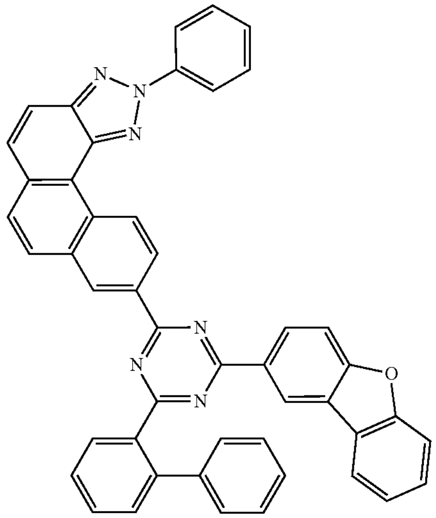
-continued
M172
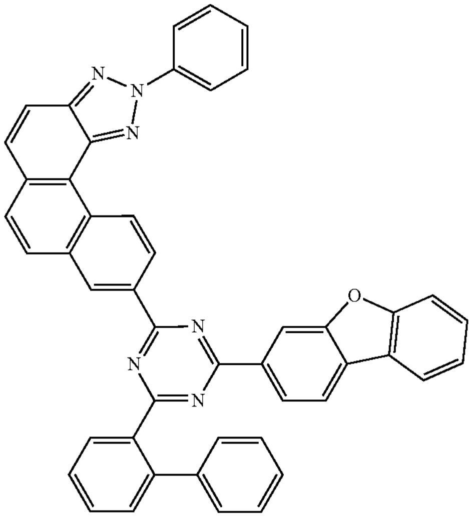
M173
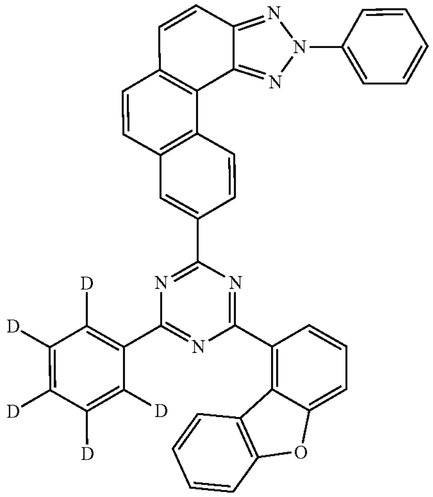
M174
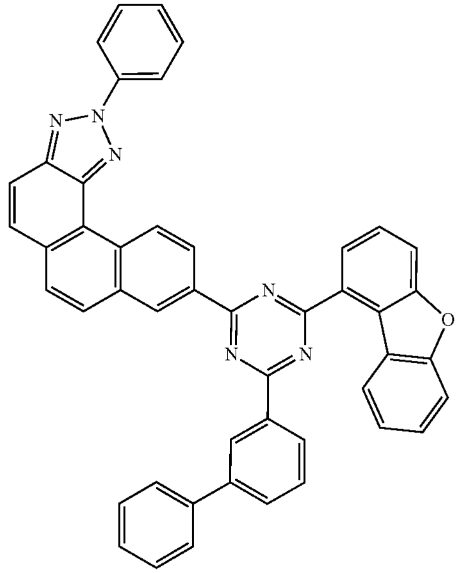

-continued
M175
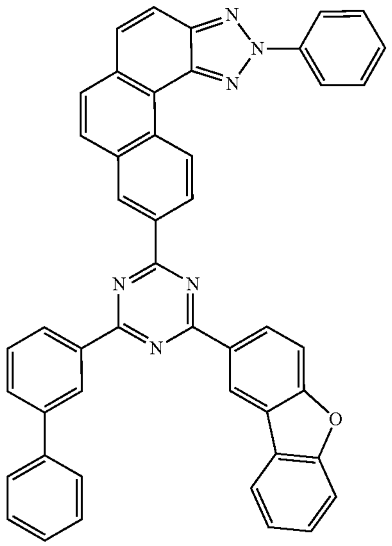
M176
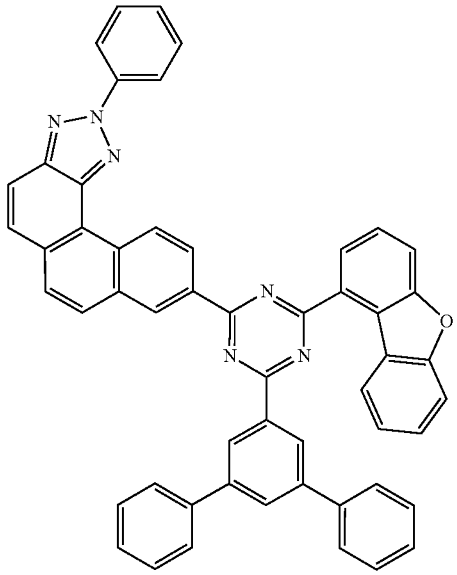
-continued
M177
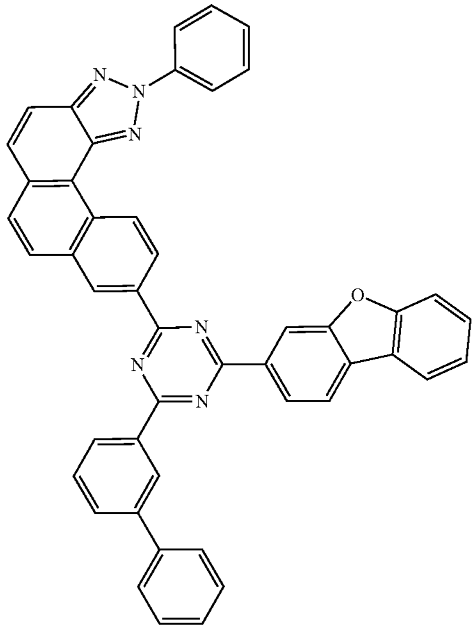
M178
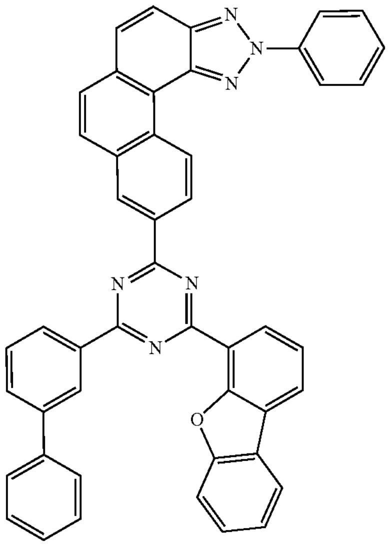

-continued
M179
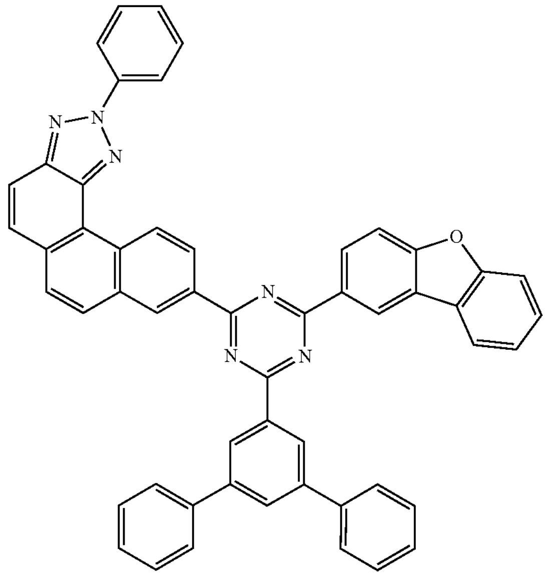
M180
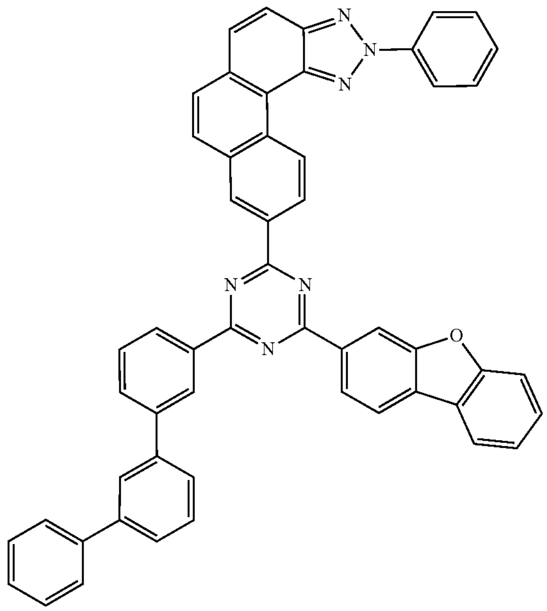
-continued
M181
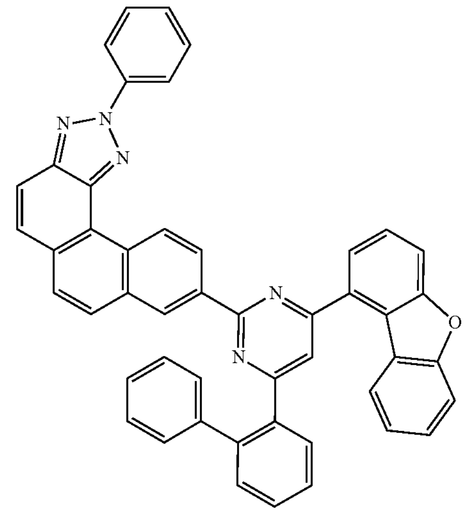
M182
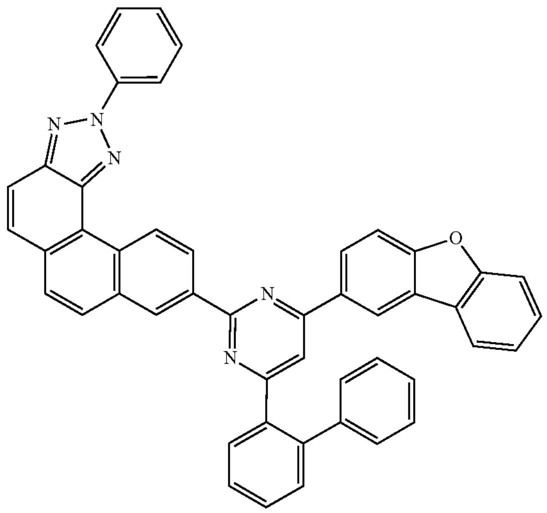
M183
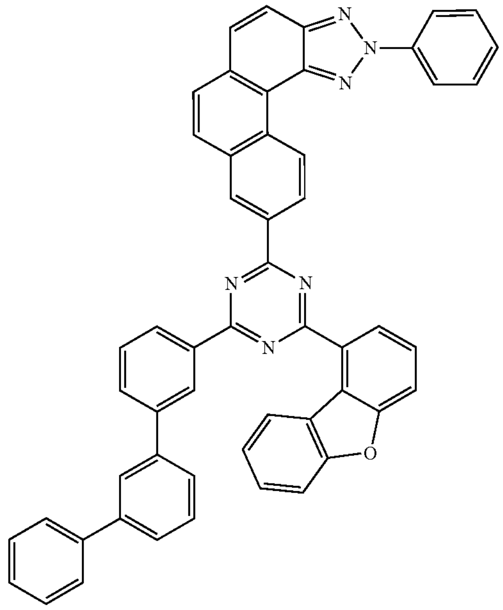

-continued
M184
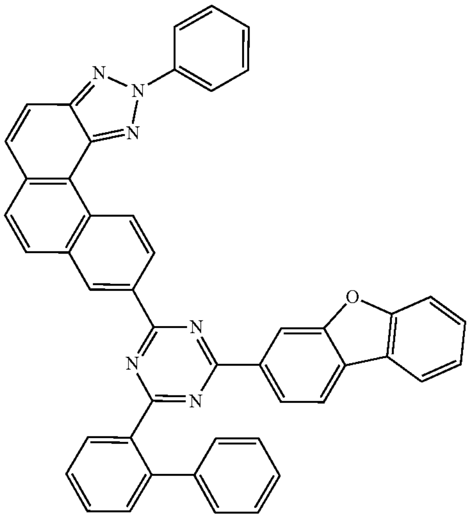
M185
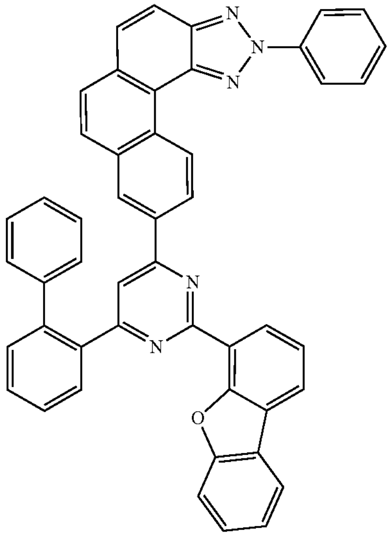
M186
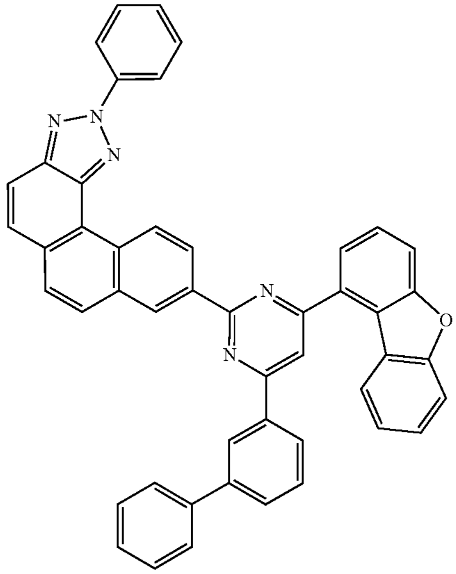
-continued
M187
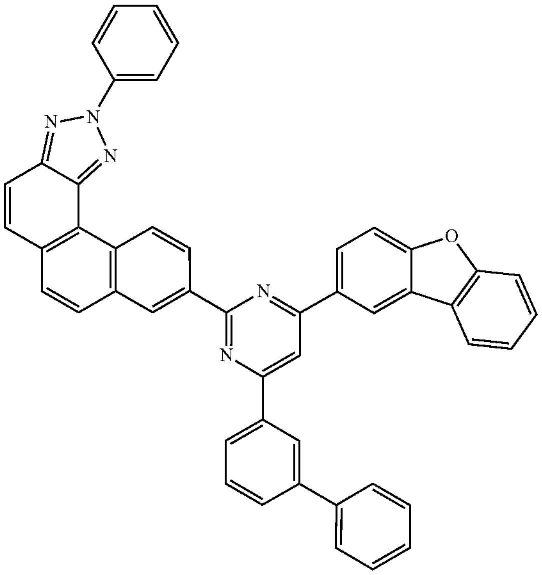
M188
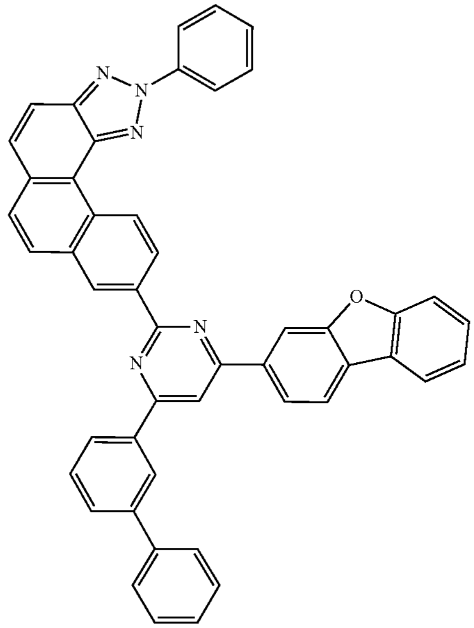

-continued
M189
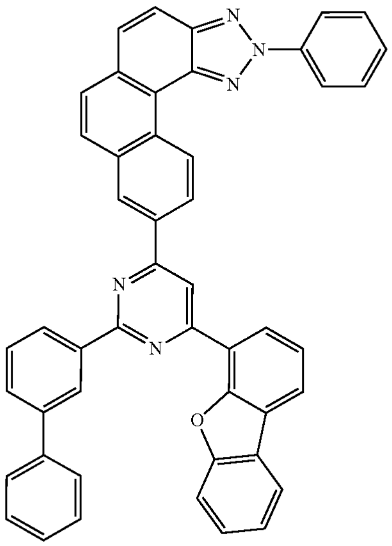
M190
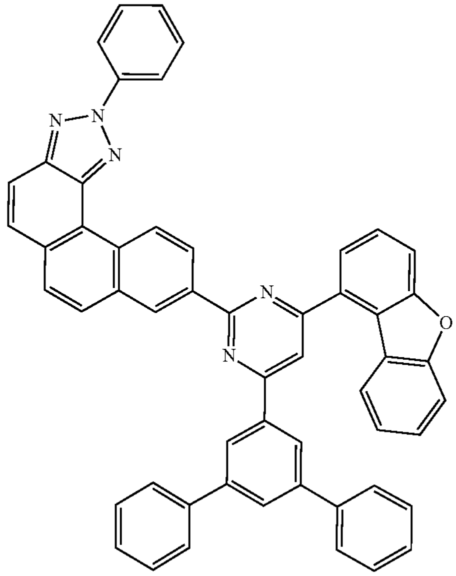
-continued
M191
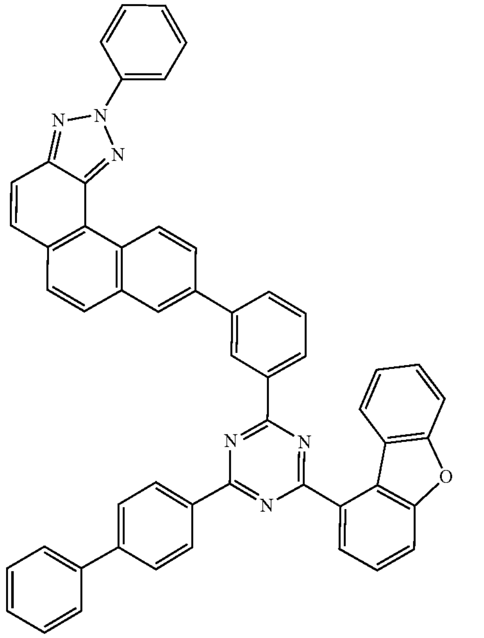
M192
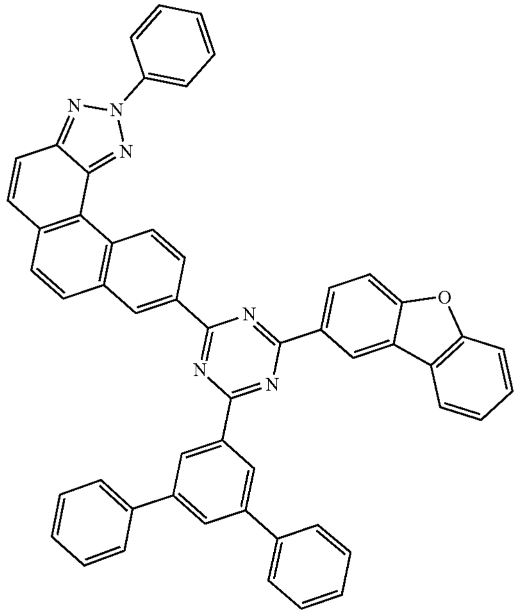

-continued
M193
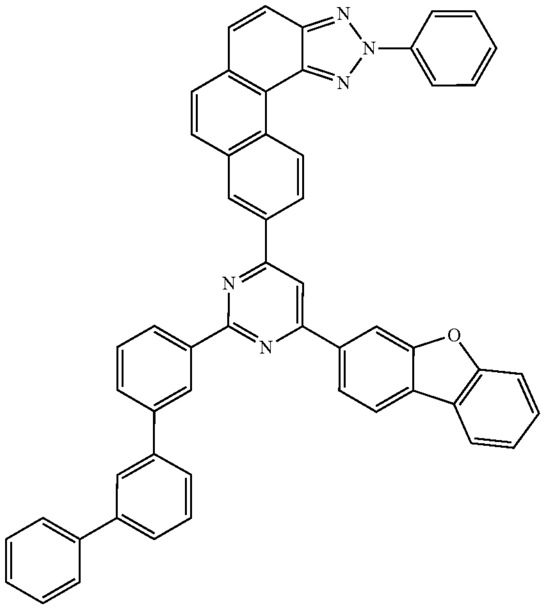
M195
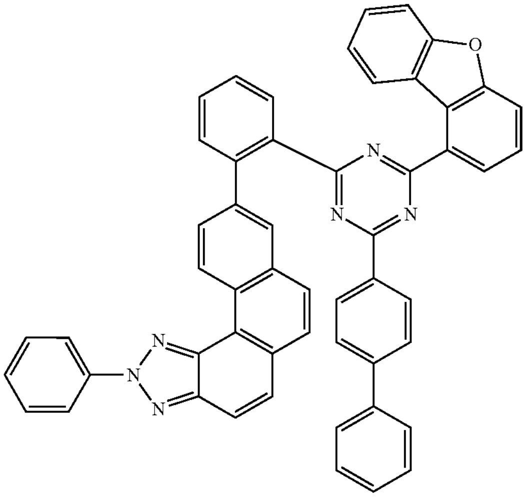
M194
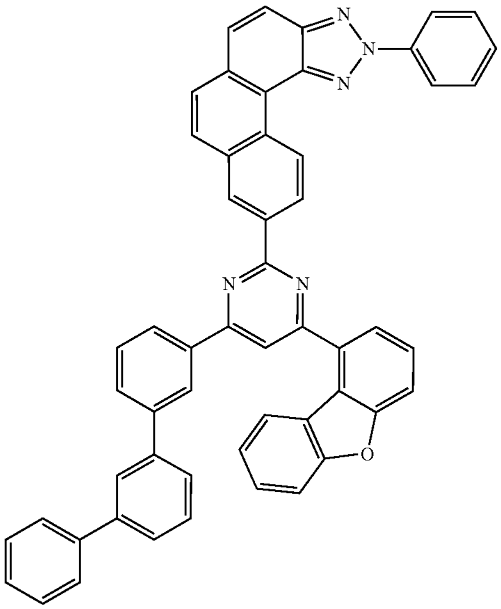
M196
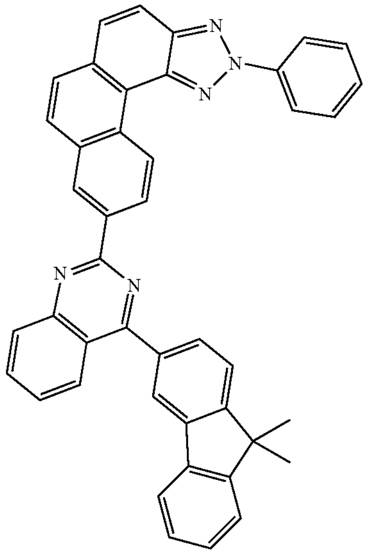

-continued
M197
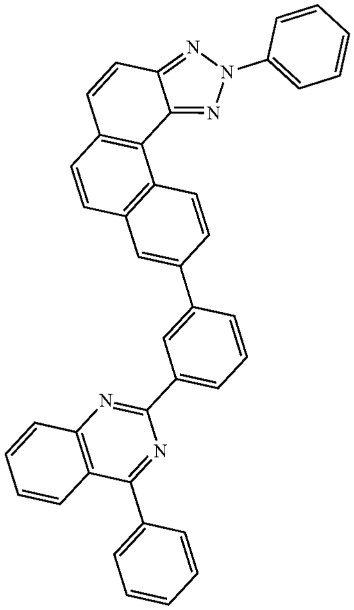
M198
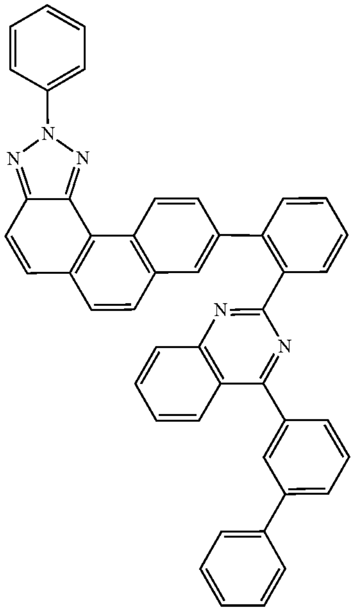
-continued
M199
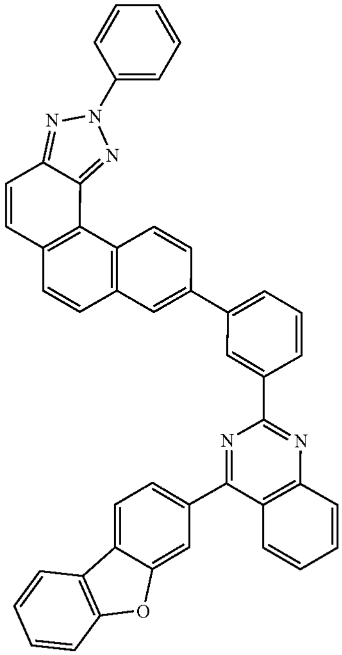
M200
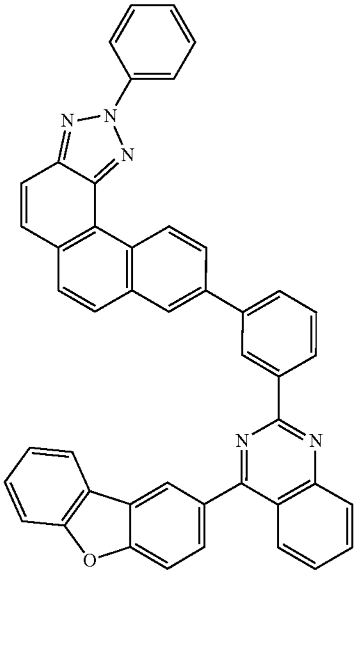

-continued
M201
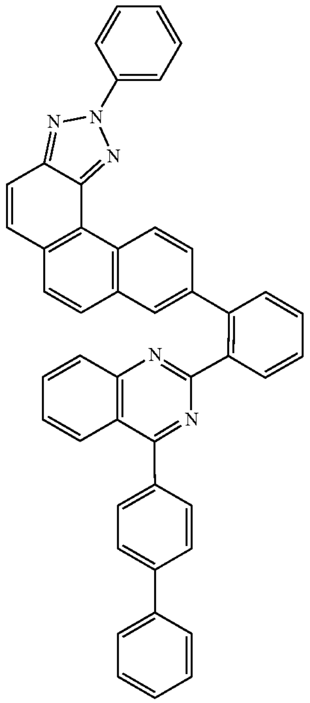
M202
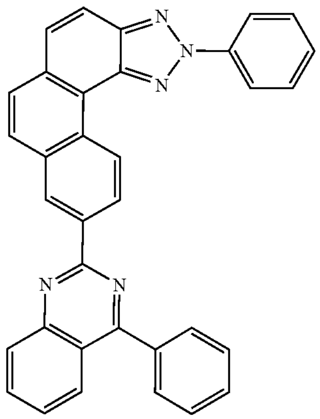
M203
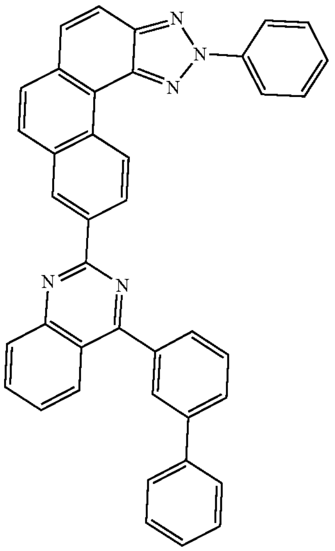
-continued
M204
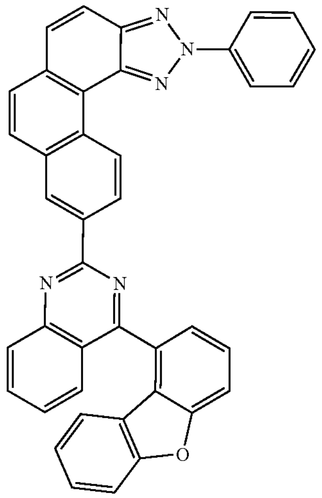
M205
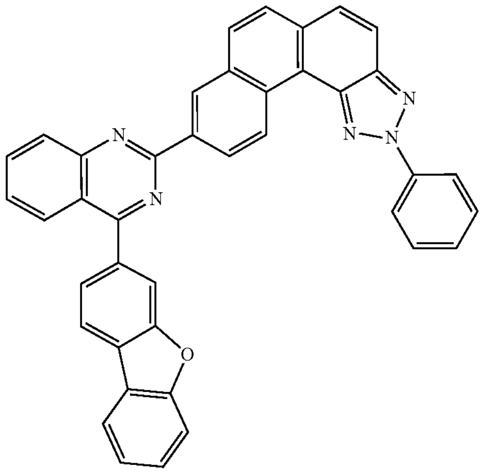
M206
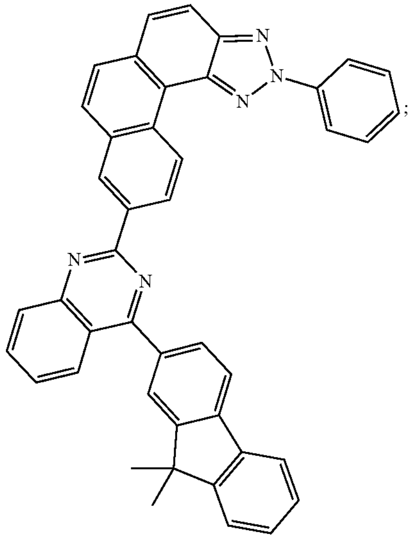
;
wherein D represents deuterium.
4. The organic material composition according to claim 1, wherein, in Formula (2), at least one of $Ar^5$ to $Ar^8$ is

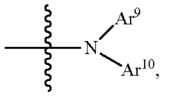

wherein $Ar^9$ and $Ar^{10}$ are each independently selected from a substituted or unsubstituted C6-C30 aryl group, and a substituted or unsubstituted C3-C30 heteroaryl group.

5. The organic material composition according to claim 1, wherein the substituent is selected from deuterium, halogen, a cyano group, a nitro group, an unsubstituted or R"-substituted C1-C4 straight or branched alkyl group, an unsubstituted or R"-substituted C6-C20 aryl group, an unsubstituted or R"-substituted C3-C20 heteroaryl group, and an unsubstituted or R"-substituted C6-C20 arylamino group; R" is selected from deuterium, halogen, a cyano group and a nitro group.

6. The organic material composition according to claim 1, wherein the compound having a structure represented by Formula (2) is any one of the following compounds N1 to N60:

N1

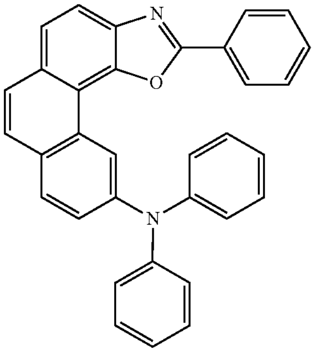

N2

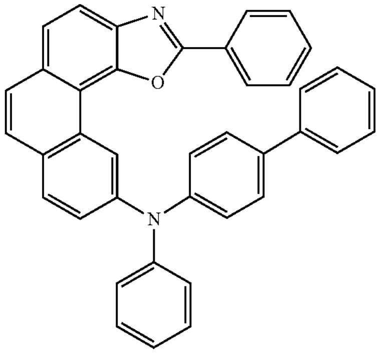

N3

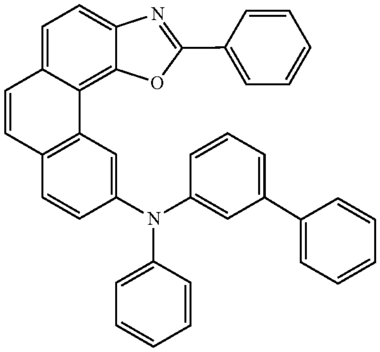

-continued

N4

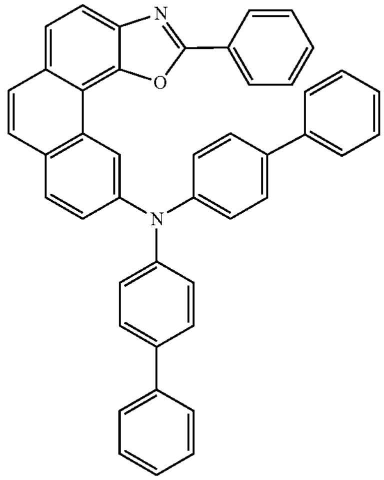

N5

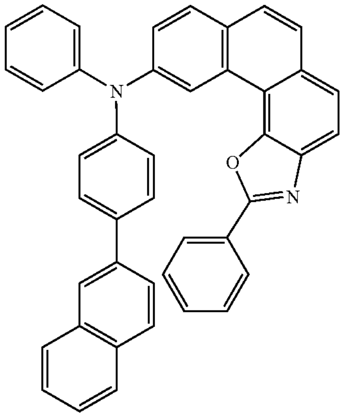

N6

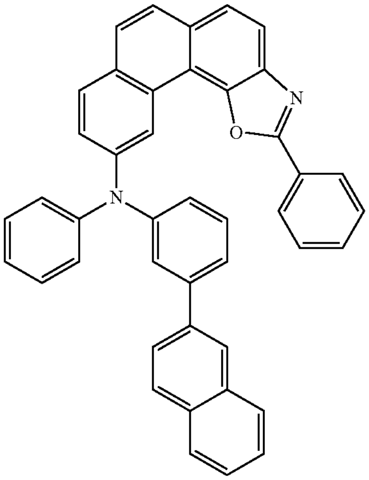

-continued
N7
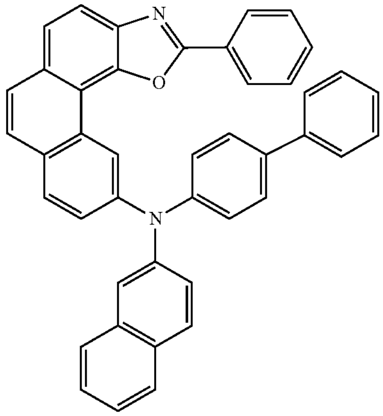
N8
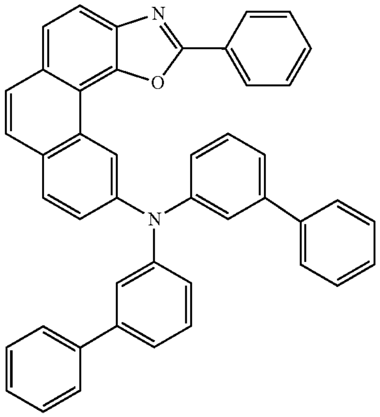
N9
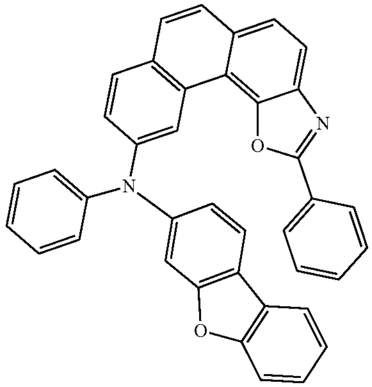
N10
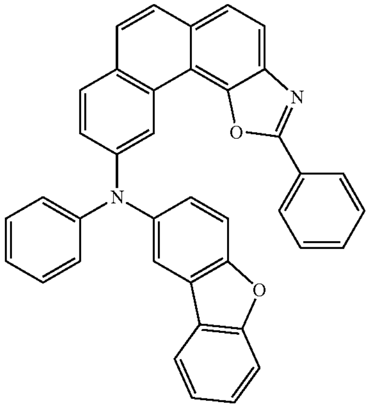
-continued
N11
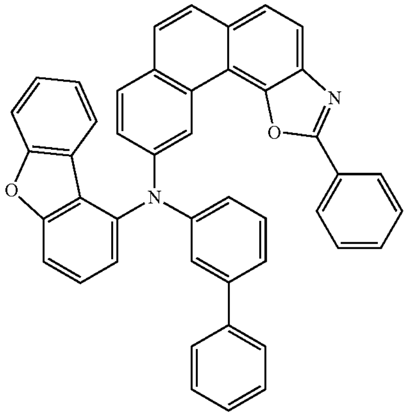
N12
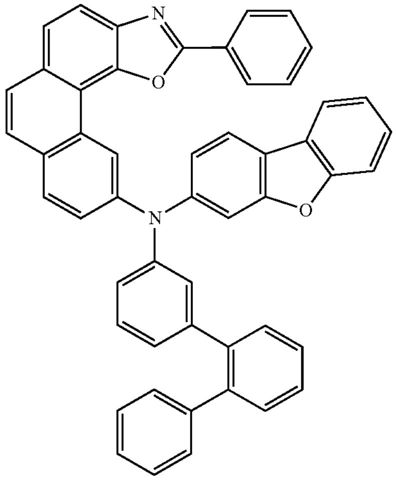
N13
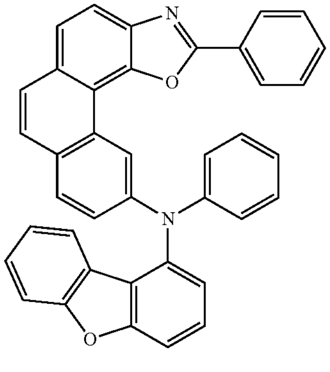

-continued
N14
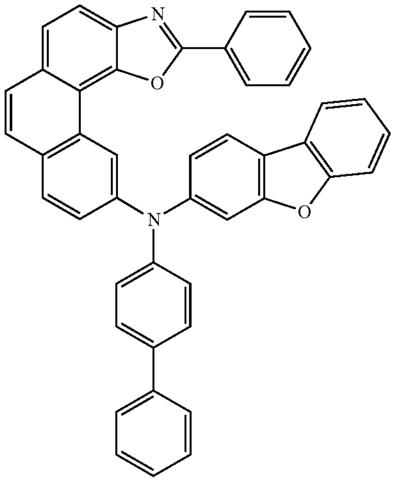
N15
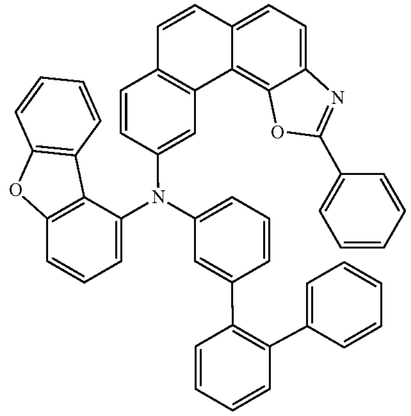
N16
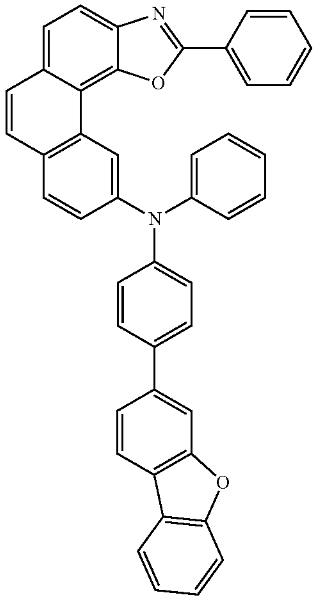
-continued
N17
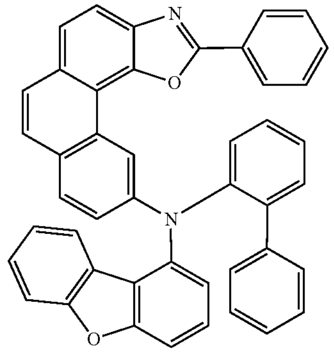
N18
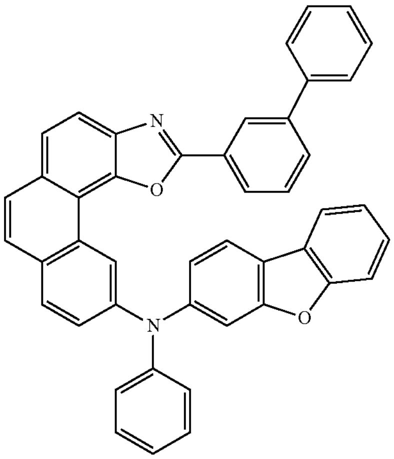
N19
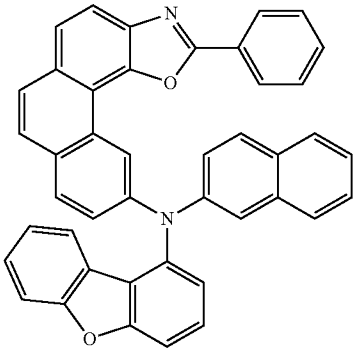
N20
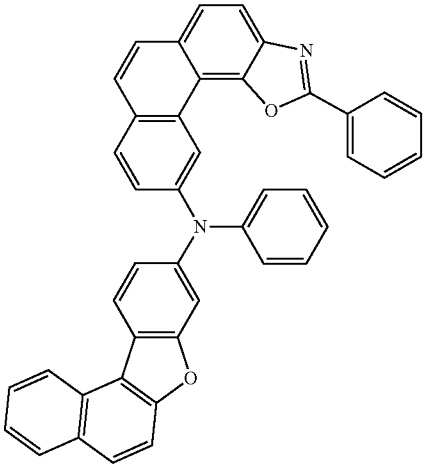

-continued
N21
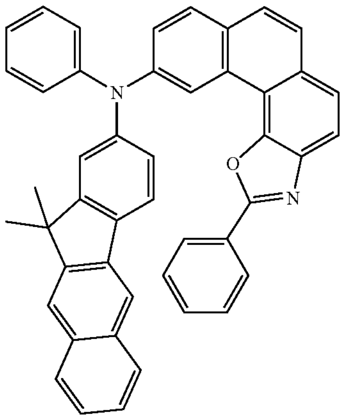
N22
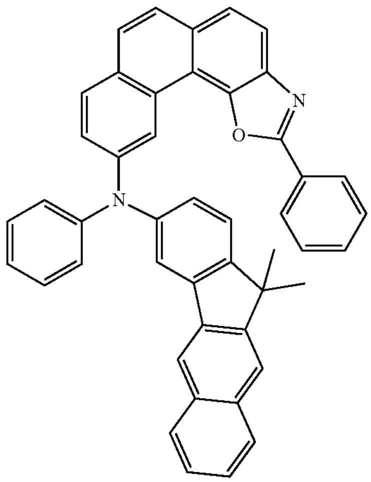
N23
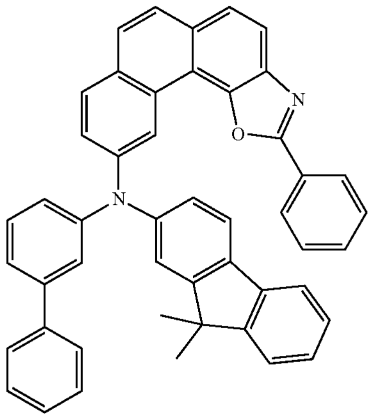
-continued
N24
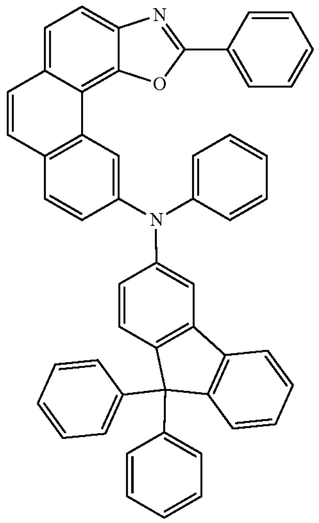
N25
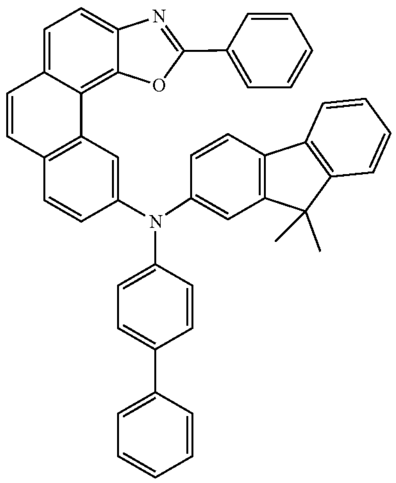
N26
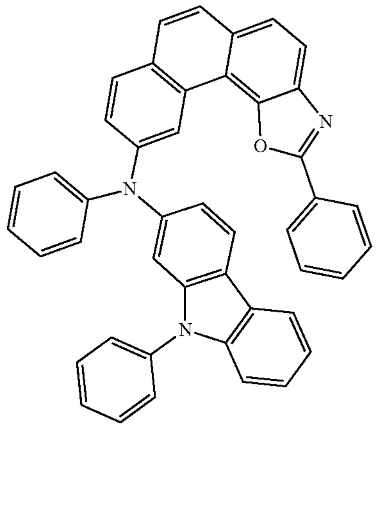

N27
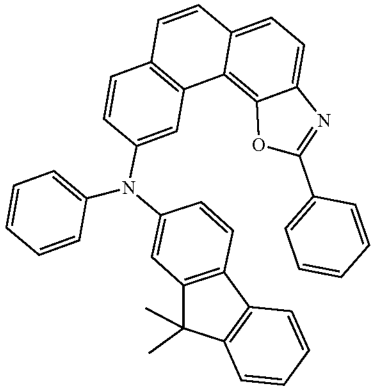
N28
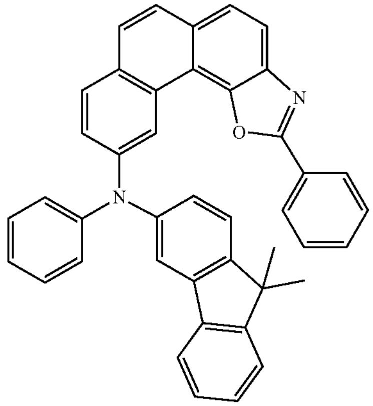
N29
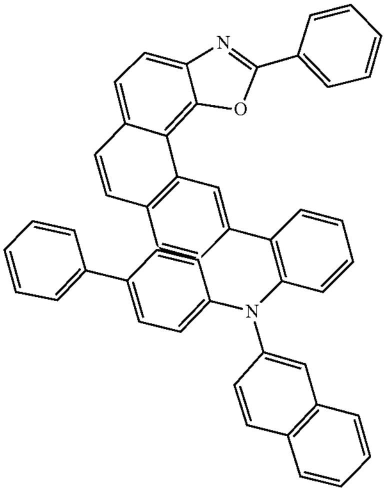
N30
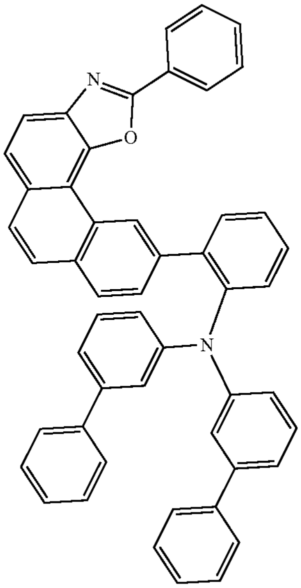
N31
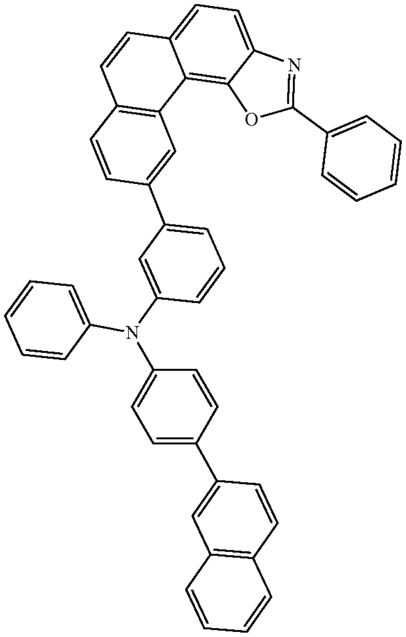

-continued
N32
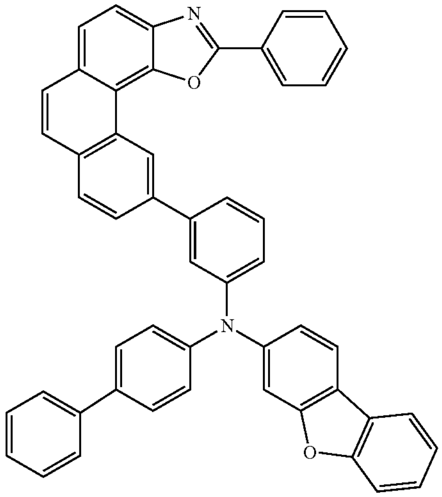
N33
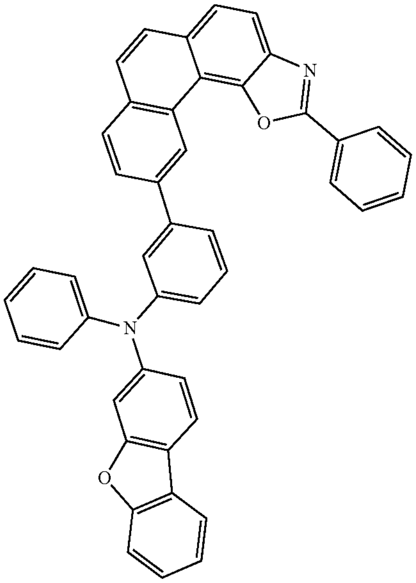
N34
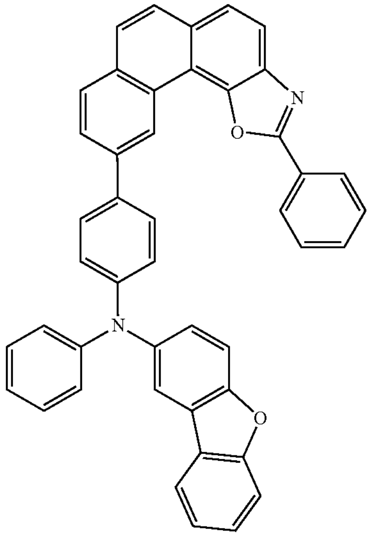
-continued
N35
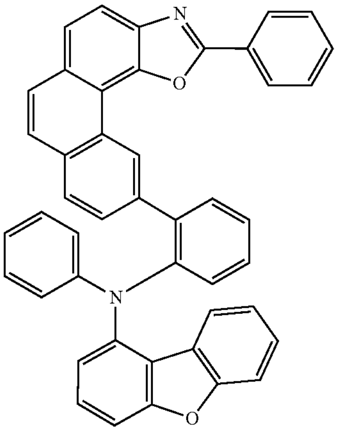
N36
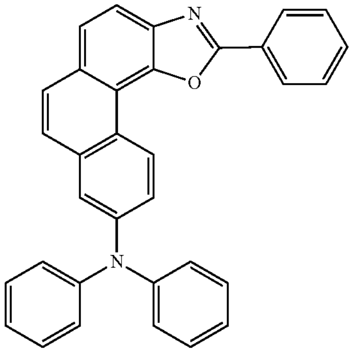
N37
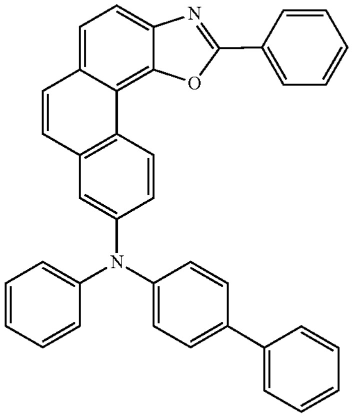

-continued
N38
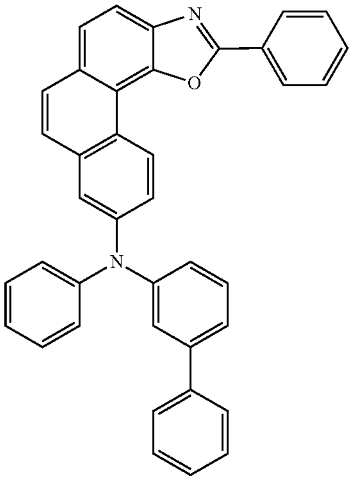
N39
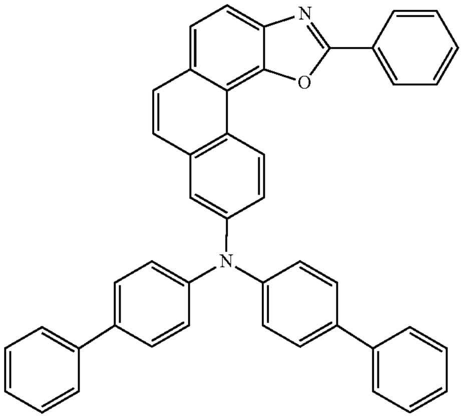
N40
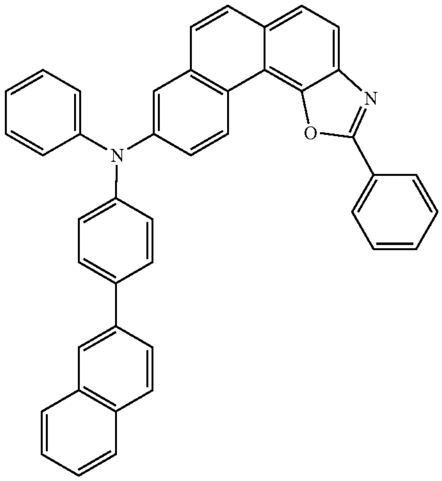
-continued
N41
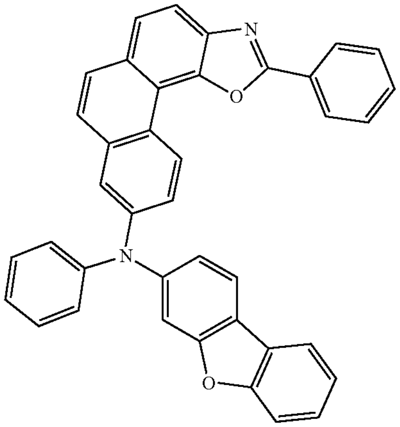
N42
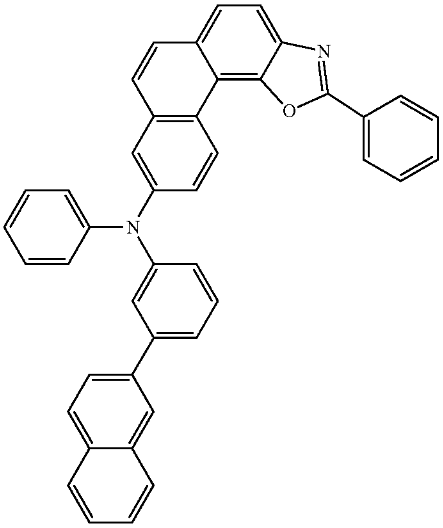
N43
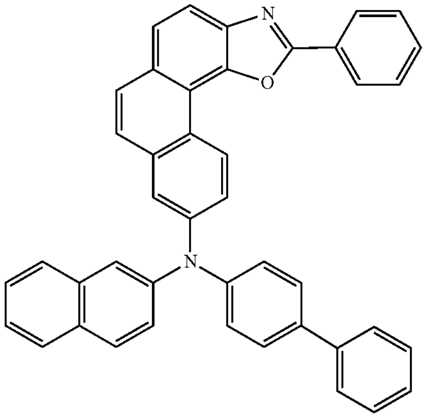

-continued
N44
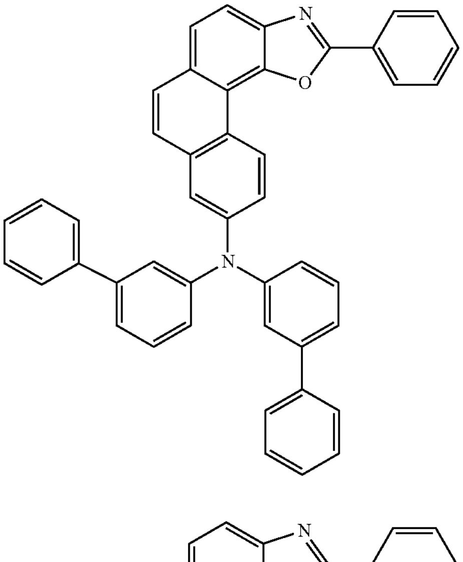
N45
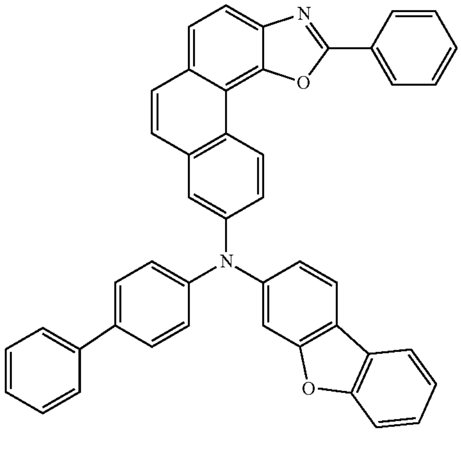
N46
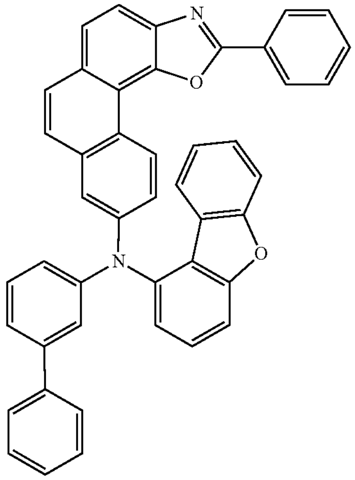
-continued
N47
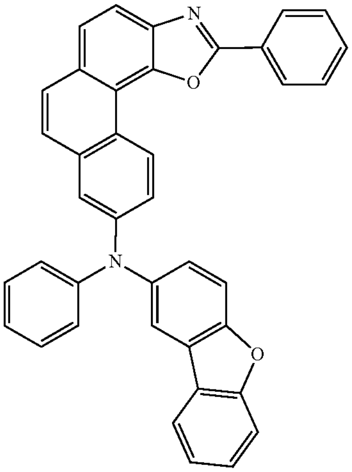
N48
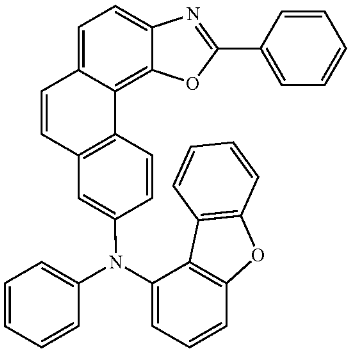
N49
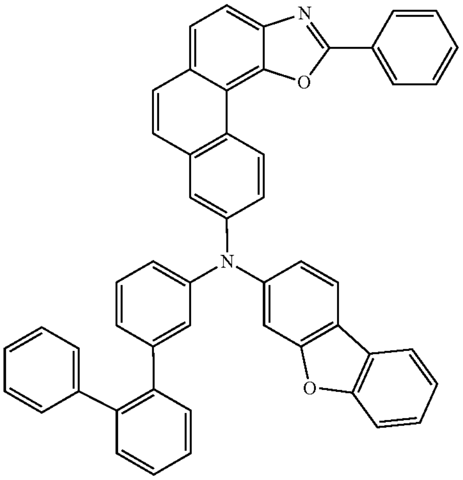

-continued
N50
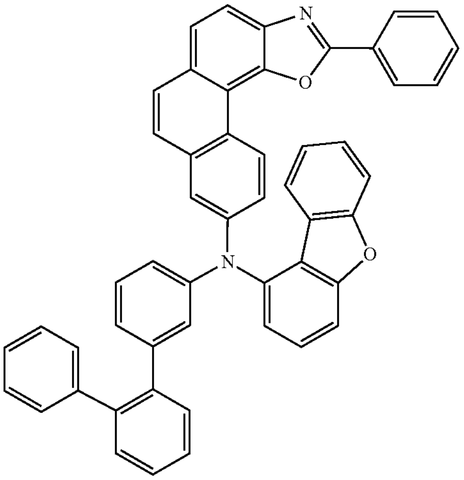
N51
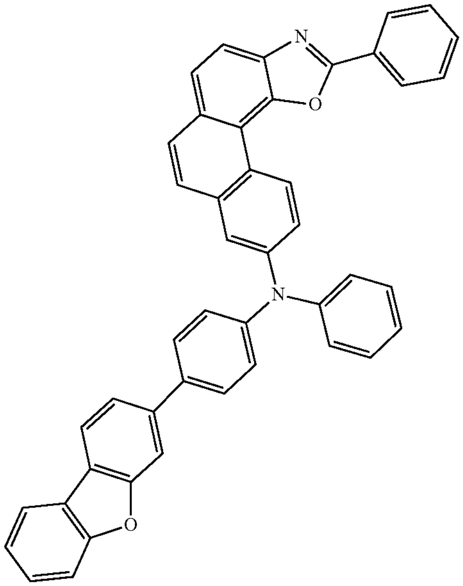
N52
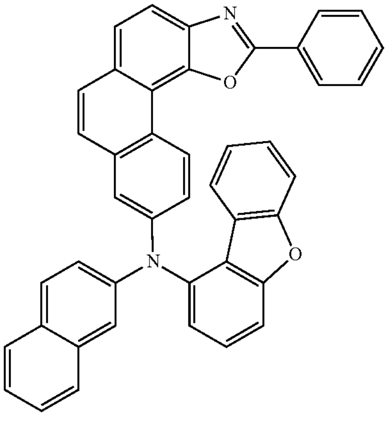
-continued
N53
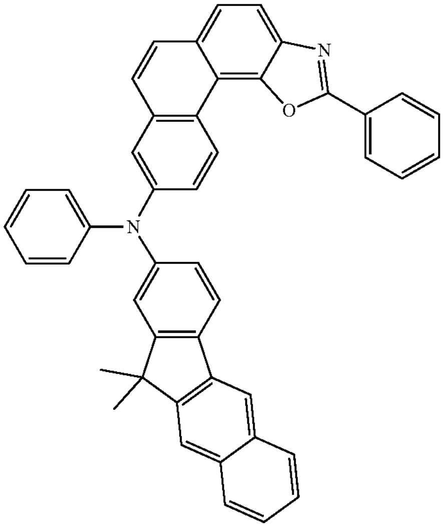
N54
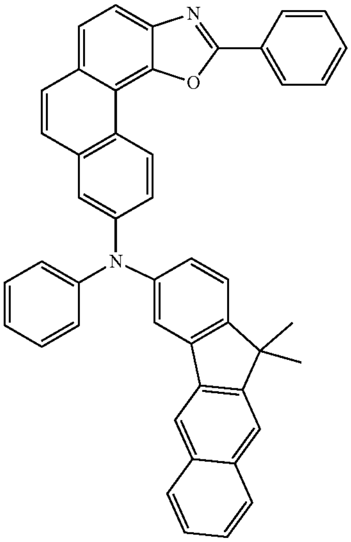
N55
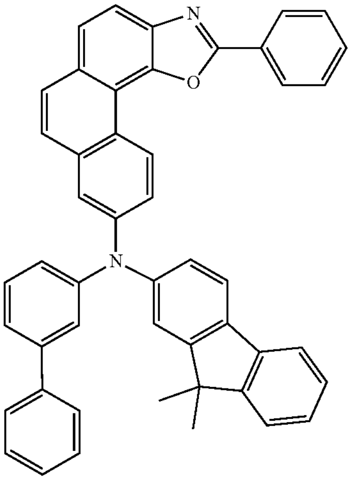

-continued

N56

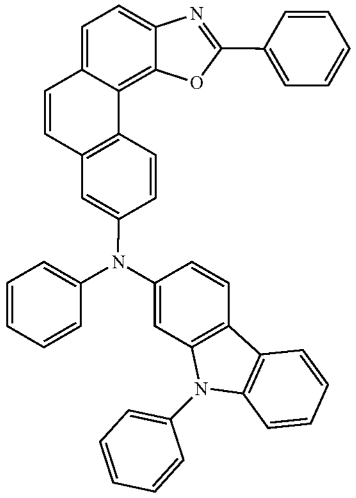

N57

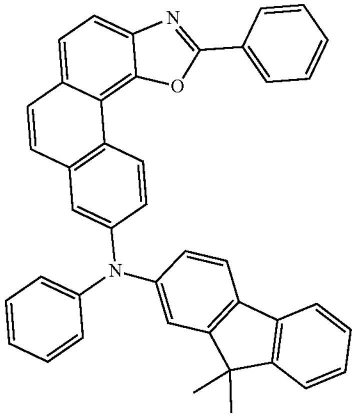

N58

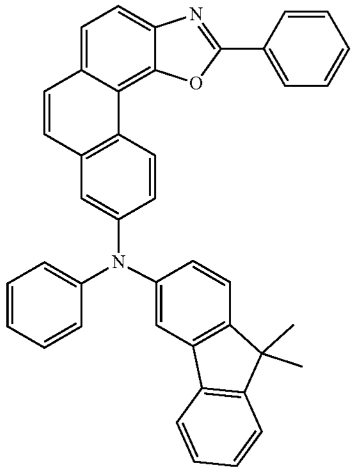

-continued

N59

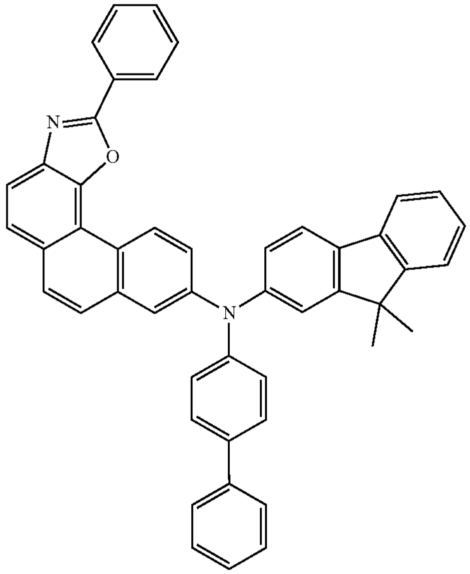

N60

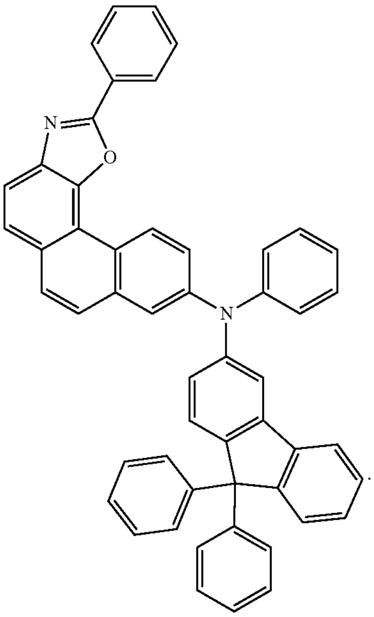

and the compound having a structure represented by Formula (1) and the compound having a structure represented by Formula (2) have a weight ratio of 1:9 to 9:1.

7. The organic material composition according to claim 6, wherein the compound having a structure represented by Formula (1) and the compound having a structure represented by Formula (2) have a weight ratio of 4:6 to 6:4.

8. An organic electroluminescence material, wherein the organic electroluminescence material comprises the organic material composition according to claim 1.

9. An application of the organic material composition according to claim 1 in preparation of an optical element.

10. An organic electroluminescence element, wherein the organic electroluminescence element comprises an anode, a cathode and an organic layer disposed between the anode and the cathode; and the organic layer comprises the organic material composition according to claim 1.

11. An electronic device, wherein the electronic device comprises the organic electroluminescence element according to claim 10.

* * * * *